(12) United States Patent
Sehgal et al.

(10) Patent No.: US 7,687,058 B2
(45) Date of Patent: *Mar. 30, 2010

(54) EX VIVO AND IN VIVO EXPRESSION OF THE THROMBOMODULIN GENE FOR THE TREATMENT OF CARDIOVASCULAR AND PERIPHERAL VASCULAR DISEASES

(75) Inventors: Lakshman R. Sehgal, Monarch Beach, CA (US); Jonathan Wong, Palo Alto, CA (US)

(73) Assignee: BioVec, LLC, Chicago, IL (US)

( * ) Notice: Subject to any disclaimer, the term of this patent is extended or adjusted under 35 U.S.C. 154(b) by 4 days.

This patent is subject to a terminal disclaimer.

(21) Appl. No.: 12/219,715

(22) Filed: Jul. 28, 2008

(65) Prior Publication Data

US 2009/0105180 A1    Apr. 23, 2009

Related U.S. Application Data

(60) Division of application No. 11/650,479, filed on Jan. 8, 2007, now Pat. No. 7,481,998, which is a continuation-in-part of application No. 10/725,013, filed on Dec. 2, 2003, now Pat. No. 7,179,459.

(60) Provisional application No. 60/430,099, filed on Dec. 2, 2002.

(51) Int. Cl.
*A01K 63/00* (2006.01)
*A61K 39/325* (2006.01)
*C12H 15/86* (2006.01)
*C07H 21/04* (2006.01)

(52) U.S. Cl. ............ 424/93.6; 424/233.1; 536/23.5; 536/24.1; 536/24.2

(58) Field of Classification Search .......... None
See application file for complete search history.

(56) References Cited

U.S. PATENT DOCUMENTS

| | | | |
|---|---|---|---|
| 4,826,811 | A | 5/1989 | Sehgal et al. |
| 5,981,225 | A | 11/1999 | Kochanek et al. |
| 6,290,949 | B1 | 9/2001 | French et al. |
| 7,179,459 | B2 | 7/2007 | Sehgal et al. |
| 7,501,114 | B2 * | 3/2009 | Sehgal et al. ........ 424/93.6 |

OTHER PUBLICATIONS

Zuckerbraun, Brian S., et al., "Vascular Gene Therapy, A Reality of the 21st Century," Arch. Surg., vol. 137, pp. 854-861 (2002). .
Kibbe, Melina R., et al., "Gene Therapy for Restenosis," Circ. Res., vol. 86, pp. 829-833 (2000).
Shears, Larry L, et al., "Efficient Inhibition of Intimal Hyperplasia by Adenovirus-Mediated Inducible Nitric Oxide Synthase Gene Transfer to Rats and Pigs In Vivo," J. Am. Coll. Surg., vol. 187, No. 3, pp. 295-306 (1998).
Ross, Russell, "The pathogenesis of atherosclerosis: a perspective for the 1990s," Nature, vol. 362, pp. 801-809 (1993).
Sadler, J. Evan, "Thrombomodulin Structure and Function," Tehomb Haemost., vol. 78, pp. 392-395 (1997).
Esmon, Charles T., "Thrombomodulin as a model of molecular mechanisms that modulate protease specificity and function at the vessel surface," Faseb J., vol. 9; pp. 946-955 (1995).
Salomaa, Veikko, et al., "Soluble thrombomodulin as a predicctor of incident coronary heart disease and symptomless carotid artery atherosclerosis in the Atherosclerosis Risk in Communities (ARIC) Study: a case-cohort study," Lancet, vol. 353, pp. 1729-1734 (1999).
Palmer, R.M.J., et al., "Nitric oxide release accounts for the biological activity of endothelium-derived relaxing factor," Nature, vol. 327, pp. 524-526 (1987).
Kubes, P., et al., "Nitric oxide: An endogenous modulator of leukocyte adhesion," Proc. Natl. Acad. Sci. USA, vol. 88, pp. 4651-4655 (1991).
Steg, P. Gabriel, M.D., et al., "Reduction of Restenosis After Angioplasty in an Atheromatous Rabbit Model by Suicide Gene Therapy," Circulation, vol. 96, pp. 408-411 (1997).
Van Belle, Eric, et al., "Accelerated Endothelialization by Local Delivery of Recombinant Human Vascular Endothelial Growth Factor Reduces In-Stent Intimal Formation," Biochem. and Biophs. Res. Communications, vol. 235, pp. 311-316 (1997).
Salyapongse, A. Neil, M.D., et al., "Gene Therapy and Tissue Engineering," Tissue Engineering, vol. 26, No. 4, pp. 663-676 (1999).
Kon, T., et al., "Bone Morphogenetic Protein-2-Stimulates Differentiation of Cultured Spinal Ligament Cells from Patients with Ossification of the Posterior Longitudinal Ligament," Calcif. Tissue Int., vol. 60; pp. 291-296 (1997).
Kibbe, Melina R., MD, et al., "Adenovirus-mediated gene transfer of human inducible nitric oxide synthase in porcine vein grafts inhibits intimal hyperplasia," J. Vasc. Surg., vol. 34, pp. 156-165 (2001).
He, Tong-Chuan, et al., "A simplified system for generating recombinant adenoviruses," Proc. Natl. Acad. Sci. USA, vol. 95, pp. 2509-2514 (1998).
Marmur, J., et al., "Strand Separation and Specific Recombination in Deoxyribonucleic Acids: Biological Studies," Proc. Natl. Acad. Sci. USA, vol. 46, pp. 453-461 (1960).
Doty, P., et al., "Strand Separation and Specific Recombination in Deoxyribonucleic Acids: Physical Chemical Studies," PNAS USA, vol. 46, pp. 461-476 (1960).
Sambrook, J. Fritsch, et al., "Analysis of Genomic DNA by Southern Hybridization," Molecular Cloning: A Laboratory Manual (Cold Spring Harbor Lab. Press, Plainview, NY), vol. II, pp. 9.31-9.62 (1989).
Curiel, David T., "Strategies to Adapt Adenoviral Vectors for Targeted Delivery," Ann NY Acad Sci 886, pp. 158-171 (1991).

(Continued)

*Primary Examiner*—Richard Schnizer
(74) *Attorney, Agent, or Firm*—Ping Wang; Morris, Manning & Martin, LLP

(57) ABSTRACT

The present invention relates to methods and compositions for treatment of cardiovascular and peripheral vascular diseases using ex vivo and in vivo gene delivery technologies. One aspect of the present invention relates to a method for treating a vascular disease by introducing a DNA sequence encoding a TM protein or its variant into a segment of a blood vessel ex vivo using a gutless adenovirus vector. Another aspect of the present invention is to provide a gutless adenovirus vector carrying a transgene, such as a gene encoding TM protein or its variant.

18 Claims, 7 Drawing Sheets
(1 of 7 Drawing Sheet(s) Filed in Color)

OTHER PUBLICATIONS

Haj-Ahmand, Yousef, et al., "Development of a Helper-Independent Human Adenovirus Vector and Its Use in the Transfer of the Herpes Simplex Virus Thymidine Kinase Gene," J. Virol. vol. 57, No. 1, 267-274 (1986).

Ragot, Thierry, et al., "Efficient adenivirus-mediated transfer of a human minidystrophin gene to skeletal muscle of mdx mice," Nature, vol. 361, pp. 647-650 (1993).

Howell, John McC., et al., "High-Level Dystrophin Expression after Adenovirus-Mediated Dystrophin Minigene Transfer to Skeletal Muscle of Dystrophic Dogs: Prolongation of Expression with Immunosuppression," Hum Gene Ther., vol. 9, pp. 629-634 (1998).

Parks, Robin J., et al., "A helper-dependent adenovirus vector system: Removal of helper virus by Cre-mediated excision of the viral packaging signal," Proc. Natl. Acad. Sci. USA, vol. 93, pp. 13565-13570 (1996).

Lieber, André, et al., "Recombinant Adenoviruses with Large Deletions Generated by Cre-Mediated Excision Exhibit Different Biological Properties Compared with First-Generation Vectors In Vitro and In Vivo," J. Virol, vol. 70, pp. 8944-8960 (1996).

Gossen, Manfred, et al., "Tight control of gene expression in mammalian cells by tetracycline-responsive promoters," Proc. Natl. Acad. Sci. USA, vol. 89, pp. 5547-5551 (1992).

Gossen, Manfred, et al., "Transcriptional Activation by Tetracyclines in Mammalian Cells," Science, vol. 268, pp. 1766-1769 (1995).

Kistner, Andreas, et al., "Doxycycline-mediated quantitative and tissue-specific control of gene expression in transgenic mice," Proc. Natl. Acad. Sci. USA, vol. 93, pp. 10933-10938 (1996).

No, David, et al., "Ecdysone-inducible gene expression in mammalian cells and transgenic mice," Proc. Natl. Acad. Sci. USA, vol. 93, pp. 3346-3351 (1996).

Wang, Yaolin, et al., "A regulatory system for use in gene transfer," PNAS USA, vol. 91, pp. 8180-8184 (1994).

Wang, Yaolin, et al., "Ligand-inducible and liver-specific target gene expression in transgenic mice," Nat. Biotech., vol. 15, pp. 239-243 (1997).

Magari, Shannon R., et al., "Pharmacologic Control of a Humanized Gene Therapy System Implanted into Nude Mice," J. Clin. Invest, vol. 100, No. 11, pp. 2865-2872 (1997).

Ye, Xuehai, et al., "Regulated Delivery of Therapeutic Proteins After in Vivo Somatic Cell Gene Transfer," Science, vol. 283, pp. 88-91 (1999).

Suzuki, Koji, et al., "Structure and expression of human thrombomodulin, a thrombin receptor on endothelium acting as a cofactor for protein C activation," EMBO J., vol. 6, No. 7, pp. 1891-1897 (1987).

Wen, Duanzhi, et al., "Human Thrombomodulin: Complete cDNA Sequence and Chromosome Localization of the Gene," Biochemistry, vol. 26, pp. 4350-4357 (1987).

Ng, Philip, et al., "Development of a FLP/frt Syste for Generating Helper-Dependent Adenoviral Vectors," Molecular Therapy, vol. 3, No. 5, pp. 809-815 (2001).

Umana, Pablo, et al., "Efficient FLPe recombinase enables scalable production of helper-dependent adenoviral vectors with negligible helper-virus contamination," Nature Biotechnology, vol. 19, pp. 582-585 (2001).

* cited by examiner

EX VIVO AND IN VIVO EXPRESSION OF THE THROMBOMODULIN GENE FOR THE TREATMENT OF CARDIOVASCULAR AND PERIPHERAL VASCULAR DISEASES

This application is a divisional application of U.S. application of 11/650,479, filed Jan. 8, 2007, which is a continuation-in-part application of U.S. Ser. No. 10/725,013, filed Dec. 2, 2003, which claims priority from U.S. Provisional Application Ser. No. 60/430,099 filed Dec. 2, 2002. The entirety of all of the aforementioned applications is incorporated herein by reference.

FIELD

The present invention is directed to methods and compositions for the treatment of cardiovascular and peripheral vascular diseases, and in particular, is directed to methods and compositions for ex vivo and in vivo expression of the thrombomodulin gene using gutless adenovirus vector.

BACKGROUND

Atherosclerosis is one of the chief causes of morbidity and mortality in the United States and many other countries of the world. (Zuckerbraun et al., *Arch Surg.* 137:854-861 [2002]; Kibbe et al., *Circ Res.* 86:829-33 [2000]). This process can result in limiting the flow of blood to the heart, kidneys and the peripheral vessels, to name a few. Current approaches to the treatment of lesions in the arteries include coronary artery by-pass graft (CABG) surgery and angioplasty with or without the placement of a stent. The latter may serve as a vehicle for drug delivery, as is currently being tested in clinical trials. A number of pharmacological agents that affect platelet function or provide anticoagulant properties have so far failed to reduce re-occlusion or intimal hyperplasia. (Kibbe et al., *Circ Res.* 86:829-33 [2000]).

Cardiovascular diseases, however, are the result of complex pathophysiologic processes that involve the expression of many proteins and molecules that can adversely affect the grafted vessel (Shears et al., *J. Am. Coll Surg.,* 187(3):295-306 [1998]; Ross et al., *Nature,* 362:801-9 [1993]). Approximately 15-30% of patients receiving vein grafts for coronary or peripheral vascular disease require follow-up treatment, either in the form of angioplasty or new grafts.

Thrombomodulin (TM) is an integral membrane glycoprotein expressed on the surface of endothelial cells (Sadler et al., *Trhomb Haemost.,* 78:392-95 [1997]). It is a high affinity thrombin receptor that converts thrombin into a protein C activator. Activated protein C then functions as an anticoagulant by inactivating two regulatory proteins of the clotting system, namely factors Va and VI [I]a (Esmon et al., *Faseb J,* 9:946-55 [1995]). The latter two proteins are essential for the function of two of the coagulation proteases, namely factors IXa and Xa. TM thus plays an active role in blood clot formation in vivo and can function as a direct or indirect anticoagulant.

There are several other proteins or enzymes that have shown to reduce the process of intimal hyperplasia, whose evolution is the cause of late graft failure. For instance, Nitric oxide synthase, an enzyme expressed by endothelial cells has been shown in animal models to inhibit intimal hyperplasia, especially the inducible enzyme (iNOS) (Salmaa et al., *Lancet,* 353:1729-34 [1999]; Palmer et al., *Nature,* 327:524-26 [1987]; Kubes et al., *PNAS USA.,* 88:4651-5 [1991]).

Animal studies shown that cytoxic gene transfection utilizing the Herpes Simplex Virus thymidine kinase gene delivered via an adenoviral vector was able to inhibit intimal hyperplasia (Steg et al., *Circulation,* 96:408-11 [1997]). Vascular endothelial growth factor (VEGF), basic fibroblast growth factor (bFGF) and platelet derived growth factor (PDGF) have all been shown to promote reendothelization and enhance the healing of vascular injury and help limit intimal hyperplasia. (Ban Bellle et al., *Biochem Biophs Res Commun.,* 235:311-16 [1997]; Salyapongse et al., *Tissue Engineering* 26(4):663-76 [1999]).

A gene therapy approach is currently under clinical investigation. It involves the injection, directly into heart muscles, of an adenoviral vector delivery system containing the gene for the expression of vascular endothelial growth factor (VEGF). This is being tested in patients whose coronary vessels are not amenable to standard grafting procedures. However, some recent adverse clinical events demonstrated that injection of large quantities of adenovirus vectors is associated with significant risks. Accordingly, there still exists a need for a method to effectively introduce therapeutic genes, such as TM, into vascular tissues.

SUMMARY

One aspect of the present invention relates to methods for treating a vascular disease in a mammal. In one embodiment, the method comprises the steps of: infecting a segment of blood vessel in vitro using a gutless adenoviral vector comprising a polynucleotide encoding a thrombomodulin protein or its variant, and grafting the virus-treated blood vessel in the mammal, wherein the thrombomodulin protein or its variant is expressed in a amount sufficient to reduce re-occlusion or intimal hyperplasia in the grafted blood vessel, and wherein the gutless adenoviral vector comprises the nucleotide sequence of SEQ ID NO: 13 or SEQ ID NO: 15.

In another embodiment, the method comprises the steps of: evacuating a clot from a blood vessel in the mammal, isolating a segment of the blood vessel around the evacuation site, and infecting the segment of blood vessel in vivo using a gutless adenoviral vector comprising a polynucleotide encoding a thrombomodulin protein or its variant, wherein the thrombomodulin protein or its variant is expressed in a amount sufficient to reduce re-occlusion or intimal hyperplasia in the infected blood vessel, and wherein said gutless adenoviral vector comprises the nucleotide sequence of SEQ ID NO: 13 or SEQ ID NO: 15.

In another embodiment, the method comprises the step of administering a therapeutically effective amount of a gutless adenovirus vector into a segment of a blood vessel in vivo using a stent, wherein the gutless adenovirus vector comprises the nucleotide sequence of SEQ ID NO: 13 or SEQ ID NO: 15, and is capable of expressing a thrombomodulin protein or a variant of the thrombomodulin protein.

In another embodiment, the method comprises the step of administering intravenously an effective amount of a gutless adenoviral vector comprising a polynucleotide encoding a thrombomodulin protein or its variant, wherein the gutless adenoviral vector comprises the nucleotide sequence of SEQ ID NO:13 or SEQ ID NO:15.

Another aspect of the present invention pertains to a gutless adenovirus vector comprising the nucleotide sequence of SEQ ID NO: 13 or SEQ ID NO: 15.

Another aspect of the present invention pertains to a gutless adenovirus vector comprising a polynucleotide encoding a thrombomodulin protein having the amino acid sequence of SEQ ID NO:2, a regulatory element operably linked to the polynucleotide sequence; and a stuffer comprising the nucleotide sequence of SEQ ID NO:13 or SEQ ID NO:15.

Yet another aspect of the present invention pertains to a pharmaceutical composition for treating a vascular disease, comprising the gutless adenovirus vector described above and a pharmaceutically acceptable carrier.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

Figure 1:
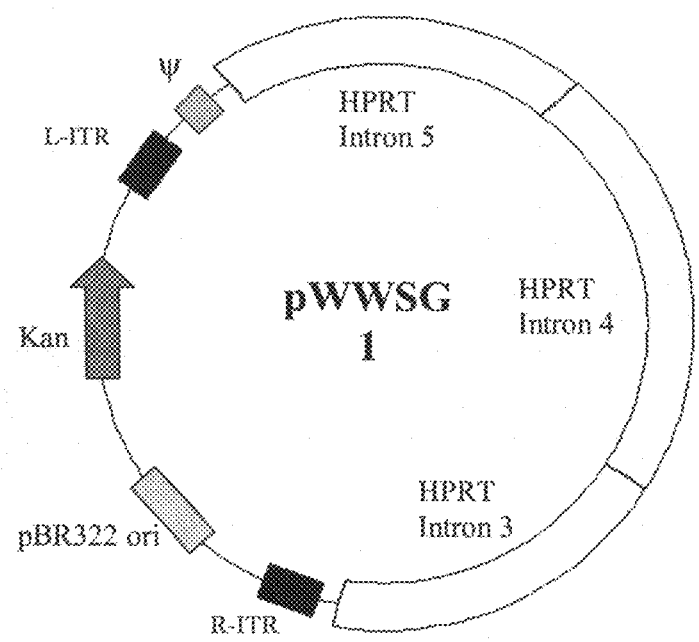
FIG. 1 is a schematic drawing of an embodiment of the backbone shuttle vector pShuttle-ITR-HPRT.

The practice of the present invention will employ, unless otherwise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

The primary object of the present invention is to provide methods for treating vascular diseases using gene delivery technologies. One aspect of the present invention relates to a method for treating a vascular disease by introducing a DNA sequence encoding a TM protein or its variant into a segment of a blood vessel in vitro using a gutless adenovirus vector and grafting the virus-treated vessel in a patient affected by a vascular disease. The virus-mediated TM expression reduces re-occlusion and intimal hyperplasia in the grafted vessel. This ex vivo approach eliminates the need to inject a large quantity of virus into a patient and hence significantly reduces the viral-related toxicity.

In one embodiment, the method is used for a coronary artery bypass. In another embodiment, the method is used for the treatment of peripheral vascular diseases. In yet another embodiment, the method is used for the maintenance of vein access in renal dialysis patients.

Another object of the present invention is to provide a method to deliver a gutless adenovirus vector carrying a DNA sequence encoding a TM protein or its variant using a stent. The viral vector is embedded in the stent and is released only at a treatment site. Since the viral infection is restricted at the treatment site and the surrounding area, only a small amount of the virus is needed and the virus-related toxicity is reduced.

Yet another object of the present invention pertains to a gutless adenovirus carrying a TM gene. In one embodiment, the gutless adenovirus, which contains a regulatory element operably linked to a DNA sequence encoding a TM protein or its variant and a polyA sequence, is produced using a novel shuttle vector containing a pBR322 replication origin, a selection marker, an adenovirus left inverted terminal repeat, an adenovirus encapsidation signal, a stuffer sequence, and an adenovirus left inverted terminal repeat.

In one embodiment, the regulatory element is a constitutive promoter such a CMV promoter and RSV promoter. In another embodiment, the regulatory element is an inducible promoter.

The fourth object of the present invention is to provide a pharmaceutical composition which comprises an effective amount of gutless adenovirus carrying a TM gene of the present invention and a pharmaceutically acceptable carrier. Such compositions may be liquids or lyophilized or otherwise dried formulations and may further include diluents of various buffer content, (e.g., Tris-HCl, acetate, phosphate) pH and ionic strength, additives such as albumin and gelatin to prevent absorption to surfaces, detergents (e.g., Tween 20, Tween 80, Pluronic F68, bile acid salts), solubilizing agents (e.g., glycerol, polyethylene glycerol); anti-oxidants (e.g., ascorbic acid, sodium metabisulfite), and preservatives (e.g. Thimerosal, benzyl alcohol, parabens).

In describing the present invention, the following terms will be employed, and are intended to be defined as indicated below.

"Gene transfer" or "gene delivery" refers to methods or systems for reliably introducing a particular nucleotide sequence (e.g., DNA) into targeted cells. The introduced nucleotide sequences may persist in vivo in episomal forms or integrate into the genome of the target cells. Gene transfer provides a unique approach for the treatment of acquired and inherited diseases, and a number of systems have been developed in the art for gene transfer into mammalian cells. See, e.g., U.S. Pat. No. 5,399,346.

As used herein, the term "effective amount" refers to a level of infection which brings about at least partially a desired therapeutic or prophylactic effect in an organ or tissue infected by the method of the present invention. The infection with an effective amount of the vector carrying genetic material of interest can then result in the modification of the cellular activities, e.g., a change in phenotype, in an organ or a tissue that has been infected by the method of the present invention. In a preferred embodiment, the infection with an effective amount of the vector carrying genetic material of interest results in modulation of cellular activity in a significant number of cells of an infected organ or a tissue.

A gene transfer "vector" refers to any agent, such as a plasmid, phage, transposon, cosmid, chromosome, liposome, DNA-viral conjugates, RNA/DNA oligonucleotides, virus, bacteria, etc., which is capable of transferring gene sequences into cells. Thus, the term includes cloning and expression vehicles including "naked" expression vectors, as well as viral and non-viral vectors. A vector may be targeted to specific cells by linking a target molecule to the vector. A targeting molecule is any agent that is specific for a cell or tissue type of interest, including for example, a ligand, antibody, sugar, receptor, or other binding molecule. The invention is also intended to include such other forms of vectors which serve equivalent functions and which become known in the art subsequently hereto.

The term "expression control element" or "regulatory element" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a, DNA regulatory sequence that is sufficient for RNA polymerase recognition, binding and transcription initiation. Additionally, a promoter includes sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, muscle creatine kinase (MCK) promoter, myosin promoter, (α-actin promoter) and the like.

The term "transduction" denotes the delivery of a DNA molecule to a recipient cell either in vivo or in vitro, via a replication-defective viral vector, such as via a recombinant adenovirus.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as the function to direct the expression thereof. Thus, for example, intervening untranslated yet transcribed sequences can be present between a promoter sequence and the coding sequence and the promoter sequence can still be considered "operably linked" to the coding sequence.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *PNAS USA* 46:453 (1960) and Doty et al., *PNAS USA* 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "Tm." The Tm. of a particular nucleic acid duplex under specified conditions is the temperature at which on average half of the base pairs have disassociated. The equation for calculating the Tm. of nucleic acids is well known in the art.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data bands, or in a Southern hybridization experiment under, for example, stringent conditions as defined for that particular system. Suitable conditions include those characterized by a hybridization buffer comprising 0.9M sodium citrate ("SSC") buffer at a temperature of about 37° C. and washing in SSC buffer at a temperature of about 37° C.; and preferably in a hybridization buffer comprising 20% formamide in 0.9M SSC buffer at a temperature of about 42° C. and washing in 0.2×SSC buffer at about 42° C. Stringency conditions can be further varied by modifying the temperature and/or salt content of the buffer, or by modifying the length of the hybridization probe as is known to those of skill in the art. Defining appropriate hybridization conditions is within the skill of the art. See e.g., Sambrook, J. Fritsch, E. J., & Maniatis, T. (1989) *Molecular Cloning: A Laboratory Manual* (Cold Spring Harbor Lab. Press, Plainview, N.Y.).

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The terms "nucleic acid substrate" and nucleic acid template" are used herein interchangeably and refer to a nucleic acid molecule which may comprise single- or double-stranded DNA or RNA.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "native thrombomodulin" refers to both the natural protein and soluble peptides having the same characteristic biological activity of membrane-bound or detergent solubilized (natural) thrombomodulin. These soluble peptides are also referred to as "wild-type" or "non-mutant" analog peptides. Biological activity is the ability to act as a receptor for thrombin, increase the activation of protein C, or other biological activity associated with native thrombomodulin. Oxidation resistant TM analogs are these soluble peptides that in addition to being soluble contain a specific artificially induced mutation in their amino acid sequence.

The term "thrombomodulin variant" is a polypeptide that differs from a native thrombomodulin polypeptide in one or more substitutions, deletions, additions and/or insertions, such that the bioactivity of the native thrombomodulin polypeptide is not substantially diminished or enhanced. In other words, the bioactivity of a thrombomodulin variant may be enhanced or diminished by, less than 50%, and preferably less than 20%, relative to the native protein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the and/or C-terminal of the mature protein.

Preferably, a thrombomodulin variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the bioactivity, secondary structure and hydropathic nature of the polypeptide.

Thrombomodulin variants preferably exhibit at least about 70%, more preferably at least about 90% and most preferably at least about 95% sequence homology to the original thrombomodulin polypeptide.

A thrombomodulin variant also includes a thrombomodulin polypeptides that is modified from the original thrombomodulin polypeptides by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cysteine, formation of pyroglutamate, formulation, gammacarboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

Adenovirus Vectors

The genome of an adenovirus can be manipulated such that it encodes and expresses a gene product of interest but is inactivated in terms of its ability to replicate in a normal lyric viral life cycle (Curie DT, *Ann NY Acad Sci* 886, 158-171 [1991]). Suitable adenoidal vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium, endothelial cells and muscle cells. Additionally, introduced adenoidal DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoidal genome for foreign DNA is large (up to 8 kilobases) relative to other gene delivery vectors (Haj-Ahmand et al. *J. Virol.* 57, 267-273 [1986]). Most replication-defective adenoidal vectors currently in use are deleted for all or parts of the viral E1 and E3 genes but retain as much as 80% of the adenoidal genetic material. Adenoidal vectors deleted for all viral coding regions are also described by Kochanek et al. and Chamberlain et al. (*U.S. Pat. No.* 5,985,846 and U.S. Pat. No. 6,083,750).

Adenovirus vectors have been successfully tested in a number of animal models (Ragot et al. *Nature* 361, 647-650 [1993]; Howell et al. *Hum Gene Ther* 9, 629-634 [1998]). Nonetheless, the toxicity and immunogenicity remain major hurdles to overcome before the adenovirus vectors can be safely used in humans.

Adenoviruses (Ad) are double-stranded DNA viruses with a linear genome of about 36 kb. The adenovirus genome is complex and contains over 50 open reading frames (ORFs). These ORFs are overlapping and genes encoding one protein are often embedded within genes coding for other Ad proteins. Expression of Ad genes is divided into an early and a late phase. The early genes comprise E1a, E1b, E2a, E2b, E3 and E4, which are transcribed prior to replication of the viral genome. The late genes (e.g., L1-5) are transcribed after replication of the viral genome. The products of the late genes are predominantly components of the virion, as well as proteins involved in the assembly of virions.

The so-called "gutless" rAd vectors contain a minimal amount of adenovirus DNA and are incapable of expressing any adenovirus antigens (hence the term "gutless"). The gutless rAd vectors provide the significant advantage of accommodating large inserts of foreign DNA while completely eliminating the problem of expressing adenoviral genes that result in an immunological response to viral proteins when a gutless rAd vector is used in gene therapy. Methods for producing gutless rAd vectors have been described, for example, in U.S. Pat. No. 5,981,225 to Kochanek et al., and U.S. Pat. Nos. 6,063,622 and 6,451,596 to Chamberlain et al; Parks et al., *PNAS* 93:13565 (1996) and Lieber et al., *J. Virol.* 70:8944-8960 (1996).

The "inverted terminal repeats (ITRs) of adenovirus" are short elements located at the 5' and 3' termini of the linear adenoviral genome, respectively and are required for replication of the viral DNA. The left ITR is located between 1-130 bp in the Ad genome (also referred to as 0-0.5 mu). The right ITR is located from about 3,7500 bp to the end of the genome (also referred to as 99.5-100 mu). The two ITRs are inverted repeats of each other. For clarity, the left ITR or 5' end is used to define the 5' and 3' ends of the ITRs. The 5' end of the left ITR is located at the extreme 5' end of the linear adenoviral genome; picturing the left ITR as an arrow extending from the 5' end of the genome, the tail of the 5' ITR is located at mu 0 and the head of the left ITR is located at about 0.5 mu (further the tail of the left ITR is referred to as the 5' end of the left ITR and the head of the left ITR is referred to as the 3' end of the left ITR). The tail of the right or 3' ITR is located at mu 100 and the head of the right ITR is located at about mu 99.5; the head of the right ITR is referred to as the 5' end of the right ITR and the tail of the right ITR is referred to as the 3' end of the right ITR. In the linear adenoviral genome, the ITRs face each other with the head of each ITR pointing inward toward the bulk of the genome. When arranged in a "tail to tail orientation" the tails of each ITR (which comprise the 5' end of the left ITR and the 3' end of the right ITR) are located in proximity to one another while the heads of each ITR are separated and face outward.

The "encapsidation signal of adenovirus" or "adenovirus packaging sequence" refers to the Ψ sequence which comprises five (AI-AV) packaging signals and is required for encapsidation of the mature linear genome; the packaging signals are located from about 194 to 358 bp in the Ad genome (about 0.5-1.0 mμ).

One aspect of the present invention relates to a viral backbone shuttle vector for the construction of gutless rAd vectors. In one embodiment, the viral backbone shuttle vector of the present invention contains a left and a right inverted terminal repeats of adenovirus, an encapsidation signal (ψ) of adenovirus, a pBR322 replication origin, a kanamycin resistance gene, and a stuffer sequence, which is the hypoxanthine phosphoribosyltransferase (HPRT) intron fragment with an approximately 10 kb. (SEQ ID NO: 1).

The viral backbone shuttle vector of the present invention contains multiple restriction endonuclease sites for the insertion of a foreign DNA sequence of interest. In one embodiment, the viral backbone shuttle vector contains seven unique cloning sites where the foreign DNA sequence can be inserted by molecular cloning techniques that are well known in the DNA cloning art. The foreign DNA sequence of interest typically comprises cDNA or genomic fragments that are of interest to transfer into mammalian cells. Foreign DNA sequence of interest may include any naturally occurring or synthetic DNA sequence. The foreign DNA may be identical in sequence to naturally-occurring DNA or may be mutated relative to the naturally occurring sequence. The foreign DNA need not be characterized as to sequence or function.

The size of foreign DNA that may be included in the shuttle vector will depend upon the size of the rest of the vector. If necessary, the stuffer sequence may be removed to adapt large size foreign DNA fragment. The total size of foreign DNA may vary from 1 kb to 35 kb. Preferably, the total size of foreign DNA is from 15 kb to 35 kb.

The foreign DNA may encode protein, or contain regulatory sites, including but not limited to, transcription factor binding sites, promoters, enhancers, silencers, ribosome binding sequences, recombination sites, origins of replication, sequences which regulate RNA stability and polyadenylation signals. The promoters used may vary in their nature, origin and properties. The choice of promoter depends in fact on the desired use and on the gene of interest, in particular. Thus, the promoter may be constitutive or regulated, strong or weak, ubiquitous or tissue/cell-specific, or even specific of physiological or pathophysiological states (activity dependent on the state of cell differentiation or the step in the cell cycle). The promoter may be of eukaryotic, prokaryotic, viral, animal, plant, artificial or human, etc., origin. Specific examples of promoters are the promoters of the genes PGK, TK, GH, α-EF1, APO, CMV, RSV etc. or artificial promoters, such as those for p53, E2F or cAMP.

In one embodiment, the viral backbone shuttle vector of the present invention comprises at least 15 contiguous bases of SEQ ID NO: 1, preferably comprises at least 90 contiguous bases of SEQ ID NO: 1, more preferably comprises at least 300 contiguous bases of SEQ ID NO: 1, and most preferably comprises 3000 or more contiguous bases of SEQ ID NO: 1.

One aspect of the present invention relates to a gutless adenoviral vector that carries a DNA sequence encoding a native TM protein or a variant of a TM protein. In one embodiment, the native TM protein is a human TM protein having the amino acid sequence recited in SEQ ID NO:2. Another aspect of the present invention also relates to a gutless adenoviral vector that carries other transgenes. These transgenes may include, but are not limited to, those coding for cytokines such as IL-1, IL-2, IL-3, IL-4, IL-5, IL-6, IL-7, IL-8, IL-9, IL-10, IL-11, IL-12, IL-13, IL-14, IL-15, IL-16, IL-17 and other interleukins; hematopoetic growth factors such as erythropoietin; colony stimulating factors such as G-CSF, GM-CSF, M-CSF, SCF and thrombopoietin; growth factors such as BNDF, BMP, GGRP, EGF, FGF, GDNF, GGF, HGF, IGF-1, IGF-2; KGF, myotrophin, NGF, OSM, PDGF, somatotrophin, TGF-β, TGF-α and VEGF; antiviral cytokines such as interferons, antiviral proteins induced by interferons, TNF-α, and TNF-β; amyloid protein and amyloid precursor protein; anti-angiogenic proteins such as angiostatin, endostatin, METH-1 and METH-2; clotting factors such as Factor IX, Factor VIII, and others in the clotting cascade; collagens; cyclins and cyclin inhibitors, such as cyclin dependent kinases, cyclin D1, cyclin E, WAF1, cdk4 inhibitor, and MTS1; cystic fibrosis transmembrane conductance regulator gene (CFTR); enzymes such as cathepsin K, cytochrome p-450 and other cytochromes, farnesyl transferase, glutathione-s transferases, heparanase, HMG CoA synthetase, n-acetyltransferase, phenylalanine hydroxylase, phosphodiesterase, ras carboxyl-terminal protease, telomerase and TNF converting enzyme; glycoproteins such as cadherins, e.g., N-cadherin and E-cadherin; cell adhesion molecules; selectins; transmembrane glycoproteins such as CD40; heat shock proteins; hormones such as 5-α reductase, atrial natriuretic factor, calcitonin, corticotrophin releasing factor, diuretic hormones, glucagon, gonadotropin, gonadotropin releasing hormone, growth hormone, growth hormone releasing factor, somatotropin, insulin, leptin, luteinizing hormone, luteinizing hormone releasing hormone, parathyroid hormone, thyroid hormone, and thyroid stimulating hormone; proteins involved in immune responses, including antibodies, CTLA4, hemagglutinin, MHC proteins, VLA-4, and kallikrein-kininogen-kinin system; ligands such as CD4; oncogene products such as sis, hst, protein tyrosine kinase receptors, ras, abl, mos, myc, fos, jun, H-ras, ki-ras, c-fns, bcl-2, L-myc, c-myc, gip, gsp, and HER-2; receptors such as bombesin receptor, estrogen receptor, GABA receptors, growth factor receptors including EGFR, PDGFR, FGFR, and NGFR, GTP-binding regulatory proteins, interleukin receptors, ion channel receptors, leukotriene receptor antagonists, lipoprotein receptors, opioid pain receptors, substance P receptors, retinoic acid and retinoid receptors, steroid receptors, T-cell receptors, thyroid hormone receptors, TNF receptors; tissue plasminogen activator; transmembrane receptors; transmembrane transporting systems, such as calcium pump, proton pump, Na/Ca exchanger, MRP1, MRP2, P170, LRP, and cMOAT; transferrin; and tumor suppressor gene products such as APC, brca1, brca2, DCC, MCC, MTS1, NF1, NF2, nm23, p53 and Rb.

In one embodiment, the DNA sequence is controlled by a regulatory element. In on embodiment, the regulatory element is a constitutive promoter such as the CMV promoter or RSV promoter. In another embodiment, the DNA sequence is controlled by a regulatable expression system. Systems to regulate expression of therapeutic genes have been developed and incorporated into the current viral gene delivery vectors. These systems are briefly described below:

Tet-on/off system. The Tet-system is based on two regulatory elements derived from the tetracycline-resistance operon of the *E. coli* Tn 10 transposon: the tet repressor protein (TetR) and the Tet operator DNA sequence (tetO) to which TetR binds. The system consists of two components, a "regulator" and a "reporter" plasmid. The "regulator" plasmid encodes a hybrid protein containing a mutated Tet repression (tetr) fused to the VP 16 activation domain of herpes simplex virus. The "reporter" plasmid contains a tet-responsive element (TRE), which controls the "reporter" gene of choice. The tetr-VP 16 fusion protein can only bind to the TRE, therefore activate the transcription of the "reporter" gene, in the presence of tetracycline. The system has been incorporated into a number of viral vectors including retrovirus, adenovirus (Gossen and Bujard, *PNAS USA* 89: 5547-5551, [1992]; Gossen et al., *Science* 268: 1766-1769, [1995]; Kistner et al., *PNAS USA* 93: 10933-10938, [1996]).

Ecdysone system. The Ecdysone system is based on the molting induction system found in *Drosophila*, but modified for inducible expression in mammalian cells. The system uses an analog of the *drosophila* steroid hormone ecdysone, muristerone A, to activate expression of the gene of interest via a heterodimeric nuclear receptor. Expression levels have been reported to exceed 200-fold over basal levels with no effect on mammalian cell physiology (No et al., *PNAS USA* 93: 3346-3351, [1996]).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., *PNAS USA* 93: 8180-8184, [1994]; Wang et al., *Nat. Biotech* 15: 239-243, [1997]).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been used to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral vectors. Long-term regulatable gene expression has been achieved in both mice and baboons (Magari et al., *J. Clin. Invest.* 100: 2865-2872, [1997]; Ye et al., *Science* 283:88-91, [1999]).

Ex Vivo and In Vivo Thrombomodulin Gene Transfer

The instant invention uses a gutless adenovirus vector to express a native thrombomodulin protein or a variant of the thrombomodulin protein at a vessel graft or angioplasty site to prevent or reduce re-occlusion and intimal hyperplasia. The amino acid sequence of human thrombomodulin (SEQ ID NO: 2) and the DNA sequence encoding human thrombomodulin (SEQ ID NO: 3) have been reported (Suzuki et al. *EMBO J.* 6:1891-1897, [1987]).

In one embodiment, the in vivo expression of thrombomodulin or a thrombomodulin variant is used for the treatment of atherosclerotic cardiovascular disease (CVD). Though venous grafts can be used for bypass surgeries, the veins eventually, become occluded by thrombosis resulting the recurrence of the diseases. In this embodiment, TM gene delivery is used in coronary artery bypass grafting, and vascular graft prostheses to block thrombosis. Specifically, TM gene is introduced into a segment of blood vessel in vitro using a gene transfer vector.

TM gene delivery can be also used for the reduction of no-intima formation, for the prevention of atherosclerosis; for the prevention of myocardial infarction and for the inhibition of fibrinolysis in hemophilic plasma. TM gene transfer at the site of thrombus formation is potent approach to reverse these vascular diseases.

In another embodiment, in vivo TM expression is achieved by embedding a gene transfer vector in a stent which is placed at the treatment site following percutaneous transluminal coronary angioplasty, peripheral artery angioplasty, thrombectomy, or an intravascular stenting procedure.

In another embodiment, the in vivo expression of thrombomodulin, or a thrombomodulin variant is used for the treatment of end stage renal failure (ESRD). ESRD patients often exhibit decreased antithrombotic activity due to low TM levels. In such patients, enhanced in vivo TM gene expression can be potentially very useful.

In another embodiment, the in vivo TM expression is achieved by administering a gene transfer vector to a mammal intravenously (i.v.), intramuscularly (i.m.), intraperitoneally (i.p.) or subcutaneously. For adenoviral and AAV vectors, intravenous administration often lead to viral infection of hepatocytes and transgene expression in the liver.

The present invention is further illustrated by the following examples which should not be construed as limiting. The contents of all references, patents and published patent applications cited throughout this application, as well as the Figures and Tables are incorporated herein by reference.

EXAMPLE 1

Construction of Gutless Viral Backbone Shuttle Vector pShuttle-ITR-HPRT 1.1 Creation of pShuttle-ITR An embodiment of a gutless viral backbone shuttle vector pShuttle-ITR-HPRT is shown in FIG. 1. Sequence portion containing R-ITR, PBR322 ori, Kan, L-ITR, and encapsidation signal was obtained from the pAdEasy® system from STRATEGENE®. At bp 3667 of the original pShuttle sequence, there is a BamHI site just beyond the R-ITR. PCR primers were designed to include the BamHI site and then were to create an EcoRI site at the end of the R-ITR. The R-ITR was PCR replicated and then digested with BamHI and EcoRI to create sticky ends. The viral backbone was then cut with both BamHI and EcoRI. The BamHI cut the backbone at bp 3667 and there was also an EcoRI site inside the MCS at bp 377. The backbone portion of the plasmid was then gel purified and the PCR replicated R-ITR was recloned into position. This essentially puts the L-ITR, encapsidation signal, MCS, and R-ITR all in close proximity to each other.

1.2 Creation of pShuttle-ITR-HPRT

Insertion of the HPRT introns was a two step cloning process. First, the viral backbone pShuttle-ITR was digested with EcoRI and XbaI, both enzyme sites are in the MCS. The HPRT source was also digested with EcoRI and XbaI yielding a 7477 bp fragment that was cloned into the EcoRI/XbaI digested viral backbone. Then the HPRT source was digested with only XbaI yielding a 2715 bp fragment. One of the XbaI sites in this cut is the same XbaI site that was cut from the EcoRI/XbaI double digest in step 1. The viral backbone was cut with only XbaI and the 2715 bp fragment was inserted.

Overall, from the HPRT source, the HPRT stuffer sequence is inserted into the viral backbone in reverse orientation, hence intron 5, then 4, then 3. The 2715 bp fragment was inserted and checked to follow the original source sequence. The new plasmid is designated as pShuttle-ITR-HPRT (SEQ ID NO: 1)

EXAMPLE 2

Construction and Preparation of Gutless Viral Shuttle Vector Carrying Human Thrombomodulin or lacZ Gene 2(a) Construction and Preparation of Gutless Viral Shuttle Vector Carrying Human Thrombomodulin Gene 2(a)-1 Creation of pCMV-hTM The insertion of hTM into the gutless adenovirus backbone first required the creation of a CMV-hTM expression cassette. The intermediate vector used was pcDNA3.1/Zeo(+) (Invitrogen). A CMV promoter is available commercially and a CMV promoter was cloned into the multiple cloning sites (MCS) at the XbaI/EcoRV restriction enzyme site locations. The CMV from ps5 was removed using XbaI/EcoRV. pcDNA3.1/Zeo(+) was cleaved inside the MCS using both XbaI and EcoRV as well. The CMV promoter was then ligated. Due to the location of the enzyme sites in the MCS, the CMV promoter (SEQ ID NO:4) was inserted in a backwards orientation relative to the pcDNA3.1/Zeo (+) plasmid. The human TM cDNA (SEQ ID NO:5) was obtained from Dr. Sadler (Dittman et al., *Biochemistry*, 26(14):4350-4357 [1987]) which the sequence was also submitted to ATCC and to GenBank. The human TM gene was removed from the plasmid using EcoRI and inserted into pcDNA3.1/Zeo(+), also in the reverse orientation to pcDNA3.1/Zeo(+) downstream of the inserted CMV promoter.

2(a)-2 Creation of pShuttle-ITR-HPRT-CMV-TM

The expression cassette in pCMV-hTM was removed by digesting with PmeI. The gutless adenovirus backbone pshuttle-ITR-HPRT was linearized using SmaI which cuts the plasmid at bp 381. The CMV-hTM cassette was ligated to the gutless virus in the forwards orientation. Sequence of the expression cassette (from PmeI site to PmeI site) is shown in SEQ ID NO:6. The new plasmid is designated as pShuttle-ITR-HPRT-CMV-TM.

2(a)-3 Creation of pTMadap

The following linker containing a BstEII and SfiI site was inserted into the BstEII and Bsu36I sites of pShuttle-ITR-HPRT-CMV-TM, resulting in the vector pTMadap (SEQ ID NO:7).

```
                                          (SEQ ID NO:8)
    5'-gtaacactgg cccaggaggc ctttctggtg acccc-3'

(SEQ ID NO:9)
    3'-tgacc gggtcctccg gaaagaccac tggggatt-5'
```

Creation of pTMadap-stuffer1

Based on the published sequence HSU71148 of the human X chromosome region q28 the following PCR primers were synthesized:

```
                                         (SEQ ID NO:10)
      Forward: 5' TAGTTCCTTCTGCCTGGAATAC 3'

(SEQ ID NO:11)
      Reverse: 5' CAAGTCACAAGGATGGACTACA 3'
```

Amplification of a human DNA sample resulted in the amplification of a 18524 bp DNA fragment (stuffer 1, SEQ ID NO: 12). Stuffer 1 was cut with the restriction enzymes BstEII and SfiI and the resulting fragment of approximately 18371 bp was inserted into the BsteII and SfiI sites of pTMadap, resulting in pTMadap-stuffer1.

2(a)-4 Creation of pTMadap-Stuffer1-Short

To reduce the size of the stuffer1 fragment in pTMadap-stuffer1, pTMadap-stuffer1 was digested with SanDI and BstEII and the resulting DNA ends were modified by a fill-in reaction with Klenow. Re-ligation resulted in the 25207 bp vector pTMadap-stuffer1-short. The sequence of stuffer1-short fragment is shown in SEQ ID NO:13.

Creation of pTMadap-Stuffer1-Short-Stuffer2

The plasmid p2-2 (SEQ ID NO: 14, obtained from GenBank) was cut with NotI and the resulting fragment of approximately 5954 bp (stuffer 2, SEQ ID NO: 15) was inserted into the NotI site of pTMadap-stuffer1 short, resulting in pTMadap-stuffer 1-short-stuffer2.

2(a)-6 Removal of PacI Site from pTMadap-Stuffer1short-Stuffer2

Figure 2:
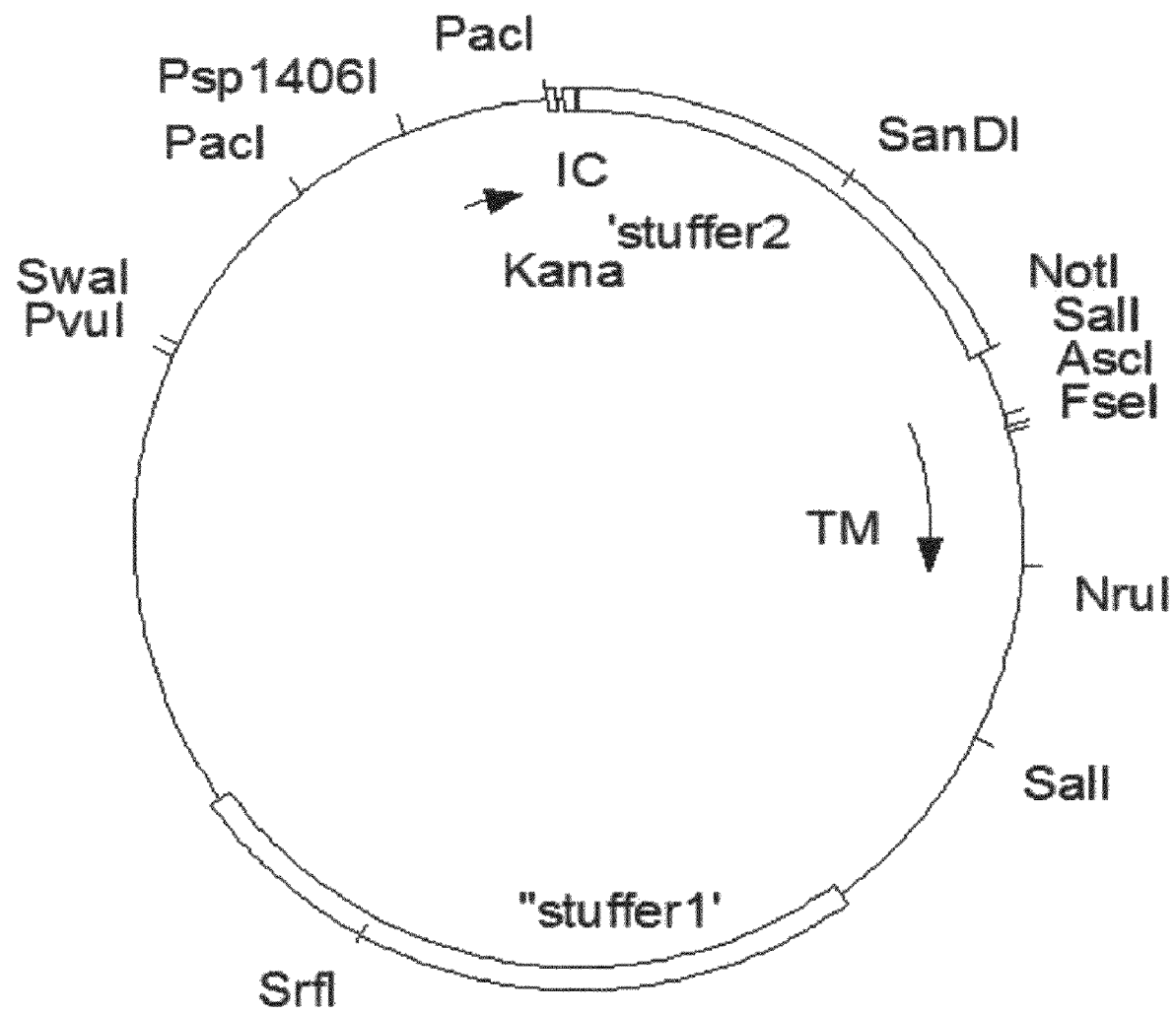
FIG. 2 is a schematic drawing of an embodiment of the full length backbone vector pTM-final.

Plasmid pTMadap-stuffer1-short-stuffer2 was cut with AclI and BsiW1. The resulting 28790 bp fragment was isolated from gel. pShuttle-ITR-HPRT (SEQ ID NO:1) was cut with AclI and Acc65I. The resulting 1966 bp fragment was ligated into the isolated 28790 bp fragment, resulting in the full length backbone vector pTM-final (FIG. 2 and SEQ ID NO: 16).

2(b) Construction and Preparation of Gutless Viral Shuttle Vector Carrying LacZ Gene The insertion of LacZ also required creation of an intermediate vector to create the expression cassette. pcDNA3.1/Zeo (+) was again used. First, a portion of the vector from the end of the MCS, restriction enzyme site ApaI, to the beginning of the SV40 poly A, restriction site NaeI, was removed and the vector relegated to itself. Then the LacZ gene was inserted into the vector MCS using NotI/XbaI. The expression cassette, containing CMV promoter, LacZ gene, and SV40 poly A, was removed using NruI/SalI retraction enzymes and blunt-end cloned into the gutless adenovirus at the SmaI restriction enzyme site.

EXAMPLE 3

Preparation of Gutless Adenovirus Carrying Human Thrombomodulin Gene (Gutless Ad.hTM)

The gutless Ad.hTM was prepared according to the following protocol:

1. Linearize pTM-final by digestion with PacI. The completeness of the digestion is confirmed by electrophoresis using a small aliquot of the digestion product. It's not necessary to gel purify the digested pTM-final for transfection described in step 2).

2. Transfect 293FLP cells grown in a 60 mm dish at about 80% confluence with about 5 μg of PacI-digested pTM-final using lipofectamine. 293FLP cells are 293 cells engineered to express the flp gene product, which recognizes the FRS flanking the encapsidation signal and cleaves out the encapsidation signal thereby not allowing helper-viral DNA to be packaged. (Beauchamp et al., *Molecular Therapy*, 3(5):809-815 [2001]; Umana et al., *Nature Biotechnology*, 19:582-585 [2001]).

3. Twenty-four hours after the transfection, infect the cells with helpervirus H10 in 2% DMEM-F12 at a multiplicity of infection (MOI) of 10.

4. Remove the cells from the plate (preferably with a cell scraper) after the appearance of cytopathic effect (CPE), place the cells in a sterile 15 ml tube, and lyse the cells by three freeze-and-thaw cycles. Precipitate the cell debris by spinning the lysate for 5 minutes at 4000 rpm and harvest the supernatant. The supernatant is designated as P0 (passage number 0) supernatant.

5. Infect 293FLP cells in two T75 flask at 80% confluency with 4 ml of P0 supernatant and with the helpervirus at MOI of 1.

6. Continue passaging virus in the manner described in steps 4 and 5 until passage 6 and confirm that helpervirus is added at an MOI of 1 at each passage.

7. Add the P6 supernatant to 8 T500 flasks containing 293FLP cells at 80% confluency and infect the cells with the helpervirus at a MOI of 1.

8. Following CPE, harvest the cells into 500 ml sterile tubes. Centrifuge the cell suspension at 4500 rpm, 4° C. for 10 minutes.

9. Resuspend the cell pellet in 2% DMEM-F12 (the pellet can be stored at −80° C. at this stage).

10. Freeze-thaw the resuspended cell pellet three times. Spin down the cell debris by centrifugation at 4000 rpm, 4° C. for 10 minutes.

11. Transfer the supernatant, which contains the released virus, to a fresh sterile culture tube and subject the supernatant to a second round of centrifugation to further remove cell debris.

12. Transfer the supernatant to a fresh sterile tube. The virus is ready for CsCl-purification.

13. To purify the virus, ultra-clear SW41 (Beckman) tubes were prepared by soaking in Ultra Pure Water, then 70% ETOH. Cotton swabs (one swab for each tube) were used to completely dry out the tube, and two tubes were used per sample.

14. Preparation of the first gradient: 2.5 mL CsCl—Density 1.25, and 2.5 mL CsCl—Density 1.40. Place the 1.25 density CsCl into the Beckman tubes first. Underlay slowly the high density, 1.40 CsCl using a sterile pasteur pipette, and overlay an equal amount (in mL) of CVL, about 4.25 ml/tube. Samples were centrifuged in a SW41 rotor with speed: 35,000 rpm at 20° C. for 1 hour and with acceleration: 1 and deceleration: 4. The lower opalescent band was collected using 1 or 3 mL syringe with green cap needles.

Preparation of second gradient: CsCl was prepared to density 1.33 g/ml. Two fresh ultra-clear tubes were placed 8 mL of CsCl and overlay the band just recovered after the first spin. (To equilibrate the tubes, measure before the volume of the recovered band and divide equally in the 2 tubes). Samples were centrifuged at the conditions above for 18 hours. The opalescent band was recovered and collected in a sterile eppendorf tube. (From this moment, keep the tube always on ice). Samples were dialyze with dialysis buffer: (1) 10× Dialysis Buffer: 100 mM Tris—pH 7.4, 10 mM $MgCl_2$; (2) 1× Dialysis Buffer (2 Liters): 400 mL Glycerol, 200 mL 10× Dialysis Buffer 140 mL, and Ultra Pure Water. The dialyzed samples were immediately stored at −70° C.

(c) Determination of Virus Titer

BioRad protein estimation kit was used with 1:5 diluting, and placing 1 ml in each disposable cuvette. Standards were set up at 0, 1, 2, 5, 10, and 15 μg/ml. (BSA is fine). Sample cuvettes were prepared using 1-10 μl of sample, depending on estimate of titer. (Sample OD must be within the linear range of the standard line.) OD was taken at 595λ and formula of the line was calculated from standards. The protein concentration of the samples was calculated using this formula. The following formula was used to convert protein concentration to titer: $[12.956+224.15 \, (\mu g/ml)] \times 10^8$.

EXAMPLE 4

Expression of Human Thrombomodulin (hTM) In Vitro

(A) Expression of hTM in HEK 293 Cells Transfected with pTM-Final

Figure 3:
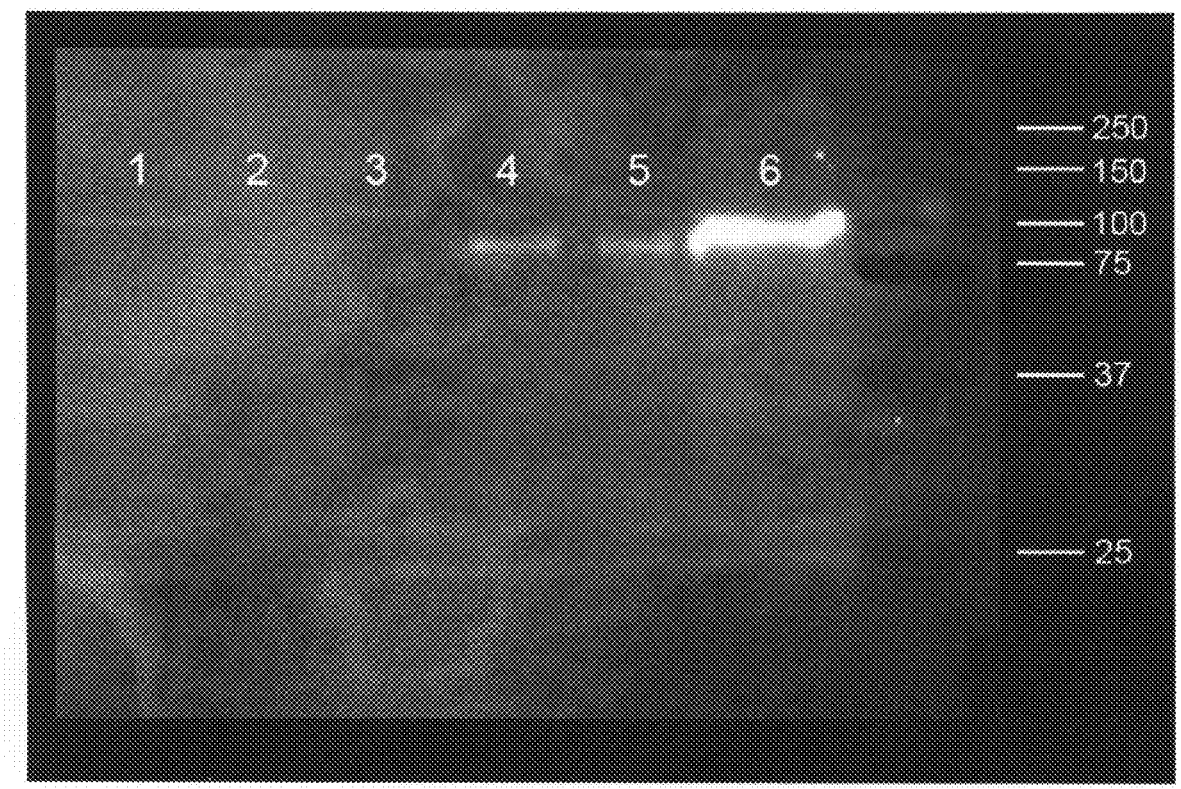
FIG. 3 is a picture of a Western blot showing hTM expression in HEK 293 cells transfected with pTM-final (the full size backbone of gutless Ad.hTM). Lanes 1-3: lysate from control cells; Lanes 4-6, lysate from pTM-final transfected cells.

HEK 293 cells were cultured in a 6 well cluster and transfected with 1 μg of pTM-final. After 24 hours, the cells were washed with PBS and lysed in 125 μl RIPA buffer with protease inhibitors Protein samples (16 μl) were separated on 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) was used to detect the proteins. As shown in FIG. 3, hTM expression was detectable in cells transfected with pTM-final.

The RIPA buffer was prepared according the following recipe: mixing 100 μl Igepal ca-630, 50 mg sodium deoxycholate, 500 μl 120% SDS, 10 mM β-mercapto ethanol, and 1 ml 10×PBS, and add water to a final volume of 10 ml at room temperature. A cocktail of protease inhibitors containing 11.5 μl PMSF (from 34.8 mg/ml in isopropanol, 64 μl Benzamidine (from 15.6 mg/ml stock), 100 μl sodium orthovanadate (100 mM), 5 μl pepstadine (from 1 mg/ml stock), 1 μl leupeptine (from 5 mg/ml stock), and 1 μl aprotin (from 5 mg/ml stock) was added to the RIPA buffer immediately before use.

(B) Expression of hTM in P2 Lysate of 293FLP Cells

Figure 4:
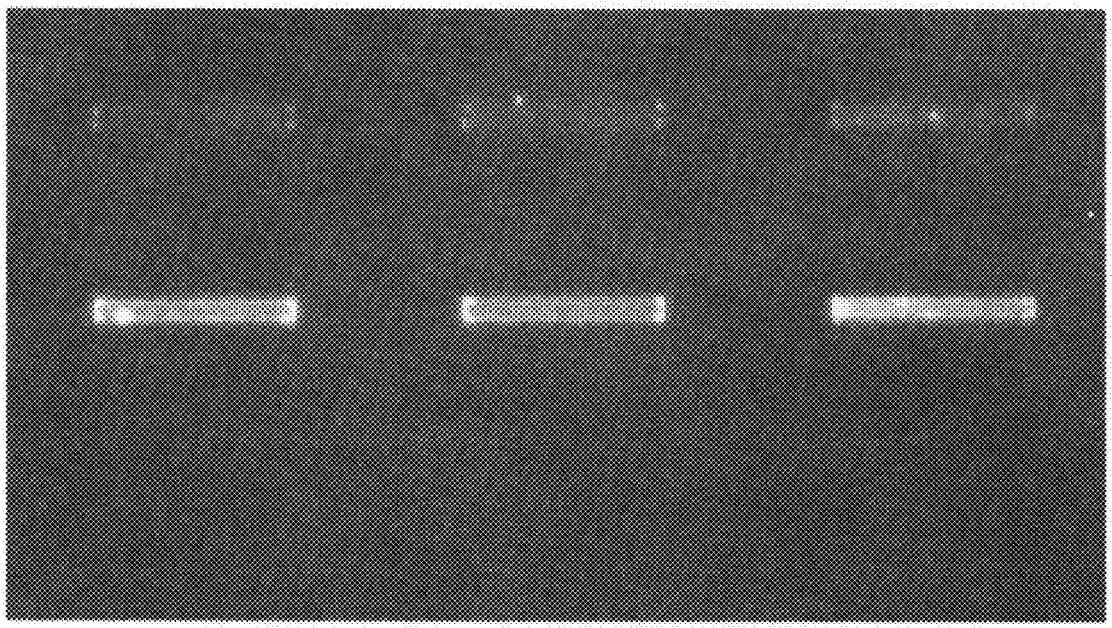
FIG. 4 is a picture of a Western slot blot showing hTM expression in 293FLP cells (passage number 2 (P2) during viral amplification). Row 1, lane 1-3: TM detection using 5 ul cell lysate of P2. Row 2, lane 1-3: TM detection using 30 ul cell lysate of P2. Row 3, lane 1-3: negative control cells.

The P2 lysate was generated as described in Example 3. After CPE was observed, 293FLP cells were detached from the bottom of the culture flask by repeated tapping of the flask. 1 ml of the total of 10 ml of cell suspension was used for the detection of TM expression. The cells in the 1 ml cell suspension were collected by centrifugation for 10 min at 300×g and lysed in 250 μl RIPA buffer. 7 ul of 5× loading buffer was added to 3511 of the lysed cells and the resulting solution was immersed in boiling water for 3 minutes. 5 and 30 ul of boiled cell lysate was diluted with 250 ul TBS (137 mM sodium chloride, 10 mM Tris, pH is 7.4 at +25° C.) and transferred to a nitrocellulose membrane using a slotblot device (Bio-Dot SF, Biorad). Primary antibody (goat anti-hTM (c-17) 1:2000 dilution, Santa Cruz) and secondary antibody (polyclonal rabbit anti-goat immunoglobulins/HRP, 1:4000 dilution, DakoCytomation)) were used to detect the proteins. As shown in FIG. 4, hTM was detectable in the P2 lysate.

The 5× loading buffer was prepared by mixing 20.0 ml 30% SDS, 11.5 ml 2M sucrose, 6.5 ml 2M Tris-HCL pH 6.8, 2.0 ml beta-mercaptoethanol and bromophenol blue. The RIPA buffer was prepared as described in Example 4(A). A cocktail of protease inhibitors containing 11, 5 μl PMSF (from 34, 8 mg/ml in isopropanol, 64 μl Benzamidine (from 15, 6 mg/ml stock), 100 μl sodium orthovanadate (100 mM), 5 μl pepstadine (from 1 mg/ml stock), 1 μl leupeptine (from 5 mg/ml stock), and 1 μl aprotin (from 5 mg/ml stock) was added to the RIPA buffer immediately before use.

(C) Expression of TM in Virus Infected Vena Cava

Vena cava was excised from rats and cut into six segments of approximately 3 mm long. The segments were incubated for 30 minutes in medium containing gutless luc or TM virus. After incubation, the segments were washed three times and transferred to a 24-well plate containing DMEM. The segments were incubated overnight in an atmosphere of 95% $O_2$ and 5% $CO_2$ with gentle shaking. After 24 hours of incubation the segments were frozen. The frozen sections were thawed in lysis buffer and loaded onto a 7.5% SDS acrylamide gel. After blotting, the blot was probed with an antibody against human TM.

Figure 5:
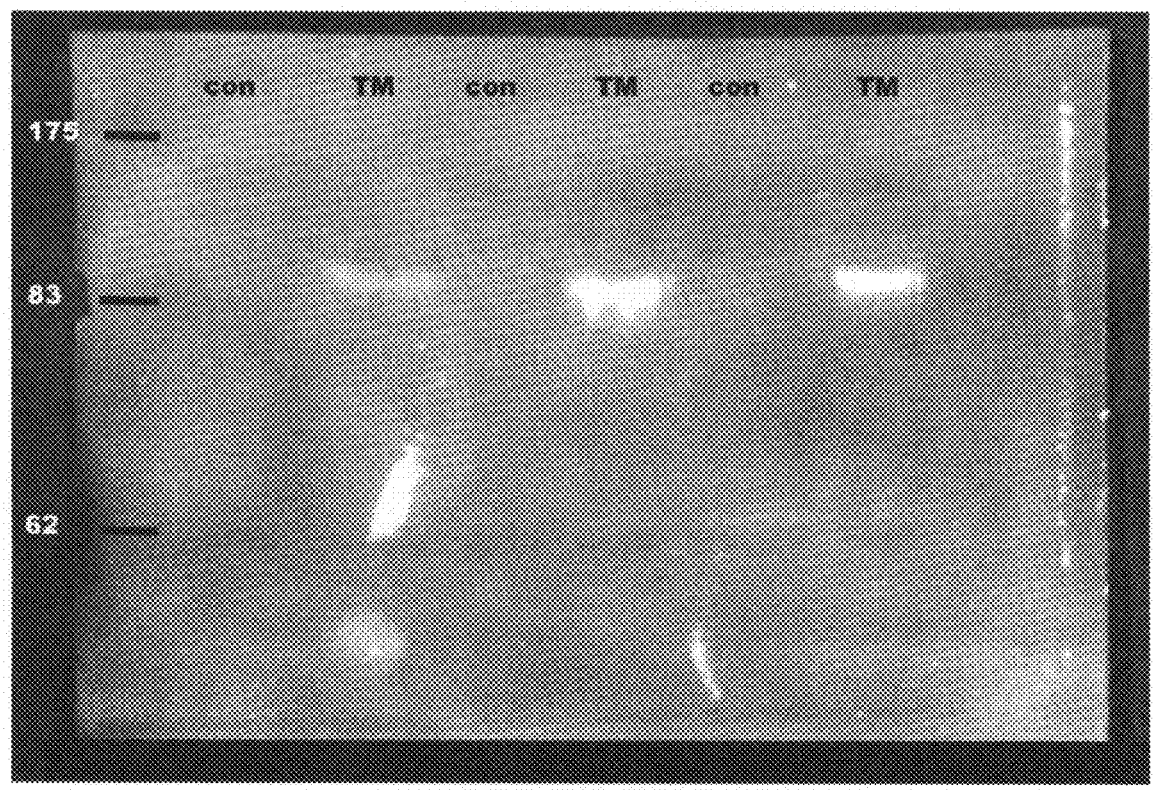
FIG. 5 is a picture of a Western blot showing hTM expression in rat vena cava infected with gutless TM virus.

The Western blot clearly shows that within 24 hours TM expression can be detected (FIG. 5).

As a control, the same HUVEC cells will be infected the gutless adenovirus expressing LacZ. These cells will subsequently be stained with X-gal to look for blue cells. This will demonstrate the viability of the gutless adenovirus backbone itself.

(D) TM expression in HEK 293 Cells Infected with TM Gutless Virus Passage 1-6

The TM-vector backbone was released by digestion with PacI. 293CRE cells were cultured in a 60 mm dish at 80% confluency. Cells were transfected with 5 μg of PacI digested TM-vector backbone. After 24 hours, 2% DMEM-F12 containing helper virus with a MOI of 10 was added. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=0.

4 ml of P=0 supernatant was added to 2 T75 dish containing 293CRE cells at 80% confluence. Cells were subsequently infected with helpervirus at MOI of 1. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=1. This procedure was repeated until P=6.

Figure 6:
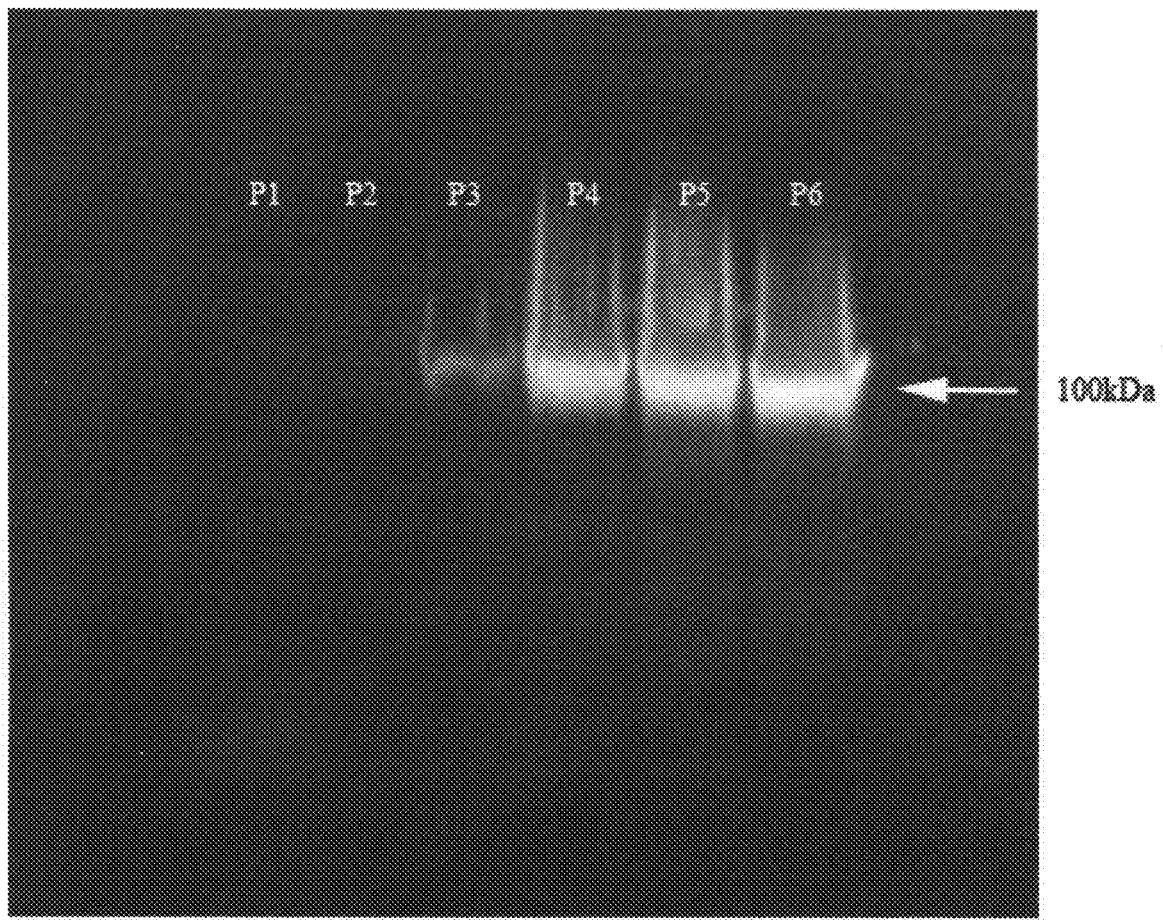
FIG. 6 is a picture of a Western bolt showing TM expression in CRE cells at passage number 1-6 (P1-P6).

HEK 293 cells were cultured in a 6 well cluster and transfected with 200 μl of TM gutless virus of passage 1-6. After 24 hours, the cells were washed with PBS and lysed in 125 μl RIPA buffer. Protein samples (16 μl) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins. As shown in FIG. 6, TM expression is higher in cells infected with virus of higher passage numbers, indicating successful amplification of TM gutless virus in 293 CRE cells.

The RIPA buffer (10 ml) was prepared as follows: 100 μl Igepal α-630, 50 mg sodium deoxycholate, 500 μl 20% SDS, 10 mM β-mercapto ethanol, 1 ml 10×PBS, add water to make up 10 ml. Immediately before use, the following protease inhibitors were added to the RIPA buffer: 115 μl PMSF (from 34.8 mg/ml in isopropanol), 64 μl Benzamidine (from 15.6 mg/ml stock), 100 μl sodium orthovanadate (100 mM), 5 μl pepstatin (from 1 mg/ml stock), 1 μl leupeptin (from 5 mg/ml stock), 1 μl aprotin (from 5 mg/ml stock).

EXAMPLE 5

Composition of the Complete Viral Delivery System (CVDS)

The Complete Viral Delivery System composes of 1:1 mixture of Ham's F12 medium and DMEM, an effective amount of a gutless virus vector carrying a polynucleotide encoding a thrombomodulin protein or a variant of a thrombomodulin protein, and an a cellular oxygen carrier. Preferred oxygen carrier includes: unmodified or chemically modified hemoglobin in the range of 3 g/dl to 10 g/dl and perfluorochemical emulsions. The CVDS may optionally contain 1 mM L-glutamine (Sigma), 1.5 g/L sodium bicarbonate (Sigma), 1× antibiotic-antimycotic (GIBCO® 15240). The CVDM maintains tissue viability during the viral treatment of blood vessel.

EXAMPLE 6

Ex Vivo Treatment of Cardiovascular Disease

A vein segment is harvested from the leg and is stored in Ham's F12 medium. Gutless adenovirus suspended in CVDM is then injected into the isolated vein segment and incubated for 10 to 40 minutes depending on the desired level of transfection. The infection may be performed under pressure to enhance efficiency.

After the incubation, the vein segment is washed several times to eliminate all viral particles that have not entered the endothelial cells of the vein segment, and is then grafted into the desired treatment site. The thorough rinse avoids the spread of the viral vector to other organs of the body following in situ grafting, and any systemic immune response to the viral vector.

EXAMPLE 7

In Vivo Treatment for Peripheral Vascular Disease

In this application, the vein in the leg is treated following evacuation of the clot. A catheter is inserted in the leg vein and both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

EXAMPLE 8

In Vivo Treatment for Renal Disease

In this application, the vein in the kidney is treated following evacuation of the clot. A catheter is inserted in the kidney vein and both the proximal and distal balloons are inflated to isolate the vein segment to be transfected. The segment is evacuated of all blood, rinsed with physiologic saline; it is then filled with the CVDS described above, under pressure. The isolated vein segment is exposed to the CVDS for a period of 10 to 45 minutes, depending upon the desired transfection efficiency.

EXAMPLE 9

In Vivo Treatment with Virus Containing Stent

In this application, a virus-coated stent is placed at a treatment site after angioplasty. The virus is a gutless adenovirus carrying a polynucleotide encoding a thrombomodulin protein or a variant of a thrombomodulin protein. Alternatively, the virus may be embedded in the stent and is releases gradually through a time-releasing mechanism well-known to one skilled in the art.

EXAMPLE 10

In Vivo Expression of Transgene by Intravenous Infusion of Viral Vectors

Figure 7:
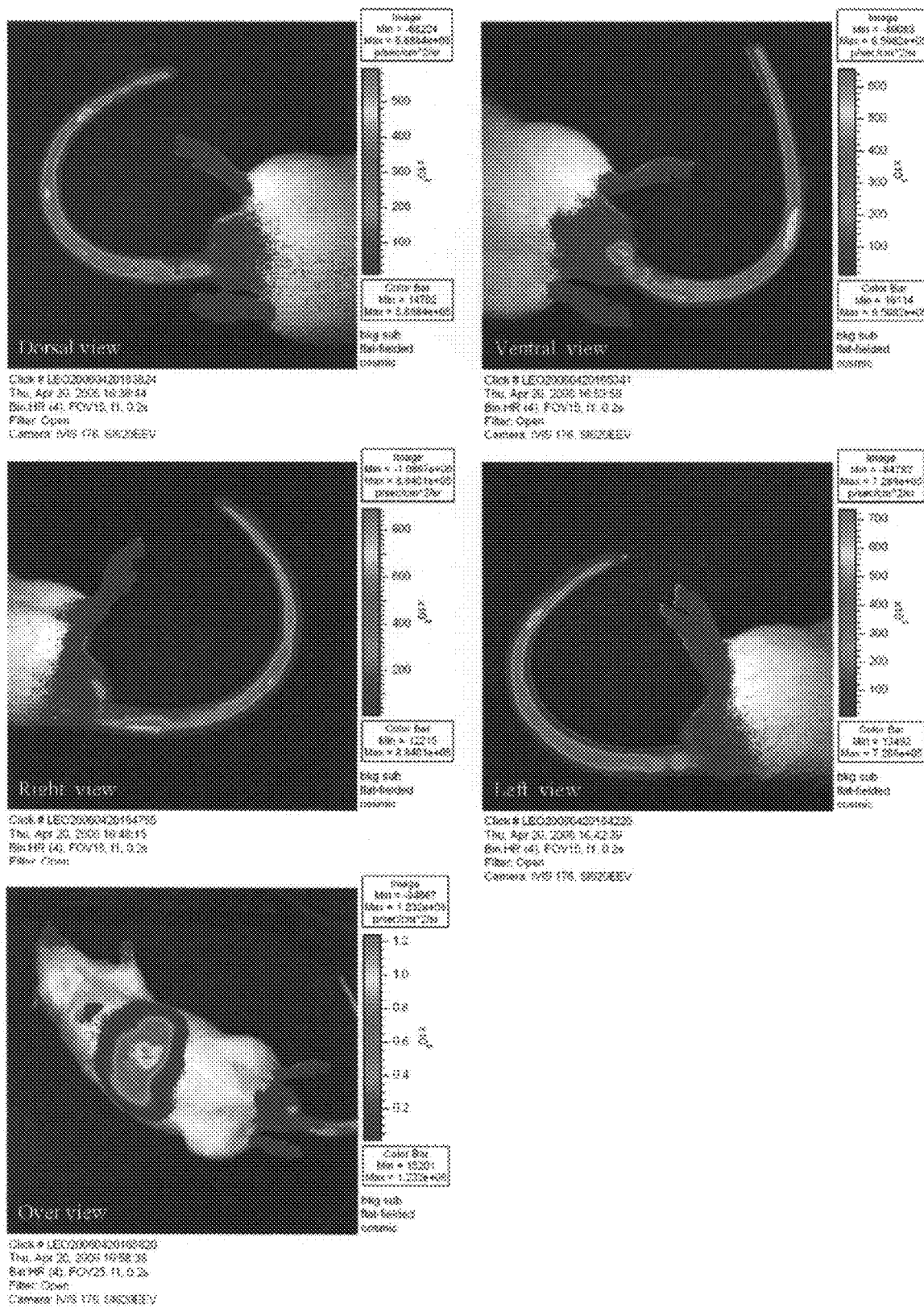
FIG. 7 is a composite of images showing gutless adenovirus-mediated luciferase expression in rat tail vein.

In one experiment, the tail vein of experimental rats was flushed with a solution containing a gutless adenoviral vector carrying a luciferase transgene. As shown in FIG. 7, the expression of luciferase was still very strong in the tail vein eight days after viral infection.

In another experiment, experimental rats were injected intravenously with the gutless TM viruses at doses ranging from $1 \times 10^8$ to $3 \times 10^1$ particles/rat. TM expression in liver will be analyzed by the rate of blood coagulation (APTT) and by Western blot of liver biopsy samples.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

SEQ ID NO:1 (pShuttle-ITR/HPRT)
CATCATCATAATAATACCTTATTTTGGATTGAAGCCAATATGATAATGAG

GGGGTGGAGTTTGTGACGTGGCGCGGGGCGTGGGAACGGGGCGGGTGACG

TAGTAGTGTGGCGGAAGTGTGATGTTGCAAGTGTGGCGGAACACATGTAA

GCGACGGATGTGGCAAAAGTGACGTTTTTGGTGTGCGCCGGTGTACACAG

GAAGTGACAATTTTCGCGCGGTTTTAGGCGGATGTTGTAGTAAATTTGGG

CGTAACCGAGTAAGATTTGGCCATTTTCGCGGGAAAACTGAATAAGAGGA

AGTGAAATCTGAATAATTTTGTGTTACTCATAGCGCGTAATACTGGTACC

GCGGCCGCCTCGAGTCTAGAACTAGTGGATCCCCCGGGCTGCAGGAATTC

TGATGGCTCTCAAAATTCCTGCCTCCTTTAGGGATAAAAGACTTTAAGAC

TTTTTAACAAAAAAGAAAAAGAAAAAAAAAATTCCTGCCTCCTGGTGTAC

ACACACAGAAGGGTTCCCTCCCCTTGAATGTGACCAGGATCTGTGAAAAT

AACGGGATAGCCGCTCCTGTGATTAGGTTATGTGGTAGACTAGAGCAAGA

TTCTCCTGCTGGTTTTGAAGAAGTCAGCTGCCATGTTGTGAGACTGTCAT

GGGCTAGGGCATGAGCCTTTAAATATCTGGGAGCAACCCCTGGCCAGCAG

CCAGTGAGAAAACGGGCCCTCAGTCCTACAATCACAAGGAACTAAATTCT

GCCAACAACCTGAAGGAACTTTGAAGAGGATCATGAGTCCCTTGATTCAG

CTTGATGAGCCCCTGAGCAGAGGATACAGCTAACTTGTACTAGGGAAGTA

TAAAAAACATGCATGGGAATGATATATATCAACTTTAAGGATAATTGTCA

TACTTCTGGGAATGAAGGGAAAGAAATGGGGCTTTAGTTGTATTATGATC

TTTAATTTCTCAAAAAAAATAAGATCAGAAGCAAATATGGCAAAATGTTA

ATACTTTTGTGGGTACGTAGGTATTCAGCATACCCTTTTTTCTGAGTTCA

AAATATTTTATAATTAAAATGAAATGCAGGCCAGGCACAGTGGCTCATGC

CTATAATACCAGCACTTTGCGAGGCCGAGGTGGGAGGATGGCTTGAGGCC

-continued

```
AGACCAGCCTGGCCAACATGGCAAAACCCCATCTCTACTTAAAAAAAAAA
AAACTATATATATATATATGTGTGTGTGTGTATATATATATATGTATA
TATATTTATATATGTGTATATATATATATGTATATATATTTATATATG
TGTGTGTATATATATATACACACACACACATATATACATACATACATA
CACACACACACACACACAATTAGCCAGGCATGGTGGCGCACACCTGTAGT
CCCAGCTACTTGGGAGGCTGAGACATGAGAATTGCTTGAACCTGGGAGGC
AGAGTAGTTAGTGAGCTGAGATCATACCACTGCACTCCAGCCTGGTGACA
GAGTGAGACTCTGTCTTAAAAAAAATAAAAATTAAAATTAAATGCAAAAG
GTCCAAGTGAATTGAAGAGGAAAGGGGTATCAAGGAAGGTTTTGTGGAGG
TGACGTTTGAGCTGGGTCTTAAATGACTTAAACATGGGATAAGAAGGGAG
GGAATAAGGACATTTCAGGTACGAGAAATAAGGAGCAAACAGTGGAAACA
ACCTAACGTCTGTCAACCAGTGAATGGATAACAAAAATGTAATTCAGATG
GTATCCAACTTACGATGGTTCAACATGAGATTTTCTGACTTTAGGATAG
ATTTATCAAAGTAGTAAATCCATTTTCAACTTATGATATTTTCAACTTCA
GATGGGTTTATCAGGACACAGTTGAGGAACACCTGTCTATCCATACAATT
TGGCAATAAAAAGGAAATGAGTGCAGATATACTCCACAACATGAATGAAC
CTTGAAAACATTAAGTGAGAGAAGCCAGATACAAAAGGCCACATATTGTA
TGATTCTATTTATACAAAATGTCCAGAATAGGCAAATCTTATAGACAGCA
AGTAGGTAGATGATCAGTTTGCTAGGTGCTGGGGGAAGGGGAAATGGGGA
GTGATGGCTAAGGGGATTGGGTTTCTTTGTGGGGCAATGAAAATGTTTTA
AAATTGAGCGTGATAATGATTGCACAATGCTGCATATATATATAATCTAT
AGATTATATATATATAAAGAGAGGCTGTTAGACAGTGATAAGTGATATAT
ATATATATATACATAGAGAGAGAGAGAGAGAGAGAGAGAGGCTGTTAGTG
ATAAGTGATCAGGAAAATAAAAGTATTGAGGAGGAATACGAAGTTGACGG
TGTGAAAACATGAGATTTTATATAGGATGGCCAGGGAAGGCCTTAATGAG
AAAGTGACTTATGAGTAAAAACAAGGGATCCTAAACCTTAGCATGCATCA
GAATCACTCGGAAACTTGTTAAAGCATAGCTTGCTGGGCCTCATCACAGA
TATTTTGATTCGGTAGGTTCTTGTCTGATATTAATACTTTTGGTCTAGGG
AACCACATTTTGAGAACCACTGAGCTAAAGGAAGTAAAGGTTTCCCTTAG
TTTACTAGCTGGTAACCCTAGGAAACTGCTTAGCCTCTCGGTGCTAAGAT
ACAAAATACTTTAGCACATAATAACACATGGAAAATAGTCTATAAATTAT
AAATATTATTTTTATGTACCAAATATTACATAAGACAAAATCTAAGCAA
GATATATATATATACATAAAATATAAGATATATATGTATATATTATAT
ATAGATAAATAGAGAGAGAGAGTTATGTTTAGAAAGAAAATACTTCAAAC
TAAAAAAAGAGAGGTAGGAAGTATACCATTCCATTATTGGTAAAAACAAA
TTACTAAGTAGTCTTTACAAAAAACCAATCTCACTCCTTTAGAACACAAG
CCCACCATTAAAACTGATGCAGAGGAATTTCTCTCCCTGGCTTACCTTTA
GGATGGTGCATACTAAGTTAGAAAAGTCATAAATGTTATATTAAAGTAA
ATGTGAACTTACTTCCACAATCAAGACATTCTAGAAGAAAAAGAGAAATG
AAAATCAGTACAATGAATAAAACGGTATTTCCAATTATAAGTCAAATCAC
```

-continued

```
ATCATAACAACCCTAAGGAATTATCCAAACTCTTGTTTTTAGATGCTTTA
TTATATCAAACTCTCCTTTAAACAAGTGGCCCATCTGCTGGGATTTGGAA
GCCTGTAATACTGAAATTTTCATCATAATGGAAATTTTAAAAACAGAATT
TGACCCACCTGTTTTTAAAACACTTTCATTACTTAACAAGAGGTCTAATC
TTGGGCAAGTCTTGAAATTTCTCTGGCCTTAGTTTCCCATGTGTTAAATG
AAACTTGAAGCAGTTGGTCTCTTATAGTCTCCTGACTCTAACATTCTAAG
AATTATATTTGTACAATAACTCAAAAATCACATAATTTAATTTACCATAT
GGACTCCAAAATATATTTTCTCATTAGGCTAAACTTGATCTGCATTTTCT
GGATGTGTCCATATTCTTGGACTACACTAAAACATGATACCAATGCTTCC
TCTCACCATAAACCCTCACTTCGCTTTCTACATTTAAGAATTTTATAGCT
GGAAGAGTCCTTAACAGAAAATACCATCTAATAATTACCCCTCAAAATCG
AGAAAGTCCTATCTGTTCTTATGCTAGTTATAAGAATGAGGCAGCATTTC
ACATAATGGTTATAAACACTGCCACAAGAAGATTCATGATGTGTTGTTTA
TCTGTAGCTCTCATCATACTCTGTCATATAACTATAGCATTAAGATTTTA
ATGTTCTATATATTCTTCTAAGACAGTGTTTACCAGAGTAAGGCACAAAA
GATCCACTGGTTTGCAAGAAAGATTAGAACTTTTAAATTTTTTACCTCAC
CTTGTTTAATCTATATTTTTGTATGTATTTTGTAACATATATATTATTAT
TACCATAAATCATATATAATTTAAAATGCATATATTAGGGGTAAATGCTC
AGGAAACTTTTTATAAATTGGGCATGCAAATACAAGTTTGAAGACTCACT
GTTCTAGGTATTAAAAGTAAAGTTATAACCAAGTAAAGCTTCCACCTTTT
CATGTCTCAAAGCAGTTTATTGTTGGAGGTAAGATCTCTTAGAAGCCTAA
ACAGGTCCAAGTACAGAATGAAGTAAGGCTAGCCCATAACTTGTGGCAAG
CAATTCATACTATTTCTCTCATGCTGAGCTCTCCTCAGTGAAGCAGCTAC
TATAGACAACTGCAGCCTATTGGTAGCCTATTTTACAGGCAGGAAAAAA
TTACTTTTTATTCAAAGTGGAACTCAGGACATGGGGAGAAAATGAATACA
AAAAATAGGGTCAATCCAAAGGCACACAGCAAATGAGTAACACAGTTATG
TTTTTTTCCCATTTGTATGAGGTCCCAGTAAATTCTAAGTAAACTGCAAA
TTTAATAATACACTAAAAAAGCCATGCAATTGTTCAAATGAATCCCAGCA
TGGTACAAGGAGTACAGACACTAGAGTCTAAAAAACAAAAGAATGCCATT
ATTGAGTTTTTGAATTATATCAAGTAGTTACATCTCTACTTAATAAATGA
GAAAACGAGGATAAGAGGCCATTTGATAAAATGAAAATAGCCAAGAAGT
GGTATTAGAGACTTGAATACAGGTATTCGGGTCCAAAGTTCATCTGCTCA
AATACTAACTGGGGAAAAGAGGGAAAAATATTTATATACATATATATCTG
CACACAAAATACCCCCAAAAGACAAAATGAGGCCAGGCAGGGTGGCTCA
CACCCGTAATCCCGGTACTTTGGGAGGCTGAGGCAGGTGGATACCTGAGA
TCAGGAGTTGGAGATCAGCCTGGTCAACATGGTGAAACCCTGTCTCTACT
AAAGATAAAAAATTAGCCAGGCATGGTGGCGTGCGCCTGTAATCCCAGC
TACTTGGGAGTCTGAGGCAGGAGAATCACTTGAACTGGGAAGGGGAGGTT
GCAGTGAGCCAAGATCGTACTACTGCACTCCAGCCTGGGCAGCAGAGTGA
GACTCCATCACAAAAATAAATAAATAAATAAAATACAATGAAACAGAAAG
```

-continued

```
TTCAAATAATCCCATAATCTTACCACCAAGAAATAACTTTCACTCGTTAT
ACTTATTGATTTTTCCATAATAAATGTACTTTACTGTGACTATCATGAAA
AGAAAGTTATTTTAGAAACAGAGAACTGTTTCAGATCAAATCTATGTAGT
AGAACAGAGCCATTAGGTGGGAAAGACGAGATCAAACTAAATCTCAGAAG
GCCTAAAAGGCTAGGTCCATTCCAGCACTAAAAACTGACCAGACAAGTAA
TGGCTTCAACAGCTTCTAAATATGGACAAAGCATGCTGAAAGGGAAGGAC
AGGTCTAACAGTGGTATATGAAATGAACAGGAGGGGCAAAGCTCATTTCT
CCTCTGAAGTTTTCCAAAGATGCTGAGGAGGACATTAGTTTGACATGACC
CTGATATGGGACAAGATAATTTCACAGAAGTTTTACATGTTAAAGTTTTC
TTATAGATACTCATTCAAGTAAGCAATGAACACTAAAATCTAAAGAAAGA
AAAGAGCTTTAGAGTCAGGTCTGTATTCAAATTCAAGCTCTACCACTTAC
TGGTTCTGTGACTTTGGGCAAGTCTTTTAACCTTATTAAGTCTTAATTTC
CTGATTTGTAAAATGGGGATATCGTCTCCCTCACAGGATTGTTGTGAAAC
TTTTATGAGATTAATGCCTTTATATTTGGCATAGTGTAAGTAAACAATAA
CTGGCAGCTTCAAAAAAAAAAGCAGTAGCATTCCATCATTTATTATTGG
TTACTCTCAAAAAGTTTTTCAATGTACTAGAAGATAAATATTCAAATACC
TTAATATCTCCATTATTTTCAGGTAAACAGCATGCTCCTGAACAACCAAT
GGGTCAACAAATAAATTAAAAGGGAAATCTAAAAACATCTTGATATTAAA
CTACATGGAAGCACAATATACCAAAACCAATGGTTCACACTAGGAGAATT
TTAAGGTACAAGAAAACTCTTTGAGATTTCTTAAAATAATAGTATGTCTG
AATTTATTGAGTGATTTACCAGAAACTGTTGTAAGAGCTCTACTTGCATT
ATAGCACTTAATCCTCTTAACTCTATGGCTGCTATTATCAACCTCACCCT
AATCACATATGGGACACAGAGAGGTTAAGTAACTTGCCCAAGGTCAGAGT
TAGGAAGTACTAAGCCATGCTTTGAATCAGTTGTCAGGCTCCGGAACTCA
CACTTTCAGCCACTACATAATACTGCTTTGCTATCTTTTAGGAAACTATG
TGAGTCTACCTCACATAGACTCACATAGGTTTGTTTTTTTTTTTTTTA
AAGGCTATCTTTTCCCCCATCAATGTTTTTTGAAGGATCCCAAATTAGAG
TCCCACAGAGGCAGACAGCAGTACTTGACAATATGGACATTTAAGGTTAA
TGTTGGATTCTACTGTCTTTTTACTACATGACCTAGGGAACGATAATTAA
CCTAGACTGCTTCCAAGGGTTAAATAACCCATTTAGTTATACTATGTAAA
TTATCTCTTAGTGATTGATTGAAAGCACACTGTTACTAATTGACTCGGTA
TGAAGTGCTTTTTTTCTTCCCTTTCAAGATACATACCTTTCCAGTTAAA
GTTGAGAGATCATCTCCACCAATTACTTTTATGTCCCCTGTTGACTGGTC
ATTCTAGTTAAAAAAAAAAAAAACTATATATATATATATCTACACACACA
TATGTATATGTATATCCTTATGTACACACACAAACTTCAAATTAAATGAG
AACTAGAAGATTTGAAGTTAGCTAGCTAATATCCATAGCATTATGATA
TTCTAAATGATATGAATTATAAGAATTAGGTTTCCTGAAATGAATGACTA
GAAAACTTTCAAGTAGAGATTAGTAAAAATTAAAAAGTCCTAATCGGCCA
TTACTGATTTGATGTTTTTAAGAGTCCTAAAAAATGGGTTACATCCATTT
TTAAGTGGGTAGTATTATAACAGCCACCCATCTTCAATCACAGTGATTTC
TGAATTGTGAGGGAAGTTATTAGCATGACAGGTGTCTGGTTCTGGCCCTG
TACGATTCCCATGAGTCAAGCAAATTGTAAGGGCTGGTCTATATCACACC
CAACCCCAAGGATATGTCCCTCAAAAGTCTAGCCCAGGCCCCGTCATCTT
CAGCATCATCTGGGAAACCAGGTCTGATTAGTAGTCCTTTAAGGAATACC
TCTTAGGCTCCCATTTTACTGCTATCACAGAATCCAATAAAACCCTTACA
GGAGATTCAATGGGAAATGCTCAACACCCACTGTAGTTGGTGGTGACAAT
GACCATAATTTGGCTGTGCTGGATTCAGGACAGAAAATTTGGGTGAAAGA
GCAGGTGAACAAAAGAGCTTCGACTTGCCCTAGCAGAGAGCAAGCCATAC
CATACCACAAAGCCACAGCAATTACAACGGTGCAGTACCAGCACAGTAAA
TGAACAAAGTAGAGCCCAGAAACAGACCCAGAACTATATGAGGATTTAGT
ATACAATAAAGATGGTATTTCGAGTCAGTAGGGAAAAGATGAATTATTCA
ATAAATGATGTTTGGCCAACTAGTAACCCATTTGGGAAAAAATAAAAGTA
TGGTCCCTACCTCACAGCATACACAAAAATAAATTCCAGACGGATTAAAA
TCTAAATGTAAAAAATAAAGCCATAAGTGGACTGGAAGAAAATAGAGAAT
TTTTTTTAACATCCGTAGAAAGGGTAAAAACCCAGGCATGACATGAACCA
AAACTGAAGAGGTTCTGTAACAAATACCCCCTTTTATATATTGGGCTCCA
ACAATAAGAACCCATAGGAAAATGGAGAATGAACACAAATAGACAATTTA
TAGAAGAGAAGGTTATAAGGTGTAAAATTATATCTATCTGAGAAACAAAC
ACTAAAACAATGTGATTCTACTGTTCTCCCACCCATACTGGCAAAACTTA
AGCCTGATAATATGCTGAGGGGAAATAAGCACTCTTGTTGGTGAGAGTAT
TAATTGGCATAGCTTCTTTTGAAAATGACATAGCAATACCTGTTAAAATT
GCAAACATGCATGTCACTTAATCCAGTAATCCCACTTCTGGGAATCAATG
CTACAAAAACACTGACAAGTATACAAAGATACATTCAAGAGTGTTCACTG
GGCCGGGTGCGGTGGCTTCATGCCTGTAATCCCAGGGAGGCAGAGGCAAG
ACGATCGCTTGACCCCAGGAGTTCAAGGCCAGCCCGAGAAACACAGCAAG
ACCCTGTCTCTCTTTTTTTATTTAAAAAATAAATGTTCACTGTATCAGT
TGTTCACAAAAACAAACCAACATGTCCATTAACAGGGAACCATTTAAATT
AATCAAGTTCATCTACACAATGTAATACCATGCAACTATTAAAAAGCACC
TGATAATCCAAAGCACACTGAGACAGAATAATGCTATTAAAAACACCAAG
TAGTGGAACACTGTGTTGCCTATGACACCATTTTTATTCAACATTTAAAC
AAATTTGTAACAGCAATTACATGAGTAGTGACAATGGCGTTTATGAGACT
TTTCACTTTTATGTGCTTCTATTTTTGTTATGCTTCTATATATACATCCA
TTTATTATGGAGTGTTACTTTCAAAAATCACAAATGGGCCAGTATTATTT
GGTGTTGCAAGGTGAGCATATGACTTCTGATATCAACCTTTGCATATTAC
TTCTCAATTTAGGGAAATTACAGACATCCCTTATTCTAACTAACTTAAAA
CCCAGCATTTCAAACATACAGAATTGATGGGGAAAAAAAGAAAGAAGAA
AGAAAGAAAAGGCAACAAGCTTCAGATGACAGTGACTCACATCAAATTAT
TTATAAAATCTGTTAAATAGTGCCATCTTCTGGAGATACCTGGTATTACA
GTCCAACTCCAGTTGATGTCTTTACAGAGACAAGAGGAATAAAGGAAAAA
ATATTCAAGAACTGAAAAGTATGGAGTCATGGAAAAATTGCTGTGATCCA
```

-continued

AAGGCTACGGTGATAGGACAAGAAACAAGAGAACTCCAAGCAGTAAGACA
CTGCTGTTCTATTAGCATCCAAACCTCCATACTCCTGTTTGCCCCAAGGC
TTTTTTAAAAAATAGAGACAGGATCTCACTATTTTGCTCAGGCTGGTCTT
GAACTCCTGGACTCAAGCTATCCTCCTGCCTCGGCCTCCTAAAGTGCCGA
GATTACAGGCTTGAGTCACCATACCTGGCTATTTATTTTTTCTTAACTCT
CTTGCCTGGCCTATAGCCACCATGGAAGCTAATAAAGAATATTAATTTAA
GAGTAATGGTATAGTTCACTACATTGGAATACAGGTATAAGTGCCTACAT
TGTACATGAATGGCATACATGGATCAATTACCCCACCTGGGTGGCCAAAG
GAACTGCGCGAACCTCCCTCCTTGGCTGTCTGGAACAAGCTTCCCACTAG
ATCCCTTTACTGAGTGCCTCCCTCATCTTTAATTATGGTTAAGTCTAGGA
TAACAGGACTGGCAAAGGTGAGGGAAAGCTTCCTCCAGAGTTGCTCTAC
CCTCTCCTCTACCGTCCTATCTCCTCACTCCTCTCAGCCAAGGAGTCCAA
TCTGTCCTGAACTCAGAGCGTCACTGTCAACTACATAAAATTGCCAGAGA
AGCTCTTTGGGACTACAAACACATACCCTTAATGTCTTTATTTCTATTTT
GTCTACCTCTTCAGTCTAGGTGAAAAAATAGGAAGGATAATAGGGAAGAA
CTTTGTTTATGCCTACTTATCCGCCCCTAGGAATTTTGAAAACCTCTAGG
TAGCAATAAGAACTGCAGCATGGTATAGAAAAGAGGAGGAAAGCTGTAT
AGAAATGCATAATAAATGGGCAGGAAAAGAACTGCTTGGAACAAACAGGG
AGGTTGAACTATAAGGAGAGAAAGCAGAGAGGCTAATCAACAAGGCTGGG
TTCCCAAGAGGGCATGATGAGACTATTACTAAGGTAGGAATTACTAAGGG
CTCCATGTCCCCTTAGTGGCTTAGTACTATGTAGCTTGCTTTCTGCAGTG
AACTTCAGACCCTTCTTTTAGGATCCTAGAATGGACTTTTTTTTTTATC
GGAAAACAGTCATTCTCTCAACATTCAAGCAGGCCCCAAGTCTACCACAC
TCAATCACATTTTCTCTTCATATCATAATCTCTCAACCATTCTCTGTCCT
TTTAACTGTTTTTCTATACCCTGATCAAATGCCAACAAAAGTGAGAATGT
TAGAATCATGTATTTTTAGAGGTAGACTGTATCTCAGATAAAAAAAAAGG
GCAGATATTCCATTTTCCAAAATATGTATGCAGAAAAAATAAGTATGAAA
GGACATATGCTCAGGTAACAAGTTAATTTGTTTACTTGTATTTTATGAAT
TCCCTAAAACCTACGTCACCCGCCCCGTTCCCACGCCCCGCGCCACGTCA
CAAACTCCACCCCCTCATTATCATATTGGCTTCAATCCAAAATAAGGTAT
ATTATTGATGATGTTAATTAACATGCATGGATCCATATGCGGTGTGAAAT
ACCGCACAGATGCGTAAGGAGAAAATACCGCATCAGGCGCTCTTCCGCTT
CCTCGCTCACTGACTCGCTGCGCTCGGTCGTTCGGCTGCGGCGAGCGGTA
TCAGCTCACTCAAAGGCGGTAATACGGTTATCCACAGAATCAGGGGATAA
CGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAG
CATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGA
AGCGTGGCGCTTTCTCATAGCTCACGCTGTAGGTATCTCAGTTCGGTGTA

-continued

GGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGA
CACGACTTATCGCCACTGGCAGCAGCCACTGGTAACAGGATTAGCAGAGC
GAGGTATGTAGGCGGTGCTACAGAGTTCTTGAAGTGGTGGCCTAACTACG
GCTACACTAGAAGGACAGTATTTGGTATCTGCGCTCTGCTGAAGCCAGTT
ACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAG
TGGAACGAAAACTCACGTTAAGGGATTTTGGTCATGAGATTATCAAAAAG
GATCTTCACCTAGATCCTTTTAAATTAAAAATGAAGTTTTAAATCAATCT
AAAGTATATATGAGTAAACTTGGTCTGACAGTTACCAATGCTTAATCAGT
GAGGCACCTATCTCAGCGATCTGTCTATTTCGTTCATCCATAGTTGCCTG
ACTCCCCGTCGTGTAGATAACTACGATACGGGAGGGCTTACCATCTGGCC
CCAGTGCTGCAATGATACCGCGAGACCCACGCTCACCGGCTCCAGATTTA
TCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAG
TAAGTAGTTCGCCAGTTAATAGTTTGCGCAACGTTGTTGCCATTGCTGCA
GCCATGAGATTATCAAAAAGGATCTTCACCTAGATCCTTTTCACGTAGAA
AGCCAGTCCGCAGAAACGGTGCTGACCCCGGATGAATGTCAGCTACTGGG
CTATCTGGACAAGGGAAAACGCAAGCGCAAAGAGAAAGCAGGTAGCTTGC
AGTGGGCTTACATGGCGATAGCTAGACTGGGCGGTTTTATGGACAGCAAG
CGAACCGGAATTGCCAGCTGGGGCGCCCTCTGGTAAGGTTGGGAAGCCCT
GCAAAGTAAACTGGATGGCTTTCTTGCCGCCAAGGATCTGATGGCGCAGG
GATCAAGCTCTGATCAAGAGACAGGATGAGGATCGTTTCGCATGATTGA
ACAAGATGGATTGCACGCAGGTTCTCCGGCCGCTTGGGTGGAGAGGCTAT
TCGGCTATGACTGGGCACAACAGACAATCGGCTGCTCTGATGCCGCCGTG
TTCCGGCTGTCAGCGCAGGGGCGCCCGGTTCTTTTTGTCAAGACCGACCT
GTCCGGTGCCCTGAATGAACTGCAAGACGAGGCAGCGCGGCTATCGTGGC
TGGCCACGACGGGCGTTCCTTGCGCAGCTGTGCTCGACGTTGTCACTGAA
GCGGGAAGGGACTGGCTGCTATTGGGCGAAGTGCCGGGGCAGGATCTCCT
GTCATCTCACCTTGCTCCTGCCGAGAAAGTATCCATCATGGCTGATGCAA
TGCGGCGGCTGCATACGCTTGATCCGGCTACCTGCCCATTCGACCACCAA
GCGAAACATCGCATCGAGCGAGCACGTACTCGGATGGAAGCCGGTCTTGT
CGATCAGGATGATCTGGACGAAGAGCATCAGGGGCTCGCGCCAGCCGAAC
TGTTCGCCAGGCTCAAGGCGAGCATGCCCGACGGCGAGGATCTCGTCGTG
ACCCATGGCGATGCCTGCTTGCCGAATATCATGGTGGAAAATGGCCGCTT
TTCTGGATTCATCGACTGTGGCCGGCTGGGTGTGGCGGACCGCTATCAGG
ACATAGCGTTGGCTACCCGTGATATTGCTGAAGAGCTTGGCGGCGAATGG
GCTGACCGCTTCCTCGTGCTTTACGGTATCGCCGCTCCCGATTCGCAGCG
CATCGCCTTCTATCGCCTTCTTGACGAGTTCTTCTGAATTTTGTTAAAAT

```
TTTTGTTAAATCAGCTCATTTTTTAACCAATAGGCCGAAATCGGCAAAAT

CCCTTATAAATCAAAAGAATAGACCGAGATAGGGTTGAGTGTTGTTCCAG

TTTGGAACAAGAGTCCACTATTAAAGAACGTGGACTCCAACGTCAAAGGG

CGAAAAACCGTCTATCAGGGCGATGGCCCACTACGTGAACCATCACCCTA

ATCAAGTTTTTTGGGGTCGAGGTGCCGTAAAGCACTAAATCGGAACCCTA

AAGGGAGCCCCCGATTTAGAGCTTGACGGGGAAAGCCGGCGAACGTGGCG

AGAAAGGAAGGGAAGAAAGCGAAAGGAGCGGGCGCTAGGGCGCTGGCAAG

TGTAGCGGTCACGCTGCGCGTAACCACCACACCCGCCGCGCTTAATGCGC

CGCTACAGGGCGCGTCCATTCGCCATTCAGGATCGAATTAATTCTTAATT

AA

SEQ ID NO:2 (human TM amino acid sequence)
MLGVLVLGALALAGLGFPAPAEPQPGGSQCVEHDCFALYPGPATFLNASQ

ICDGLRGHLMTVRSSVAADVISLLLNGDGGVGRRRLWIGLQLPPGCGDPK

RLGPLRGFQWVTGDNNTSYSRWARLDLNGAPLCGPLCVAVSAAEATVPSE

PIWEEQQCEVKADGFLCEFHFPATCRPLAVEPGAAAAAVSITYGTPFAAR

GADFQALPVGSSAAVAPLGLQLMCTAPPGAVQGHWAREAPGAWDCSVENG

GCEHACNAIPGAPRCQCPAGAALQADGRSCTASATQSCNDLCEHFCVPNP

DQPGSYSCMCETGYRLAADQHRCEDVDDCILEPSPCPQRCVNTQGGFECH

CYPNYDLVDGECVEPVDPCFRANCEYQCQPLNQTSYLCVCAEGFAPIPHE

PHRCQMFCNQTACPADCDPNTQASCECPEGYILDDGFICTDIDECENGGF

CSGVCHNLPGTFECICGPDSALARHIGTDCDSGKVDGGDSGSGEPPPSPT

PGSTLTPPAVGLVHSGLLIGISIASLCLVVALLALLCHLRKKQGAARAKM

EYKCAAPSKEVVLQHV RTERTPQRL

SEQ ID NO:3 (human TM nucleotide sequence)
atgcttggg gtcctggtcc ttggcgcgct ggccctggcc ggcctggggt tccccgcacc cgcagagccg cagccgggtg gcagccagtg cgtcgagcac gactgcttcg cgctctaccc gggccccgcg accttcctca atgccagtca gatctgcgac ggactgcggg gccacctaat gacagtcgcg tcctcggtgg ctgccgatgt catttccttg ctactgaacg gcgacgcgg cgttggccgc cggcgcctct ggatcggcct gcagctgcca cccggctgcg gcgaccccaa gcgcctcggg ccctgcgcg gcttccagtg ggttacggga gacaacaaca ccagctatag caggtgggca cggctcgacc tcaatgggc tcccctctgc ggcccgttgt gcgtcgctgt ctccgctgct gaggccactg tgcccagcga gccgatctgg gaggagcagc agtgcgaagt gaaggccgat ggcttcctct gcgagttcca cttcccagcc acctgcaggc cactggctgt ggagcccggc gccgcggctg ccgccgtctc gatcacctac ggcaccccgt tcgcggcccg cggagcggac ttccaggcgc tgccggtggg cagctccgcc gcggtggctc ccctcggctt acagctaatg tgcaccgcgc
```

```
cgcccggagc ggtccagggg cactgggcca gggaggcgcc gggcgcttgg gactgcagcg tggagaacgg cggctgcgag cacgcgtgca atgcgatccc tggggctccc cgctgccagt gcccagccgg cgccgccctg caggcagacg ggcgctcctg caccgcatcc gcgacgcagt cctgcaacga cctctgcgag cacttctgcg ttcccaaccc cgaccagccg ggctcctact cgtgcatgtg cgagaccggc taccggctgg cggccgacca acaccggtgc gaggacgtgg atgactgcat actggagccc agtccgtgtc cgcagcgctg tgtcaacaca cagggtggct tcgagtgcca ctgctaccct aactacgacc tggtggacgg cgagtgtgtg gagcccgtgg acccgtgctt cagagccaac tgcgagtacc agtgccagcc cctgaaccaa actagctacc tctgcgtctg cgccgagggc ttcgcgccca ttccccacga gccgcacagg tgccagatgt tttgcaacca gactgcctgt ccagccgact gcgaccccaa cacccaggct agctgtgagt gccctgaagg ctacatcctg gacgacggtt tcatctgcac ggacatcgac gagtgcgaaa acggcggctt ctgctccggg gtgtgccaca acctccccgg taccttcgag tgcatctgcg ggcccgactc ggcccttgcc cgccacattg gcaccgactg tgactccggc aaggtggacg gtggcgacag cggctctggc gagccccgc ccagcccgac gccggctcc accttgactc ctccggccgt ggggctcgtg cattcgggct tgctcatagg catctccatc gcgagcctgt gcctggtggt ggcgcttttg gcgctcctct gccacctgcg caagaagcag ggcgccgcca gggccaagat ggagtacaag tgcgcggccc cttccaagga ggtagtgctg cagcacgtgc ggaccgagcg gacgccgcag agactc SEQ ID NO:4 (CMV promoter)
TCTAGACGCGTTGACATTGATTATTGACTAGTTATTAATAGTAATCAATT

ACGGGGTCATTAGTTCATAGCCCATGATATCATATGGAGTTCCGCGTTAC

ATAACTTACGGTAAATGGCCCGCCTGGCTGACCGCCCAACGACCCCCGCC

CATTGACGTCAATAATGACGTATGTTCCCATAGTAACGCCAATAGGGACT

TTCCATTGACGTCAATGGGTGGAGTATTTACGGTAAACTGCCCACTTGGC

AGTACATCAAGTGTATCATATGCCAAGTACGCCCCCTATTGACGTCAAT

GACGGTAAATGGCCCGCCTGGCATTATGCCCAGTNCATGACCTTATGGGA

CTTTCCTACTTGGCAGACATCTACGTATTAGTCATCGCTATTACCATGGT

GATGCGGTTTTGGCAGTACATCAATGGGCGTGGATAGCGGTTTGACTCAC

GGGGATTTCCAAGTCTCCACCCCATTGACGTCAATGGGAGTTTGTTTTG

GCACCAAAATCAACGGGACTTTCCAAAATGTCGTAACAACTCCGCCCCAT

TGACGCAAATGGGCGGTAGGCGTGTACGGTGGGAGGTCTATATAAGCAGA
```

-continued
GCTCTCTGGCTAACTAGAGAACCCCTGCTTACTGGCTTATCGAGATATC

SEQ ID NO:5 (hTM cDNA)
GGCAGCGCGCAGCGGCAAGAAGTGTCTGGGCTGGGACGGACAGGAGAGGC
TGTCGCCATCGGCGTCCTGTGCCCCTCTGCTCCGGCACGGCCCTGTCGCA
GTGCCCGCGCTTTCCCCGGCGCCTGCACGCGGCGCGCCTGGGTAACATGC
TTGGGGTCCTGGTCCTTGGCGCGCTGGCCCTGGCCGGCCTGGGGTTCCCC
GCACCCGCAGAGCCGCAGCCGGGTGGCAGCCAGTGCGTCGAGCACGACTG
CTTCGCGCTCTACCCGGGCCCCGCGACCTTCCTCAATGCCAGTCAGATCT
GCGACGGACTGCGGGGCCACCTAATGACAGTGCGCTCCTCGGTGGCTGCC
GATGTCATTTCCTTGCTACTGAACGGCGACGGCGGCGTTGGCCGCCGGCG
CCTCTGGATCGGCCTGCAGCTGCCACCCGGCTGCGGCGACCCCAAGCGCC
TCGGGCCCCTGCGCGGCTTCCAGTGGGTTACGGGAGACAACAACACCAGC
TATAGCAGGTGGGCACGGCTCGACCTCAATGGGGCTCCCCTCTGCGGCCC
GTTGTGCGTCGCTGTCTCCGCTGCTGAGGCCACTGTGCCCAGCGAGCCGA
TCTGGGAGGAGCAGCAGTGCGAAGTGAAGGCCGATGGCTTCCTCTGCGAG
TTCCACTTCCCAGCCACCTGCAGGCCACTGGCTGTGGAGCCCGGCGCCGC
GGCTGCCGCCGTCTCGATCACCTACGGCACCCCGTTCGCGGCCCGCGGAG
CGGACTTCCAGGCGCTGCCGGTGGGCAGCTCCGCCGCGGTGGCTCCCCTC
GGCTTACAGCTAATGTGCACCGCGCCGCCCGGAGCGGTCCAGGGGCACTG
GGCCAGGGAGGCGCCGGGCGCTTGGGACTGCAGCGTGGAGAACGGCGGCT
GCGAGCACGCGTGCAATGCGATCCCTGGGGCTCCCCGCTGCCAGTGCCCA
GCCGGCGCCGCCCTGCAGGCAGACGGGCGCTCCTGCACCGCATCCGCGAC
GCAGTCCTGCAACGACCTCTGCGAGCACTTCTGCGTTCCCAACCCCGACC
AGCCGGGCTCCTACTCGTGCATGTGCGAGACCGGCTACCGGCTGGCGGCC
GACCAACACCGGTGCGAGGACGTGGATGACTGCATACTGGAGCCCAGTCC
GTGTCCGCAGCGCTGTGTCAACACACAGGGTGGCTTCGAGTGCCACTGCT
ACCCTAACTACGACCTGGTGGACGGCGAGTGTGTGGAGCCCGTGGACCCG
TGCTTCAGAGCCAACTGCGAGTACCAGTGCCAGCCCCTGAACCAAACTAG
CTACCTCTGCGTCTGCGCCGAGGGCTTCGCGCCCATTCCCCACGAGCCGC
ACAGGTGCCAGATGTTTTGCAACCAGACTGCCTGTCCAGCCGACTGCGAC
CCCAACACCCAGGCTAGCTGTGAGTGCCCTGAAGGCTACATCCTGGACGA
CGGTTTCATCTGCACGGACATCGACGAGTGCGAAAACGGCGGCTTCTGCT
CCGGGGTGTGCCACAACCTCCCCGGTACCTTCGAGTGCATCTGCGGGCCC
GACTCGGCCCTTGCCCGCCACATTGGCACCGACTGTGACTCCGGCAAGGT
GGACGGTGGCGACAGCGGCTCTGGCGAGCCCCCGCCCAGCCCGACGCCCG
GCTCCACCTTGACTCCTCCGGCCGTGGGGCTCGTGCATTCGGGCTTGCTC
ATAGGCATCTCCATCGCGAGCCTGTGCCTGGTGGTGGCGCTTTTGGCGCT
CCTCTGCCACCTGCGCAAGAAGCAGGGCGCCGCCAGGGCCAAGATGGAGT
ACAAGTGCGCGGCCCCTTCCAAGGAGGTAGTGCTGCAGCACGTGCGGACC
GAGCGGACGCCGCAGAGACTCTGAGCGGCCTCCGTCCAGGAGCCTGGCTC
CGTCCAGGAGCCTGTGCCTCCTCACCCCCAGCTTTGCTACCAAAGCACCT

-continued
TAGCTGGCATTACAGCTGGAGAAGACCCTCCCCGCACCCCCCAAGCTGTT
TTCTTCTATTCCATGGCTAACTGGCGAGGGGTGATTAGAGGGAGGAGAA
TGAGCCTCGGCCTCTTCCGTGACGTCACTGGACCACTGGGCAATGATGGC
AATTTTGTAACGAAGACACAGACTGCGATTTGTCCCAGGTCCTCACTACC
GGGCGCAGGAGGGTGAGCGTTATTGGTCGGCAGCCTTCTGGGCAGACCTT
GACCTCGTGGGCTAGGGATGACTAAAATATTTATTTTTTTAAGTATTTA
GGTTTTGTTTGTTTCCTTTGTTCTTACCTGTATGTCTCCAGTATCCACT
TTGCACAGCTCTCCGGTCTCTCTCTCTCTACAAACTCCCACTTGTCATGT
GACAGGTAAACTATCTTGGTGAATTTTTTTTTCCTAGCCCTCTCACATTT
ATGAAGCAAGCCCCACTTATTCCCCATTCTTCCTAGTTTTCTCCTCCCAG
GAACTGGGCCAACTCACCTGAGTCACCCTACCTGTGCCTGACCCTACTTC
TTTTGCTCTTAGCTGTCTGCTCAGACAGAACCCCTACATGAAACAGAAAC
AAAAACACTAAAAATAAAAATGGCCATTTGCTTTTTCACCAGATTTGCTA
ATTTATCCTGAAATTTCAGATTCCCAGAGCAAAATAATTTTAAACAAAGG
TTGAGATGTAAAAGGTATTAAATTGATGTTGCTGGACTGTCATAGAAATT
ACACCCAAAGAGGTATTTATCTTTACTTTTAAACAGTGAGCCTGAATTTT
GTTGCTGTTTTGATTTGTACTGAAAAATGGTAATTGTTGCTAATCTTCTT
ATGCAATTTCCTTTTTTGTTATTATTACTTATTTTTGACAGTGTTGAAAA
TGTTCAGAAGGTTGCTCTAGATTGAGAGAAGAGACAAACACCTCCCAGGA
GACAGTTCAAGAAAGCTTCAAACTGCATGATTCATGCCAATTAGCAATTG
ACTGTCACTGTTCCTTGTCACTGGTAGACCAAAATAAAACCAGCTCTACT
GGTCTTGTGGAATTGGGAGCTTGGGAATGGATCCTGGAGGATGCCCAATT
AGGGCCTAGCCTTAATCAGGTCCTCAGAGAATTTCTACCATTTCAGAGAG
GCCTTTTGGAATGTGGCCCCTGAACAAGAATTGGAAGCTGCCCTGCCCAT
GGGAGCTGGTTAGAAATGCAGAATCCTAGGCTCCACCCCATCCAGTTCAT
GAGAATCTATATTTAACAAGATCTGCAGGGGTGTGTCTGCTCAGTAATT
TGAGGACAACCATTCCAGACTGCTTCCAATTTTCTGGAATACATGAAATA
TAGATCAGTTATAAGTAGCAGGCAAGTCAGGCCCTTATTTTCAAGAAAC
TGAGGAATTTTCTTTGTGTAGCTTTGCTCTTTGGTAGAAAAGGCTAGGTA
CACAGCTCTAGACACTGCCACACAGGGTCTGCAAGGTCTTTGGTTCAGCT
AAGCTAGGAATGAAATCCTGCTTCAGTGTATGGAAATAAATGTATCATAG
AAATGTAACTTTTGTAAGACAAAGGTTTTCCTCTTCTATTTTGTAAACTC
AAAATATTTGTACATAGTTATTTATTTATTGGAGATAATCTAGAACACAG
GCAAATCCTTGCTTATGACATCACTTGTACAAAATAAACAAATAACAAT
GTGAAAAAAAAAAAAAAAAAAAAAAAAAAAAAAAAAAAAAA SEQ ID NO:6 (CMV-hTM expression cassette)
GTTTAAACGGGCCCTCTAGACGCGTTGACATTGATTATTGACTAGTTATT
AATAGTAATCAATTACGGGGTCATTAGTTCATAGCCCATGATATCATATG
GAGTTCCGCGTTACATAACTTACGGTAAATGGCCCGCCTGGCTGACCGCC
CAACGACCCCCGCCCATTGACGTCAATAATGACGTATGTTCCCATAGTAA -continued

```
CGCCAATAGGGACTTTCCATTGACGTCAATGGGTGGAGTATTTACGGTAA
ACTGCCCACTTGGCAGTACATCAAGTGTATCATATGCCAAGTACGCCCCC
CTATTGACGTCAATGACGGTAAATGGCCCGCCTGGCATTATGCCCAGTNC
ATGACCTTATGGGACTTTCCTACTTGGCAGACATCTACGTATTAGTCATC
GCTATTACCATGGTGATGCGGTTTTGGCAGTACATCAATGGGCGTGGATA
GCGGTTTGACTCACGGGGATTTTCCAAGTCTCCACCCCATTGACGTCAAT
GGGAGTTTGTTTTGGCACCAAAATCAACGGGACTTTCCAAAATGTCGTAA
CAACTCCGCCCCATTGACGCAAATGGGCGGTAGGCGTGTACGGTGGGAGG
TCTATATAAGCAGAGCTCTCTGGCTAACTAGAGAACCCCTGCTTACTGGC
TTATCGAGATATCTGCAGAATTCATCTGTCGACTGCTACCGGCAGCGCGC
AGCGGCAAGAAGTGTCTGGGCTGGACGGACAGGAGAGGCTGTCGCCATC
GGCGTCCTGTGCCCCTCTGCTCCGGCACGGCCCTGTCGCAGTGCCCGCGC
TTTCCCCGGCGCCTGCACGCGGCGCGCCTGGGTAACATGCTTGGGGTCCT
GGTCCTTGGCGCGCTGGCCCTGGCCGGCCTGGGGTTCCCCGCACCCGCAG
AGCCGCAGCCGGGTGGCAGCCAGTGCGTCGAGCACGACTGCTTCGCGCTC
TACCCGGGCCCCGCGACCTTCCTCAATGCCAGTCAGATCTGCGACGGACT
GCGGGGCCACCTAATGACAGTGCGCTCCTCGGTGGCTGCCGATGTCATTT
CCTTGCTACTGAACGGCGACGGCGGCGTTGGCCGCCGGCGCCTCTGGATC
GGCCTGCAGCTGCCACCCGGCTGCGGCGACCCCAAGCGCCTCGGGCCCCT
GCGCGGCTTCCAGTGGGTTACGGGAGACAACAACACCAGCTATAGCAGGT
GGGCACGGCTCGACCTCAATGGGGCTCCCCTCTGCGGCCCGTTGTGCGTC
GCTGTCTCCGCTGCTGAGGCCACTGTGCCCAGCGAGCCGATCTGGGAGGA
GCAGCAGTGCGAAGTGAAGGCCGATGGCTTCCTCTGCGAGTTCCACTTCC
CAGCCACCTGCAGGCCACTGGCTGTGGAGCCCGGCGCCGCGGCTGCCGCC
GTCTCGATCACCTACGGCACCCCGTTCGCGGCCCGCGGAGCGGACTTCCA
GGCGCTGCCGGTGGGCAGCTCCGCCGCGGTGGCTCCCCTCGGCTTACAGC
TAATGTGCACCGCGCCGCCCGGAGCGGTCCAGGGGCACTGGGCCAGGGAG
GCGCCGGGCGCTTGGGACTGCAGCGTGGAGAACGGCGGCTGCGAGCACGC
GTGCAATGCGATCCCTGGGGCTCCCCGCTGCCAGTGCCCAGCCGGCGCCG
CCCTGCAGGCAGACGGGCGCTCCTGCACCGCATCCGCGACGCAGTCCTGC
AACGACCTCTGCGAGCACTTCTGCGTTCCCAACCCCGACCAGCCGGGCT
CTACTCGTGCATGTGCGAGACCGGCTACCGGCTGGCGGCCGACCAACACC
GGTGCGAGGACGTGGATGACTGCATACTGGAGCCCAGTCCGTGTCCGCAG
CGCTGTGTCAACACACAGGGTGGCTTCGAGTGCCACTGCTACCCTAACTA
CGACCTGGTGGACGGCGAGTGTGTGGAGCCCGTGGACCCGTGCTTCAGAG
CCAACTGCGAGTACCAGTGCCAGCCCCTGAACCAAACTAGCTACCTCTGC
GTCTGCGCCGAGGGCTTCGCGCCCATTCCCCACGAGCCGCACAGGTGCCA
GATGTTTTGCAACCAGACTGCCTGTCCAGCCGACTGCGACCCCAACACCC
AGGCTAGCTGTGAGTGCCCTGAAGGCTACATCCTGGACGACGGTTTCATC
TGCACGGACATCGACGAGTGCGAAAACGGCGGCTTCTGCTCCGGGGTGTG
```

-continued

```
CCACAACCTCCCCGGTACCTTCGAGTGCATCTGCGGGCCCGACTCGGCCC
TTGCCCGCCACATTGGCACCGACTGTGACTCCGGCAAGGTGGACGGTGGC
GACAGCGGCTCTGGCGAGCCCCCGCCCAGCCCGACGCCCGGCTCCACCTT
GACTCCTCCGGCCGTGGGGCTCGTGCATTCGGGCTTGCTCATAGGCATCT
CCATCGCGAGCCTGTGCCTGGTGGTGGCGCTTTTGGCGCTCCTCTGCCAC
CTGCGCAAGAAGCAGGGCGCCGCCAGGGCCAAGATGGAGTACAAGTGCGC
GGCCCCTTCCAAGGAGGTAGTGCTGCAGCACGTGCGGACCGAGCGGACGC
CGCAGAGACTCTGAGCGGCCTCCGTCCAGGAGCCTGGCTCCGTCCAGGAG
CCTGTGCCTCCTCACCCCAGCTTTGCTACCAAAGCACCTTAGCTGGCAT
TACAGCTGGAGAAGACCCTCCCCGCACCCCCCAAGCTGTTTTCTTCTATT
CCATGGCTAACTGGCGAGGGGGTGATTAGAGGGAGGAGAATGAGCCTCGG
CCTCTTCCGTGACGTCACTGGACCACTGGGCAATGATGGCAATTTTGTAA
CGAAGACACAGACTGCGATTTGTCCCAGGTCCTCACTACCGGGCGCAGGA
GGGTGAGCGTTATTGGTCGGCAGCCTTCTGGGCAGACCTTGACCTCGTGG
GCTAGGGATGACTAAAATATTTATTTTTTTTAAGTATTTAGGTTTTTGTT
TGTTTCCTTTGTTCTTACCTGTATGTCTCCAGTATCCACTTTGCACAGCT
CTCCGGTCTCTCTCTCTACAAACTCCCACTTGTCATGTGACAGGTAAA
CTATCTTGGTGAATTTTTTTTCCTAGCCCTCTCACATTTATGAAGCAAG
CCCCACTTATTCCCCATTCTTCCTAGTTTTCTCCTCCCAGGAACTGGGCC
AACTCACCTGAGTCACCCTACCTGTGCCTGACCCTACTTCTTTTGCTCTT
AGCTGTCTGCTCAGACAGAACCCCTACATGAAACAGAAACAAAAACACTA
AAAATAAAAATGGCCATTTGCTTTTTCACCAGATTTGCTAATTTATCCTG
AAATTTCAGATTCCCAGAGCAAAATAATTTTAAACAAAGGTTGAGATGTA
AAAGGTATTAAATTGATGTTGCTGGACTGTCATAGAAATTACACCCAAAG
AGGTATTTATCTTTACTTTTAAACAGTGAGCCTGAATTTGTTGCTGTTT
TGATTTGTACTGAAAAATGGTAATTGTTGCTAATCTTCTTATGCAATTTC
CTTTTTTGTTATTATTACTTATTTTTGACAGTGTTGAAAATGTTCAGAAG
GTTGCTCTAGATTGAGAGAAGAGACAAACACCTCCCAGGAGACAGTTCAA
GAAAGCTTCAAACTGCATGATTCATGCCAATTAGCAATTGACTGTCACTG
TTCCTTGTCACTGGTAGACCAAAATAAAACCAGCTCTACTGGTCTTGTGG
AATTGGGAGCTTGGGAATGGATCCTGGAGGATGCCCAATTAGGGCCTAGC
CTTAATCAGGTCCTCAGAGAATTTCTACCATTTCAGAGAGGCCTTTTGGA
ATGTGGCCCCTGAACAAGAATTGGAAGCTGCCCTGCCCATGGGAGCTGGT
TAGAAATGCAGAATCCTAGGCTCCACCCCATCCAGTTCATGAGAATCTAT
ATTTAACAAGATCTGCAGGGGGTGTGTCTGCTCAGTAATTTGAGGACAAC
CATTCCAGACTGCTTCCAATTTTCTGGAATACATGAAATATAGATCAGTT
ATAAGTAGCAGGCAAGTCAGGCCCTTATTTTTCAAGAAACTGAGGAATTT
TCTTTGTGTAGCTTTGCTCTTTGGTAGAAAAGGCTAGGTACACAGCTCTA
GACACTGCCACACAGGGTCTGCAAGGTCTTTGGTTCAGCTAAGCTAGGAA
TGAAATCCTGCTTCAGTGTATGGAAATAAATGTATCATAGAAATGTAACT
```

-continued

```
TTTGTAAGACAAAGGTTTTCCTCTTCTATTTTGTAAACTCAAAATATTTG
TACATAGTTATTTATTTATTGGAGATAATCTAGAACACAGGCAAAATCCT
TGCTTATGACATCACTTGTACAAAATAAACAAATAACAATGTGAAAAAA
AAAAAAAAAAAAAAAAAAAAAAAAAAAAAAAAAAAGGTAGCAGTCGACAGAT
GAATTCCACCACACTGGACTAGTGGATCCGAGCTCGGTACCAAGCTTAAG
TTTAAAC
```

SEQ ID NO:7 (pTMadap)
```
CATCATCAATAATATACCTTATTTTGGATTGAAGCCAATATGATAATGAG
GGGGTGGAGTTTGTGACGTGGCGCGGGGCGTGGGAACGGGGCGGGTGACG
TAGTAGTGTGGCGGAAGTGTGATGTTGCAAGTGTGGCGGAACACATGTAA
GCGACGGATGTGGCAAAAGTGACGTTTTTGGTGTGCGCCGGTGTACACAG
GAAGTGACAATTTTCGCGCGGTTTTAGGCGGATGTTGTAGTAAATTTGGG
CGTAACCGAGTAAGATTGGCCATTTTCGCGGGAAAACTGAATAAGAGGA
AGTGAAATCTGAATAATTTTGTGTTACTCATAGCGCGTAATACTGGTACC
GCGGCCGCCTCGAGTCTAGAACTAGTGGATCCCCCAAACGGGCCCTCTAG
ACGCGTTGACATTGATTATTGACTAGTTATTAATAGTAATCAATTACGGG
GTCATTAGTTCATAGCCCATGATATCATATGGAGTTCCGCGTTACATAAC
TTACGGTAAATGGCCCGCCTGGCTGACCGCCCAACGACCCCCGCCCATTG
ACGTCAATAATGACGTATGTTCCCATAGTAACGCCAATAGGGACTTTCCA
TTGACGTCAATGGGTGGAGTATTTACGGTAAACTGCCCACTTGGCAGTAC
ATCAAGTGTATCATATGCCAAGTACGCCCCCCTATTGACGTCAATGACGG
TAAATGGCCCGCCTGGCATTATGCCCAGTNCATGACCTTATGGGACTTTC
CTACTTGGCAGACATCTACGTATTAGTCATCGCTATTACCATGGTGATGC
GGTTTTGGCAGTACATCAATGGGCGTGGATAGCGGTTTGACTCACGGGA
TTTTCCAAGTCTCCACCCCATTGACGTCAATGGGAGTTTGTTTTGGCACC
AAAATCAACGGGACTTTCCAAAATGTCGTAACAACTCCGCCCCATTGACG
CAAATGGGCGGTAGGCGTGTACGGTGGGAGGTCTATATAAGCAGAGCTCT
CTGGCTAACTAGAGAACCCCTGCTTACTGGCTTATCGAGATATCTGCAGA
ATTCATCTGTCGACTGCTACCGGCAGCGCGCAGCGGCAAGAAGTGTCTGG
GCTGGGACGGACAGGAGAGGCTGTCGCCATCGGCGTCCTGTGCCCCTCTG
CTCCGGCACGGCCCTGTCGCAGTGCCCGCGCTTTCCCCGGCGCCTGCACG
CGGCGCGCCTGGGTAACATGCTTGGGGTCCTGGTCCTTGGCGCGCTGGCC
CTGGCCGGCCTGGGGTTCCCCGCACCCGCAGAGCCGCAGCCGGGTGGCAG
CCAGTGCGTCGAGCACGACTGCTTCGCGCTCTACCCGGGCCCCGCGACCT
TCCTCAATGCCAGTCAGATCTGCGACGGACTGCGGGCCACCTAATGACA
GTGCGCTCCTCGGTGGCTGCCGATGTCATTTCCTTGCTACTGAACGGCGA
CGGCGGCGTTGGCCGCCGGCGCCTCTGGATCGGCCTGCAGCTGCCACCCG
GCTGCGGCGACCCCAAGCGCCTCGGGCCCTGCGCGGCTTCCAGTGGGTT
ACGGGAGACAACAACACCAGCTATAGCAGGTGGGCACGGCTCGACCTCAA
TGGGGCTCCCCTCTGCGGCCCGTTGTGCGTCGCTGTCTCCGCTGCTGAGG
CCACTGTGCCCAGCGAGCCGATCTGGGAGGAGCAGCAGTGCGAAGTGAAG
```

-continued

```
GCCGATGGCTTCCTCTGCGAGTTCCACTTCCCAGCCACCTGCAGGCCACT
GGCTGTGGAGCCCGGCGCCGCGGCTGCCGCCGTCTCGATCACCTACGGCA
CCCCGTTCGCGGCCCGCGGAGCGGACTTCCAGGCGCTGCCGGTGGGCAGC
TCCGCCGCGGTGGCTCCCCTCGGCTTACAGCTAATGTGCACCGCGCCGCC
CGGAGCGGTCCAGGGGCACTGGGCCAGGGAGGCGCCGGGCGCTTGGGACT
GCAGCGTGGAGAACGGCGGCTGCGAGCACGCGTGCAATGCGATCCCTGGG
GCTCCCCGCTGCCAGTGCCCAGCCGGCGCCGCCCTGCAGGCAGACGGGCG
CTCCTGCACCGCATCCGCGACGCAGTCCTGCAACGACCTCTGCGAGCACT
TCTGCGTTCCCAACCCCGACCAGCCGGGCTCCTACTCGTGCATGTGCGAG
ACCGGCTACCGGCTGGCGGCCGACCAACACCGGTGCGAGGACGTGGATGA
CTGCATACTGGAGCCCAGTCCGTGTCCGCAGCGCTGTGTCAACACACAGG
GTGGCTTCGAGTGCCACTGCTACCCTAACTACGACCTGGTGGACGGCGAG
TGTGTGGAGCCCGTGGACCCGTGCTTCAGAGCCAACTGCGAGTACCAGTG
CCAGCCCTGAACCAAACTAGTACCTCTGCGTCTGCGCCGAGGGCTTCG
CGCCCATTCCCCACGAGCCGCACAGGTGCCAGATGTTTTGCAACCAGACT
GCCTGTCCAGCCGACTGCGACCCCAACACCCAGGCTAGCTGTGAGTGCCC
TGAAGGCTACATCCTGGACGACGGTTTCATCTGCACGGACATCGACGAGT
GCGAAAACGGCGGCTTCTGCTCCGGGGTGTGCCACAACCTCCCCGGTACC
TTCGAGTGCATCTGCGGGCCCGACTCGGCCCTTGCCCGCCACATTGGCAC
CGACTGTGACTCCGGCAAGGTGGACGGTGGCGACAGCGGCTCTGGCGAGC
CCCCGCCCAGCCCGACGCCCGGCTCCACCTTGACTCCTCCGGCCGTGGGG
CTCGTGCATTCGGGCTTGCTCATAGGCATCTCCATCGCGAGCCTGTGCCT
GGTGGTGGCGCTTTTGGCGCTCCTCTGCCACCTGCGCAAGAAGCAGGGCG
CCGCCAGGGCCAAGATGGAGTACAAGTGCGCGGCCCCTTCCAAGGAGGTA
GTGCTGCAGCACGTGCGGACCGAGCGGACGCCGCAGAGACTCTGAGCGGC
CTCCGTCCAGGAGCCTGGCTCCGTCCAGGAGCCTGTGCCTCCTCACCCCC
AGCTTTGCTACCAAAGCACCTTAGCTGGCATTACAGCTGGGAAGACCCT
CCCCGCACCCCCCAAGCTGTTTTCTTCTATTCCATGGCTAACTGGCGAGG
GGGTGATTAGAGGGAGGAGAATGAGCCTCGGCCTCTTCCGTGACGTCACT
GGACCACTGGGCAATGATGGCAATTTTGTAACGAAGACACAGACTGCGAT
TTGTCCCAGGTCCTCACTACCGGGCGCAGGAGGGTGAGCGTTATTGGTCG
GCAGCCTTCTGGGCAGACCTTGACCTCGTGGGCTAGGGATGACTAAAATA
TTTATTTTTTTAAGTATTTAGGTTTTTGTTTGTTTCCTTTGTTCTTACC
TGTATGTCTCCAGTATCCACTTTGCACAGCTCTCCGGTCTCTCTCTCTCT
ACAAACTCCCACTTGTCATGTGACAGGTAAACATATCTTGGTGAATTTTTT
TTTCCTAGCCCTCTCACATTTATGAAGCAAGCCCCACTTATTCCCCATTC
TTCCTAGTTTTCTCCTCCCAGGAACTGGGCCAACTCACCTGAGTCACCCT
ACCTGTGCCTGACCCTACTTCTTTTGCTCTTAGCTGTCTGCTCAGACAGA
ACCCCTACATGAAACAGAAACAAAAACACTAAAAATAAAAATGGCCATTT
GCTTTTTCACCAGATTTGCTAATTTATCCTGAAATTTCAGATTCCCAGAG
```

-continued

```
CAAAATAATTTTAAACAAAGGTTGAGATGTAAAAGGTATTAAATTGATGT
TGCTGGACTGTCATAGAAATTACACCCAAAGAGGTATTTATCTTTACTTT
TAAACAGTGAGCCTGAATTTTGTTGCTGTTTTGATTTGTACTGAAAAATG
GTAATTGTTGCTAATCTTCTTATGCAATTTCCTTTTTTGTTATTATTACT
TATTTTTGACAGTGTTGAAAATGTTCAGAAGGTTGCTCTAGATTGAGAGA
AGAGACAAACACCTCCCAGGAGACAGTTCAAGAAAGCTTCAAACTGCATG
ATTCATGCCAATTAGCAATTGACTGTCACTGTTCCTTGTCACTGGTAGAC
CAAAATAAAACCAGCTCTACTGGTCTTGTGGAATTGGGAGCTTGGGAATG
GATCCTGGAGGATGCCCAATTAGGGCCTAGCCTTAATCAGGTCCTCAGAG
AATTTCTACCATTTCAGAGAGGCCTTTTGGAATGTGGCCCCTGAACAAGA
ATTGGAAGCTGCCCTGCCCATGGGAGCTGGTTAGAAATGCAGAATCCTAG
GCTCCACCCCATCCAGTTCATGAGAATCTATATTTAACAAGATCTGCAGG
GGGTGTGTCTGCTCAGTAATTTGAGGACAACCATTCCAGACTGCTTCCAA
TTTTCTGGAATACATGAAATATAGATCAGTTATAAGTAGCAGGCCAAGTC
AGGCCCTTATTTTCAAGAAACTGAGGAATTTTCTTTGTGTAGCTTTGCTC
TTTGGTAGAAAAGGCTAGGTACACAGCTCTAGACACTGCCACACAGGGTC
TGCAAGGTCTTTGGTTCAGCTAAGCTAGGAATGAAATCCTGCTTCAGTGT
ATGGAAATAAATGTATCATAGAAATGTAACTTTTGTAAGACAAAGGTTTT
CCTCTTCTATTTTGTAAACTCAAAATATTTGTACATAGTTATTTATTTAT
TGGAGATAATCTAGAACACAGGCAAAATCCTTGCTTATGACATCACTTGT
ACAAAATAAACAAATAACAATGTGAAAAAAAAAAAAAAAAAAAAAAAAA
AAAAAAAAAAAAAAGGTAGCAGTCGACAGATGAATTCCACCACACTGGAC
TAGTGGATCCGAGCTCGGTACCAAGCTTAAGTTTGGGCTGCAGGAATTCT
GATGGCTCTCAAAATTCCTGCCTCCTTTAGGGATAAAAGACTTTAAGACT
TTTTAACAAAAAGAAAAAGAAAAAAAAAATTCCTGCCTCCTGGTGTACA
CACACAGAAGGGTTCCCTCCCCTTGAATGTGACCAGGATCTGTGAAAATA
ACGGGATAGCCGCTCCTGTGATTAGGTTATGTGGTAGACTAGAGCAAGAT
TCTCCTGCTGGTTTTGAAGAAGTCAGCTGCCATGTTGTGAGACTGTCATG
GGCTAGGGCATGAGCCTTTAAATATCTGGGAGCAACCCCTGGCCAGCAGC
CAGTGAGAAAACGGGCCCTCAGTCCTACAATCACAAGGAACTAAATTCTG
CCAACAACCTGAAGGAACTTTGAAGAGGATCATGAGTCCCTTGATTCAGC
TTGATGAGCCCCTGAGCAGAGGATACAGCTAACTTGTACTAGGGAAGTAT
AAAAAACATGCATGGGAATGATATATATCAACTTTAAGGATAATTGTCAT
ACTTCTGGGAATGAAGGGAAAGAAATGGGGCTTTAGTTGTATTATGATCT
TTAATTTCTCAAAAAAAATAAGATCAGAAGCAAATATGGCAAATGTTAA
TACTTTTGTGGGTACGTAGGTATTCAGCATACCCTTTTTTCTGAGTTCAA
AATATTTTATAATTAAAATGAAATGCAGGCCAGGCACAGTGGCTCATGCC
TATAATACCAGCACTTTGCGAGGCCGAGGTGGGAGGATGGCTTGAGGCCA
GACCAGCCTGGCCAACATGGCAAAACCCCATCTCTACTTAAAAAAAAAA
AACTATATATATATATATGTGTGTGTGTGTATATATATATATGTATAT

ATATTTATATATGTGTGTATATATATATGTATATATATTTATATATGT
GTGTGTATATATATATACACACACACATATATACATACATACATAC
ACACACACACACACAATTAGCCAGGCATGGTGGCGCACACCTGTAGTC
CCAGCTACTTGGGAGGCTGAGACATGAGAATTGCTTGAACCTGGGAGGCA
GAGTAGTTAGTGAGCTGAGATCATACCACTGCACTCCAGCCTGGTGACAG
AGTGAGACTCTGTCTTAAAAAAAATAAAAATTAAAATTAAATGCAAAAGG
TCCAAGTGAATTGAAGAGGAAAGGGGTATCAAGGAAGGTTTTGTGGAGGT
GACGTTTGAGCTGGGTCTTAAATGACTTAAACATGGGATAAGAAGGGAGG
GAATAAGGACATTTCAGGTACGAGAAATAAGGAGCAAACAGTGGAAACAA
CCTAACGTCTGTCAACCAGTGAATGGATAACAAAAATGTAATTCAGATGG
TATCCAACTTACGATGGTTCAACATGAGATTTTTCTGACTTTAGGATAGA
TTTATCAAAGTAGTAAATCCATTTTCAACTTATGATATTTTCAACTTCAG
ATGGGTTTATCAGGACACAGTTGAGGAACACCTGTCTATCCATACAATTT
GGCAATAAAAAGGAAATGAGTGCAGATATACTCCACAACATGAATGAACC
TTGAAAACATTAAGTGAGAGAAGCCAGATACAAAAGGCCACATATTGTAT
GATTCTATTTATCAAAATGTCCAGAATAGGCAAATCTTATAGACAGCAA
GTAGGTAGATGATCAGTTTGCTAGGTGCTGGGGGAAGGGGAAATGGGGAG
TGATGGCTAAGGGGATTGGGTTTCTTTGTGGGGCAATGAAAATGTTTTAA
AATTGAGCGTGATAATGATTGCACAATGCTGCATATATATATAATCTATA
GATTATATATATATAAAGAGAGGCTGTTAGACAGTGATAAGTGATATATA
TATATATATACATAGAGAGAGAGAGAGAGAGAGAGAGAGGCTGTTAGTGA
TAAGTGATCAGGAAAATAAAAGTATTGAGGAGGAATACGAAGTTGACGGT
GTGAAAACATGAGATTTTATATAGGATGGCCAGGGAAGGCCTTAATGAGA
AAGTGACTTATGAGTAAAAACAAGGGATCCTAAACCTTAGCATGCATCAG
AATCACTCGGAAACTTGTTAAAGCATAGCTTGCTGGGCCTCATCACAGAT
ATTTTGATTCGGTAGGTTCTTGTCTGATATTAATACTTTTGGTCTAGGGA
ACCACATTTTGAGAACCACTGAGCTAAAGGAAGTAAAGGTTTCCCTTAGT
TTACTAGCTGGTAACACTGGCCCAGGAGGCCTTTCTGGTGACCCCTAAGG
AATTATCCAAACTCTTGTTTTTAGATGCTTTATTATATCAAACTCTCCTT
TAAACAAGTGGCCCATCTGCTGGGATTTGGAAGCCTGTAATACTGAAATT
TTCATCATAATGGAAATTTTAAAAACAGAATTTGACCCACCTGTTTTTAA
AACACTTTCATTACTTAACAAGAGGTCTAATCTTGGGCAAGTCTTGAAAT
TTCTCTGGCCTTAGTTTCCCATGTGTTAAATGAAACTTGAAGCAGTTGGT
CTCTTATAGTCTCCTGACTCTAACATTCTAAGAATTATATTTGTACAATA
ACTCAAAAATCACATAATTTAATTTACCATATGGACTCCAAAATATATTT
TCTCATTAGGCTAAACTTGATCTGCATTTTCTGGATGTGTCCATATTCTT
GGACTACACTAAAACATGATACCAATGCTTCCTCTCACCATAAACCCTCA
CTTCGCTTTCTACATTTAAGAATTTTATAGCTGGAAGAGTCCTTAACAGA
AAATACCATCTAATAATTACCCCTCAAAATCGAGAAAGTCCTATCTGTTC
TTATGCTAGTTATAAGAATGAGGCAGCATTTCACATAATGGTTATAAACA
```

```
CTGCCACAAGAAGATTCATGATGTGTTGTTTATCTGTAGCTCTCATCATA
CTCTGTCATATAACTATAGCATTAAGATTTTAATGTTCTATATATTCTTC
TAAGACAGTGTTTACCAGAGTAAGGCACAAAAGATCCACTGGTTTGCAAG
AAAGATTAGAACTTTTAAATTTTTTACCTCACCTTGTTTAATCTATATTT
TTGTATGTATTTTGTAACATATATATTATTATTACCATAAATCATATATA
ATTTAAAATGCATATATTAGGGGTAAATGCTCAGGAAACTTTTTATAAAT
TGGGCATGCAAATACAAGTTTGAAGACTCACTGTTCTAGGTATTAAAAGT
AAAGTTATAACCAAGTAAAGCTTCCACCTTTTCATGTCTCAAAGCAGTTT
ATTGTTGGAGGTAAGATCTCTTAGAAGCCTAAACAGGTCCAAGTACAGAA
TGAAGTAAGGCTAGCCCATAACTTGTGGCAAGCAATTCATACTATTTCTC
TCATGCTGAGCTCTCCTCAGTGAAGCAGCTACTATAGACAACTGCAGCCT
ATTGGTAGCCTATTTTACAGGCAGGAAAAAAATTACTTTTTATTCAAAGT
GGAACTCAGGACATGGGGAGAAAATGAATACAAAAAATAGGGTCAATCCA
AAGGCACACAGCAAATGAGTAACACAGTTATGTTTTTTCCCATTTGTAT
GAGGTCCCAGTAAATTCTAAGTAAACTGCAAATTTAATAATACACTAAAA
AAGCCATGCAATTGTTCAAATGAATCCCAGCATGGTACAAGGAGTACAGA
CACTAGAGTCTAAAAAACAAAAGAATGCCATTATTGAGTTTTTGAATTAT
ATCAAGTAGTTACATCTCTACTTAATAAATGAGAAAAACGAGGATAAGAG
GCCATTTGATAAAATGAAAATAGCCAAGAAGTGGTATTAGAGACTTGAAT
ACAGGTATTCGGGTCCAAAGTTCATCTGCTCAAATACTAACTGGGGAAAA
GAGGGAAAAATATTTATATACATATATATCTGCACACAAAAATACCCCCA
AAAGACAAAATGAGGCCAGGCAGGGTGGCTCACACCCGTAATCCCGGTAC
TTTGGGAGGCTGAGGCAGGTGGATACCTGAGATCAGGAGTTGGAGATCAG
CCTGGTCAACATGGTGAAACCCTGTCTCTACTAAAGATAAAAAAATTAGC
CAGGCATGGTGGCGTGCGCCTGTAATCCCAGCTACTTGGGAGTCTGAGGC
AGGAGAATCACTTGAACTGGGAAGGGGAGGTTGCAGTGAGCCAAGATCGT
ACTACTGCACTCCAGCCTGGGCAGCAGAGTGAGACTCCATCACAAAAATA
AATAAATAAATAAAATACAATGAAACAGAAAGTTCAAATAATCCCATAAT
CTTACCACCAAGAAATAACTTTCACTCGTTATACTTATTGATTTTTCCAT
AATAAATGTACTTTACTGTGACTATCATGAAAAGAAAGTTATTTTAGAAA
CAGAGAACTGTTTCAGATCAAATCTATGTAGTAGAACAGAGCCATTAGGT
GGGAAAGACGAGATCAAACTAAATCTCAGAAGGCCTAAAAGGCTAGGTCC
ATTCCAGCACTAAAAACTGACCAGACAAGTAATGGCTTCAACAGCTTCTA
AATATGGACAAAGCATGCTGAAAGGGAAGGACAGGTCTAACAGTGGTATA
TGAAATGAACAGGAGGGGCAAAGCTCATTTCTCCTCTGAAGTTTTCCAAA
GATGCTGAGGAGGACATTAGTTTGACATGACCCTGATATGGGACAAGATA
ATTTCACAGAAGTTTTACATGTTAAAGTTTTCTTATAGATACTCATTCAA
GTAAGCAATGAACACTAAAATCTAAAGAAAGAAAAGAGCTTTAGAGTCAG
GTCTGTATTCAAATTCAAGCTCTACCACTTACTGGTTCTGTGACTTTGGG
CAAGTCTTTTAACCTTATTAAGTCTTAATTTCCTGATTTGTAAAATGGGG
```

```
ATATCGTCTCCCTCACAGGATTGTTGTGAAACTTTTATGAGATTAATGCC
TTTATATTTGGCATAGTGTAAGTAAACAATAACTGGCAGCTTCAAAAAAA
AAAAGCAGTAGCATTCCATCATTTATTATTGGTTACTCTCAAAAAGTTTT
TCAATGTACTAGAAGATAAATATTCAAATACCTTAATATCTCCATTATTT
TCAGGTAAACAGCATGCTCCTGAACAACCAATGGGTCAACAAATAAATTA
AAAGGGAAATCTAAAAACATCTTGATATTAAACTACATGGAAGCACAATA
TACCAAAACCAATGGTTCACACTAGGAGAATTTTAAGGTACAAGAAAACT
CTTTGAGATTTCTTAAAATAATAGTATGTCTGAATTTATTGAGTGATTTA
CCAGAAACTGTTGTAAGAGCTCTACTTGCATTATAGCACTTAATCCTCTT
AACTCTATGGCTGCTATTATCAACCTCACCCTAATCACATATGGGACACA
GAGAGGTTAAGTAACTTGCCCAAGGTCAGAGTTAGGAAGTACTAAGCCAT
GCTTTGAATCAGTTGTCAGGCTCCGGAACTCACACTTTCAGCCACTACAT
AATACTGCTTTGCTATCTTTTAGGAAACTATGTGAGTCTACCTCACATAG
ACTCACATAGGTTTGTTTTTTTTTTTTTTAAAGGCTATCTTTTCCCCC
ATCAATGTTTTTTGAAGGATCCCAAATTAGAGTCCCACAGAGGCAGACAG
CAGTACTTGACAATATGGACATTTAAGGTTAATGTTGGATTCTACTGTCT
TTTTACTACATGACCTAGGGAACGATAATTAACCTAGACTGCTTCCAAGG
GTTAAATAACCCATTTAGTTATACTATGTAAATTATCTCTTAGTGATTGA
TTGAAAGCACACTGTTACTAATTGACTCGGTATGAAGTGCTTTTTTTCT
TCCCTTTCAAGATACATACCTTTCCAGTTAAAGTTGAGAGATCATCTCCA
CCAATTACTTTTATGTCCCCTGTTGACTGGTCATTCTAGTTAAAAAAAA
AAAAACTATATATATATATATCTACACACACATATGTATATGTATATCCT
TATGTACACACACAAACTTCAAATTAAATGAGAACTAGAAGATTTGAGAA
GTTAGCTAGCTAATATCCATAGCATTATGATATTCTAAATGATATGAATT
ATAAGAATTAGGTTTCCTGAAATGAATGACTAGAAAACTTTCAAGTAGAG
ATTAGTAAAATTAAAAAGTCCTAATCGGCCATTACTGATTTGATGTTTT
TAAGAGTCCTAAAAAATGGGTTACATCCATTTTTAAGTGGGTAGTATTAT
AACAGCCACCCATCTTCAATCACAGTGATTTCTGAATTGTGAGGGAAGTT
ATTAGCATGACAGGTGTCTGGTTCTGGCCCTGTACGATTCCCATGAGTCA
AGCAAATTGTAAGGGCTGGTCTATATCACACCCAACCCCAAGGATATGTC
CCTCAAAAGTCTAGCCCAGGCCCCGTCATCTTCAGCATCATCTGGGAAAC
CAGGTCTGATTAGTAGTCCTTTAAGGAATACCTCTTAGGCTCCCATTTTA
CTGCTATCACAGAATCAATAAAACCCTTACAGGAGATTCAATGGGAAAT
GCTCAACACCCACTGTAGTTGGTGGTGACAATGACCATAATTTGGCTGTG
CTGGATTCAGGACAGAAAATTTGGGTGAAAGAGCAGGTGAACAAAAGAGC
TTCGACTTGCCCTAGCAGAGAGCAAGCCATACCATACCACAAAGCCACAG
CAATTACAACGGTGCAGTACCAGCACAGTAAATGAACAAAGTAGAGCCCA
GAAACAGACCCAGAACTATATGAGGATTTAGTATACAATAAAGATGGTAT
TTCGAGTCAGTAGGGAAAAGATGAATTATTCAATAAATGATGTTTGGCCA
ACTAGTAACCCATTTGGGAAAAAATAAAAGTATGGTCCCTACCTCACAGC
```

-continued

ATACACAAAAATAAATTCCAGACGGATTAAAATCTAAATGTAAAAAATAA
AGCCATAAGTGGACTGGAAGAAAATAGAGAATTTTTTTTAACATCCGTAG
AAAGGGTAAAAACCCAGGCATGACATGAACCAAAACTGAAGAGGTTCTGT
AACAAATACCCCCTTTTATATATTGGGCTCCAACAATAAGAACCCATAGG
AAAATGGAGAATGAACACAAATAGACAATTTATAGAAGAGAAGGTTATAA
GGTGTAAAATTATATCTATCTGAGAAACAAACACTAAAACAATGTGATTC
TACTGTTCTCCCACCCATACTGGCAAAACTTAAGCCTGATAATATGCTGA
GGGGAAATAAGCACTCTTGTTGGTGAGAGTATTAATTGGCATAGCTTCTT
TTGAAAATGACATAGCAATACCTGTTAAAATTGCAAACATGCATGTCACT
TAATCCAGTAATCCCACTTCTGGGAATCAATGCTACAAAAACACTGACAA
GTATACAAAGATACATTCAAGAGTGTTCACTGGGCCGGGTGCGGTGGCTT
CATGCCTGTAATCCCAGGGAGGCAGAGGCAAGACGATCGCTTGACCCCAG
GAGTTCAAGGCCAGCCCGAGAAACACAGCAAGACCCTGTCTCTCTTTTTT
TTATTTAAAAAATAAATGTTCACTGTATCAGTTGTTCACAAAAACAAACC
AACATGTCCATTAACAGGGAACCATTTAAATTAATCAAGTTCATCTACAC
AATGTAATACCATGCAACTATTAAAAAGCACCTGATAATCCAAAGCACAC
TGAGACAGAATAATGCTATTAAAAACACCAAGTAGTGGAACACTGTGTTG
CCTATGACACCATTTTTATTCAACATTTAAACAAATTTGTAACAGCAATT
ACATGAGTAGTGACAATGGCGTTTATGAGACTTTTCACTTTTATGTGCTT
CTATTTTGTTATGCTTCTATATATACATCCATTTATTATGGAGTGTTAC
TTTCAAAAATCACAAATGGGCCAGTATTATTTGGTGTTGCAAGGTGAGCA
TATGACTTCTGATATCAACCTTTGCATATTACTTCTCAATTTAGGGAAAT
TACAGACATCCCTTATTCTAACTAACTTAAAACCCAGCATTTCAAACATA
CAGAATTGATGGGAAAAAAAGAAAGAAGAAAGAAAGAAAAGGCAACAA
GCTTCAGATGACAGTGACTCACATCAAATTATTTATAAAATCTGTTAAAT
AGTGCCATCTTCTGGAGATACCTGGTATTACAGTCCAACTCCAGTTGATG
TCTTTACAGAGACAAGAGGAATAAAGGAAAAAATATTCAAGAACTGAAAA
GTATGGAGTCATGGAAAAATTGCTGTGATCCAAAGGCTACGGTGATAGGA
CAAGAAACAAGAGAACTCCAAGCAGTAAGACACTGCTGTTCTATTAGCAT
CCAAACCTCCATACTCCTGTTTGCCCCAAGGCTTTTTTAAAAAATAGAGA
CAGGATCTCACTATTTTGCTCAGGCTGGTCTTGAACTCCTGGACTCAAGC
TATCCTCCTGCCTCGGCCTCCTAAAGTGCCGAGATTACAGGCTTGAGTCA
CCATACCTGGCTATTTATTTTTTCTTAACTCTCTTGCCTGGCCTATAGCC
ACCATGGAAGCTAATAAAGAATATTAATTTAAGAGTAATGGTATAGTTCA
CTACATTGGAATACAGGTATAAGTGCCTACATTGTACATGAATGGCATAC
ATGGATCAATTACCCCACCTGGGTGGCCAAAGGAACTGCGCGAACCTCCC
TCCTTGGCTGTCTGGAACAAGCTTCCCACTAGATCCCTTTACTGAGTGCC
TCCCTCATCTTTAATTATGGTTAAGTCTAGGATAACAGGACTGGCAAAGG
TGAGGGGAAAGCTTCCTCCAGAGTTGCTCTACCCTCTCCTCTACCGTCCT
ATCTCCTCACTCCTCTCAGCCAAGGAGTCCAATCTGTCCTGAACTCAGAG

CGTCACTGTCAACTACATAAAATTGCCAGAGAAGCTCTTTGGGACTACAA
ACACATACCCTTAATGTCTTTATTTCTATTTTGTCTACCTCTTCAGTCTA
GGTGAAAAAATAGGAAGGATAATAGGGAAGAACTTTGTTTATGCCTACTT
ATCCGCCCCTAGGAATTTTGAAAACCTCTAGGTAGCAATAAGAACTGCAG
CATGGTATAGAAAAGAGGAGGAAAGCTGTATAGAAATGCATAATAAATG
GGCAGGAAAAGAACTGCTTGGAACAAACAGGGAGGTTGAACTATAAGGAG
AGAAAGCAGAGAGGCTAATCAACAAGGCTGGGTTCCCAAGAGGGCATGAT
GAGACTATTACTAAGGTAGGAATTACTAAGGGCTCCATGTCCCCTTAGTG
GCTTAGTACTATGTAGCTTGCTTTCTGCAGTGAACTTCAGACCCTTCTTT
TAGGATCCTAGAATGGACTTTTTTTTTTTATCGGAAAACAGTCATTCTCT
CAACATTCAAGCAGGCCCCAAGTCTACCACACTCAATCACATTTTCTCTT
CATATCATAATCTCTCAACCATTCTCTGTCCTTTTAACTGTTTTTCTATA
CCCTGATCAAATGCCAACAAAAGTGAGAATGTTAGAATCATGTATTTTTA
GAGGTAGACTGTATCTCAGATAAAAAAAAAGGGCAGATATTCCATTTTCC
AAAATATGTATGCAGAAAAAATAAGTATGAAAGGACATATGCTCAGGTAA
CAAGTTAATTTGTTTACTTGTATTTTATGAATTCCCTAAAACCTACGTCA
CCCGCCCCGTTCCCACGCCCCGCGCCACGTCACAAACTCCACCCCCTCAT
TATCATATTGGCTTCAATCCAAAATAAGGTATATTATTGATGATGTTAAT
TAACATGCATGGATCCATATGCGGTGTGAAATACCGCACAGATGCGTAAG
GAGAAAATACCGCATCAGGCGCTCTTCCGCTTCCTCGCTCACTGACTCGC
TGCGCTCGGTCGTTCGGCTGCGGCGAGCGGTATCAGCTCACTCAAAGGCG
GTAATACGGTTATCCACAGAATCAGGGGATAACGCAGGAAAGAACATGTG
AGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGC
TCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTA
CCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCT
GGGCTGTGTGCACGAACCCCCCGTTCAGCCCGACCGCTGCGCCTTATCCG
GTAACTATCGTCTTGAGTCCAACCCGGTAAGACACGACTTATCGCCACTG
GCAGCAGCCACTGGTAACAGGATTAGCAGAGCGAGGTATGTAGGCGGTGC
TACAGAGTTCTTGAAGTGGTGGCCTAACTACGGCTACACTAGAAGGACAG
TATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATC
CTTTGATCTTTTCTACGGGGTCTGACGCTCAGTGGAACGAAAACTCACGT
TAAGGGATTTTGGTCATGAGATTATCAAAAGGATCTTCACCTAGATCCTT
TTTAAATTAAAAATGAAGTTTTAAATCAATCTAAAGTATATATGAGTAAA
CTTGGTCTGACAGTTACCAATGCTTAATCAGTGAGGCACCTATCTCAGCG
ATCTGTCTATTTCGTTCATCCATAGTTGCCTGACTCCCCGTCGTGTAGAT

-continued

AACTACGATACGGGAGGGCTTACCATCTGGCCCCAGTGCTGCAATGATAC
CGCGAGACCCACGCTCACCGGCTCCAGATTTATCAGCAATAAACCAGCCA
GCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTA
ATAGTTTGCGCAACGTTGTTGCCATTGCTGCAGCCATGAGATTATCAAAA
AGGATCTTCACCTAGATCCTTTTCACGTAGAAAGCCAGTCCGCAGAAACG
GTGCTGACCCCGGATGAATGTCAGCTACTGGGCTATCTGGACAAGGGAAA
ACGCAAGCGCAAAGAGAAAGCAGGTAGCTTGCAGTGGGCTTACATGGCGA
TAGCTAGACTGGGCGGTTTTATGGACAGCAAGCGAACCGGAATTGCCAGC
TGGGGCGCCCTCTGGTAAGGTTGGGAAGCCCTGCAAAGTAAACTGGATGG
CTTTCTTGCCGCCAAGGATCTGATGGCGCAGGGGATCAAGCTCTGATCAA
GAGACAGGATGAGGATCGTTTCGCATGATTGAACAAGATGGATTGCACGC
AGGTTCTCCGGCCGCTTGGGTGGAGAGGCTATTCGGCTATGACTGGGCAC
AACAGACAATCGGCTGCTCTGATGCCGCCGTGTTCCGGCTGTCAGCGCAG
GGGCGCCCGGTTCTTTTTGTCAAGACCGACCTGTCCGGTGCCCTGAATGA
ACTGCAAGACGAGGCAGCGCGGCTATCGTGGCTGGCCACGACGGGCGTTC
CTTGCGCAGCTGTGCTCGACGTTGTCACTGAAGCGGGAAGGGACTGGCTG
CTATTGGGCGAAGTGCCGGGGCAGGATCTCCTGTCATCTCACCTTGCTCC
TGCCGAGAAAGTATCCATCATGGCTGATGCAATGCGGCGGCTGCATACGC
TTGATCCGGCTACCTGCCCATTCGACCACCAAGCGAAACATCGCATCGAG
CGAGCACGTACTCGGATGGAAGCCGGTCTTGTCGATCAGGATGATCTGGA
CGAAGAGCATCAGGGGCTCGCGCCAGCCGAACTGTTCGCCAGGCTCAAGG
CGAGCATGCCCGACGGCGAGGATCTCGTCGTGACCCATGGCGATGCCTGC
TTGCCGAATATCATGGTGGAAAATGGCCGCTTTTCTGGATTCATCGACTG
TGGCCGGCTGGGTGTGGCGGACCGCTATCAGGACATAGCGTTGGCTACCC
GTGATATTGCTGAAGAGCTTGGCGGCGAATGGGCTGACCGCTTCCTCGTG
CTTTACGGTATCGCCGCTCCCGATTCGCAGCGCATCGCCTTCTATCGCCT
TCTTGACGAGTTCTTCTGAATTTTGTTAAAATTTTTGTTAAATCAGCTCA
TTTTTTAACCAATAGGCCGAAATCGGCAAAATCCCTTATAAATCAAAAGA
ATAGACCGAGATAGGGTTGAGTGTTGTTCCAGTTTGGAACAAGAGTCCAC
TATTAAAGAACGTGGACTCCAACGTCAAAGGGCGAAAAACCGTCTATCAG
GGCGATGGCCCACTACGTGAACCATCACCCTAATCAAGTTTTTTGGGGTC
GAGGTGCCGTAAAGCACTAAATCGGAACCCTAAAGGGAGCCCCCGATTTA
GAGCTTGACGGGAPAGCCGGCGAACGTGGCGAGAAAGGAAGGGAAGAAA
GCGAAAGGAGCGGGCGCTAGGGCGCTGGCAAGTGTAGCGGTCACGCTGCG
CGTAACCACCACACCCGCCGCGCTTAATGCGCCGCTACAGGGCGCGTCCA
TTCGCCATTCAGGATCGAATTAATTCTTAATTAA

SEQ ID NO:8 (BstII linker)
5'-gtaacactgg cccaggaggc ctttctggtg acccc-3'

SEQ ID NO:9 (SfiI linker)
3'-tgacc gggtcctccg aaagaccac tggggatt-5'

SEQ ID NO:10 (Forward PCR primer)
5' TAGTTTCCTTCTGCCTGGAATAC 3'

SEQ ID NO:11 (Reverse PCR primer)
5' CAAGTCACAAGGATGGACTACA 3'

SEQ ID NO:12 (Stuffer1)
TAGTTCCTTCTGCCTGGAATACTTCCTCATCTCACTTGCTTTCCTGCCTG
GCAGCTTCCTACTTGCCCTCTGGAACCAGCTCTAGGGTCACCACATCTCT
GCTTCTGAGTGCCTCCTCAGACACAGTCTGTATTTCCTCTTCCAAGCTCT
CATCACAAACATTGTGCTGTATTATATGTTTCTGTGTGGTCTTCCTTCTA
TGAGGAAGCCTTGGAAAGCAGGAGACTTATTTTAGTCTTCTTTATGTTTC
TTTTATTCCCAACACATTATGTCTGCCCCATAGACCTTTTCAATAAATGA
TTATTGAGTTAGTGACTCCTTTTACATGCTGACAAATGTGGCTCTTATTA
CTCCCCATTTCAGTATCACATATTTGTAAAAGTGAATCCTTCTTAATCGT
TTTACTTTTCTCCTAGTAAATTCCTCATCTATGCCTGTCTGCTGCTGTTC
TCTGTGCTGCTGGCCCTTCGTTTGGATGGCATCATACAGTGGAGTTACTG
GGCTGTCTTTGCTCCAATATGGCTGTGGAAGTTAATGGTCATTGTTGGAG
CCTCAGTTGGAACTGGAGTCTGGGCACGAAATCCTCAATATCGGTAATAC
TGCTTTATACAACCCATTGGTCTCTAGCATGAGGGAGCAATATCTTGACT
TTTCTCACTTTTGATGAAGTAAGGACCATTTTATTTTCTACCTATCTGGG
GTCTTAGAACTATAGTATAAGCTAACAGATCTCTTCTGTGTTTTTGAAAA
TTTAGTCTTTGGTATGTATTTCTTACAAAAGCAGTGCCATTTGGGGGTA
AGTTGCCAGCCAGCTCACAGATGCCTATATAATCCAAAATGCACCCAAAA
TACAGAACTGGTATGCCATACTAGACTAAGCAGCATGAAACCACCCTGTT
TTTAGGAAAAGACACTCATATTATGTTTGGTCATGAAAGATCTTTCTCCA
ATACAGTTTTGGAACTGGGGCTCCCCTTGTCCCACCCTCCTAGTCCCAGA
GCTTAGGACTATTAGCAGTGTAGGGGAGGTGGCTTGACCAGGAGACCAT
GAGTCCCTGAGACAGCAGCTGGGGAATGAGGAAAGTCAAAGATTGGATGC
CGAGAAGGAAAGCAGAGCCTTTGGGGGCAGGGGAGAGGGGTACCCTTTAC
CGTTTCCAACTCTTGCCCTCCCTGCTCTTGGATGCCTCCGCTGGCCCAAA
TTCCTGGGAGTTGCTCACGCCAGCATGCAACCTGCTTGTTGCTGGGACCT
GCGAGAGTCTTTCCCTTCTCTGCCACAGAGACTGTAACTACATAAAGGGA
AAAAGGGGGACTTAAGACTGGGAGGCTATTATGAACCTCCACTGGGAAAA
TGAGGAGTACAGGAATTCCCAGAAGGCAGCTGCTCATGTGGGAAAAGTGT
AAAGTTGAAACTACCGCACCTTTTTTTTTTTTTTTTTTTTTTTTTTTTTT
TTGAGACAGAGTTTCGCTCTTGTTGCCCAGGCTGGAGTGCAATGGTGTGA
TCTCGGCCCACTGCAGCCTCCACATCCCGGGTTCAAGTGATTCTCCTGCC
TCGGCCTCCTGAGTAGCTGGGATTACAGGCACCTGCCACCATGCCCAGCT
AATTTTTTGTATTTTTAGTAGAGATAGGGTTTCACCATGCCAGGCTAGTT
TTGAACTCCTGACATCAGGTGATCCACCCGCCTTGGCCTCCTGAAGTGCT
GGGATTACAGGTGTGAGCCACCACGTCCGGCCACTACATCAACTTTTTAA
ATTTTTGTTTACTAAATATGAAAATGATTCAGATTGTGTAAATTACATAT

```
CACATACATGTCTAAGAACTGTAAAACAGTTACACAGAGAGCCTTGGCAG
GTGAGGGACATTCATGTATAGCTGTTTCAGAGTTCTTAGATTTTTTTGA
AAGATTGATGACCTGTGTGGCTGTATGTGTTTTATTTTTTTATGAGATAT
TTTCAGATATCTAATATTAATTGCTTCTCAAAGAATGCAAAGTTAAATAA
ACATTTAGGTTCTACTAATTGATATTTAGAATATATTCAAACTTCTCTTT
GTTGGTCTTATTTAAGATGTTTTGAGCAAGGAAAGGAATTGTGTATGTGG
GGTTGAATGTAAGGAATGTACAGGCGTGGTCATTCTCATGTTAACATTAA
CCAGTGGAACATGGTTGGGTCCTACAGGAATAACCTCTGATAGCATTTTC
TCTATGATCTAACTTCCGGTGTATTTGTCACCCACAATACATGTATATCA
TAAATGTTCATCTGTATTTTGAATAAACATTGTAGGCCTTTCAGATGCAT
TATAGAGCCTTTTCCTGATTAGCGGCCTTACCATTGCTCAATTGTAGATC
TGTTAAGGTTATTGTGCATGATACTTAGCTAATTAAACTGATTTTGTTTG
AGAACAGTTTTAACTCTTGTTCTTCTTTCTCTTTCATGTGCAGGTGTTAA
TTTATCTTAATGGAATAGAAAGGAAAATGAAAATCATTTATACGTTTTAT
TTGCATTTAAAAATAGCACCTAACAATAGTTACTACTATCTTGAAATATA
ACTGGCACTTGTTCATAGAACTAGAGTTATTTTTATAATATTGTGTGAAG
GGTGGTTTACATGGTTTCTTGAAAAATGAGGATCATGAGACTTAAGGGGT
ATTTGCCTGGTTTTAGCAGCAGAAGCAAATCAGCTTGAATAATCTTGGAA
GTAACTCTTGTTGTTGAATTTAAAGATGTGAACAGAAGTGTTTATGTACA
TTGTCAGGGAAATAAGAACTGGCTATTACTTTTGAGAATATCCTTATACG
GTTAAAACATTAAATTCTGGTTTGTTGTAATGTTCATTTTGTATTATGT
AGTAGTTCTTCGATGTTTCAGAGATTGCCTACCAAAGCTTAGGTTTAAGT
TAGCTTTCTACCTGATTTCCCTTTGCTTTTGTCAAATTTTCAAGTAAAAT
TCAAAGTATAAATATAAGTTGGTATTTGCCCTGAACTGCTTGCTTATAGT
GGAGATTCTGAACTGAGGGTGTTTTCTTCTTCTCTCCCTTTTTTAGAGCA
GAAGGAGAAACGTGTGTGGAGTTTAAAGCCATGTTGATTGCAGTGGGCAT
CCACTTGCTCTTGTTGATGTTTGAAGTTCTGGTCTGTGACAGAATCGAGA
GAGGAAGCCATTTCTGGCTCCTGGTCTTCATGCCGCTGTTCTTTGTTTCC
CCGGTGTCTGTTGCAGCTTGCGTTTGGGGCTTTCGACATGACAGGTCACT
AGAGGTGAGATTTCATATATTTAAGAATGTTTTCCACTTTGGGAGGTCAA
GGCAGGTGGATCACTTGAGGTCAGGAGTTTGAGACCAGCCTGGCCAACAT
GGTGAAACCCCATCTCTACTAATAATACAAAAATTAGCCGGGTGTGGTGG
CATGCGCCAGTAATCCCAGCTTCTCCGGAGGCTGAGGCGGGAGAATCTCT
TGAACCCAGGAGGCGGAGGTTGCAGTGAGCCAAGATTGAACCATTGCACT
CCAGCCTGGGTGACAGAATGAAACTCCGTCTTAAAAAAAAAAAAAAGAA
TGTTTTCAAAAGTAAAATATTTTGCTCAGTTATTCAGATGTCAATTTCTT
ACCCTTTGTTAGGAAGAGCTTGATCATTACCAACTCTACATCATGAGACA
ACAAGGCAACAAAAGATGATGGAAATAACAATTTTTCTTTCTTCACTTAG
AACACTAGCTTTTCACCCAGGACATCAGCCTTCTCCCAGCTTCACATCCT
GTATCAATCAGACAGAAACAGAACTGATAGGTTAGATACAGATATATGTA
TAAAGAGAGTTAAGGAACTGGCTCACATTACTGTGGGGCTGGCAAGTCTG
AAATCTCCAGGGCAGGTGAACAGGCTGGAGACCTAGGAGGAGTTGACACT
GCAGTCCTGGCACAGAATTTTTTCCTCTCCAGGAAACCACAGTTTTTGCT
TTTAAGGCCTTCACCTGATTGCATGAGGCCCACCCATGCTATGGAGGGTA
GTCTCCTTTATTCAAAGTCAGTACCTTCACTGCAACAGCAAGCTTAGTGT
TTGATTAAATAACTGGGTACTATAGCCCAGCCAAGTTGACACTCAAAACT
GACCATCTCCCCACCTCAGACCCCATGATTTAGCACCTCCCCTGCTGTCT
GGTTAGCTTATCCTGATGTGCCCCTGTGTTTGTTTATTCATTCAATAAAC
ATTTATCAAGTATTTACTAGATGCCAAGCCCTTTTTCCCTAAGCATAGAG
GATATGCAGATGAATAAAATACCAGGACTAGTAATAATAGTAATGAAAGT
AATTGCAGATAACGTTTATTGAGCACTTACTGTGTGCCAGGCATTGTGCG
AGGCACATTACATGTGGTAGTTTTCTTACTAACTAACTCTGTGAGGTAGG
TCCAGAGAAGATAAGTCATTTGTTCATGGCCACATGTGAAGGGGCAGGAC
CAGGATTCCGTTTGAGTCAGCCCGACTCTAAAGCCCGGGCACATAACTAC
ATAACTGCATAGAAGCTGAGGGCCCAAAGCTGAATACTGATGGGTTGAGG
GGAGAACTAGAGGCTGTAGATGCCTGGTTTTGAGCCGTGTGGATGAAGAG
TGAAGGGAGAAGACTGCAGTTGGCTTAGGAAGTAAACATAGCAGCTGTAG
GGTGGGTCAGGCATATAAGCCTAGACCCCAGGTATGGGCGTGAGGGAAG
GTATGTAGACAGAGGGACGGTGATGGAGCAAGGCCCTGTGGGACTCAGGG
AGAATGGGACCTAGAGCACCAGGAAGGGTTTGGCCTTGAACAAGGGGAGC
TATTCCCTGATTTTCATGCTGGTGGAAAGGCCACAGCATGGGTATAGTGG
TAGGTAGGAGTGAGCCGTGGAGGGAGAGTATCTGATGGTCCACTTTCACC
CTCCCTACAATTCCCAGTTTATATCAGGGACTTGAGCATCCATGGATTTT
GGTATCCACAGGGGGTCCTGGAACCAATCCCCCACAGATACTGAGGGACA
ACTATACAAGGACTAGGACTGCATTGGGCCTGAATTACAGAAAGTAAGTC
TTTCATATATTCACACTCTAGGCATTCCTGCCCTTGGAAGAAACAACATA
CCAGGAGCTGAGCTCCCTCCTCCTGTGATGCAAGAACAGTACCTATGTTG
GTGAGGGGTGGTCTGGAGTAGGCTCATACAGAGATGGGAAGGAGGAGTT
GAGGGTCTGCCAGGAAGCCCTGTGTTGGGAGGGAAGGGATGGCATTTTTG
GGACACATTGAAGCCTAGAGGCAGGAAACACTCCATCAGCTGAGTGGACT
GTGGCGATTCAGATCCGACGGGAGCACAAGGTGGAAAGGAAGGAACTGTG
GGAGTTGAGAAGAGGGAGCCTCTACAGAGGGATTGGGGCAAATAGGGG
CCACGTCCTCAGCCCACAGAGCATGTGCTGAAGTGCCCCAGGCACCCCAG
TGCACTCACAGGGCACCAGGGGATAGTGGACATTTTGAGGAAAACAGTAA
TACCTGACATTTGTTGGGACACCATACAAACTACTAGCTTGAAATAGTTT
ACAGGTTTATTTTTAGGCCACACTGCATTCCTTTCAGTGACGTCGTATCT
TTAAGAAGCTGGGTTTTCAGCAGTTGCTGTGAAAACAAAAAAGGCTAATG
CTGTGTGAAAATCCGGGTGAAGAACAGGTAACGAGTGGGAGCACCTTGTC
TGATTCCAAGGCGTGGGAAATGGTGAGCTACCTGACAGGCACACGCATCC
CACTGGGAATTAGTTTTGGTTATTTAAGAATAATATTAACATTTTTCTTT
```

-continued

```
AGATTTATATGAATTATTTTTTCTAGTGGCTACTTAGAAATACTTACTAA
GTTAGATGTAATTACTTAAATCAGTGCAACTGTTGGCATTCCCAGCCACA
TTAGGGATTTCTTTTGGCCTAGAGGTCTATGGAGGAATTACTAAATTCCC
CATGTACCTATGTACTGAGAACTTTTGGGAAGCTCTGGGCCTGGTCCCAG
ATTTCAATTTTGTGGGCAAGAATGTACTTTACCAGAGTGAGGAGCAGCCT
GCAGGGCGTTTGGGCTGGAGGCGGGAGGTTAGTAAGGGGTTGCTGAAGTG
GTAGGCGGATGGTGCCGAAGAAGGCCTCACTAGGCAGTCATCATCAGGAT
AGGAAGTGGGCACGGGATTCAGGAGAAATCTGGACTTTACAGTGGACAGG
ATGTGGTGACTGAACGTGACAGTGTGGGAAAAAGAATGCAGGGTGATTCC
CGGGCTCATGGCTTGAGAAATGAGACCACTGTTGTGCCTCCAAGTGACAT
GGGAGGCTATAGAAAGTGACATGGGAGGCTATAGAAAGTGACATGGGAGG
CCATAGAAAGTGACATGGGAGGCCATAGAAAGTGACATGGGAGGCCATAG
AAAGTGACAAGGGAGGCCATAGAAAGTGACATGGGAGGCCATAGTGACAT
GGGAGGCCATAGAAAGTGACATGGGAGGCTATAGAAAGTGACATGGGAGG
CCATAGAAAGTGACATGGGAGGCCATAGAAAGTGACATGGGAGGCCATAG
TGACATGGGAGGCCATAGAAAGTGACATGGGAGGCTATAGAAAGAGGAGA
TACAAGGTTCTAAGTGCAGGCGATAATGATCTCTATTTGGGACTGGCTTC
ATTTGAGGTGCCTTTAGGAGAGCCGAGTGGCCTATGCACAGCTGGGTCTG
CTATGCAGCAGGAAGGCTAAGTTGGAGACAGATGTGAGAACTAACCATGA
AGGAGGTAATAATGCAGACCAAGGGTCTGGTTGAAATTTCTTCTCCCCCA
GTCCAGGGTGCAGCGGGTGAGTGAAAATATGTGTGTTTGTGTGTCTGTCT
TCCTAGTCGGGAGAGAAGACTGAGTTTGTGGCTCTGCGGAGCATCACCAT
TTAAGGAGGGGGAAAAGGAGACAGAAGGAATTACCAGAACACTCCAGAGG
GCTCCAAGACTGTATGGTGGGATCTAGATGGCCAGGAGGAGGGGAGCAAA
AAGGAAAGAGTCATCCACAGTATCAGTAGGATGCCAGTTGAAGTGTTTTT
GCTGCCTCCCGGTTATCGGTGACTTTGATGAAAGCTGTCTTCTGGTGGTC
ATGGGGGTGGAGGCCAGATCACAAGGAAGCTGGGAATGGTAGATGAGATA
GTAGGGCTTGCATATTCATTACTGTCTCGCAGAGAGAAACCTGAGGCTA
AGAGGGGTCTTGGATCAAAGGATGGGGTGGGTTTATCTGGTTTCGGGGCT
TTTGTTTTTAATGAGAAGGAGTCATTTCTGTGCTGCTAGGAGGGATCAAT
GGAATAGGTGGGGTTAAAGATACAGTACGGAATCTACAGTTGATGGCTTG
ATGTGACAAGGTCCTCAAGGAGCCTGAAAGGAAGGGGTGGGGTCCAAGGG
CAAAACCGAGGTATGAGAAGAAGGATGCACAAGGATGGTTTCGAGTAGAC
AGTATTGTTGGTAGGGACATGAAGGAAGTTTAGTGGTCTATTGCAGCTAG
CCTGTGTTCCCAGTGAACCTGGAAACAAGGTTCTCATCTGTGCTCAGGCC
TCAGGCCAGAAAGGGCAAGGCAGCAGAGGGGCAAGGCAGCAGGCTGAGCC
CCATTTCCCCTTGCCATAATACTGCTGTGCCCCTCTGGTACCGAAAATCA
GGAGTTTCCAGTGCAATATAATATTATACAAGTTACACTGTATTATAATG
TGTATTGTCTTTTAGTGTGTTAACCAAATTACTGCAGTATTAAATGCAAA
TTATACTTTGTTTAACTGATTCTTCTCTTCATTTTTAGTTAGAAATCCTG
```

```
TGTTCTGTCAACATTCTCCAGTTTATATTCATTGCCTTAAGACTGGACAA
GATCATCCACTGGCCCTGGCTTGTATGTAACTTTTAAAATCCTTAAATAA
ACTTCTTTTTTATTATAAAAGTAATTCATATTCACTGTACAAAGCTTGGA
AAAGACGGACAAGCAGAAGTAATAGCCTAATAGTCACCCATAATCCCACC
ATGGGGAGATAACATGGTTAGTGTTTTTATGTCTGTGTTTTATACAAACA
GTTTGGATATAACTGTGTGCACCATTTTGTATCCTGATTTTTTGTTTTA
ATGTTGTATCATAAACATTTTATCATGTTAATAAAAGGTCTTTATAAACA
TGACTTCTAAAGTTTAATTGATACAAAATATTCTTCAAGTGCATGTATCA
GACCATCCTCTTATTTCTAAAATATGGTATTTCCATTGTTGCCAGTGTTG
AATGATTTTAAATCATACTGCAGTATATATGTTTATGCATTAAAATTTTT
GCCTTTTGTTTTTTGGTTGTTTTCTTAGGAAATAGTCCAGAAATAGTGTT
ACTGAGCTAGAGGTTGGGAACTATTTGAGATTCCTATATACGTATACTGC
ACTGCCAACTTGCTTTTCCAAAAGCCATACCTGGCCAGGCGCAGTGGCTT
ACACTTACAGTCCCAGCACTTTGGGAGGCCGAGGTGAGCTGATCACTTGA
GCTCAGGAGTTCGAGACCAACCTGTGCAATGTAGCAAGACCCTGTCTCAA
AAGAAAAAAAAAAAAGCCATACCCATTTACACTCTTGCTGGTGGTGGCA
TCTATGTCATGCTTCTAAACTGTGACTTCAGTTACTGGGCATTTGGTTGA
AATTAACTGTGAATAAATGGGTAGATGGATGCAGAGATAGAAAGATAAGT
GGCAAGGTAGAAATTAGAGAACACAGTATAGATTCCACTATTAAATGCAT
GGAAAAAAGATGGAGACTAAAGGCAGAAGAGTTCCATTGCCACTGGGAGG
TAAGGTCATGCTAGTGTTTTTGTTCGGTTTTATTTTCTCTGTTGTTTGAT
GTATAATTTTGCATACAATATATTTTATGTATTAAATATAGCTACCCTTA
AAAAGTGAAAAGTATAGTAAAGAATTGGGAGCAGAGAAGAAATGAAGGGA
ACCTAAGTATACTCCATATTTAAAGATGGGAATAATCACTTCTGCCCAAA
GTCTTTGATAAAACATTCATAATAAAAAATATTCAGTCACTCATCCTACA
ACTTCACAGTGCTGTATCTGGAGAATGGTCATTGGGTTCAAAACTGTTTC
TGTTGTGACGTGAAGGAAACATATCTAAACAAGACCAAATTTTTTCGTAT
AAGATACTGTCAGGGAAAAAAAAGATTAGTAATTTTGAGAGCTTTCCACA
AATGAGAAGAAAGATTTTTTCTGCCCTTCATCCTCTGTAGATCCCAGTTG
ATGAAGCAGTCTGAGTACATGTTTCCCATAGTGAGCAAGAGAAAACAAGG
AAGCCTATTGAGATCTAACATTCCACCCATGAAGGGAACTTCAGTAAAAA
GGAGAATCTCATCACAGAATGGGGAACGGGAAGAAAGGCTGTGCATAGA
CTCTGCAGAGAAACCTACAATCAAGAACTGGTCAGGAGAAGTAAAATTCG
TATGCCAACTCAAATCATAGATCTAAAAGAAAATGTAAAACTATAGATCT
GTTAGGAAATAACATAGGACAGAATCTTTGGGGTTTGCAATTAGGCAGAG
AGTACTTAGAAATGGCACTGTTAATATGGTCCATACGAGAGAGAAATCAT
AAATTTGGACTTCCTCAAAATTAAAATGAAATGAAGACAGGCCACAGACT
GGGAGAAAATATTTGCAAAGCACACATCAAAACACTGACTTGCACCCAGA
ACATACAGAGAACTCTTAAAAACTCAAAACTGCAAAAAGAAACACCTAAA
AATTGGCAAAGAGTTGACAATTTGCGAAGGGGATATACACATGGCGAAA
```

-continued

```
AAGCACAGGAAAAGATGCTCAACGCCATTACAGGTTAGGGAAGACAAACT
ACAACCAGGATGAGGGCCCGAAACACATGGCTTCAGAATGGTGAAACTCA
GCAACACTGACGAGGCCACGTGCCTGGGAGGATGCAGAGGAACTGGGACA
CTCCAGTGTTACTGGCGGGAAGGCAGGTGGTACGGGCACTGTAGAAAATG
GTTTGGCCATCTCTGATGCAGTTAAAAGCGCACTTCCCGTGGGACTTGGC
TGCCCCACTCCTGGGTATAAGATTTACCCCCAGAGAAGTGAAAGCGCGCA
GCCTTGTAGAAACCCACACACCAGTGTTTGTAGCAGTCTTGTTTGCATTT
TGGATAGCGGCCTTGTTTGGTTTTCACAAACCACCCTCAGCGGACAGTCA
GATAAACTGTAGGCATCCATACAATGGAATACCACTCAGATCTGAGAGGG
AACGACCTGTGGATACAGGGAGGGAACAACTTGGATGAATCTCATTAGAG
ACATTATGTGGATGGCGGGAAGCCAGTCTCAACAGGTTACTTGTCTCGCG
ATGCCATCTACATAAAGTTCCAGCAGAGACAAAAGTACAGTGAGAGAACA
GATCAGTGTTTGCCGGGGCTAATGGTGGGGACGGTGTGATAGTGAAGGGA
CAGCACGGAGAGTTTTGCAGGGTGACAGACCTCTTCTGCATCCTGCCAAC
GGCTGTGTGAATCTACTTGTGTGAAGACTCAGGGAACTCACACCAAAGGA
AGACGGTCACTTTTCCTACTGTATGATAGATAATTAATAAAAAGGGAGAA
CGGAGGAGTGTCGTCCCAGGAGGCAGGGCAGGAGGGCGAAGACGTGTCAC
AGGGGAGCCTGGCCAAGTGGCGCCCCCGGAACTCGTCCTCTGGGCTTGTG
TGTGGATGAGACAAGGTCTACCTGGTACGACAGGGACATACTGGGAATGC
GCCCTTGCCGTGGAGGCGGGGACCCGGCAGCGCTACGTATCCAGCATCAA
CCTGTATCCAGCATCAACCCGCCAAGTTCACTAACTTGGTAGGGGTGAGG
TTAGGGATCCTTAGGAGCCCAGGCAGCCAGACTTTCTGGGGAGCCCATTC
CCATTTGTGTTGCCAAAGTACCCCCAGCAGGTTGTGGGAATGTTGCCTGT
GAAGAGAGTCTGTTGGGGTGAGATCTTGTGTGTGTGCACAGGGTGACAGT
TGTGTCCCATTTCCCGGGAAGCTGTGATGGCAGCAGAACCTAGAGGAGCC
TGAGAGAGTGTGGGAGAGTGGGCCTCTGGAAGAGTAGAGGCTGCGGAGCC
AGGTGCAGGGCTGTCTGTCACCCAAAGGAAGAGGGACTGATGACTCACTG
AGCGTGTGTGTCCCCTGGTGGCAGCAGGCCCCATAGTGAACATACCATAC
CTTTTCTGTCCTGAGCGATGCTCCCAGCAGTCCTGGGAGATGGAACGGTC
CTTATTCGGCTCACAGGAAGGACCGCCTTAACTGGACAGACACAGCAAGG
TGCTAAAGATGCCTTCCATCAGAGGCCAGGTTGGAAGCTCTAAAGAGACT
TCTCTTGCTGTTCTCTCACCCACCCCCAGGTTGTGTGTGTCCCGCTGTGG
ATTCTCATGTCCTTTCTGTGCCTGGTGGTCCTCTACTACATTGTGTGGTC
CGTCTTGTTCTTGCGCTCTATGGATGTGATTGCGGACAGCGCAGGACACA
CATAACCATGGCCCTGAGCTGGATGACCATCGTCGTGCCCCTTCTTACAT
TTGAGGTAAGCGTTCCACGGGAAGCCTCTTCAGCCCCTGAAGCTTGCGCT
TCCCCTGACAGGATTCTGCACCCCTAGAAAGGCAGCCTCTGTCCCTCGAG
CTCACAGTGAGCCCACTCCAGGAGAGGGGAGAGAACACAGCCATCTCCGA
GAGGGAGCTTCGGTGAAAGGAGAGCATCCTTCCTTTCTCTTGGGGGCAGC
ACGTGGGGCTGGCAGGGAGAAGAGTGCACCTTTTTAGCCATGGTGCCTCT
```

-continued

```
GTATGGCTCCAGTTTCCACTCTGGGGAAAGCAGAGTGGGATGTCAGATTT
GTGTATTGGAGTCACGTGGAGAATTCTAGAATGGGAGCTGTTGACTCCTT
AGAACAAACACCCGGAGGAGTTTGCCATAAAACTGCTGGCACTGGGAACT
TTTCAAGTGGATAGGCTATTGCCGAGCTCTGAAGAGGGACATAAAAGCTC
ATTTCGAGCTTTCCCCAGGGATAGGTGGTTTCCTGCCTTTTTCTGGCGGT
GCTGATGTTCCCTCTTGTGGGAGCTCACGCGGGGGTGGGGTGGTGGGGAG
GAACTGCCTAATGAAGTCTGGCTTCCGCCTCTGCCCATTTTCGGTGCTGG
CATCAACCGGGACTATGTCTCTTTCTTTAGATTCTGCTGGTTCACAAACT
GGATGCCACAACGCCTTCTCCTGCATCCCGATCTTTGTCCCCCTTTGGC
TCTCGTTGATCACGCTGATGGCAACCACATTTGGACAGAAGGGAGGAAAC
CACTGTATGTACTCAGCATTTCAGAAGTCCTTGGTGTGTGTCTGGGGGGG
GACCAGGGGTGGGGGTGGCGGATAGAAGTCTAGGAAGGGATGAGTCCC
CGAGGGCCCCAATTTAGAAGCTTGTGTGGGAAAGTGAGGGCTGAGGAAAT
TCTGGGACCTTCTAAGGGAAGGGCATGCCGTAACTCTGGTGTTCTGCTGG
CCTGCACCGGGACTTTTCTCGCAGTGCACGCTGCCATTTGAGGTAGAACC
AGACACGGCAGGCAACCTCTCAGAGATCCCGTTCCCTCCTCTGCAAATG
GGGATCAAGACAGATTCTTCCCAGGCCCGGGAGGGTTTGATGGAAAATCC
ACATCTCCCACCCAAACCTGGGATTCATCCTAGGTCCCTGTTGGCCGCTC
TGCCTCCCCCATATCCTTGCTGCCATCACCCGAGTCTTGCCTGTCTTGCC
TTGCTAACACTCTATTCCCCTCCACCTGCTTGCTGAGGCAGACACTTCCA
AAACGATCTCTGCAGAGGGTGCCTTCCTGGCAAGGCTGTGGGCTCCATGG
CACGGAAGCCCAGAGCATTGCCCTTCGGAAAGCCAGTGGGTTTGGGGGCA
GGGCCTCACTGCAGCCCAGCAGCCCGGGCTGTGCTTGCTGTTTGTGCCTC
TGCCCCCTACCCCGCACCCGGGAGCAGGGAGGGCTTGCACCGAGCTGACA
CTCCAGTAGCCTACAGAGAGGAGTAGTGGGACTGGGAAAGTGGCTTTAAG
GTGGCTCCATGAGTTCAGGCCCCCTCCTGGCCAACCCGTGCATGACTACC
GCCCTCACGGATTCCAGAGGGTGACAGAAATCTTGTTCTTGGGTGGCACT
GTCATCCATGAGTTTATCCTGGCTGGAGAAGATTAGCGGAAGACACCGTA
GTCTGCGCACCACAGATATTTTGAGACTCACTGGAGCAGTAGTTCTCAAA
TTTGGGCATCCAGCAGAATCCCAAAAGGGCCAGGAAAAGGGGACCGCTGG
AGCCCACCCTAGCCCGACTCAGTTTCTGGAGGTCTGGGCTGGGGCCCGAG
AATGGCATCCCTAACTAGGCCCCGTGGACGCTGTCCCTGCCGGTCCGGGA
ACCCCACTCCAAGCACCACAGAGCTAGCATTTGCACTTCTTCCCCATTTT
GGGTACTCAAGCCCTGTTCAGGCTTTGTGACTCAGGAGTCTGGATAAAGT
ATGTTATGACATTGTAGGAGTGAAACTTCTTGTTACGGAAAGAAAGTTAA
CAGGAAGGTCAGTTGAGCCTCGTGTGTGAAATAAAAAATTCTTATTTTTC
AGGGTGGTTTGGTATCCGCAAAGATTTCTGTCAGTTTCTGCTTGAAATCT
TCCCATTTCTACGAGAATATGGAAACATTTCCTATGATCTCCATCACGAA
GATAATGAAGAAACCGAAGAGACCCCAGTTCCGGAGCCCCCTAAAATCGC
ACCCATGTTTCGAAAGAAGGCCAGGGTGGTCATTACCCAGAGCCCTGGGA
```

```
AGTATGTGCTCCCACCTCCCAAATTAAATATCGAAATGCCAGATTAGATG
CCACTTCCGGGGACAGAGCTTAAGTGGACTGGGACGCACTCTCTCCGCCT
TCCTCTGCCCCCTCGTTCACCCCGCAGACCAGAACCAGTACTGGAGCTGG
GTCTCCAGGTACGTCCATCTCATGCCTTGTTTGCATCCAGCGCCTATCAG
CCACTCACCACGACGGGACGCGGAAGTGGCAGGTGACGGGGGTGTGTGCC
AGCAGATGCGGATGCCAGGAAGAGTGTGAGAACAGGGGTGGGATTACCGT
CTGTCTGGGAGGGGCTCCAGGTACCCCTCTTCCCCGTCAGACCCACTGGG
AGATGGCTGCTTGCCAGGCCCCCAGAAGGAACATCTGTCTATACGGTGCT
GAAATCCCAATCAAAAGTATTGTTTAGAAATGTATTTCTCCACAGGGCTG
ACCTCCTGCAGCTCGCTGAGCACTCCCAGGTCCTCAGCACTCCCAGGTCG
TGGCTGGGGCAGTCAGTAGGAACTGTAACTATGTCTCTGATGCACCACGT
GTTTAGACACAGCACAGTCCTTTTTTCTGTTCCTACTGTGGAAGTAGTTT
CTCTTTGGGCATGCTGACAGCAGTTTTTCATAGCCTCACGGATGAGCCCT
TTCTACGGGAGTGACTCCATGCTTGTATACAGAGTATTTATACAAATGTT
TTAGCATCTTCATATGCGGTGTTAACCCCTAGTTCTGTACAGCATATTCT
GTTCAAGTATTTTTTTACAAGCTTGTGCTGTAGGCACATGCCTTCTGCTG
CAGAAGTGGACGCCCGTGGCACACTCCCCCCCCCCCCCCGTGGGGTGCCA
CGCCTTCATGGGACATTGCCACTTCTGCCCTGGAACTCGTGCAGGTACGT
AGTAGCTGCTACTGCCACAACGGCAACACCAAGCAAGAGATGGTCCATGC
TTTTCTGACGTTCTCAGAATAGTGGCTAGCTTCAAACCTGACAAGCGCTG
CTTGAAGCCGGAACACTAGAGAATGTTGCTGAGAGCAGAAACGGCCACGC
GGGTCACGACTATGCGTGGGAAAGTCTCAAGCTTCCCTCCTGCCAGCAAC
AAGAAGGCTTTGGAGTAGGCATGATGTTTTCACGTGTGCGTGCCGTTTCT
CCAAGCACTGCAGGTTCCACCGTGTGTCAGAGGCTGCAAGTTTAACATCC
TCCTGCCTGAAAACAAATAGGTCCTTTGCTGAAAAGAGGGTAAAAAAGA
GCTTTGATCTTCTCAGCCAGGAGAAGAGGGTGGTGTTTTCACGCGGGCAA
CTGCTCGCCGGCCTACATGGGGTTAATTCAAGTCTGCTGCGAGCACGACT
CCGCCCTTGGCACTGGCCTCCAGCAAGCCCTGTTCTCTTTGGGGTACAGG
GGAACGGGATGGTTTAGACTTTCCTGCTCAGTGTGTAAAAAATGTAGCTA
AAGCCACTATTTTTGCTCTCCTTAAGCTGTTCAATAAACCGGTTCCTCAT
TTTACACGTGCATGATGTGTATCTTCTTTGCTGGATGGGCCAGGAAACTG
GAGTGGTCCTCTCAGCCAGCCTCAGAGGAAAGAAATCTCTAGCTGGCACA
GGCAGCCAGTGAGTGAGGCTGGCGGCTGCAGGGGCACAGCCTTTAGAATG
AGTCCTTCAGTGCACAGGTCCCAGGGTATACGGGGTAGTGGGAGGAAGGA
GGGGACGCCTCGCAGATGCCACTGTTGGCTGGGCTACACCTTGCCACACT
TGTTACTGCTTAGGAGGCTTTCTGGAGTGTTCCTTGGGTGCTACGACAAT
CTGCAGCAGACACTGTCCTTTCACCGCTCCTGGTCCTCGTTTGCTCCCCA
GTGATGTCAACAGCTGAGGACTGCTCACGCTGCAACAAAAGGCTCTGCAG
TCGCTGTCTAGCTTGCCCTAGTCGTCTCTAGAGTTCTGCCTGAACTGAAA
CTCAAGTGGGGTTCAGCTCATGACTTGTGGCAATTGACCAGGAAATTCAC
CAGTTGCTGTGGCTGGAAGGATTTTCAGTCCTGTGGGTTGTAACCAGAGG
CCACAGGTGGATTCTGCCTTAGGCTCATGAGATTTCCGACTTGCTGTTGA
AGAAAATGCCTTGTGAAGTGACAACAGTAGCTCTGACCCAACTGCCGGTG
CCTCGCTAGTTCCTATACGTCCCACTGGATCCTCACAGCCCCGGGAAGCA
GGTGCTACTACTCTTATCCCCGGGAGGAGACAGAGGCCGAGAGAGGTTAA
GTGACGTGCCCAAGTCACACAGCTCGGCAGCGGCCGGGTTGAGCATCAGC
AGTCTGTTTGCAGACCCCTCACTGTCACCCCCTGAGCCAGTGCGCCTTGG
GCCCTGCGGTCAGGATGTCTCAAGCGTGGAGGCATCACCGGTTCGTGGCA
GTCTCTGGAAGGTCACTGAGCTCTGTGCCCAGAATCGAGTCGGGGGAGTC
TGTGCAGAGGTGGCCCTGTGTGTGGGGACAGTGTGTGACACAGACACTGC
TTTGGATGGACACCTCTCCCGTGACCTCCTAGCATCCAATCCCAAAGGAA
CAACTGTTGCAGAGATGGACCGCTGGACACAAACCCACGTGCGTTTCTCT
GGAGACACTGGCCAAGGAAAACAAAACATGCTCGAAGGCCAACAGCTGCA
TGCCCCACCGCGATGTGACCGCAGACACCCGGGGTGTAGAAGGGTCTCTG
CCTGGTGGGGGACACGTGCAGGCCGAGGAGAGGCAGGAAGGAGGCTGCC
TCCGACTCCCCACTGGACTGCATGGCGACGGCGTGTGGTGGGGCAGTCAG
CTAAGCCATTTGCCTAAGGGGCTGTCGGGCATCTGCGTGCTGGGGACCGA
CAGTGTGGGTGTGTTAGGAGGATCTGTATGGAGCACATTGCTGCCTCTGG
CTAGGACAGGGTGGAAAGGGTGGCGTGGCTACAGCCTGACCCATGGGCAC
CGTCCTACCCTTTGTTCTGTGCTTCCGAGTGTCAGTCATGTGCTGGGGTC
TGTGGGCCCATGACTCAGACGGTGAGCTCTGACCTTCCTGAGCCAGGGCT
TTGCTGTAGTTGTGCCTGGCTCAGGAGCTCTAGGACAAGGGGACCGCTCC
AGGTCTGCATCTACGGTGTGGCAGGGCCCCTCGGCACTCTTGTGCACTAG
TGTCATCTTTCCCATTGAAATGACTGTGAGGACCAGAATGTGCACATGCA
GATGGGCAGCTACTTGTCTGCCTTGGCCCTTTATTACACAACTTGCTGGG
GGTGGAGATGCCACCCCCCGGCAGTCAGAGCCCCTTTATGATGTCATGGG
GCTGGTTACATGACTGCCAAGGGGTGCTGCTGGCCACACTGCACTAGCAA
GTTTGCCAGATGGAGGACAAGCGATCATTGAGTATGGCTCGCTGTGAAGA
AAGAAATTCGAGAGGACAGGATCATGGCTTGGAAAGGGTGCCTTTCCCTC
CCCCAGTTGCAGTCAGAGACCTACCTTCACCCAGCAGATCCTTCCCCTGCC
TGGGACGACCCGGGGTCCACTGGGAGCCCTAACTTGAGGCTGCTGACAGA
AGAAATCGCTTTCCAACCTCTGGCCGAGGAAGCTTCGTTCAGAAGGCCGC
ACCCTGACGGTGACGTCCCGCCCCAGGGAGAAGATAATCTCCTCTCCCTC
CCCTTTCCACAGAAACTGTGGAGACTGGTCAGCAGCAACCAGTTTTCGTC
CATCTGGTGGGATGACAGTGGGGCTTGTAGAGTGATCAATCAAAAACTCT
TTGAAAAGGAGATTCTCAAAAGGGACGTCGCACACAAAGTGTTTGCCACA
ACTTCGATAAAGAGCTTCTTCCGCCAGCTAAACTTGTATGGCTTCCGAAA
ACGGCGTCAATGCACTTTCAGGACCTTCACCCGCATTTTCTCCGCAAAAA
GGCTGGTCTCCATCTTGAATAAGGTAATGAACGACAAGCCTCTGGAGGGG
TTAAGTCGGTGGGCTCTGGGGCCTGGTCGGGTGGAAGTCCCAGGACTGCC
```

```
TCCTGGGAAGTGGGCGACCTCAGGCAGGGTGTGGGGCCATCGCTGTGGGC

CTGTGTCCCCCTCTGGGTGGAGGTGACATGAACTAAGAGTGAATGTGGGG

AGAGGGCTGAGGATGGTGCGGGCCCCTCTCGAGTGTGTAAAATATCACAG

GTGCCAAGTAGCCGTATCTGCGTGTCGTCCTCCCCGGGGCCAGCCATGTC

ATCTGGTGGTTGCTGTGTCCCCCTGACTCCACAGCACATTACCCTGTGAG

GTGAGCAGGCCAGGGGAGTCTGGTATTTGTACCACTGTCACCCTAGCTGG

TGTCTGGAGAGGTGCTCAAGTGGAAGCACTGAAGGGCGCCTGGCGCAGGA

GGTGCAGATGCTCCTGCTGCCCTTGGTAGGTGGGCCCCTGGTGTGGAAGA

GCCAGTACCCAGGGCCTCCAACCCAGCCGGGGTGCATTCTGTTGCCAGCT

GACACTGCATGGGGAGGCCCAGAATCTTCTTCCCTCCTGGTCTGCAACT

TCAAAGACCCTTTCCGCCGGCCATGGACACCCTAATCTGCCATTTTGAGG

CTTTTTCCAAGACGGAAAGGCCCGCCACAACTTGGTAAACCTTGACGATG

TGAACGCGAGTCCCCAGCTTCCTTTGGGGACTGGGACCTTTTCCAGAAAG

GCCTCCTGGGCCAGTAGAGTTCTCTTGCACAGGGGCGTAGATGGTTGGTA

GTTGTAGTCCATCCTTGTGACTTG

SEQ ID NO:13 (Stuffer 1-Short)
GGCCCAGGAGGCCTTTCTGGAAAAGGTCCCAGTCCCCAAAGGAAGCTGGG

GACTCGCGTTCACATCGTCAAGGTTTACCAAGTTGTGGCGGGCCTTTCCG

TCTTGGAAAAAGCCTCAAAATGGCAGATTAGGGTGTCCATGGCCGGCGGA

AAGGGTCTTTGAAGTTGCAGACCAGGAGGGAAGAAGATTCTGGGCCTCCC

CCATGCAGTGTCAGCTGGCAACAGAATGCACCCCGGCTGGGTTGGAGGCC

CTGGGTACTGGCTCTTCCACACCAGGGGCCCACCTACCAAGGGCAGCAGG

AGCATCTGCACCTCCTGCGCCAGGCGCCCTTCAGTGCTTCCACTTGAGCA

CCTCTCCAGACACCAGCTAGGGTGACAGTGGTACAAATACCAGACTCCCC

TGGCCTGCTCACCTCACAGGGTAATGTGCTGTGGAGTCAGGGGGACACAG

CAACCACCAGATGACATGGCTGGCCCCGGGGAGGACGACACGCAGATACG

GCTACTTGGCACCTGTGATATTTTACACACTCGAGAGGGGCCCGCACCAT

CCTCAGCCCTCTCCCCACATTCACTCTTAGTTCATGTCACCTCCACCCAG

AGGGGGACACAGGCCCACAGCGATGGCCCCACACCCTGCCTGAGGTCGCC

CACTTCCCAGGAGGCAGTCCTGGGACTTCCACCCGACCAGGCCCCAGAGC

CCACCGACTTAACCCCTCCAGAGGCTTGTCGTTCATTACCTTATTCAAGA

TGGAGACCAGCCTTTTTGCGGAGAAAATGCGGGTGAAGGTCCTGAAAGTG

CATTGACGCCGTTTTCGGAAGCCATACAAGTTTAGCTGGCGGAAGAAGCT

CTTTATCGAAGTTGTGGCAAACACTTTGTGTGCGACGTCCCTTTTGAGAA

TCTCCTTTTCAAAGAGTTTTTGATTGATCACTCTACAAGCCCCACTGTCA

TCCCACCAGATGGACGAAAACTGGTTGCTGCTGACCAGTCTCCACAGTTT

CTGTGGAAAGGGGAGGGAGAGGAGATTATCTTCTCCCTGGGGCGGGACGT

CACCGTCAGGGTGCGGCCTTCTGAACGAAGCTTCCTCGGCCAGAGGTTGG

AAAGCGATTTCTTCTGTCAGCAGCCTCAAGTTAGGGCTCCCAGTGGACCC

CGGGTCGTCCCAGGCAGGGGAAGGATCTGCTGGGTGAAGGTAGGTCTCTG

ACTGCAACTGGGGAGGGAAAGGCACCCTTTCCAAGCCATGATCCTGTCCT

CTCGAATTTCTTTCTTCACAGCGAGCCATACTCAATGATCGCTTGTCCTC

CATCTGGCAAACTTGCTAGTGCAGTGTGGCCAGCAGCACCCCTTGGCAGT

CATGTAACCAGCCCCATGACATCATAAAGGGGCTCTGACTGCCGGGGGGT

GGCATCTCCACCCCCAGCAAGTTGTGTAATAAAGGGCCAAGGCAGACAAG

TAGCTGCCCATCTGCATGTGCACATTCTGGTCCTCACAGTCATTTCAATG

GGAAAGATGACACTAGTGCACAAGAGTGCCGAGGGCCCTGCCACACCGT

AGATGCAGACCTGGAGCGGTCCCCTTGTCCTAGAGCTCCTGAGCCAGGCA

CAACTACAGCAAAGCCCTGGCTCAGGAAGGTCAGAGCTCACCGTCTGAGT

CATGGGCCCACAGACCCCAGCACATGACTGACACTCGGAAGCACAGAACA

AAGGGTAGGACGGTGCCCATGGGTCAGGCTGTAGCCACGCCACCCTTTCC

ACCCTGTCCTAGCCAGAGGCAGCAATGTGCTCCATACAGATCCTCCTAAC

ACACCCACACTGTCGGTCCCCAGCACGCAGATGCCCGACAGCCCCTTAGG

CAAATGGCTTAGCTGACTGCCCCACCACACGCCGTCGCCATGCAGTCCAG

TGGGGAGTCGGAGGCAGCCTCCTTCCTGCCTCTCCTCGGCCTGCACGTGT

CCCCCCACCAGGCAGAGACCCTTCTACACCCCGGGTGTCTGCGGTCACAT

CGCGGTGGGCATGCAGCTGTTGGCCTTCGAGCATGTTTTGTTTTCCTTG

GCCAGTGTCTCCAGAGAAACGCACGTGGGTTTGTGTCCAGCGGTCCATCT

CTGCAACAGTTGTTCCTTTGGGATTGGATGCTAGGAGGTCACGGGAGAGG

TGTCCATCCAAAGCAGTGTCTGTGTCACACACTGTCCCCACACACAGGGC

CACCTCTGCACAGACTCCCCCGACTCGATTCTGGGCACAGAGCTCAGTGA

CCTTCCAGAGACTGCCACGAACCGGTGATGCCTCCACGCTTGAGACATCC

TGACCGCAGGGCCAAGGCGCACTGGCTCAGGGGTGACAGTGAGGGGTC

TGCAAACAGACTGCTGATGCTCAACCCGGCCGCTGCCGAGCTGTGTGACT

TGGGCACGTCACTTAACCTCTCTCGGCCTCTGTCTCCTCCCGGGATAAG

AGTAGTAGCACCTGCTTCCCGGGGCTGTGAGGATCCAGTGGGACGTATAG

GAACTAGCGAGGCACCGGCAGTTGGGTCAGAGCTACTGTTGTCACTTCAC

AAGGCATTTTCTTCAACAGCAAGTCGGAAATCTCATGAGCCTAAGGCAGA

ATCCACCTGTGGCCTCTGGTTACAACCCACAGGACTGAAAATCCTTCCAG

CCACAGCAACTGGTGAATTTCCTGGTCAATTGCCACAAGTCATGAGCTGA

ACCCCACTTGAGTTTCAGTTCAGGCAGAACTCTAGAGACGACTAGGGCAA

GCTAGACAGCGACTGCAGAGCCTTTTGTTGCAGCGTGAGCAGTCCTCAGC

TGTTGACATCACTGGGAGCAAACGAGGACCAGGAGCGGTGAAAGGACAG

TGTCTGCTGCAGATTGTCGTAGCACCCAAGGAACACTCCAGAAAGCCTCC

TAAGCAGTAACAAGTGTGGCAAGGTGTAGCCCAGCCAACAGTGGCATCTG

CGAGGCGTCCCCTCCTTCCTCCCACTACCCCGTATACCCTGGGACCTGTG

CACTGAAGGACTCATTCTAAAGGCTGTGCCCCTGCAGCCGCCAGCCTCAC

TCACTGGCTGCCTGTGCCAGCTAGAGATTTCTTTCCTCTGAGGCTGGCTG

AGAGGACCACTCCAGTTTCCTGGCCCATCCAGCAAAGAAGATACACATCA

TGCACGTGTAAAATGAGGAACCGGTTTATTGAACAGCTTAAGGAGAGCAA
```

-continued

```
AAATAGTGGCTTTAGCTACATTTTTTACACACTGAGCAGGAAAGTCTAAA
CCATCCCGTTCCCCTGTACCCCAAAGAGAACAGGGCTTGCTGGAGGCCAG
TGCCAAGGGCGGAGTCGTGCTCGCAGCAGACTTGAATTAACCCCATGTAG
GCCGGCGAGCAGTTGCCCGCGTGAAAACACCACCCTCTTCTCCTGGCTGA
GAAGATCAAAGCTCTTTTTTTACCCTCTTTTCAGCAAAGGACCTATTTGT
TTTCAGGCAGGAGGATGTTAAACTTGCAGCCTCTGACACACGGTGGAACC
TGCAGTGCTTGGAGAAACGGCACGCACACGTGAAAACATCATGCCTACTC
CAAAGCCTTCTTGTTGCTGGCAGGAGGGAAGCTTGAGACTTTCCCACGCA
TAGTCGTGACCCGCGTGGCCGTTTCTGCTCTCAGCAACATTCTCTAGTGT
TCCGGCTTCAAGCAGCGCTTGTCAGGTTTGAAGCTAGCCACTATTCTGAG
AACGTCAGAAAAGCATGGACCATCTCTTGCTTGGTGTTGCCGTTGTGGCA
GTAGCAGCTACTACGTACCTGCACGAGTTCCAGGGCAGAAGTGGCAATGT
CCCATGAAGGCGTGGCACCCCACGGGGGGGGGGGGAGTGTGCCACGGG
CGTCCACTTCTGCAGCAGAAGGCATGTGCCTACAGCACAAGCTTGTAAAA
AAATACTTGAACAGAATATGCTGTACAGAACTAGGGGTTAACACCGCATA
TGAAGATGCTAAAACATTTGTATAAATACTCTGTATACAAGCATGGAGTC
ACTCCCGTAGAAAGGGCTCATCCGTGAGGCTATGAAAAACTGCTGTCAGC
ATGCCCAAAGAGAAACTACTTCCACAGTAGGAACAGAAAAAAGGACTGTG
CTGTGTCTAAACACGTGGTGCATCAGAGACATAGTTACAGTTCCTACTGA
CTGCCCCAGCCACGACCTGGGAGTGCTGAGGACCTGGGAGTGCTCAGCGA
GCTGCAGGAGGTCAGCCCTGTGGAGAAATACATTTCTAAACAATACTTTT
GATTGGGATTTCAGCACCGTATAGACAGATGTTCCTTCTGGGGGCCTGGC
AAGCAGCCATCTCCCAGTGGGTCTGACGGGGAAGAGGGGTACCTGGAGCC
CCTCCCAGACAGACGGTAATCCCACCCCTGTTCTCACACTCTTCCTGGCA
TCCGCATCTGCTGGCACACACCCCCGTCACCTGCCACTTCCGCGTCCCGT
CGTGGTGAGTGGCTGATAGGCGCTGGATGCAAACAAGGCATGAGATGGAC
GTACCTGGAGACCCAGCTCCAGTACTGGTTCTGGTCTGCGGGGTGAACGA
GGGGGCAGAGGAAGGCGGAGAGAGTGCGTCCCAGTCCACTTAAGCTCTGT
CCCCGGAAGTGGCATCTAATCTGGCATTTCGATATTTAATTTGGGAGGTG
GGAGCACATACTTCCCAGGGCTCTGGGTAATGACCACCCTGGCCTTCTTT
CGAAACATGGGTGCGATTTAGGGGGCTCCGGAACTGGGGTCTCTTCGGT
TTCTTCATTATCTTCGTGATGGAGATCATAGGAAATGTTTCCATATTCTC
GTAGAAATGGGAAGATTTCAAGCAGAAACTGACAGAAATCTTTGCGGATA
CCAAACCACCCTGAAAAATAAGAATTTTTTATTTCACACACGAGGCTCAA
CTGACCTTCCTGTTAACTTTCTTTCCGTAACAAGAAGTTTCACTCCTACA
ATGTCATAACATACTTTATCCAGACTCCTGAGTCACAAAGCCTGAACAGG
GCTTGAGTACCCAAAATGGGGAAGAAGTGCAAATGCTAGCTCTGTGGTGC
TTGGAGTGGGGTTCCCGGACCGGCAGGGACAGCGTCCACGGGGCCTAGTT
AGGGATGCCATTCTCGGGCCCCAGCCCAGACCTCCAGAAACTGAGTCGGG
CTAGGGTGGGCTCCAGCGGTCCCCTTTTCCTGGCCCTTTTGGGATTCTGC
```

-continued

```
TGGATGCCCAAATTTGAGAACTACTGCTCCAGTGAGTCTCAAAATATCTG
TGGTGCGCAGACTACGGTGTCTTCCGCTAATCTTCTCCAGCCAGGATAAA
CTCATGGATGACAGTGCCACCCAAGAACAAGATTTCTGTCACCCTCTGGA
ATCCGTGAGGGCGGTAGTCATGCACGGGTTGGCCAGGAGGGGCCTGAAC
TCATGGAGCCACCTTAAAGCCACTTTCCCAGTCCCACTACTCCTCTCTGT
AGGCTACTGGAGTGTCAGCTCGGTGCAAGCCCTCCCTGCTCCCGGGTGCG
GGGTAGGGGGCAGAGGCACAAACAGCAAGCACAGCCCGGGCTGCTGGGCT
GCAGTGAGGCCCTGCCCCCAAACCCACTGGCTTTCCGAAGGGCAATGCTC
TGGGCTTCCGTGCCATGGAGCCCACAGCCTTGCCAGGAAGGCACCCTCTG
CAGAGATCGTTTTGGAAGTGTCTGCCTCAGCAAGCAGGTGGAGGGGAATA
GAGTGTTAGCAAGGCAAGACAGGCAAGACTCGGGTGATGGCAGCAAGGAT
ATGGGGGAGGCAGAGCGGCCAACAGGGACCTAGGATGAATCCCAGGTTTG
GGTGGGAGATGTGGATTTTCCATCAAACCCTCCCGGGCCTGGGAAGAATC
TGTCTTGATCCCCATTTTGCAGAGGAGGGAACGGGATCTCTGAGAGGTTG
CCTGCCGTGTCTGGTTCTACCTCAAATGGCAGCGTGCACTGCGAGAAAAG
TCCCGGTGCAGGCCAGCAGAAACACCAGAGTTACGGCATGCCCTTCCCTTA
GAAGGTCCCAGAATTTCCTCAGCCCTCACTTTCCCACACAAGCTTCTAAA
TTGGGGCCCTCGGGGACTCATCCCTTCCTAGACTTCTATCCGCCACCCCC
CACCCCCTGGTCCCCCCCAGACACACACCAAGGACTTCTGAAATGCTGA
GTACATACAGTGGTTTCCTCCCTTCTGTCCAAATGTGGTTGCCATCAGCG
TGATCAACGAGAGCCAAAGGGGGACAAAGATCGGGATGCAGGAGAAGGCG
TTGTGGCCATCCAGTTTGTGAACCAGCAGAATCTAAAGAAAGAGACATAG
TCCCGGTTGATGCCAGCACCGAAAATGGGCAGAGGCGGAAGCCAGACTTC
ATTAGGCAGTTCCTCCCCACCACCCCACCCCCGCGTGAGCTCCCACAAGA
GGGAACATCAGCACCGCCAGAAAAGGCAGGAAACCACCTATCCCTGGGG
AAAGCTCGAAATGAGCTTTTATGTCCCTCTTCAGAGCTCGGCAATAGCCT
ATCCACTTGAAAAGTTCCCAGTGCCAGCAGTTTTATGGCAAACTCCTCCG
GGTGTTTGTTCTAAGGAGTCAACAGCTCCCATTCTAGAATTCTCCACGTG
ACTCCAATACACAAATCTGACATCCCACTCTGCTTTCCCCAGAGTGGAAA
CTGGAGCCATACAGAGGCACCATGGCTAAAAAGGTGCACTCTTCTCCCTG
CCAGCCCCACGTGCTGCCCCCAAGAGAAAGGAAGGATGCTCTCCTTTCAC
CGAAGCTCCCTCTCGGAGATGGCTGTGTTCTCTCCCCTCTCCTGGAGTGG
GCTCACTGTGAGCTCGAGGGACAGAGGCTGCCTTTCTAGGGGTGCAGAAT
CCTGTCAGGGGAAGCGCAAGCTTCAGGGGCTGAAGAGGCTTCCCGTGGAA
CGCTTACCTCAAATGTAAGAAGGGGCACGACGATGGTCATCCAGCTCAGG
GCCATGGTTATGTGTGTCCTGCGCTGTCCGCAATCACATCCATAGAGCGC
AAGAACAAGACGGACCACACAATGTAGTAGAGGACCACCAGGCACAGAAA
GGACATGAGAATCCACAGCGGGACACACACAACCTGGGGGTGGGTGAGAG
AACAGCAAGAGAAGTCTCTTTAGAGCTTCCAACCTGGCCTCTGATGGAAG
GCATCTTTAGCACCTTGCTGTGTCTGTCCAGTTAAGGCGGTCCTTCCTGT
```

-continued
GAGCCGAATAAGGACCGTTCCATCTCCCAGGACTGCTGGGAGCATCGCTC
AGGACAGAAAAGGTATGGTATGTTCACTATGGGGCCTGCTGCCACCAGGG
GACACACACGCTCAGTGAGTCATCAGTCCCTCTTCCTTTGGGTGACAGAC
AGCCCTGCACCTGGCTCCGCAGCCTCTACTCTTCCAGAGGCCCACTCTCC
CACACTCTCTCAGGCTCCTCTAGGTTCTGCTGCCATCACAGCTTCCCGGG
AAATGGGACACAACTGTCACCCTGTGCACACACACAAGATCTCACCCCAA
CAGACTCTCTTCACAGGCAACATTCCCACAACCTGCTGGGGTACTTTGG
CAACACAAATGGGAATGGGCTCCCCAGAAAGTCTGGCTGCCTGGGCTCCT
AAGGATCCCTAACCTCACCCCTACCAAGTTAGTGAACTTGGCGGGTTGAT
GCTGGATACAGGTTGATGCTGGATACGTAGCGCTGCCGGGTGACC SEQ ID NO:14 (p2-2)
GGGCGAATTGGGCCCGACGTCGCATGCTCCCGGCCGCCATGGCGGCCGCG
GGAATTCGATATCACTAGTGAATTCGCGGCCGGCGATTGGGCCCGACGTC
GCATGCTCCCGGCCGCCATGGCGGCCGCGGGAATTCGATTCCTTAATTAA
GTCGACTGGGACCCAAACTTTGGAGTCGTTGACAGATGTGACAGGTGAAG
CCTGGGATGACATCGCCAAAAATGCAACGTCTCACTCATTGTCACTACTC
CCAGGGCTCAGTCGTCACTGGGGAAAATCTCCAGAAGGTAGCGCGGGCCA
AGGTGACAGGTGTCTGCCAAGATCTGCCCGCCAGACTCCCGGGCGGCGCG
CTCCCTCCCTGCAGGCCTTCAGCCCGTCAGCATCCCCTTCCTCGGGGCCC
TGCTCACTCCCAGCCTCCATCCCCCTGCCATCTCCTCCGCCGGTCGCGTG
CGGACACAAGGATGGGGACCTCCCAGCGAGGAGCGCTCTGGGCGGGGCTC
CGGACGCATGCGCGGCCCTCGTACGGAAGCCCGGAAGGAGGGGCAGGGGG
CGGTGGCTCAGGTTTCTCCGGGCGGCGGCGGCGGCGGCGGCGGACGGC
GACGGCGACGGCAGCGGGACGGCAGCAGTAGCGGGAGCAGCAGCGTGGA
CGCGGCTGGCGCTGGCGCCATGAACCCGCTGTAAGGCGCAGGCTGTGCAG
CACGGGGTGCGGGGAGGAGGAGGAGGACGCCGCGGTGAAGTTCTCCGCC
ATGAACCTGAGGGGCCTCTTCCAGGACTTCAACCCGAGGTGAGGCGGCGT
CGTTGGCGCCCCCGGGAGTCCGCGCTGCGGGCTCGGGCGCGGGCTGGTGT
TCGGCTCCGGGGAGGCACGGCGGGCGAGATGCTGCAGCCCGAGGACCCGG
GCGCCTGCCCGAGCCTCCCTGCGGGTGCAAGCGGTCCCCAGGCAAAACAG
TCGGCCTCGGCGCCCGCCCGCTTCCTCCTCCCGTGCCCGGTGCTTTCAGC
CCCTGCCCGGCCACGGCCGGAAGGGCCCGGCCGCGAGCCCCGTCCTGCCC
CAAGGGAACCCCATTCTTTTCTGCTTGCTGTCCCTCATTGGTGTCCCAAC
TTCTTCGTCTCGGTTCCATCCTCTTCTGCGCCGCTGCGGGCCCTCCATTC
TCCGCGTCAGGGCCGTCTCACTCGACCCAACACCCCTACCCCCACCCCAG
CTGTTTCCTCCAGTTCCTCGCAGTCCTTGGGGTTTTCCTTGGGTTTATGC
CCATCCCTCTCTTGTTTGCTTCTTTGTTGAACGGATACCTGAAACACTGT
TGAATCCTTGGAGTCAGTGTCGGGGTATGGCAATACCTTATATAATGCAT
TTCTGGGTGAGCCTGATCATTTTCCATACTCATTTTCTCATCAGTCTTCA
CTACAAGTTTATTTGCAGGAAGTAGATATTGCTGTCCTTCTTTTCCAGAT
GGGGAACACCCAGTGGACAGTGTGGAGAAAACACTGGCTAAGCACTCAAG -continued
CGCCTGTCCTTGCACTTGCCCGACTGTTTTGTAACTGTTCTTTACCCCAG
GCTGTGAGCTCCCTGAAGCTGAGACCATCTCCTGCTCATCTCAGTGTCCC
CAGCGCCTCCCACCCACCGTATCTGGCACATAGTAGGCACATATAAATG
TTTGTGGAACTAAACTGAGCCCAAAGACTTGGATTGGAGACGAGGCCATA
TGTAACTGGGTGATTCTCTGCCCTTCTTTGGCCCTTCTGTAAAATGAGGA
GTTGGCCTAACTGATCTCTTAAATGCACTACTCTCCGAAAGGAGTATCCG
TTTCCCTTATTTGCCAGTTGGGAAGACGTGCTCAGTAAATATTTGTGTGC
TGTAACCTATGTTAGGTGCTTTAGATGCTGGCGGTCTCAGCATGGGGTGA
AGAAGGGCTTGTACACTTAAGATGCCTTACAGTACTGTGCAGTGCTGTAC
TGCGGGGGCCAACTCTGGGGACCTATGCCTTGGCTGCTTGTTGAGGATGA
AAGGAAGTTTTAGGGGAGTATTTGTATGTTGAGGGTGCAGTCTCCCTAGG
GATGGTGACATTTTAACTTGTGAGTCATTGTGACTTTGTATGTGCCCTTA
TTCCACTTTGAGTTCATGTTCTGGTTAGGAGTGCCAGTGTCTCTAACACG
GTGCAGACATTATCATTGTTGGCTTGAAGGCATAGAGGAGGTAACAGAA
CTAACTGCAGTCCCTTCCTCTGCTGCATCAGGGGGTTAAGATTGGTCTGC
AGGGTAGTAGGGTTGGTGCTGTGGCTGGACAAGCCCTGTATGTCTTCTAT
TTGGAGATGGTGATAAGAAAGTTAAGTAAAAACTGAATTGTTTTGTGCCC
TTGGGCAACTCACTTATCTATTGTTTTATCTGTAGAATGAGTATAATCTC
TCAGTGGGGTAGGGAGGCCAATTAAGGATTGATTACAAAGTGCCTTACAA
ATAGAAAGCTACAGTGACTTGTTTGCAAGGTGACAGAGAATTCAGAAGCC
TCAAGAAACTGCCTTAAGTGATCAAACAGGCTAACGGAGTTGCCAAAGCA
AAATAGTGCTGCACTGATACTACCTTTAACCGTTTTTTCCTTTAGCCCTT
TTCCCCCCAAAAAAATTAGTATATGAAATTACAGTGAAATACCTGGTATC
TAAGCAGATTTATAGTAATTCTCAACATATTCATCAATCTCTTAATTCTA
CCTGCATTAAAATGTATTTCTACCTGAAAAGTTTAAAGGTCTTTTATACT
GTGCCATTTTCCTGATTCATTGTTGCCAGAGGTAGTGAGTTCCTTAATTT
TACAGATATTTCAAGAGGACATTGGCCAGGTATTATTGGTAAATCAGATT
TGTTTTTTTAGCTGGTAGTGTTTCACCTCTCCTGAGCACTCCTAGTTTTT
GACAGTGTGCTTTAGTCTCCTTCCATGCTGAGGAAGGCCTTCTCTATAGG
AGAAAGAAAACTGAGGGGTGTACACAGGAAGTTACCTTATGCTGGGGACT
CAAACCTTGATGCTACTGCTTTGCTCCCTGCCTCTATTTTTGAACCAATT
CAACATCTCCCTCCTACCCCAGGACCTTGTCACACACTGTTCTCTTTACC
AGGAATGTTTCCCTCTCTTTTCCTCTCCTCCAGACCTAGTGAACTCCTAT
TTATCCTCACTTGGCACTTGCTAAGGGAAGCATTCCTGACTTCCCTGACC
AGATTTACTGCTCCCTGTTTCTACAGTTCCTGTAGTATTTACTACTCCTC
CATCATAGTGCATATTTGTACCCTTGTGTCTGTCTGGATGCTTATTTGAT
TAATACCTGCCTCCCCCACTAAACTTAAGCTCCATGGGGTCAAGGCCGT
GACTGTGTCAGTATCGTAGCCTGCATACTTGGAATAGTACCTGGCTCAAT
AAATATTTGTGGAGTAAATAACTGAATAACTCTCCAGAGCCTATAAGATA
AATCTAGAGCTGCTGCTTTCAATCACTGCTTTCCTGGTGGTCTGTGGCCT

```
GGTTCTCTTTCTTCTCACACTCTTCCCACCTTCAGAGTGCAGCCATTGCT
TTGGAGAGATGGGAGAGAACATGGCACTAAGGCAGAATATGGCTATATTT
ACTTTGAAGAGCATGTCTTTGTCATAGAAATAGTCACTGTCATGGTTTGG
TGGGTCCCAAGGCATGGGTCATGGCTCCAGATCCCCTTTCCAGCCTTTTG
GATCTTGGTAAGTCTGAACCCACTGCTGCGTTGGCAAGGCTCTGGAAACT
ATAGTGACAGAGAATGATTCACAAGTGTCAACACTCAGATGTACAGGGCT
GCCAGCTGACCCACTCTACCTATTTCCATCTGGCACTGAACTGGTTGATC
ATGAACTTCTTTTCATAATTGCTTTTTAGTTATGCAGGTTAAGACATGCC
GAAACAGATGTACCGGACCCACAAACAAGTCCTTCCTTGAATGCCTGAGG
CTTCCTAACAGTGAAAGAGCCCTGTTCTTAGAGTAGGCAAACTGATTCTG
AGGCATTGTAGGTGGTAGGGATCTGGTAGTAGGTAGCATTAGGTGGGCTC
CCGGCACTCACCATGGAGCCTTGAAATTTTCTGCTACTTTGGGGGAGTTG
CTGGTTCAGAGAAGGCCCTTCCACCCTGGTAGCCATGTGGCACTGGAAGG
CTGTGAAAACTCTGCTGGGCCTTCTTAGTCATCTGTTGTGAGCTCCTGAT
GGGAGTGTGGTGTATCCCTCAGGTGTGCTAGACTGGAACAAAGGCTGAGA
AGTGTTGCTCTGGGGGTTCCAACTTGTGGGCATGGGGTACTGATGAGATC
AGTAGTGTTTGGAGACTTCTGTATGCTCCATCTTCAGAAGACATTCTGGA
GTCCATATAAGTTATCTTGTCTCTTGTTTGAAGCAGGAAAAAGGAATGCG
ATTGCTGGTAATATAGTTCACTAAAGTCAGCTACCTGGCCTCTAACAGTT
ATTTGCAAAGTATATTATAACATTGATTCCTCAAACATCTAGATTCCTAT
CTCGTGCCAAGTGATGTACTAGGTGCTCTAAGTACAAAAATAAAGGAATA
TAGTCCTCCTCTCAATGCGTAAGCCTAGTGGAAGAAGCAGAAATGAAAGG
GAAATAAGAATTCAATAGAGTATGAGGCATTACAGTGAAAGAAACCAAAT
GTCTTAGAAGTACAAATGGCAGAGCTACTAATTCTGTCTCGAGCAGGCAG
GGAAGAGTCTATAGTGGAAATGACTTTTGAGCTAGATTTTGAATTGAGCT
AGTCTTTTGAGCCAGACTTTTGAGCTAGAATTGTAGGGTTGTCATCAGAC
CAGAGAGTAGGAAGGGTACCTTGTGAGGAAGAGAGAGAGAGATCAGATTG
TTACTGTGTCTATGTAGAAAAGGAAGACATAAGAAACTCCATTTTGATCT
GTACTAAGAAAAATTGTTTCTGCTTTGAGATGCTGTTAACCTGTAACTTT
AGTCCCAACCCTGTGCTCACAGAAACCTGTGCTGTAATGAATCAAGGTTT
AATGGATTTAGGGCTGTGCAGGATGTACCTTGTTAACAATATGTTTGCAG
GCAGTATGCTTGGTAAAAGTCATCGCCATTCTCCATTCTCGATTAACCAG
GGACACAGTGCACTGCGGAAGGCCGCAGGGACATCTGCCCAAGAAAGCCT
GGGTATTGTCCAAGGTTTCCCCCCACTGAGACAGCCTGAGATATGGCCTT
GTGGGAAAGGAAAGACCTTACCACCCCCAGCCCGACACCCGTAAAGTGT
CTGTGCTGAGGAGGAGTAGTGAAAGAGCGGGGCCTCTTTGCAGTTGAGAT
AAGAGGAAGGCTTCTGTCTCCTGCTCATCCCTGGGAATGGAATGTCTCTG
TGTAAAGCTGACCATTCCCATTCGTTCTATTCTGAGATAGGAGAAAACCA
CCCTGTGGCTGGAGGCGAAGTATGCTGGCAGCAATACTGCTCTGTTACTC
TTTGCTACACTGAGTTGTTTGGGTAAAGAGAAACATAAATCTAGCCTGCG
TGCACATCCAGGCACAGTACCTTTCCTTGAACTTATTCATGATACAGATT
CCTTTGCTCACGTTTCCCTGCTGACCTTCTCCCCACCTGTTGCCCTGCTA
CACTCCCCTCGCTAAGATAGTAAAAATAATGATCAGTAAATACTGAGGTA
ACTCAGAGGCTAGCGCTGGTGCGGGTCCTCCGTATGCTGAGTGCCGGTCC
CCTGGGCCCACTGTTCTTTTCTCTATACTTTGTTTCTGTGTCTTATTTCTT
TTCTCAGTCTCGTCCCACCTGACGAGAAATACCCACAGGTGTGGAGGGGC
TGGCCCCTTTCAGTATCTCAGAAGGGACAAAGTACACAAAGGCATGGGGT
CATGATAGTGCCTGGTATGTTCAGGTAGTGAAGAGGTCCATGTGGTATGA
GCACTGCAGATGATATGTGTCGTATGAATTAAAAATACATAGTTACTGCA
AATAGTTTTTACAGGTTATTGTTTTTAAGAAAGCAGTATCTAATGCACGA
GTGTACTGTCAGTACTGTCAATGAACTACTTACCACTCAAGTGACTGCTT
ACGCGTCGAATCACTAGTGAATTCGCGGCCGCCTGCAGGTCGACCATATG
GGAGAGCTCCCAACGCGTTGGATGCATAGCTTGAGTATTCTATAGTGTCA
CCTAAATAGCTTGGCGTAATCATGGTCATAGCTGTTTCCTGTGTGAAATT
GTTATCCGCTCACAATTCCACACAACATACGAGCCGGAAGCATAAAGTGT
AAAGCCTGGGGTGCCTAATGAGTGAGCTAACTCACATTAATTGCGTTGCG
CTCACTGCCCGCTTTCCAGTCGGGAAACCTGTCGTGCCAGCTGCATTAAT
GAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGG
ATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCCTGA
CGAGCATCACAAAAATCGACGCTCAAGTCAGAGGTGGCGAAACCCGACAG
GACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGG
TGTAGGTCGTTCGCTCCAAGCTGGGCTGTGTGCACGAACCCCCCGTTCAG
CCCGACCGCTGCGCCTTATCCGGTAACTATCGTCTTGAGTCCAACCCGGT
AAGACACGACTTATCGCCACTGGCAGCAGCCACTGGTAACAGGATTAGCA
GAGCGAGGTATGTAGGCGGTGCTACAGAGTTCTTGAAGTGGTGGCCTAAC
TACGGCTACACTAGAAGAACAGTATTTGGTATCTGCGCTCTGCTGAAGCC
AGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGA
AAAAAAGGATCTCAAGAAGATCCTTTGATCTTTTCTACGGGGTCTGACGC
TCAGTGGAACGAAAACTCACGTTAAGGGATTTTGGTCATGAGATTATCAA
AAAGGATCTTCACCTAGATCCTTTTAAATTAAAAATGAAGTTTTAAATCA
ATCTAAAGTATATATGAGTAAACTTGGTCTGACAGTTACCAATGCTTAAT
CAGTGAGGCACCTATCTCAGCGATCTGTCTATTTCGTTCATCCATAGTTG
CCTGACTCCCCGTCGTGTAGATAACTACGATACGGGAGGGCTTACCATCT
GGCCCCAGTGCTGCAATGATACCGCGAGACCCACGCTCACCGGCTCCAGA
```

-continued

```
TTTATCAGCAATAAACCAGCCAGCCGGAAGGGCCGAGCGCAGAAGTGGTC

CTGCAACTTTATCCGCCTCCATCCAGTCTATTAATTGTTGCCGGGAAGCT

AGAGTAAGTAGTTCGCCAGTTAATAGTTTGCGCAACGTTGTTGCCATTGC

TACAGGCATCGTGGTGTCACGCTCGTCGTTTGGTATGGCTTCATTCAGCT

CCGGTTCCCAACGATCAAGGCGAGTTACATGATCCCCCATGTTGTGCAAA

AAAGCGGTTAGCTCCTTCGGTCCTCCGATCGTTGTCAGAAGTAAGTTGGC

CGCAGTGTTATCACTCATGGTTATGGCAGCACTGCATAATTCTCTTACTG

TCATGCCATCCGTAAGATGCTTTTCTGTGACTGGTGAGTACTCAACCAAG

TCATTCTGAGAATAGTGTATGCGGCGACCGAGTTGCTCTTGCCCGGCGTC

AATACGGGATAATACCGCGCCACATAGCAGAACTTTAAAAGTGCTCATCA

TTGGAAAACGTTCTTCGGGGCGAAAACTCTCAAGGATCTTACCGCTGTTG

AGATCCAGTTCGATGTAACCCACTCGTGCACCCAACTGATCTTCAGCATC

TTTTACTTTCACCAGCGTTTCTGGGTGAGCAAAAACAGGAAGGCAAAATG

CCGCAAAAAAGGGAATAAGGGCGACACGGAAATGTTGAATACTCATACTC

TTCCTTTTTCAATATTATTGAAGCATTTATCAGGGTTATTGTCTCATGAG

CGGATACATATTTGAATGTATTTAGAAAAATAAACAAATAGGGGTTCCGC

GCACATTTCCCCGAAAAGTGCCACCTGATGCGGTGTGAAATACCGCACAG

ATGCGTAAGGAGAAAATACCGCATCAGGAAATTGTAAGCGTTAATATTTT

GTTAAAATTCGCGTTAAATTTTTGTTAAATCAGCTCATTTTTTAACCAAT

AGGCCGAAATCGGCAAAATCCCTTATAAATCAAAAGAATAGACCGAGATA

GGGTTGAGTGTTGTTCCAGTTTGGAACAAGAGTCCACTATTAAAGAACGT

GGACTCCAACGTCAAAGGGCGAAAAACCGTCTATCAGGGCGATGGCCCAC

TACGTGAACCATCACCCTAATCAAGTTTTTTGGGGTCGAGGTGCCGTAAA

GCACTAAATCGGAACCCTAAAGGGAGCCCCCGATTTAGAGCTTGACGGGG

AAAGCCGGCGAACGTGGCGAGAAAGGAAGGGAAGAAAGCGAAAGGAGCGG

GCGCTAGGGCGCTGGCAAGTGTAGCGGTCACGCTGCGCGTAACCACCACA

CCCGCCGCGCTTAATGCGCCGCTACAGGGCGCGTCCATTCGCCATTCAGG

CTGCGCAACTGTTGGGAAGGGCGATCGGTGCGGGCCTCTTCGCTATTACG

CCAGCTGGCGAAAGGGGGATGTGCTGCAAGGCGATTAAGTTGGGTAACGC

CAGGGTTTTCCCAGTCACGACGTTGTAAAACGACGGCCAGTGAATTGTAA

TACGACTCACTATA
```

NEED SEQ ID NO:15 (Stuffer 2)
```
GGCCGCGGGAATTCGATTCCTTAATTAAGTCGACTGGGACCCAAACTTTG

GAGTCGTTGACAGATGTGACAGGTGAAGCCTGGGATGACATCGCCAAAAA

TGCAACGTCTCACTCATTGTCACTACTCCCAGGGCTCAGTCGTCACTGGG

GAAAATCTCCAGAAGGTAGCGCGGGCCAAGGTGACAGGTGTCTGCCAAGA

TCTGCCCGCCAGACTCCCGGGCGGCGCGCTCCCTCCCTGCAGGCCTTCAG

CCCGTCAGCATCCCCTTCCTCGGGGCCCTGCTCACTCCCAGCCTCCATCC

CCCTGCCATCTCCTCCGCCGGTCGCGTGCGGACACAAGGATGGGGACCTC

CCAGCGAGGAGCGCTCTGGGCGGGGCTCCGGACGCATGCGCGGCCCTCGT

ACGGAAGCCCGGAAGGAGGGGCAGGGGGCGGTGGCTCAGGTTTCTCCGGG

CGGCGGCGGCGGCGGCGGCGACGGCGACGGCGACGGCAGCGGGGACG

GCAGCAGTAGCGGGAGCAGCAGCGTGGACGCGGCTGGCGCTGGCGCCATG

AACCCGCTGTAAGGCGCAGGCTGTGCAGCACGGGGTGCGGGGGAGGAGGA

GGAGGACGCCGCGGTGAAGTTCTCCGCCATGAACCTGAGGGGCCTCTTCC

AGGACTTCAACCCGAGGTGAGGCGGCGTCGTTGGCGCCCCCGGGAGTCCG

CGCTGCGGGCTCGGGCGCGGGCTGGTGTTCGGCTCCGGGAGGCACGGCG

GGCGAGATGCTGCAGCCCGAGGACCCGGGCGCCTGCCCGAGCCTCCCTGC

GGGTGCAAGCGGTCCCCAGGCAAAACAGTCGGCCTCGGCGCCCGCCCGCT

TCCTCCTCCCGTGCCCGGTGCTTTCAGCCCCTGCCCGGCCACGGCCGGAA

GGGCCCGGCCGCGAGCCCCGTCCTGCCCCAAGGGAACCCCATTCTTTTCT

GCTTGCTGTCCCTCATTGGTGTCCCAACTTCTTCGTCTCGGTTCCATCCT

CTTCTGCGCCGCTGCGGGCCCTCCATTCTCCGCGTCAGGGCCGTCTCACT

CGACCCAACACCCCTACCCCCACCCCAGCTGTTTCCTCCAGTTCCTCGCA

GTCCTTGGGGTTTTCCTTGGGTTTATGCCCATCCCTCTCTTGTTTGCTTC

TTTGTTGAACGGATACCTGAAACACTGTTGAATCCTTGGAGTCAGTGTCG

GGGTATGGCAATACCTTATATAATGCATTTCTGGGTGAGCCTGATCATTT

TCCATACTCATTTTCTCATCAGTCTTCACTACAAGTTTATTTGCAGGAAG

TAGATATTGCTGTCCTTCTTTTCCAGATGGGAACACCCAGTGGACAGTG

TGGAGAAAACACTGGCTAAGCACTCAAGCGCCTGTCCTTGCACTTGCCCG

ACTGTTTTGTAACTGTTCTTTACCCCAGGCTGTGAGCTCCCTGAAGCTGA

GACCATCTCCTGCTCATCTCAGTGTCCCCAGCGCCTCCCACCCACCGTAT

CTGGCACATAGTAGGCACATATAAAATGTTTGTGGAACTAAACTGAGCCC

AAAGACTTGGATTGGAGACGAGGCCATATGTAACTGGGTGATTCTCTGCC

CTTCTTTGGCCCTTCTGTAAAATGAGGAGTTGGCCTAACTGATCTCTTAA

ATGCACTACTCTCCGAAAGGAGTATCCGTTTCCCTTATTTGCCAGTTGGG

AAGACGTGCTCAGTAAATATTTGTGTGCTGTAACCTATGTTAGGTGCTTT

AGATGCTGGCGGTCTCAGCATGGGTGAAGAAGGGCTTGTACACTTAAGA

TGCCTTACAGTACTGTGCAGTGCTGTACTGCGGGGGCCAACTCTGGGGAC

CTATGCCTTGGCTGCTTGTTGAGGATGAAAGGAAGTTTTAGGGGAGTATT

TGTATGTTGAGGGTGCAGTCTCCCTAGGGATGGTGACATTTTAACTTGTG

AGTCATTGTGACTTTGTATGTGCCCTTATTCCACTTTGAGTTCATGTTCT

GGTTAGGAGTGCCAGTGTCTCTAACACGGTGCAGACATTATCATTGTTGG

CTTCGAAGGCATAGAGGAGGTAACAGAACTAACTGCAGTCCCTTCCTCTG

CTGCATCAGGGGGTTAAGATTGGTCTGCAGGGTAGTAGGGTTGGTGCTGT

GGCTGGACAAGCCCTGTATGTCTTCTATTTGGAGATGGTGATAAGAAAGT

TAAGTAAAAACTGAATTGTTTTGTGCCCTTGGGCAACTCACTTATCTATT

GTTTTATCTGTAGAATGAGTATAATCTCTCAGTGGGGTAGGGAGGCCAAT

TAAGGATTGATTACAAAGTGCCTTACAAATAGAAAGCTACAGTGACTTGT

TTGCAAGGTGACAGAGAATTCAGAAGCCTCAAGAAACTGCCTTAAGTGAT
```

```
CAAACAGGCTAACGGAGTTGCCAAAGCAAAATAGTGCTGCACTGATACTA
CCTTTAACCGTTTTTTCCTTTAGCCCTTTTCCCCCCAAAAAAATTAGTAT
ATGAAATTACAGTGAAATACCTGGTATCTAAGCAGATTTATAGTAATTCT
CAACATATTCATCAATCTCTTAATTCTACCTGCATTAAAATGTATTTCTA
CCTGAAAAGTTTAAAGGTCTTTTATACTGTGCCATTTTCCTGATTCATTG
TTGCCAGAGGTAGTGAGTTCCTTAATTTTACAGATATTTCAAGAGGACAT
TGGCCAGGTATTATTGGTAAATCAGATTTGTTTTTTTAGCTGGTAGTGTT
TCACCTCTCCTGAGCACTCCTAGTTTTTGACAGTGTGCTTTAGTCTCCTT
CCATGCTGAGGAAGGCCTTCTCTATAGGAGAAAGAAAACTGAGGGGTGTA
CACAGGAAGTTACCTTATGCTGGGGACTCAAACCTTGATGCTACTGCTTT
GCTCCCTGCCTCTATTTTTGAACCAATTCAACATCTCCCTCCTACCCCAG
GACCTTGTCACACACTGTTCTCTTTACCAGGAATGTTTCCCTCTCTTTTC
CTCTCCTCCAGACCTAGTGAACTCCTATTTATCCTCACTTGGCACTTGCT
AAGGGAAGCATTCCTGACTTCCCTGACCAGATTTACTGCTCCCTGTTTCT
ACAGTTCCTGTAGTATTTACTACTCCTCCATCATAGTGCATATTTGTACC
CTTGTGTCTGTCTGGATGCTTATTTGATTAATACCTGCCTCCCCCACTAA
ACTTTAAGCTCCATGGGGTCAAGGCCGTGACTGTGTCAGTATCGTAGCCT
GCATACTTGGAATAGTACCTGGCTCAATAAATATTTGTGGAGTAAATAAC
TGAATAACTCTCCAGAGCCTATAAGATAAATCTAGAGCTGCTGCTTTCAA
TCACTGCTTTCCTGGTGGTCTGTGGCCTGGTTCTCTTTCTTCTCACACTC
TTCCCACCTTCAGAGTGCAGCCATTGCTTTGGAGAGATGGGAGAGAACAT
GGCACTAAGGCAGAATATGGCTATATTTACTTTGAAGAGCATGTCTTTGT
CATAGAAATAGTCACTGTCATGGTTTGGTGGGTCCCAAGGCATGGGTCAT
GGCTCCAGATCCCCTTTCCAGCCTTTTGGATCTTGGTAAGTCTGAACCCA
CTGCTGCGTTGGCAAGGCTCTGGAAACTATAGTGACAGAGAATGATTCAC
AAGTGTCAACACTCAGATGTACAGGGCTGCCAGCTGACCCACTCTACCTA
TTTCCATCTGGCACTGAACTGGTTGATCATGAACTTCTTTTCATAATTGC
TTTTTAGTTATGCAGGTTAAGACATGCCGAAACAGATGTACCGGACCCAC
AAACAAGTCCTTCCTTGAATGCCTGAGGCTTCCTAACAGTGAAAGAGCCC
TGTTCTTAGAGTAGGCAAACTGATTCTGAGGCATTGTAGGTGGTAGGGAT
CTGGTAGTAGGTAGCATTAGGTGGGCTCCCGGCACTCACCATGGAGCCTT
GAAATTTTCTGCTACTTTGGGGGAGTTGCTGGTTCAGAGAAGGCCCTTCC
ACCCTGGTAGCCATGTGGCACTGGAAGGCTGTGAAAACTCTGCTGGGCCT
TCTTAGTCATCGTTGTGAGCTCCTGATGGGAGTGTGGTGTATCCCTCAG
GTGTGCTAGACTGGAACAAAGGCTGAGAAGTGTTGCTCTGGGGGTTCCAA
CTTGTGGGCATGGGGTACTGATGAGATCAGTAGTGTTTGGAGACTTCTGT
ATGCTCCATCTTCAGAAGACATTCTGGAGTCCATATAAGTTATCTTGTCT
CTTGTTTGAAGCAGGAAAAAGGAATGCGATTGCTGGTAATATAGTTCACT
AAAGTCAGCTACCTGGCCTCTAACAGTTATTTGCAAAGTATATTATAACA
TTGATTCCTCAAACATCTAGATTCCTATCTCGTGCCAAGTGATGTACTAG
GTGCTCTAAGTACAAAAATAAAGGAATATAGTCCTCCTCTCAATGCGTAA
GCCTAGTGGAAGAAGCAGAAATGAAAGGGAAATAAGAATTCAATAGAGTA
TGAGGCATTACAGTGAAAGAAACCAAATGTCTTAGAAGTACAAATGGCAG
AGCTACTAATTCTGTCTCGAGCAGGCAGGGAAGAGTCTATAGTGGAAATG
ACTTTTGAGCTAGATTTTGAATTGAGCTAGTCTTTTGAGCCAGACTTTTG
AGCTAGAATTGTAGGGTTGTCATCAGACCAGAGAGTAGGAAGGGTACCTT
GTGAGGAAGAGAGAGAGAGATCAGATTGTTACTGTGTCTATGTAGAAAAG
GAAGACATAAGAAACTCCATTTTGATCTGTACTAAGAAAAATTGTTTCTG
CTTTGAGATGCTGTTAACCTGTAACTTTAGTCCCAACCCTGTGCTCACAG
AAACCTGTGCTGTAATGAATCAAGGTTTAATGGATTAGGGCTGTGCAGG
ATGTACCTTGTTAACAATATGTTTGCAGGCAGTATGCTTGGTAAAAGTCA
TCGCCATTCTCCATTCTCGATTAACCAGGGACACAGTGCACTGCGGAAGG
CCGCAGGGACATCTGCCCAAGAAAGCCTGGGTATTGTCCAAGGTTTCCCC
CCACTGAGACAGCCTGAGATATGGCCTTGTGGGAAAGGAAAGACCTTACC
ACCCCCCAGCCCGACACCCGTAAAGTGTCTGTGCTGAGGAGGAGTAGTGA
AAGAGCGGGGCCTCTTTGCAGTTGAGATAAGAGGAAGGCTTCTGTCTCCT
GCTCATCCCTGGGAATGGAATGTCTCTGTGTAAAGCTGACCATTCCCATT
CGTTCTATTCTGAGATAGGAGAAAACCACCCTGTGGCTGGAGGCGAAGTA
TGCTGGCAGCAATACTGCTCTGTTACTCTTTGCTACACTGAGTTGTTTGG
GTAAAGAGAAACATAAATCTAGCCTGCGTGCACATCCAGGCACAGTACCT
TTCCTTGAACTTATTCATGATACAGATTCCTTTGCTCACGTTTCCCTGCT
GACCTTCTCCCCACCTGTTGCCCTGCTACACTCCCCTCGCTAAGATAGTA
AAAATAATGATCAGTAAATACTGAGGTAACTCAGAGGCTAGCGCTGGTGC
GGGTCCTCCGTATGCTGAGTGCCGGTCCCCTGGGCCCACTGTTCTTTCTC
TATACTTTGTTTCTGTGTCTTATTTCTTTTCTCAGTCTCGTCCCACCTGA
CGAGAAATACCCACAGGTGTGGAGGGGCTGGCCCCTTTCAGTATCTCAGA
AGGGACAAAGTACACAAAGGCATGGGGTCATGATAGTGCCTGGTATGTTC
AGGTAGTGAAGAGGTCCATGTGGTATGAGCACTGCAGATGATATGTGTCG
TATGAATTAAAAATACATAGTTACTGCAAATAGTTTTTACAGGTTATTGT
TTTTAAGAAAGCAGTATCTAATGCACGAGTGTACTGTCAGTACTGTCAAT
GAACTACTTACCACTCAAGTGACTGCTTACGCGTCGAATCACTAGTGAAT
TCGC

SEQ ID NO:16 (pTM-final)
GTACGGAAGCCCGGAAGGAGGGGCAGGGGGCGGTGGCTCAGGTTTCTCCG
GGCGGCGGCGGCGGCGGCGGCGGCGACGGCGACGGCGACGGCAGCGGGGA
CGGCAGCAGTAGCGGGAGCAGCAGCGTGGACGCGGCTGGCGCTGGCGCCA
TGAACCCGCTGTAAGGCGCAGGCTGTGCAGCACGGGGTGCGGGGGAGGAG
GAGGAGGACGCCGCGGTGAAGTTCTCCGCCATGAACCTGAGGGGCCTCTT
CCAGGACTTCAACCCGAGGTGAGGCGGCGTCGTTGGCGCCCCCGGGAGTC
CGCGCTGCGGGCTCGGCGCGGGCTGGTGTTCGGCTCCGGGGAGGCACGG
CGGGCGAGATGCTGCAGCCCGAGGACCCGGGCGCCTGCCCGAGCCTCCCT
```

-continued

```
GCGGGTGCAAGCGGTCCCCAGGCAAAACAGTCGGCCTCGGCGCCCGCCCG
CTTCCTCCTCCCGTGCCCGGTGCTTTCAGCCCCTGCCCGGCCACGGCCGG
AAGGGCCCGGCCGCGAGCCCCGTCCTGCCCCAAGGGAACCCCATTCTTTT
CTGCTTGCTGTCCCTCATTGGTGTCCCAACTTCTTCGTCTCGGTTCCATC
CTCTTCTGCGCCGCTGCGGGCCCTCCATTCTCCGCGTCAGGGCCGTCTCA
CTCGACCCAACACCCCTACCCCCACCCCAGCTGTTTCCTCCAGTTCCTCG
CAGTCCTTGGGGTTTTCCTTGGGTTTATGCCCATCCCTCTCTTGTTTGCT
TCTTTGTTGAACGGATACCTGAAACACTGTTGAATCCTTGGAGTCAGTGT
CGGGGTATGGCAATACCTTATATAATGCATTTCTGGGTGAGCCTGATCAT
TTTCCATACTCATTTTCTCATCAGTCTTCACTACAAGTTTATTTGCAGGA
AGTAGATATTGCTGTCCTTCTTTTCCAGATGGGGAACACCCAGTGGACAG
TGTGGAGAAAACACTGGCTAAGCACTCAAGCGCCTGTCCTTGCACTTGCC
CGACTGTTTTGTAACTGTTCTTTACCCCAGGCTGTGAGCTCCCTGAAGCT
GAGACCATCTCCTGCTCATCTCAGTGTCCCCAGCGCCTCCCACCCACCGT
ATCTGGCACATAGTAGGCACATATAAAATGTTTGTGGAACTAAACTGAGC
CCAAAGACTTGGATTGGAGACGAGGCCATATGTAACTGGGTGATTCTCTG
CCCTTCTTTGGCCCTTCTGTAAAATGAGGAGTTGGCCTAACTGATCTCTT
AAATGCACTACTCTCCGAAAGGAGTATCCGTTTCCCTTATTTGCCAGTTG
GGAAGACGTGCTCAGTAAATATTTGTGTGCTGTAACCTATGTTAGGTGCT
TTAGATGCTGGCGGTCTCAGCATGGGGTGAAGAAGGGCTTGTACACTTAA
GATGCCTTACAGTACTGTGCAGTGCTGTACTGCGGGGCCAACTCTGGGG
ACCTATGCCTTGGCTGCTTGTTGAGGATGAAAGGAAGTTTTAGGGGAGTA
TTTGTATGTTGAGGGTGCAGTCTCCCTAGGGATGGTGACATTTTAACTTG
TGAGTCATTGTGACTTTGTATGTGCCCTTATTCCACTTTGAGTTCATGTT
CTGGTTAGGAGTGCCAGTGTCTCTAACACGGTGCAGACATTATCATTGTT
GGCTTCGAAGGCATAGAGGAGGTAACAGAACTAACTGCAGTCCCTTCCTC
TGCTGCATCAGGGGGTTAAGATTGGTCTGCAGGGTAGTAGGGTTGGTGCT
GTGGCTGGACAAGCCCTGTATGTCTTCTATTTGGAGATGGTGATAAGAAA
GTTAAGTAAAAACTGAATTGTTTTGTGCCCTTGGGCAACTCACTTATCTA
TTGTTTTATCTGTAGAATGAGTATAATCTCTCAGTGGGGTAGGGAGGCCA
ATTAAGGATTGATTACAAAGTGCCTTACAAATAGAAAGCTACAGTGACTT
GTTTGCAAGGTGACAGAGAATTCAGAAGCCTCAAGAAACTGCCTTAAGTG
ATCAAACAGGCTAACGGAGTTGCCAAAGCAAAATAGTGCTGCACTGATAC
TACCTTTAACCGTTTTTTCCTTTAGCCCTTTTCCCCCCAAAAAAATTAGT
ATATGAAATTACAGTGAAATACCTGGTATCTAAGCAGATTTATAGTAATT
CTCAACATATTCATCAATCTCTTAATTCTACCTGCATTAAAATGTATTTC
TACCTGAAAAGTTTAAAGGTCTTTTATACTGTGCCATTTTCCTGATTCAT
TGTTGCCAGAGGTAGTGAGTTCCTTAATTTTACAGATATTTCAAGAGGAC
ATTGGCCAGGTATTATTGGTAAATCAGATTTGTTTTTTTAGCTGGTAGTG
TTTCACCTCTCCTGAGCACTCCTAGTTTTTGACAGTGTGCTTTAGTCTCC
```

```
TTCCATGCTGAGGAAGGCCTTCTCTATAGGAGAAAGAAAACTGAGGGGTG
TACACAGGAAGTTACCTTATGCTGGGGACTCAAACCTTGATGCTACTGCT
TTGCTCCCTGCCTCTATTTTTGAACCAATTCAACATCTCCCTCCTACCCC
AGGACCTTGTCACACACTGTTCTCTTTACCAGGAATGTTTCCCTCTCTTT
TCCTCTCCTCCAGACCTAGTGAACTCCTATTTATCCTCACTTGGCACTTG
CTAAGGGAAGCATTCCTGACTTCCCTGACCAGATTTACTGCTCCCTGTTT
CTACAGTTCCTGTAGTATTTACTACTCCTCCATCATAGTGCATATTTGTA
CCCTTGTGTCTGTCTGGATGCTTATTTGATTAATACCTGCCTCCCCCACT
AAACTTTAAGCTCCATGGGGTCAAGGCCGTGACTGTGTCAGTATCGTAGC
CTGCATACTTGGAATAGTACCTGGCTCAATAAATATTTGTGGAGTAAATA
ACTGAATAACTCTCCAGAGCCTATAAGATAAATCTAGAGCTGCTGCTTTC
AATCACTGCTTTCCTGGTGGTCTGTGGCCTGGTTCTCTTTCTTCTCACAC
TCTTCCCACCTTCAGAGTGCAGCCATTGCTTTGGAGAGATGGGAGAGAAC
ATGGCACTAAGGCAGAATATGGCTATATTTACTTTGAAGAGCATGTCTTT
GTCATAGAAATAGTCACTGTCATGGTTTGGTGGGTCCCAAGGCATGGGTC
ATGGCTCCAGATCCCCTTTCCAGCCTTTTGGATCTTGGTAAGTCTGAACC
CACTGCTGCGTTGGCAAGGCTCTGGAAACTATAGTGACAGAGAATGATTC
ACAAGTGTCAACACTCAGATGTACAGGGCTGCCAGCTGACCCACTCTACC
TATTTCCATCTGGCACTGAACTGGTTGATCATGAACTTCTTTTCATAATT
GCTTTTTAGTTATGCAGGTTAAGACATGCCGAAACAGATGTACCGGACCC
ACAAACAAGTCCTTCCTTGAATGCCTGAGGCTTCCTAACAGTGAAAGAGC
CCTGTTCTTAGAGTAGGCAAACTGATTCTGAGGCATTGTAGGTGGTAGGG
ATCTGGTAGTAGGTAGCATTAGGTGGGCTCCCGGCACTCACCATGGAGCC
TTGAAATTTTCTGCTACTTTGGGGGAGTTGCTGGTTCAGAGAAGGCCCTT
CCACCCTGGTAGCCATGTGGCACTGGAAGGCTGTGAAAACTCTGCTGGGC
CTTCTTAGTCATCTGTTGTGAGCTCCTGATGGGAGTGTGGTGTATCCCTC
AGGTGTGCTAGACTGGAACAAAGGCTGAGAAGTGTTGCTCTGGGGGTTCC
AACTTGTGGGCATGGGGTACTGATGAGATCAGTAGTGTTTGGAGACTTCT
GTATGCTCCATCTTCAGAAGACATTCTGGAGTCCATATAAGTTATCTTGT
CTCTTGTTTGAAGCAGGAAAAAGGAATGCGATTGCTGGTAATATAGTTCA
CTAAAGTCAGCTACCTGGCCTCTAACAGTTATTTGCAAAGTATATTATAA
CATTGATTCCTCAAACATCTAGATTCCTATCTCGTGCCAAGTGATGTACT
AGGTGCTCTAAGTACAAAAATAAAGGAATATAGTCCTCCTCTCAATGCGT
AAGCCTAGTGGAAGAAGCAGAAATGAAAGGGAAATAAGAATTCAATAGAG
TATGAGGCATTACAGTGAAAGAAACCAAATGTCTTAGAAGTACAAATGGC
AGAGCTACTAATTCTGTCTCGAGCAGGCAGGGAAGAGTCTATAGTGGAAA
TGACTTTTGAGCTAGATTTTGAATTGAGCTAGTCTTTTGAGCCAGACTTT
TGAGCTAGAATTGTAGGGTTGTCATCAGACCAGAGAGTAGGAAGGGTACC
TTGTGAGGAAGAGAGAGAGAGATCAGATTGTTACTGTGTCTATGTAGAAA
AGGAAGACATAAGAAACTCCATTTTGATCTGTACTAAGAAAAATTGTTTC
```

-continued

TGCTTTGAGATGCTGTTAACCTGTAACTTTAGTCCCAACCCTGTGCTCAC
AGAAACCTGTGCTGTAATGAATCAAGGTTTAATGGATTTAGGGCTGTGCA
GGATGTACCTTGTTAACATATGTTTGCAGGCAGTATGCTTGGTAAAAGT
CATCGCCATTCTCCATTCTCGATTAACCAGGGACACAGTGCACTGCGGAA
GGCCGCAGGGACATCTGCCCAAGAAAGCCTGGGTATTGTCCAAGGTTTCC
CCCCACTGAGACAGCCTGAGATATGGCCTTGTGGGAAAGGAAAGACCTTA
CCACCCCCCAGCCCGACACCCGTAAAGTGTCTGTGCTGAGGAGGAGTAGT
GAAAGAGCGGGGCCTCTTTGCAGTTGAGATAAGAGGAAGGCTTCTGTCTC
CTGCTCATCCCTGGGAATGGAATGTCTCTGTGTAAAGCTGACCATTCCCA
TTCGTTCTATTCTGAGATAGGAGAAAACCACCCTGTGGCTGGAGGCGAAG
TATGCTGGCAGCAATACTGCTCTGTTACTCTTTGCTACACTGAGTTGTTT
GGGTAAAGAGAAACATAAATCTAGCCTGCGTGCACATCCAGGCACAGTAC
CTTTCCTTGAACTTATTCATGATACAGATTCCTTTGCTCACGTTTCCCTG
CTGACCTTCTCCCCACCTGTTGCCCTGCTACACTCCCCTCGCTAAGATAG
TAAAAATAATGATCAGTAAATACTGAGGTAACTCAGAGGCTAGCGCTGGT
GCGGGTCCTCCGTATGCTGAGTGCCGGTCCCCTGGGCCCACTGTTCTTTC
TCTATACTTTGTTTCTGTGTCTTATTTCTTTTCTCAGTCTCGTCCCACCT
GACGAGAAATACCCACAGGTGTGGAGGGGCTGGCCCCTTTCAGTATCTCA
GAAGGGACAAAGTACACAAAGGCATGGGTCATGATAGTGCCTGGTATGT
TCAGGTAGTGAAGAGGTCCATGTGGTATGAGCACTGCAGATGATATGTGT
CGTATGAATTAAAAATACATAGTTACTGCAAATAGTTTTTACAGGTTATT
GTTTTTAAGAAAGCAGTATCTAATGCACGAGTGTACTGTCAGTACTGTCA
ATGAACTACTTACCACTCAAGTGACTGCTTACGCGTCGAATCACTAGTGA
ATTCGCGGCCGCCTCGAGTCTAGAACTAGTGGATCCCCCAAACGGGCCCT
CTAGACGCGTTGACATTGATTATTGACTAGTTATTAATAGTAATCAATTA
CGGGGTCATTAGTTCATAGCCCATGATATCATATGGAGTTCCGCGTTACA
TAACTTACGGTAAATGGCCCGCCTGGCTGACCGCCCAACGACCCCCGCCC
ATTGACGTCAATAATGACGTATGTTCCCATAGTAACGCCAATAGGGACTT
TCCATTGACGTCAATGGGTGGAGTATTTACGGTAAACTGCCCACTTGGCA
GTACATCAAGTGTATCATATGCCAAGTACGCCCCCCTATTGACGTCAATG
ACGGTAAATGGCCCGCCTGGCATTATGCCCAGTNCATGACCTTATGGGAC
TTTCCTACTTGGCAGACATCTACGTATTAGTCATCGCTATTACCATGGTG
ATGCGGTTTTGGCAGTACATCAATGGGCGTGGATAGCGGTTTGACTCACG
GGGATTTTCCAAGTCTCCACCCCATTGACGTCAATGGGAGTTTGTTTTGG
CACCAAAATCAACGGGACTTTCCAAAATGTCGTAACAACTCCGCCCCATT
GACGCAAATGGGCGGTAGGCGTGTACGGTGGGAGGTCTATATAAGCAGAG
CTCTCTGGCTAACTAGAGAACCCCTGCTTACTGGCTTATCGAGATATCTG
CAGAATTCATCTGTCGACTGCTACCGGCAGCGCGCAGCGGCAAGAAGTGT
CTGGGCTGGGACGGACAGGAGAGGCTGTCGCCATCGGCGTCCTGTGCCCC
TCTGCTCCGGCACGGCCCTGTCGCAGTGCCCGCGCTTTCCCCGGCGCCTG

-continued

CACGCGGCGCGCCTGGGTAACATGCTTGGGGTCCTGGTCCTTGGCGCGCT
GGCCCTGGCCGGCCTGGGGTTCCCCGCACCCGCAGAGCCGCAGCCGGGTG
GCAGCCAGTGCGTCGAGCACGACTGCTTCGCGCTCTACCCGGGCCCCGCG
ACCTTCCTCAATGCCAGTCAGATCTGCGACGGACTGCGGGGCCACCTAAT
GACAGTGCGCTCCTCGGTGGCTGCCGATGTCATTTCCTTGCTACTGAACG
GCGACGGCGGCGTTGGCCGCCGGCGCCTCTGGATCGGCCTGCAGCTGCCA
CCCCGGCTGCGGCGACCCCAAGCGCCTCGGGCCCCTGCGCGGCTTCCAGTG
GGTTACGGGAGACAACAACACCAGCTATAGCAGGTGGGCACGGCTCGACC
TCAATGGGCTCCCCTCTGCGGCCCGTTGTGCGTCGCTGTCTCCGCTGCT
GAGGCCACTGTGCCCAGCGAGCCGATCTGGGAGGAGCAGCAGTGCGAAGT
GAAGGCCGATGGCTTCCTCTGCGAGTTCCACTTCCCAGCCACCTGCAGGC
CACTGGCTGTGGAGCCCGGCGCCGCGGCTGCCGCCGTCTCGATCACCTAC
GGCACCCCGTTCGCGGCCCGCGGAGCGGACTTCCAGGCGCTGCCGGTGGG
CAGCTCCGCCGCGGTGGCTCCCCTCGGCTTACAGCTAATGTGCACCGCGC
CGCCCGGAGCGGTCCAGGGGCACTGGGCCAGGGAGGCGCCGGGCGCTTGG
GACTGCAGCGTGGAGAACGGCGGCTGCGAGCACGCGTGCAATGCGATCCC
TGGGGCTCCCCGCTGCCAGTGCCCAGCCGGCGCCGCCCTGCAGGCAGACG
GGCGCTCCTGCACCGCATCCGCGACGCAGTCCTGCAACGACCTCTGCGAG
CACTTCTGCGTTCCCAACCCCGACCAGCCGGGCTCCTACTCGTGCATGTG
CGAGACCGGCTACCGGCTGGCGGCCGACCAACACCGGTGCGAGGACGTGG
ATGACTGCATACTGGAGCCCAGTCCGTGTCCGCAGCGCTGTGTCAACACA
CAGGGTGGCTTCGAGTGCCACTGCTACCCTAACTACGACCTGGTGGACGG
CGAGTGTGTGGAGCCCGTGGACCCGTGCTTCAGAGCCAACTGCGAGTACC
AGTGCCAGCCCCTGAACCAAACTAGCTACCTCTGCGTCTGCGCCGAGGGC
TTCGCGCCCATTCCCCACGAGCCGCACAGGTGCCAGATGTTTTGCAACCA
GACTGCCTGTCCAGCCGACTGCGACCCCAACACCCAGGCTAGCTGTGAGT
GCCCTGAAGGCTACATCCTGGACGACGGTTTCATCTGCACGGACATCGAC
GAGTGCGAAAACGGCGGCTTCTGCTCCGGGGTGTGCCACAACCTCCCCGG
TACCTTCGAGTGCATCTGCGGGCCCGACTCGGCCCTTGCCCGCCACATTG
GCACCGACTGTGACTCCGGCAAGGTGGACGGTGGCGACAGCGGCTCTGGC
GAGCCCCCGCCCAGCCCGACGCCCGGCTCCACCTTGACTCCTCCGGCCGT
GGGGCTCGTGCATTCGGGCTTGCTCATAGGCATCTCCATCGCGAGCCTGT
GCCTGGTGGTGGCGCTTTTGGCGCTCCTCTGCCACCTGCGCAAGAAGCAG
GGCGCCGCCAGGGCCAAGATGGAGTACAAGTGCGCGGCCCCTTCCAAGGA
GGTAGTGCTGCAGCACGTGCGGACCGAGCGGACGCCGCAGAGACTCTGAG
CGGCCTCCGTCCAGGAGCCTGGCTCCGTCCAGGAGCCTGTGCCTCCTCAC
CCCCAGCTTTGCTACCAAAGCACCTTAGCTGGCATTACAGCTGGAGAAGA
CCCTCCCCGCACCCCCCAAGCTGTTTTCTTCTATTCCATGGCTAACTGGC
GAGGGGGTGATTAGAGGGAGGAGAATGAGCCTCGGCCTCTTCCGTGACGT
CACTGGACCACTGGGCAATGATGGCAATTTTGTAACGAAGACACAGACTG

```
CGATTTGTCCCAGGTCCTCACTACCGGGCGCAGGAGGGTGAGCGTTATTG
GTCGGCAGCCTTCTGGGCAGACCTTGACCTCGTGGGCTAGGGATGACTAA
AATATTTATTTTTTTTAAGTATTTAGGTTTTTGTTTGTTTCCTTTGTTCT
TACCTGTATGTCTCCAGTATCCACTTTGCACAGCTCTCCGGTCTCTCTCT
CTCTACAAACTCCCACTTGTCATGTGACAGGTAAACTATCTTGGTGAATT
TTTTTTTCCTAGCCCTCTCACATTTATGAAGCAAGCCCCACTTATTCCCC
ATTCTTCCTAGTTTTCTCCTCCCAGGAACTGGGCCAACTCACCTGAGTCA
CCCTACCTGTGCCTGACCCTACTTCTTTTGCTCTTAGCTGTCTGCTCAGA
CAGAACCCCTACATGAAACAGAAACAAAAACACTAAAAATAAAAATGGCC
ATTTGCTTTTTCACCAGATTTGCTAATTTATCCTGAAATTTCAGATTCCC
AGAGCAAAATAATTTTAAACAAAGGTTGAGATGTAAAAGGTATTAAATTG
ATGTTGCTGGACTGTCATAGAAATTACACCCAAAGAGGTATTTATCTTTA
CTTTTAAACAGTGAGCCTGAATTTTGTTGCTGTTTTGATTTGTACTGAAA
AATGGTAATTGTTGCTAATCTTCTTATGCAATTTCCTTTTTTGTTATTAT
TACTTATTTTTGACAGTGTTGAAAATGTTCAGAAGGTTGCTCTAGATTGA
GAGAAGAGACAAACACCTCCCAGGAGACAGTTCAAGAAAGCTTCAAACTG
CATGATTCATGCCAATTAGCAATTGACTGTCACTGTTCCTTGTCACTGGT
AGACCAAAATAAAACCAGCTCTACTGGTCTTGTGGAATTGGGAGCTTGGG
AATGGATCCTGGAGGATGCCCAATTAGGGCCTAGCCTTAATCAGGTCCTC
AGAGAATTTCTACCATTTCAGAGAGGCCTTTTGGAATGTGGCCCCTGAAC
AAGAATTGGAAGCTGCCCTGCCCATGGGAGCTGGTTAGAAATGCAGAATC
CTAGGCTCCACCCCATCCAGTTCATGAGAATCTATATTTAACAAGATCTG
CAGGGGGTGTGTCTGCTCAGTAATTTGAGGACAACCATTCCAGACTGCTT
CCAATTTTCTGGAATACATGAAATATAGATCAGTTATAAGTAGCAGGCCA
AGTCAGGCCCTTATTTTCAAGAAACTGAGGAATTTTCTTTGTGTAGCTTT
GCTCTTTGGTAGAAAAGGCTAGGTACACAGCTCTAGACACTGCCACACAG
GGTCTGCAAGGTCTTTGGTTCAGCTAAGCTAGGAATGAAATCCTGCTTCA
GTGTATGGAAATAAATGTATCATAGAAATGTAACTTTTGTAAGACAAAGG
TTTTCCTCTTCTATTTTGTAAACTCAAAATATTTGTACATAGTTATTTAT
TTATTGGAGATAATCTAGAACACAGGCAAAATCCTTGCTTATGACATCAC
TTGTACAAAATAAACAAATAACAATGTGAAAAAAAAAAAAAAAAAAAA
AAAAAAAAAAAAAAAAGGTAGCAGTCGACAGATGAATTCCACCACACT
GGACTAGTGGATCCGAGCTCGGTACCAAGCTTAAGTTTGGGCTGCAGGAA
TTCTGATGGCTCTCAAAATTCCTGCCTCCTTTAGGGATAAAAGACTTTAA
GACTTTTTAACAAAAAGAAAAAGAAAAAAAAATTCCTGCCTCCTGGTG
TACACACACAGAAGGGTTCCCTCCCCTTGAATGTGACCAGGATCTGTGAA
AATAACGGGATAGCCGCTCCTGTGATTAGGTTATGTGGTAGACTAGAGCA
AGATTCTCCTGCTGGTTTTGAAGAAGTCAGCTGCCATGTTGTGAGACTGT
CATGGGCTAGGGCATGAGCCTTTAAATATCTGGGAGCAACCCCTGGCCAG
CAGCCAGTGAGAAAACGGGCCCTCAGTCCTACAATCACAAGGAACTAAAT
TCTGCCAACAACCTGAAGGAACTTTGAAGAGGATCATGAGTCCCTTGATT
CAGCTTGATGAGCCCCTGAGCAGAGGATACAGCTAACTTGTACTAGGGAA
GTATAAAAAACATGCATGGGAATGATATATATCAACTTTAAGGATAATTG
TCATACTTCTGGGAATGAAGGGAAAGAAATGGGGCTTTAGTTGTATTATG
ATCTTTAATTTCTCAAAAAAAATAAGATCAGAAGCAAATATGGCAAATG
TTAATACTTTTGTGGGTACGTAGGTATTCAGCATACCCTTTTTTCTGAGT
TCAAAATATTTTATAATTAAAATGAAATGCAGGCCAGGCACAGTGGCTCA
TGCCTATAATACCAGCACTTTGCGAGGCCGAGGTGGGAGGATGGCTTGAG
GCCAGACCAGCCTGGCCAACATGGCAAAACCCCATCTCTACTTAAAAAAA
AAAAAACTATATATATATATGTGTGTGTGTGTATATATATATGT
ATATATATTTATATATGTGTGTATATATATATATGTATATATATTTATAT
ATGTGTGTGTATATATATATACACACACACACATATATACATACATAC
ATACACACACACACACACAATTAGCCAGGCATGGTGGCGCACACCTGT
AGTCCCAGCTACTTGGGAGGCTGAGACATGAGAATTGCTTGAACCTGGGA
GGCAGAGTAGTTAGTGAGCTGAGATCATACCACTGCACTCCAGCCTGGTG
ACAGAGTGAGACTCTGTCTTAAAAAAAATAAAAATTAAAATTAAATGCAA
AAGGTCCAAGTGAATTGAAGAGGAAAGGGGTATCAAGGAAGGTTTTGTGG
AGGTGACGTTTGAGCTGGGTCTTAAATGACTTAAACATGGGATAAGAAGG
GAGGGAATAAGGACATTTCAGGTACGAGAAATAAGGAGCAAACAGTGGAA
ACAACCTAACGTCTGTCAACCAGTGAATGGATAACAAAAATGTAATTCAG
ATGGTATCCAACTTACGATGGTTCAACATGAGATTTTTCTGACTTTAGGA
TAGATTTATCAAAGTAGTAAATCCATTTTCAACTTATGATATTTTCAACT
TCAGATGGGTTTATCAGGACACAGTTGAGGAACACCTGTCTATCCATACA
ATTTGGCAATAAAAAGGAAATGAGTGCAGATATACTCCACAACATGAATG
AACCTTGAAAACATTAAGTGAGAGAAGCCAGATACAAAAGGCCACATATT
GTATGATTCTATTTATACAAAATGTCCAGAATAGGCAAATCTTATAGACA
GCAAGTAGGTAGATGATCAGTTTGCTAGGTGCTGGGGGAAGGGGAAATGG
GGAGTGATGGCTAAGGGGATTGGGTTTCTTTGTGGGGCAATGAAAATGTT
TTAAAATTGAGCGTGATAATGATTGCACAATGCTGCATATATATATAATC
TATAGATTATATATATAAAGAGAGGCTGTTAGACAGTGATAAGTGATA
TATATATATATACATAGAGAGAGAGAGAGAGAGAGAGGCTGTTA
GTGATAAGTGATCAGGAAAATAAAAGTATTGAGGAGGAATACGAAGTTGA
CGGTGTGAAAACATGAGATTTTATATAGGATGGCCAGGGAAGGCCTTAAT
GAGAAAGTGACTTATGAGTAAAAACAAGGGATCCTAAACCTTAGCATGCA
TCAGAATCACTCGGAAACTTGTTAAAGCATAGCTTGCTGGGCCTCATCAC
AGATATTTTGATTCGGTAGGTTCTTGTCTGATATTAATACTTTTGGTCTA
GGGAACCACATTTTGAGAACCACTGAGCTAAAGGAAGTAAAGGTTTCCCT
TAGTTTACTAGCTGGTAACACTGGCCCAGGAGGCCTTTCTGGAAAAGGTC
CCAGTCCCCAAAGGAAGCTGGGGACTCGCGTTCACATCGTCAAGGTTTAC
CAAGTTGTGGCGGGCCTTTCCGTCTTGGAAAAAGCCTCAAAATGGCAGAT
```

-continued

TAGGGTGTCCATGGCCGGCGGAAAGGGTCTTTGAAGTTGCAGACCAGGAG
GGAAGAAGATTCTGGGCCTCCCCCATGCAGTGTCAGCTGGCAACAGAATG
CACCCCGGCTGGGTTGGAGGCCCTGGGTACTGGCTCTTCCACACCAGGGG
CCCACCTACCAAGGGCAGCAGGAGCATCTGCACCTCCTGCGCCAGGCGCC
CTTCAGTGCTTCCACTTGAGCACCTCTCCAGACACCAGCTAGGGTGACAG
TGGTACAAATACCAGACTCCCCTGGCCTGCTCACCTCACAGGGTAATGTG
CTGTGGAGTCAGGGGGACACAGCAACCACCAGATGACATGGCTGGCCCCG
GGGAGGACGACACGCAGATACGGCTACTTGGCACCTGTGATATTTTACAC
ACTCGAGAGGGCCCGCACCATCCTCAGCCCTCTCCCCACATTCACTCTT
AGTTCATGTCACCTCCACCCAGAGGGGACACAGGCCCACAGCGATGGCC
CCACACCCTGCCTGAGGTCGCCCACTTCCCAGGAGGCAGTCCTGGGACTT
CCACCCGACCAGGCCCCAGAGCCCACCGACTTAACCCCTCCAGAGGCTTG
TCGTTCATTACCTTATTCAAGATGGAGACCAGCCTTTTTGCGGAGAAAAT
GCGGGTGAAGGTCCTGAAAGTGCATTGACGCCGTTTTCGGAAGCCATACA
AGTTTAGCTGGCGGAAGAAGCTCTTTATCGAAGTTGTGGCAAACACTTTG
TGTGCGACGTCCCTTTTGAGAATCTCCTTTTCAAAGAGTTTTTGATTGAT
CACTCTACAAGCCCCACTGTCATCCCACCAGATGGACGAAAACTGGTTGC
TGCTGACCAGTCTCCACAGTTTCTGTGGAAAGGGGAGGGAGAGGAGATTA
TCTTCTCCCTGGGGCGGGACGTCACCGTCAGGGTGCGGCCTTCTGAACGA
AGCTTCCTCGGCCAGAGGTTGGAAAGCGATTTCTTCTGTCAGCAGCCTCA
AGTTAGGGCTCCCAGTGGACCCCGGGTCGTCCCAGGCAGGGGAAGGATCT
GCTGGGTGAAGGTAGGTCTCTGACTGCAACTGGGGAGGGAAAGGCACCCT
TTCCAAGCCATGATCCTGTCCTCTCGAATTTCTTTCTTCACAGCGAGCCA
TACTCAATGATCGCTTGTCCTCCATCTGGCAAACTTGCTAGTGCAGTGTG
GCCAGCAGCACCCCTTGGCAGTCATGTAACCAGCCCCATGACATCATAAA
GGGGCTCTGACTGCCGGGGGGTGGCATCTCCACCCCCAGCAAGTTGTGTA
ATAAAGGGCCAAGGCAGACAAGTAGCTGCCCATCTGCATGTGCACATTCT
GGTCCTCACAGTCATTTCAATGGGAAAGATGACACTAGTGCACAAGAGTG
CCGAGGGGCCCTGCCACACCGTAGATGCAGACCTGGAGCGGTCCCCTTGT
CCTAGAGCTCCTGAGCCAGGCACAACTACAGCAAAGCCCTGGCTCAGGAA
GGTCAGAGCTCACCGTCTGAGTCATGGGCCCACAGACCCCAGCACATGAC
TGACACTCGGAAGCACAGAACAAAGGGTAGGACGGTGCCCATGGGTCAGG
CTGTAGCCACGCCACCCTTTCCACCCTGTCCTAGCCAGAGGCAGCAATGT
GCTCCATACAGATCCTCCTAACACACCCACACTGTCGGTCCCCAGCACGC
AGATGCCCGACAGCCCCTTAGGCAAATGGCTTAGCTGACTGCCCCACCAC
ACGCCGTCGCCATGCAGTCCAGTGGGAGTCGGAGGCAGCCTCCTTCCTG
CCTCTCCTCGGCCTGCACGTGTCCCCCACCAGGCAGAGACCCTTCTACA
CCCCGGGTGTCTGCGGTCACATCGCGGTGGGGCATGCAGCTGTTGGCCTT
CGAGCATGTTTTGTTTTCCTTGGCCAGTGTCTCCAGAGAAACGCACGTGG
GTTTGTGTCCAGCGGTCCATCTCTGCAACAGTTGTTCCTTTGGGATTGGA

-continued

TGCTAGGAGGTCACGGGAGAGGTGTCCATCCAAAGCAGTGTCTGTGTCAC
ACACTGTCCCCACACACAGGGCCACCTCTGCACAGACTCCCCCGACTCGA
TTCTGGGCACAGAGCTCAGTGACCTTCCAGAGACTGCCACGAACCGGTGA
TGCCTCCACGCTTGAGACATCCTGACCGCAGGGCCCAAGGCGCACTGGCT
CAGGGGGTGACAGTGAGGGGTCTGCAAACAGACTGCTGATGCTCAACCCG
GCCGCTGCCGAGCTGTGTGACTTGGGCACGTCACTTAACCTCTCTCGGCC
TCTGTCTCCTCCCGGGGATAAGAGTAGTAGCACCTGCTTCCCGGGGCTGT
GAGGATCCAGTGGGACGTATAGGAACTAGCGAGGCACCGGCAGTTGGGTC
AGAGCTACTGTTGTCACTTCACAAGGCATTTTCTTCAACAGCAAGTCGGA
AATCTCATGAGCCTAAGGCAGAATCCACCTGTGGCCTCTGGTTACAACCC
ACAGGACTGAAAATCCTTCCAGCCACAGCAACTGGTGAATTTCCTGGTCA
ATTGCCACAAGTCATGAGCTGAACCCCACTTGAGTTTCAGTTCAGGCAGA
ACTCTAGAGACGACTAGGGCAAGCTAGACAGCGACTGCAGAGCCTTTTGT
TGCAGCGTGAGCAGTCCTCAGCTGTTGACATCACTGGGGAGCAAACGAGG
ACCAGGAGCGGTGAAAGGACAGTGTCTGCTGCAGATTGTCGTAGCACCCA
AGGAACACTCCAGAAAGCCTCCTAAGCAGTAACAAGTGTGGCAAGGTGTA
GCCCAGCCAACAGTGGCATCTGCGAGGCGTCCCCTCCTTCCTCCCACTAC
CCCGTATACCCTGGGACCTGTGCACTGAAGGACTCATTCTAAAGGCTGTG
CCCCTGCAGCCGCCAGCCTCACTCACTGGCTGCCTGTGCCAGCTAGAGAT
TTCTTTCCTCTGAGGCTGGCTGAGAGGACCACTCCAGTTTCCTGGCCCAT
CCAGCAAAGAAGATACACATCATGCACGTGTAAAATGAGGAACCGGTTTA
TTGAACAGCTTAAGGAGAGCAAAAATAGTGGCTTTAGCTACATTTTTTAC
ACACTGAGCAGGAAAGTCTAAACCATCCCGTTCCCCTGTACCCCAAAGAG
AACAGGGCTTGCTGGAGGCCAGTGCCAAGGGCGGAGTCGTGCTCGCAGCA
GACTTGAATTAACCCCATGTAGGCCGGCGAGCAGTTGCCCGCGTGAAAAC
ACCACCCTCTTCTCCTGGCTGAGAAGATCAAAGCTCTTTTTTTACCCTCT
TTTCAGCAAAGGACCTATTTGTTTTCAGGCAGGAGGATGTTAAACTTGCA
GCCTCTGACACACGGTGGAACCTGCAGTGCTTGGAGAAACGGCACGCACA
CGTGAAAACATCATGCCTACTCCAAAGCCTTCTTGTTGCTGGCAGGAGGG
AAGCTTGAGACTTTCCCACGCATAGTCGTGACCCGCGTGGCCGTTTCTGC
TCTCAGCAACATTCTCTAGTGTTCCGGCTTCAAGCAGCGCTTGTCAGGTT
TGAAGCTAGCCACTATTCTGAGAACGTCAGAAAAGCATGGACCATCTCTT
GCTTGGTGTTGCCGTTGTGGCAGTAGCAGCTACTACGTACCTGCACGAGT
TCCAGGGCAGAAGTGGCAATGTCCCATGAAGGCGTGGCACCCCACGGGGG
GGGGGGGGAGTGTGCCACGGGCGTCCACTTCTGCAGCAGAAGGCATGTG
CCTACAGCACAAGCTTGTAAAAAAATACTTGAACAGAATATGCTGTACAG
AACTAGGGGTTAACACCGCATATGAAGATGCTAAAACATTTGTATAAATA
CTCTGTATACAAGCATGGAGTCACTCCCGTAGAAAGGGCTCATCCGTGAG
GCTATGAAAAACTGCTGTCAGCATGCCCAAAGAGAAACTACTTCCACAGT
AGGAACAGAAAAAAGGACTGTGCTGTGTCTAAACACGTGGTGCATCAGAG

-continued

ACATAGTTACAGTTCCTACTGACTGCCCCAGCCACGACCTGGGAGTGCTG
AGGACCTGGGAGTGCTCAGCGAGCTGCAGGAGGTCAGCCCTGTGGAGAAA
TACATTTCTAAACAATACTTTTGATTGGGATTTCAGCACCGTATAGACAG
ATGTTCCTTCTGGGGGCCTGGCAAGCAGCCATCTCCCAGTGGGTCTGACG
GGGAAGAGGGGTACCTGGAGCCCCTCCCAGACAGACGGTAATCCCACCCC
TGTTCTCACACTCTTCCTGGCATCCGCATCTGCTGGCACACACCCCCGTC
ACCTGCCACTTCCGCGTCCCGTCGTGGTGAGTGGCTGATAGGCGCTGGAT
GCAAACAAGGCATGAGATGGACGTACCTGGAGACCCAGCTCCAGTACTGG
TTCTGGTCTGCGGGGTGAACGAGGGGGCAGAGGAAGGCGGAGAGAGTGCG
TCCCAGTCCACTTAAGCTCTGTCCCCGGAAGTGGCATCTAATCTGGCATT
TCGATATTTAATTTGGGAGGTGGGAGCACATACTTCCCAGGGCTCTGGGT
AATGACCACCCTGGCCTTCTTTCGAAACATGGGTGCGATTTTAGGGGCT
CCGGAACTGGGGTCTCTTCGGTTTCTTCATTATCTTCGTGATGGAGATCA
TAGGAAATGTTTCCATATTCTCGTAGAAATGGGAAGATTTCAAGCAGAAA
CTGACAGAAATCTTTGCGGATACCAAACCACCCTGAAAAATAAGAATTTT
TTATTTCACACACGAGGCTCAACTGACCTTCCTGTTAACTTTCTTTCCGT
AACAAGAAGTTTCACTCCTACAATGTCATAACATACTTTATCCAGACTCC
TGAGTCACAAAGCCTGAACAGGGCTTGAGTACCCAAAATGGGGAAGAAGT
GCAAATGCTAGCTCTGTGGTGCTTGGAGTGGGGTTCCCGGACCGGCAGGG
ACAGCGTCCACGGGGCCTAGTTAGGGATGCCATTCTCGGGCCCCAGCCCA
GACCTCCAGAAACTGAGTCGGGCTAGGGTGGGCTCCAGCGGTCCCCTTTT
CCTGGCCCTTTTGGGATTCTGCTGGATGCCCAAATTTGAGAACTACTGCT
CCAGTGAGTCTCAAAATATCTGTGGTGCGCAGACTACGGTGTCTTCCGCT
AATCTTCTCCAGCCAGGATAAACTCATGGATGACAGTGCCACCCAAGAAC
AAGATTTCTGTCACCCTCTGGAATCCGTGAGGGCGGTAGTCATGCACGGG
TTGGCCAGGAGGGGGCCTGAACTCATGGAGCCACCTTAAAGCCACTTTCC
CAGTCCCACTACTCCTCTCTGTAGGCTACTGGAGTGTCAGCTCGGTGCAA
GCCCTCCCTGCTCCCGGGTGCGGGTAGGGGGCAGAGGCACAAACAGCAA
GCACAGCCCGGGCTGCTGGGCTGCAGTGAGGCCCTGCCCCCAAACCCACT
GGCTTTCCGAAGGGCAATGCTCTGGGCTTCCGTGCCATGGAGCCCACAGC
CTTGCCAGGAAGGCACCCTCTGCAGAGATCGTTTTGGAAGTGTCTGCCTC
AGCAAGCAGGTGGAGGGAATAGAGTGTTAGCAAGGCAAGACAGGCAAGA
CTCGGGTGATGGCAGCAAGGATATGGGGAGGCAGAGCGGCCAACAGGGA
CCTAGGATGAATCCCAGGTTTGGGTGGGAGATGTGGATTTTCCATCAAAC
CCTCCCGGGCCTGGAAGAATCTGTCTTGATCCCCATTTTGCAGAGGAGG
GAACGGGATCTCTGAGAGGTTGCCTGCCGTGTCTGGTTCTACCTCAAATG
GCAGCGTGCACTGCGAGAAAAGTCCCGGTGCAGGCCAGCAGAACACCAGA
GTTACGGCATGCCCTTCCCTTAGAAGGTCCCAGAATTTCCTCAGCCCTCA
CTTTCCCACACAAGCTTCTAAATTGGGGCCCTCGGGGACTCATCCCTTCC
TAGACTTCTATCCGCCACCCCCCACCCCCTGGTCCCCCCCCAGACACACA

CCAAGGACTTCTGAAATGCTGAGTACATACAGTGGTTTCCTCCCTTCTGT
CCAAATGTGGTTGCCATCAGCGTGATCAACGAGAGCCAAAGGGGGACAAA
GATCGGGATGCAGGAGAAGGCGTTGTGGCCATCCAGTTTGTGAACCAGCA
GAATCTAAAGAAAGAGACATAGTCCCGGTTGATGCCAGCACCGAAAATGG
GCAGAGGCGGAAGCCAGACTTCATTAGGCAGTTCCTCCCCACCACCCCAC
CCCCGCGTGAGCTCCCACAAGAGGGAACATCAGCACCGCCAGAAAAAGGC
AGGAAACCACCTATCCCTGGGGAAAGCTCGAAATGAGCTTTTATGTCCCT
CTTCAGAGCTCGGCAATAGCCTATCCACTTGAAAAGTTCCCAGTGCCAGC
AGTTTTATGGCAAACTCCTCCGGGTGTTTGTTCTAAGGAGTCAACAGCTC
CCATTCTAGAATTCTCCACGTGACTCCAATACACAAATCTGACATCCCAC
TCTGCTTTCCCCAGAGTGGAAACTGGAGCCATACAGAGGCACCATGGCTA
AAAAGGTGCACTCTTCTCCCTGCCAGCCCCACGTGCTGCCCCCAAGAGAA
AGGAAGGATGCTCTCCTTTCACCGAAGCTCCCTCTCGGAGATGGCTGTGT
TCTCTCCCCTCTCCTGGAGTGGGCTCACTGTGAGCTCGAGGGACAGAGGC
TGCCTTTCTAGGGGTGCAGAATCCTGTCAGGGGAAGCGCAAGCTTCAGGG
GCTGAAGAGGCTTCCCGTGGAACGCTTACCTCAAATGTAAGAAGGGGCAC
GACGATGGTCATCCAGCTCAGGGCCATGGTTATGTGTGTCCTGCGCTGTC
CGCAATCACATCCATAGAGCGCAAGAACAAGACGGACCACACAATGTAGT
AGAGGACCACCAGGCACAGAAAGGACATGAGAATCCACAGCGGGACACAC
ACAACCTGGGGGTGGGTGAGAGAACAGCAAGAGAAGTCTCTTTAGAGCTT
CCAACCTGGCCTCTGATGGAAGGCATCTTTAGCACCTTGCTGTGTCTGTC
CAGTTAAGGCGGTCCTTCCTGTGAGCCGAATAAGGACCGTTCCATCTCCC
AGGACTGCTGGGAGCATCGCTCAGGACAGAAAAGGTATGGTATGTTCACT
ATGGGGCCTGCTGCCACCAGGGGACACACACGCTCAGTGAGTCATCAGTC
CCTCTTCCTTTGGGTGACAGACAGCCCTGCACCTGGCTCCGCAGCCTCTA
CTCTTCCAGAGGCCCACTCTCCCACACTCTCTCAGGCTCCTCTAGGTTCT
GCTGCCATCACAGCTTCCCGGGAAATGGGACACAACTGTCACCCTGTGCA
CACACACAAGATCTCACCCCAACAGACTCTCTTCACAGGCAACATTCCCA
CAACCTGCTGGGGGTACTTTGGCAACACAAATGGGAATGGGCTCCCAGA
AAGTCTGGCTGCCTGGGCTCCTAAGGATCCCTAACCTCACCCCTACCAAG
TTAGTGAACTTGGCGGGTTGATGCTGGATACAGGTTGATGCTGGATACGT
AGCGCTGCCGGGTCGTGACCCCTAAGGAATTATCCAAACTCTTGTTTTTA
GATGCTTTATTATATCAAACTCTCCTTTAAACAAGTGGCCCATCTGCTGG
GATTTGGAAGCCTGTAATACTGAAATTTTCATCATAATGGAAATTTTAAA
AACAGAATTTGACCCACCTGTTTTTAAAACACTTTCATTACTTAACAAGA
GGTCTAATCTTGGGCAAGTCTTGAAATTTCTCTGGCCTTAGTTTCCCATG
TGTTAAATGAAACTTGAAGCAGTTGGTCTCTTATAGTCTCCTGACTCTAA
CATTCTAAGAATTATATTTGTACAATAACTCAAAAATCACATAATTTAAT
TTACCATATGGACTCCAAAATATATTTTCTCATTAGGCTAAACTTGATCT
GCATTTTCTGGATGTGTCCATATTCTTGGACTACACTAAAACATGATACC

```
AATGCTTCCTCTCACCATAAACCCTCACTTCGCTTTCTACATTTAAGAAT
TTTATAGCTGGAAGAGTCCTTAACAGAAAATACCATCTAATAATTACCCC
TCAAAATCGAGAAAGTCCTATCTGTTCTTATGCTAGTTATAAGAATGAGG
CAGCATTTCACATAATGGTTATAAACACTGCCACAAGAAGATTCATGATG
TGTTGTTTATCTGTAGCTCTCATCATACTCTGTCATATAACTATAGCATT
AAGATTTTAATGTTCTATATATTCTTCTAAGACAGTGTTTACCAGAGTAA
GGCACAAAAGATCCACTGGTTTGCAAGAAAGATTAGAACTTTTAAATTTT
TTACCTCACCTTGTTTAATCTATATTTTTGTATGTATTTTGTAACATATA
TATTATTATTACCATAAATCATATATAATTTAAAATGCATATATTAGGGG
TAAATGCTCAGGAAACTTTTTATAAATTGGGCATGCAAATACAAGTTTGA
AGACTCACTGTTCTAGGTATTAAAAGTAAAGTTATAACCAAGTAAAGCTT
CCACCTTTTCATGTCTCAAAGCAGTTTATTGTTGGAGGTAAGATCTCTTA
GAAGCCTAAACAGGTCCAAGTACAGAATGAAGTAAGGCTAGCCCATAACT
TGTGGCAAGCAATTCATACTATTTCTCTCATGCTGAGCTCTCCTCAGTGA
AGCAGCTACTATAGACAACTGCAGCCTATTGGTAGCCTATTTTACAGGCA
GGAAAAAATTACTTTTTATTCAAAGTGGAACTCAGGACATGGGGAGAAA
ATGAATACAAAAATAGGGTCAATCCAAAGGCACACAGCAAATGAGTAAC
ACAGTTATGTTTTTTCCCATTTGTATGAGGTCCCAGTAAATTCTAAGTA
AACTGCAAATTTAATAATACACTAAAAAAGCCATGCAATTGTTCAAATGA
ATCCCAGCATGGTACAAGGAGTACAGACACTAGAGTCTAAAAAACAAAG
AATGCCATTATTGAGTTTTTGAATTATATCAAGTAGTTACATCTCTACTT
AATAAATGAGAAAACGAGGATAAGAGGCCATTTGATAAAATGAAAATAG
CCAAGAAGTGGTATTAGAGACTTGAATACAGGTATTCGGGTCCAAAGTTC
ATCTGCTCAAATACTAACTGGGGAAAAGAGGGAAAAATATTTATATACAT
ATATATCTGCACACAAAAATACCCCCAAAAGACAAAATGAGGCCAGGCAG
GGTGGCTCACACCCGTAATCCCGGTACTTTGGGAGGCTGAGGCAGGTGGA
TACCTGAGATCAGGAGTTGGAGATCAGCCTGGTCAACATGGTGAAACCCT
GTCTCTACTAAAGATAAAAAAATTAGCCAGGCATGGTGGCGTGCGCCTGT
AATCCCAGCTACTTGGGAGTCTGAGGCAGGAGAATCACTTGAACTGGGAA
GGGGAGGTTGCAGTGAGCCAAGATCGTACTACTGCACTCCAGCCTGGGCA
GCAGAGTGAGACTCCATCACAAAAATAAATAAATAAATAAAATACAATGA
AACAGAAAGTTCAAATAATCCCATAATCTTACCACCAAGAAATAACTTTC
ACTCGTTATACTTATTGATTTTTCCATAATAAATGTACTTTACTGTGACT
ATCATGAAAAGAAAGTTATTTTAGAAACAGAGAACTGTTTCAGATCAAAT
CTATGTAGTAGAACAGAGCCATTAGGTGGGAAAGACGAGATCAAACTAAA
TCTCAGAAGGCCTAAAAGGCTAGGTCCATTCCAGCACTAAAAACTGACCA
GACAAGTAATGGCTTCAACAGCTTCTAAATATGGACAAAGCATGCTGAAA
GGGAAGGACAGGTCTAACAGTGGTATATGAAATGAACAGGAGGGGCAAAG
CTCATTTCTCCTCTGAAGTTTTCCAAAGATGCTGAGGAGGACATTAGTTT
GACATGACCCTGATATGGGACAAGATAATTTCACAGAAGTTTTACATGTT
AAAGTTTTCTTATAGATACTCATTCAAGTAAGCAATGAACACTAAAATCT
AAAGAAAGAAAAGAGCTTTAGAGTCAGGTCTGTATTCAAATTCAAGCTCT
ACCACTTACTGGTTCTGTGACTTTGGGCAAGTCTTTTAACCTTATTAAGT
CTTAATTTCCTGATTTGTAAAATGGGGATATCGTCTCCCTCACAGGATTG
TTGTGAAACTTTTATGAGATTAATGCCTTTATATTTGGCATAGTGTAAGT
AAACAATAACTGGCAGCTTCAAAAAAAAAAGCAGTAGCATTCCATCATTT
ATTATTGGTTACTCTCAAAAAAGTTTTTCAATGTACTAGAAGATAAATAT
TCAAATACCTTAATATCTCCATTATTTTCAGGTAAACAGCATGCTCCTGA
ACAACCAATGGGTCAACAAATAAATTAAAAGGGAAATCTAAAAACATCTT
GATATTAAACTACATGGAAGCACAATATACCAAAACCAATGGTTCACACT
AGGAGAATTTTAAGGTACAAGAAAACTCTTTGAGATTTCTTAAAATAATA
GTATGTCTGAATTTATTGAGTGATTTACCAGAAACTGTTGTAAGAGCTCT
ACTTGCATTATAGCACTTAATCCTCTTAACTCTATGGCTGCTATTATCAA
CCTCACCCTAATCACATATGGGACACAGAGAGGTTAAGTAACTTGCCCAA
GGTCAGAGTTAGGAAGTACTAAGCCATGCTTTGAATCAGTTGTCAGGCTC
CGGAACTCACACTTTCAGCCACTACATAATACTGCTTTGCTATCTTTTAG
GAAACTATGTGAGTCTACCTCACATAGACTCACATAGGTTTGTTTTTTTT
TTTTTTTTAAAGGCTATCTTTTCCCCCATCAATGTTTTTTGAAGGATCCC
AAATTAGAGTCCCACAGAGGCAGACAGCAGTACTTGACAATATGGACATT
TAAGGTTAATGTTGGATTCTACTGTCTTTTTACTACATGACCTAGGGAAC
GATAATTAACCTAGACTGCTTCCAAGGGTTAAATAACCCATTTAGTTATA
CTATGTAAATTATCTCTTAGTGATTGATTGAAAGCACACTGTTACTAATT
GACTCGGTATGAAGTGCTTTTTTTTCTTCCCTTTCAAGATACATACCTTT
CCAGTTAAAGTTGAGAGATCATCTCCACCAATTACTTTTATGTCCCCTGT
TGACTGGTCATTCTAGTTAAAAAAAAAAAAAACTATATATATATATATCT
ACACACACATATGTATATGTATATCCTTATGTACACACACAAACTTCAAA
TTAAATGAGAACTAGAAGATTTGAGAAGTTAGCTAGCTAATATCCATAGC
ATTATGATATTCTAAATGATATGAATTATAAGAATTAGGTTTCCTGAAAT
GAATGACTAGAAAACTTTCAAGTAGAGATTAGTAAAAATTAAAAAGTCCT
AATCGGCCATTACTGATTTGATGTTTTTAAGAGTCCTAAAAAATGGGTTA
CATCCATTTTTAAGTGGGTAGTATTATAACAGCCACCCATCTTCAATCAC
AGTGATTTCTGAATTGTGAGGGAAGTTATTAGCATGACAGGTGTCTGGTT
CTGGCCCTGTACGATTCCCATGAGTCAAGCAAATTGTAAGGGCTGGTCTA
TATCACACCCAACCCCAAGGATATGTCCCTCAAAAGTCTAGCCCAGGCCC
CGTCATCTTCAGCATCATCTGGGAAACCAGGTCTGATTAGTAGTCCTTTA
AGGAATACCTCTTAGGCTCCCATTTTACTGCTATCACAGAATCCAATAAA
ACCCTTACAGGAGATTCAATGGGAAATGCTCAACACCCACTGTAGTTGGT
GGTGACAATGACCATAATTTGGCTGTGCTGGATTCAGGACAGAAAATTTG
GGTGAAAGAGCAGGTGAACAAAAGAGCTTCGACTTGCCCTAGCAGAGAGC
AAGCCATACCATACCACAAAGCCACAGCAATTACAACGGTGCAGTACCAG
```

-continued

```
CACAGTAAATGAACAAAGTAGAGCCCAGAAACAGACCCAGAACTATATGA
GGATTTAGTATACAATAAAGATGGTATTTCGAGTCAGTAGGGAAAAGATG
AATTATTCAATAAATGATGTTTGGCCAACTAGTAACCCATTTGGGAAAAA
ATAAAAGTATGGTCCCTACCTCACAGCATACACAAAAATAAATTCCAGAC
GGATTAAAATCTAAATGTAAAAAATAAAGCCATAAGTGGACTGGAAGAAA
ATAGAGAATTTTTTTTAACATCCGTAGAAAGGGTAAAAACCCAGGCATGA
CATGAACCAAAACTGAAGAGGTTCTGTAACAAATACCCCCTTTTATATAT
TGGGCTCCAACAATAAGAACCCATAGGAAAATGGAGAATGAACACAAATA
GACAATTTATAGAAGAGAAGGTTATAAGGTGTAAAATTATATCTATCTGA
GAAACAAACACTAAAACAATGTGATTCTACTGTTCTCCCACCCATACTGG
CAAAACTTAAGCCTGATAATATGCTGAGGGGAAATAAGCACTCTTGTTGG
TGAGAGTATTAATTGGCATAGCTTCTTTTGAAAATGACATAGCAATACCT
GTTAAAATTGCAAACATGCATGTCACTTAATCCAGTAATCCCACTTCTGG
GAATCAATGCTACAAAAACACTGACAAGTATACAAAGATACATTCAAGAG
TGTTCACTGGGCCGGGTGCGGTGGCTTCATGCCTGTAATCCCAGGGAGGC
AGAGGCAAGACGATCGCTTGACCCCAGGAGTTCAAGGCCAGCCCGAGAAA
CACAGCAAGACCCTGTCTCTCTTTTTTTATTTAAAAAATAAATGTTCAC
TGTATCAGTTGTTCACAAAAACAAACCAACATGTCCATTAACAGGGAACC
ATTTAAATTAATCAAGTTCATCTACACAATGTAATACCATGCAACTATTA
AAAAGCACCTGATAATCCAAAGCACACTGAGACAGAATAATGCTATTAAA
AACACCAAGTAGTGGAACACTGTGTTGCCTATGACACCATTTTTATTCAA
CATTTAAACAAATTTGTAACAGCAATTACATGAGTAGTGACAATGGCGTT
TATGAGACTTTTCACTTTTATGTGCTTCTATTTTTGTTATGCTTCTATAT
ATACATCCATTTATTATGGAGTGTTACTTTCAAAAATCACAAATGGGCCA
GTATTATTTGGTGTTGCAAGGTGAGCATATGACTTCTGATATCAACCTTT
GCATATTACTTCTCAATTTAGGGAAATTACAGACATCCCTTATTCTAACT
AACTTAAAACCCAGCATTTCAAACATACAGAATTGATGGGGAAAAAAAG
AAAGAAGAAAGAAAGAAAGGCAACAAGCTTCAGATGACAGTGACTCACA
TCAAATTATTTATAAAATCTGTTAAATAGTGCCATCTTCTGGAGATACCT
GGTATTACAGTCCAACTCCAGTTGATGTCTTTACAGAGACAAGAGGAATA
AAGGAAAAATATTCAAGAACTGAAAGTATGGAGTCATGGAAAAATTGC
TGTGATCCAAAGGCTACGGTGATAGGACAAGAAACAAGAGAACTCCAAGC
AGTAAGACACTGCTGTTCTATTAGCATCCAAACCTCCATACTCCTGTTTG
CCCCAAGGCTTTTTAAAAAATAGAGACAGGATCTCACTATTTTGCTCAG
GCTGGTCTTGAACTCCTGGACTCAAGCTATCCTCCTGCCTCGGCCTCCTA
AAGTGCCGAGATTACAGGCTTGAGTCACCATACCTGGCTATTTATTTTTT
CTTAACTCTCTTGCCTGGCCTATAGCCACCATGGAAGCTAATAAAGAATA
TTAATTTAAGAGTAATGGTATAGTTCACTACATTGGAATACAGGTATAAG
TGCCTACATTGTACATGAATGGCATACATGGATCAATTACCCCACCTGGG
TGGCCAAAGGAACTGCGCGAACCTCCCTCCTTGGCTGTCTGGAACAAGCT
```

-continued

```
TCCCACTAGATCCCTTTACTGAGTGCCTCCCTCATCTTTAATTATGGTTA
AGTCTAGGATAACAGGACTGGCAAAGGTGAGGGGAAAGCTTCCTCCAGAG
TTGCTCTACCCTCTCCTCTACCGTCCTATCTCCTCACTCCTCTCAGCCAA
GGAGTCCAATCTGTCCTGAACTCAGAGCGTCACTGTCAACTACATAAAAT
TGCCAGAGAAGCTCTTTGGGACTACAAACACATACCCTTAATGTCTTTAT
TTCTATTTTGTCTACCTCTTCAGTCTAGGTGAAAAAATAGGAAGGATAAT
AGGGAAGAACTTTGTTTATGCCTACTTATCCGCCCCTAGGAATTTTGAAA
ACCTCTAGGTAGCAATAAGAACTGCAGCATGGTATAGAAAAGAGGAGGA
AAGCTGTATAGAAATGCATAATAAATGGGCAGGAAAAGAACTGCTTGGAA
CAAACAGGGAGGTTGAACTATAAGGAGAGAAAGCAGAGAGGCTAATCAAC
AAGGCTGGGTTCCCAAGAGGGCATGATGAGACTATTACTAAGGTAGGAAT
TACTAAGGGCTCCATGTCCCCTTAGTGGCTTAGTACTATGTAGCTTGCTT
TCTGCAGTGAACTTCAGACCCTTCTTTTAGGATCCTAGAATGGACTTTTT
TTTTTTATCGGAAAACAGTCATTCTCTCAACATTCAAGCAGGCCCCAAGT
CTACCACACTCAATCACATTTTCTCTTCATATCATAATCTCTCAACCATT
CTCTGTCCTTTTAACTGTTTTTCTATACCCTGATCAAATGCCAACAAAAG
TGAGAATGTTAGAATCATGTATTTTTAGAGGTAGACTGTATCTCAGATAA
AAAAAAGGGCAGATATTCCATTTTCCAAAATATGTATGCAGAAAAAATA
AGTATGAAAGGACATATGCTCAGGTAACAAGTTAATTTGTTTACTTGTAT
TTTATGAATTCCCTAAAACCTACGTCACCCGCCCCGTTCCCACGCCCCGC
GCCACGTCACAAACTCCACCCCCTCATTATCATATTGGCTTCAATCCAAA
ATAAGGTATATTATTGATGATGTTAATTAACATGCATGGATCCATATGCG
GTGTGAAATACCGCACAGATGCGTAAGGAGAAAATACCGCATCAGGCGCT
CTTCCGCTTCCTCGCTCACTGACTCGCTGCGCTCGGTCGTTCGGCTGCGG
CGAGCGGTATCAGCTCACTCAAAGGCGGTAATACGGTTATCCACAGAATC
AGGGGATAACGCAGGAAAGAACATGTGAGCAAAAGGCCAGCAAAAGGCCA
GGAACCGTAAAAAGGCCGCGTTGCTGGCGTTTTTCCATAGGCTCCGCCCC
CCTGACGAGCATCACAAAAATCGACGCTCAAGTCAGAGGTGGCGAAACCC
GACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTC
CCTTCGGGAAGCGTGGCGCTTTCTCATAGCTCACGCTGTAGGTATCTCAG
TTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAAC
CCGGTAAGACACGACTTATCGCCACTGGCAGCAGCCACTGGTAACAGGAT
TAGCAGAGCGAGGTATGTAGGCGGTGCTACAGAGTTCTTGAAGTGGTGGC
CTAACTACGGCTACACTAGAAGGACAGTATTTGGTATCTGCGCTCTGCTG
AAGCCAGTTACCTTCGGAAAAAGAGTTGGTAGCTCTTGATCCGGCAAACA
AACCACCGCTGGTAGCGGTGGTTTTTTTGTTTGCAAGCAGCAGATTACGC
GCAGAAAAAAAGGATCTCAAGAAGATCCTTTGATCTTTTCTACGGGGTCT
GACGCTCAGTGGAACGAAAACTCACGTTAAGGGATTTTGGTCATGAGATT
```

ATCAAAAGGATCTTCACCTAGATCCTTTTAAATTAAAAATGAAGTTTTA

AATCAATCTAAAGTATATATGAGTAAACTTGGTCTGACAGTTACCAATGC

TTAATCAGTGAGGCACCTATCTCAGCGATCTGTCTATTTCGTTCATCCAT

AGTTGCCTGACTCCCCGTCGTGTAGATAACTACGATACGGGAGGGCTTAC

CATCTGGCCCCAGTGCTGCAATGATACCGCGAGACCCACGCTCACCGGCT

CCAGATTTATCAGCAATAAACCAGCCAGCCGGAAGGGCCGAGCGCAGAAG

TGGTCCTGCAACTTTATCCGCCTCCATCCAGTCTATTAATTGTTGCCGGG

AAGCTAGAGTAAGTAGTTCGCCAGTTAATAGTTTGCGCAACGTTGTTGCC

ATTGCTGCAGCCATGAGATTATCAAAAAGGATCTTCACCTAGATCCTTTT

CACGTAGAAAGCCAGTCCGCAGAAACGGTGCTGACCCCGGATGAATGTCA

GCTACTGGGCTATCTGGACAAGGGAAAACGCAAGCGCAAAGAGAAAGCAG

GTAGCTTGCAGTGGGCTTACATGGCGATAGCTAGACTGGGCGGTTTTATG

GACAGCAAGCGAACCGGAATTGCCAGCTGGGGCGCCCTCTGGTAAGGTTG

GGAAGCCCTGCAAAGTAAACTGGATGGCTTTCTTGCCGCCAAGGATCTGA

TGGCGCAGGGGATCAAGCTCTGATCAAGAGACAGGATGAGGATCGTTTCG

CATGATTGAACAAGATGGATTGCACGCAGGTTCTCCGGCCGCTTGGGTGG

AGAGGCTATTCGGCTATGACTGGGCACAACAGACAATCGGCTGCTCTGAT

GCCGCCGTGTTCCGGCTGTCAGCGCAGGGGCGCCCGGTTCTTTTTGTCAA

GACCGACCTGTCCGGTGCCCTGAATGAACTGCAAGACGAGGCAGCGCGGC

TATCGTGGCTGGCCACGACGGGCGTTCCTTGCGCAGCTGTGCTCGACGTT

GTCACTGAAGCGGGAAGGGACTGGCTGCTATTGGGCGAAGTGCCGGGGCA

GGATCTCCTGTCATCTCACCTTGCTCCTGCCGAGAAAGTATCCATCATGG

CTGATGCAATGCGGCGGCTGCATACGCTTGATCCGGCTACCTGCCCATTC

GACCACCAAGCGAAACATCGCATCGAGCGAGCACGTACTCGGATGGAAGC

CGGTCTTGTCGATCAGGATGATCTGGACGAAGAGCATCAGGGGCTCGCGC

CAGCCGAACTGTTCGCCAGGCTCAAGGCGAGCATGCCCGACGGCGAGGAT

CTCGTCGTGACCCATGGCGATGCCTGCTTGCCGAATATCATGGTGGAAAA

TGGCCGCTTTTCTGGATTCATCGACTGTGGCCGGCTGGGTGTGGCGGACC

GCTATCAGGACATAGCGTTGGCTACCCGTGATATTGCTGAAGAGCTTGGC

GGCGAATGGGCTGACCGCTTCCTCGTGCTTTACGGTATCGCCGCTCCCGA

TTCGCAGCGCATCGCCTTCTATCGCCTTCTTGACGAGTTCTTCTGAATTT

TGTTAAAATTTTTGTTAAATCAGCTCATTTTTTAACCAATAGGCCGAAAT

CGGCAAAATCCCTTATAAATCAAAAGAATAGACCGAGATAGGGTTGAGTG

TTGTTCCAGTTTGGAACAAGAGTCCACTATTAAAGAACGTGGACTCCAAC

GTCAAAGGGCGAAAAACCGTCTATCAGGGCGATGGCCCACTACGTGAACC

ATCACCCTAATCAAGTTTTTTGGGGTCGAGGTGCCGTAAAGCACTAAATC

GGAACCCTAAGGGAGCCCCCGATTTAGAGCTTGACGGGGAAAGCCGGCGA

ACGTGGCGAGAAAGGAAGGGAAGAAAGCGAAAGGAGCGGGCGCTAGGGCG

CTGGCAAGTGTAGCGGTCACGCTGCGCGTAACCACCACACCCGCCGCGCT

TAATGCGCCGCTACAGGGCGCGTCCATTCGCCATTCAGGATCGAATTAAT

TCTTAATTAACATCATCAATAATATACCTTATTTTGGATTGAAGCCAATA

TGATAATGAGGGGGTGGAGTTTGTGACGTGGCGCGGGGCGTGGGAACGGG

GCGGGTGACGTAGTAGTGTGGCGGAAGTGTGATGTTGCAAGTGTGGCGGA

ACACATGTAAGCGACGGATGTGGCAAAAGTGACGTTTTTGGTGTGCGCCG

GTGTACACAGGAAGTGACAATTTTCGCGCGGTTTTAGGCGGATGTTGTAG

TAAATTTGGGCGTAACCGAGTAAGATTTGGCCATTTTCGCGGGAAAACTG

AATAAGAGGAAGTGAAATCTGAATAATTTTGTGTTACTCATAGCGCGTAA

TACTG

What is claimed is:

1. A gutless adenovirus vector comprising the nucleotide sequence of SEQ ID NO:13 or SEQ ID NO:15.

2. The vector of claim 1 further comprising a polynucleotide encoding a functional thrombomodulin protein and a regulatory element operably linked to said polynucleotide sequence.

3. The vector of claim 2, wherein said regulatory element is a promoter.

4. The vector of claim 3, wherein said regulatory element is a CMV promoter or a RSV promoter.

5. The vector of claim 2, wherein said thrombomodulin protein has the amino acid sequence of SEQ ID NO:2.

6. The vector of claim 2, wherein said gutless adenoviral vector is produced by transfecting 293FLP cells with a linearized plasmid having the nucleotide sequence of SEQ ID NO: 16 followed with infection of a helper virus.

7. The vector of claim 1 comprising the nucleotide sequence of SEQ ID NO:13 and SEQ ID NO:15.

8. A gutless adenovirus vector comprising a polynucleotide encoding a thrombomodulin protein having the amino acid sequence of SEQ ID NO:2, a regulatory element operably linked to said polynucleotide sequence; and a stuffer comprising the nucleotide sequence of SEQ ID NO:13 or SEQ ID NO:15.

9. The vector of claim 8, wherein said stuffer comprises the nucleotide sequence of SEQ ID NO: 13 and SEQ ID NO: 15.

10. The vector of claim 8, wherein said gutless adenoviral vector is produced by transfecting 293FLP cells with a linearized plasmid having the nucleotide sequence of SEQ ID NO: 16 followed with infection of a helper virus.

11. The vector of claim 8, wherein said regulatory element is a promoter.

12. The gutless adenovirus vector of claim 11, wherein said promoter is a CMV promoter or a RSV promoter.

13. A pharmaceutical composition for treating a vascular disease, comprising the gutless adenovirus vector and a pharmaceutically acceptable carrier, wherein said vector comprises a polynucleotide encoding a functional thrombomodulin protein, a regulatory element operably linked to said polynucleotide sequence, and a stuffer comprising the nucleotide sequence of SEQ ID NO:13 or SEQ ID NO:15.

14. The pharmaceutical composition of claim 13, wherein said regulatory element is a promoter.

15. The pharmaceutical composition of claim 14, wherein said promoter is a CMV promoter or a RSV promoter.

16. The pharmaceutical composition of claim 13, wherein said thrombomodulin protein has the amino acid sequence of SEQ ID NO:2.

17. The pharmaceutical composition of claim 13, wherein said gutless adenoviral vector is produced by transfecting 293FLP cells with a linearized plasmid having the nucleotide sequence of SEQ ID NO: 16 followed with infection of a helper virus.

18. The pharmaceutical composition of claim 13, wherein said stuffer comprises the nucleotide sequence of SEQ ID NO: 13 and SEQ ID NO: 15.

* * * * *

SEQUENCE LISTING

<160> NUMBER OF SEQ ID NOS: 16

<210> SEQ ID NO 1
<211> LENGTH: 13602
<212> TYPE: DNA
<213> ORGANISM: Artificial Sequence
<220> FEATURE:
<223> OTHER INFORMATION: Description of Artificial Sequence: Synthetic
      plasmid <400> SEQUENCE: 1

```
catcatcaat aatataccttattttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactggtacc gcggccgcct     360
```

-continued

```
cgagtctaga actagtggat cccccgggct gcaggaattc tgatggctct caaaattcct    420
gcctccttta gggataaaag actttaagac ttttaacaa aaaagaaaaa gaaaaaaaaa    480
attcctgcct cctggtgtac acacacagaa gggttccctc cccttgaatg tgaccaggat    540
ctgtgaaaat aacgggatag ccgctcctgt gattaggtta tgtggtagac tagagcaaga    600
ttctcctgct ggttttgaag aagtcagctg ccatgttgtg agactgtcat gggctagggc    660
atgagccttt aaatatctgg gagcaacccc tggccagcag ccagtgagaa acgggccct     720 cagtcctaca atcacaagga actaaattct gccaacaacc tgaaggaact ttgaagagga    780
tcatgagtcc cttgattcag cttgatgagc ccctgagcag aggatacagc taacttgtac    840
tagggaagta taaaaaacat gcatgggaat gatatatatc aactttaagg ataattgtca    900
tacttctggg aatgaaggga agaaatggg gctttagttg tattatgatc tttaatttct     960
caaaaaaaat aagatcagaa gcaaatatgg caaaatgtta atactttgt gggtacgtag    1020 gtattcagca taccttttt tctgagttca aatattttta taattaaaat gaaatgcagg    1080
ccaggcacag tggctcatgc ctataatacc agcactttgc gaggccgagg tgggaggatg    1140
gcttgaggcc agaccagcct ggccaacatg gcaaaacccc atctctactt aaaaaaaaaa    1200
aaactatata tatatatatg tgtgtgtgtg tgtatatata tatatgtata tatatttata    1260
tatgtgtgta tatatatata tgtatatata tttatatatg tgtgtgtata tatatatata    1320
cacacacaca catatataca tacatacata cacacacaca cacacacaat tagccaggca    1380
tggtggcgca cacctgtagt cccagctact tgggaggctg agacatgaga attgcttgaa    1440
cctgggaggc agagtagtta gtgagctgag atcataccac tgcactccag cctggtgaca    1500
gagtgagact ctgtcttaaa aaaataaaa attaaaatta aatgcaaaag gtccaagtga    1560
attgaagagg aaaggggtat caaggaaggt tttgtggagg tgacgtttga gctgggtctt    1620
aaatgactta aacatgggat aagaagggag ggaataagga catttcaggt acgagaaata    1680
aggagcaaac agtggaaaca acctaacgtc tgtcaaccag tgaatggata acaaaaatgt    1740
aattcagatg gtatccaact tacgatggtt caacatgaga tttttctgac tttaggatag    1800
atttatcaaa gtagtaaatc cattttcaac ttatgatatt ttcaacttca gatgggttta    1860
tcaggacaca gttgaggaac acctgtctat ccatacaatt tggcaataaa aggaaatga    1920 gtgcagatat actccacaac atgaatgaac cttgaaaaca ttaagtgaga gaagccagat    1980
acaaaaggcc acatattgta tgattctatt tatacaaaat gtccagaata ggcaaatctt    2040
atagacagca agtaggtaga tgatcagttt gctaggtgct gggggaaggg gaaatgggga    2100
gtgatggcta aggggattgg gtttctttgt ggggcaatga aaatgtttta aaattgagcg    2160
tgataatgat tgcacaatgc tgcatatata tataatctat agattatata tatataaaga    2220
gaggctgtta gacagtgata agtgatatat atatatatat acatagagag agagagagag    2280
agagagagag gctgttagtg ataagtgatc aggaaaataa aagtattgag gaggaatacg    2340
aagttgacgg tgtgaaaaca tgagatttta tataggatgg ccaggaagg ccttaatgag    2400 aaagtgactt atgagtaaaa acaagggatc ctaaaccttga gcatgcatca gaatcactcg    2460
gaaacttgtt aaagcatagc ttgctgggcc tcatcacaga tattttgatt cggtaggttc    2520
ttgtctgata ttaatacttt tggtctaggg aaccacattt tgagaaccac tgagctaaag    2580
gaagtaaagg tttcccttag tttactagct ggtaacccta ggaaactgct tagcctctcg    2640
gtgctaagat acaaaatact ttagcacata ataacacatg gaaaatagtc tataaattat    2700
```

```
aaatattatt ttttatgtac caaatattac ataagacaaa atctaagcaa gatatatata   2760
tatatacata aaatataaga tatatatgta tatattatat atagataaat agagagagag   2820
agttatgttt agaaagaaaa tacttcaaac taaaaaaaga gaggtaggaa gtataccatt   2880
ccattattgg taaaaacaaa ttactaagta gtctttacaa aaaaccaatc tcactccttt   2940
agaacacaag cccaccatta aaactgatgc agaggaattt ctctccctgg cttaccttta   3000
ggatggtgca tactaagtta gaaaagtcat aaatgttata ttaaaagtaa atgtgaactt   3060
acttccacaa tcaagacatt ctagaagaaa aagagaaatg aaaatcagta caatgaataa   3120
aacggtattt ccaattataa gtcaaatcac atcataacaa ccctaaggaa ttatccaaac   3180
tcttgttttt agatgcttta ttatatcaaa ctctccttta aacaagtggc ccatctgctg   3240
ggatttggaa gcctgtaata ctgaaatttt catcataatg gaaattttaa aaacagaatt   3300
tgacccacct gttttttaaaa cactttcatt acttaacaag aggtctaatc ttgggcaagt   3360
cttgaaattt ctctggcctt agtttcccat gtgttaaatg aaacttgaag cagttggtct   3420
cttatagtct cctgactcta acattctaag aattatattt gtacaataac tcaaaaatca   3480
cataatttaa tttaccatat ggactccaaa atatattttc tcattaggct aaacttgatc   3540
tgcattttct ggatgtgtcc atattcttgg actacactaa acatgatac caatgcttcc    3600 tctcaccata aaccctcact tcgctttcta catttaagaa ttttatagct ggaagagtcc   3660
ttaacagaaa ataccatcta ataattaccc ctcaaaatcg agaaagtcct atctgttctt   3720
atgctagtta taagaatgag gcagcatttc acataatggt tataaacact gccacaagaa   3780
gattcatgat gtgttgttta tctgtagctc tcatcatact ctgtcatata actatagcat   3840
taagatttta atgttctata tattcttcta agacagtgtt taccagagta aggcacaaaa   3900
gatccactgg tttgcaagaa agattagaac ttttaaattt tttacctcac cttgtttaat   3960
ctatattttt gtatgtattt tgtaacatat atattattat taccataaat catatataat   4020
ttaaaatgca tatattaggg gtaaatgctc aggaaacttt ttataaattg ggcatgcaaa   4080
tacaagtttg aagactcact gttctaggta ttaaaagtaa agttataacc aagtaaagct   4140 tccaccttt catgtctcaa agcagtttat tgttggaggt aagatctctt agaagcctaa    4200
acaggtccaa gtacagaatg aagtaaggct agcccataac ttgtggcaag caattcatac   4260
tatttctctc atgctgagct ctcctcagtg aagcagctac tatagacaac tgcagcctat   4320
tggtagccta ttttacaggc aggaaaaaaa ttacttttta ttcaaagtgg aactcaggac   4380
atggggagaa aatgaataca aaaaataggg tcaatccaaa ggcacacagc aaatgagtaa   4440
cacagttatg ttttttttccc atttgtatga ggtcccagta aattctaagt aaactgcaaa   4500
tttaataata cactaaaaaa gccatgcaat tgttcaaatg aatcccagca tggtacaagg   4560
agtacagaca ctagagtcta aaaaacaaaa gaatgccatt attgagtttt tgaattatat   4620
caagtagtta catctctact taataaatga aaaacgag gataagaggc catttgataa     4680
aatgaaaata gccaagaagt ggtattagag acttgaatac aggtattcgg gtccaaagtt   4740
catctgctca aatactaact ggggaaaaga gggaaaaata tttatataca tatatatctg   4800
cacacaaaaa taccccccaaa agacaaaatg aggccaggca gggtggctca cacccgtaat   4860
cccggtactt tgggaggctg aggcaggtgg atacctgaga tcaggagttg gagatcagcc   4920
tggtcaacat ggtgaaaccc tgtctctact aaagataaaa aaattagcca ggcatggtgg   4980
cgtgcgcctg taatcccagc tacttgggag tctgaggcag gagaatcact tgaactggga   5040
aggggaggtt gcagtgagcc aagatcgtac tactgcactc cagcctgggc agcagagtga   5100
```

```
gactccatca caaaaataaa taaataaata aaatacaatg aaacagaaag ttcaaataat    5160
cccataatct taccaccaag aaataacttt cactcgttat acttattgat ttttccataa    5220
taaatgtact ttactgtgac tatcatgaaa agaaagttat tttagaaaca gagaactgtt    5280
tcagatcaaa tctatgtagt agaacagagc cattaggtgg aaagacgag  atcaaactaa    5340 atctcagaag gcctaaaagg ctaggtccat tccagcacta aaaactgacc agacaagtaa    5400
tggcttcaac agcttctaaa tatggacaaa gcatgctgaa agggaaggac aggtctaaca    5460
gtggtatatg aaatgaacag gaggggcaaa gctcatttct cctctgaagt tttccaaaga    5520
tgctgaggag gacattagtt tgacatgacc ctgatatggg acaagataat ttcacagaag    5580
ttttacatgt taaagttttc ttatagatac tcattcaagt aagcaatgaa cactaaaatc    5640
taaagaaaga aaagagcttt agagtcaggt ctgtattcaa attcaagctc taccacttac    5700
tggttctgtg actttgggca agtcttttaa ccttattaag tcttaatttc ctgatttgta    5760
aaatggggat atcgtctccc tcacaggatt gttgtgaaac ttttatgaga ttaatgcctt    5820
tatatttggc atagtgtaag taaacaataa ctggcagctt caaaaaaaaa aagcagtagc    5880
attccatcat ttattattgg ttactctcaa aaagtttttc aatgtactag aagataaata    5940
ttcaaatacc ttaatatctc cattatttc  aggtaaacag catgctcctg aacaaccaat    6000
gggtcaacaa ataaattaaa agggaaatct aaaaacatct tgatattaaa ctacatggaa    6060
gcacaatata ccaaaaccaa tggttcacac taggagaatt ttaaggtaca agaaaactct    6120
ttgagatttc ttaaaataat agtatgtctg aatttattga gtgatttacc agaaactgtt    6180
gtaagagctc tacttgcatt atagcactta atcctcttaa ctctatggct gctattatca    6240
acctcacccc aatcacatat gggacacaga gaggttaagt aacttgccca aggtcagagt    6300
taggaagtac taagccatgc tttgaatcag ttgtcaggct ccggaactca cactttcagc    6360
cactacataa tactgctttg ctatctttta ggaaactatg tgagtctacc tcacatagac    6420
tcacataggt ttgttttttt tttttttta aaggctatct tttcccccat caatgttttt    6480
tgaaggatcc caaattagag tcccacagag gcagacagca gtacttgaca atatggacat    6540
ttaaggttaa tgttggattc tactgtcttt ttactacatg acctagggaa cgataattaa    6600
cctagactgc ttccaagggt taaataaccc atttagttat actatgtaaa ttatctctta    6660
gtgattgatt gaaagcacac tgttactaat tgactcggta tgaagtgctt ttttttcttc    6720
cctttcaaga tacataccctt tccagttaaa gttgagagat catctccacc aattactttt    6780
atgtcccctg ttgactggtc attctagtta aaaaaaaaaa aaactatata tatatatatc    6840
tacacacaca tatgtatatg tatatcctta tgtacacaca caaacttcaa attaaatgag    6900
aactagaaga tttgagaagt tagctagcta atatccatag cattatgata ttctaaatga    6960
tatgaattat aagaattagg tttcctgaaa tgaatgacta gaaaactttc aagtagagat    7020
tagtaaaaat taaaaagtcc taatcggcca ttactgattt gatgttttta agagtcctaa    7080
aaaatgggtt acatccattt ttaagtgggt agtattataa cagccaccca tcttcaatca    7140
cagtgatttc tgaattgtga gggaagttat tagcatgaca ggtgtctggt tctggccctg    7200
tacgattccc atgagtcaag caaattgtaa gggctggtct atatcacacc caaccccaag    7260
gatatgtccc tcaaaagtct agcccaggcc ccgtcatctt cagcatcatc tgggaaacca    7320
ggtctgatta gtagtcctttt aaggaatacc tcttaggctc ccatttttact gctatcacag    7380 aatccaataa aacccttaca ggagattcaa tgggaaatgc tcaacaccca ctgtagttgg    7440
```

```
tggtgacaat gaccataatt tggctgtgct ggattcagga cagaaaattt gggtgaaaga    7500
gcaggtgaac aaaagagctt cgacttgccc tagcagagag caagccatac cataccacaa    7560
agccacagca attaacggg tgcagtacca gcacagtaaa tgaacaaagt agagcccaga    7620
aacagaccca gaactatatg aggatttagt atacaataaa gatggtattt cgagtcagta    7680
gggaaaagat gaattattca ataaatgatg tttggccaac tagtaaccca tttgggaaaa    7740
aataaaagta tggtccctac ctcacagcat acacaaaaat aaattccaga cggattaaaa    7800
tctaaatgta aaaataaag ccataagtgg actggaagaa atagagaat ttttttttaac    7860 atccgtagaa agggtaaaaa cccaggcatg acatgaacca aaactgaaga ggttctgtaa    7920 caaataccc cttttatata ttgggctcca acaataagaa cccataggaa aatggagaat    7980
gaacacaaat agacaattta tagaagagaa ggttataagg tgtaaaatta tatctatctg    8040
agaaacaaac actaaaacaa tgtgattcta ctgttctccc acccatactg gcaaaactta    8100
agcctgataa tatgctgagg ggaaataagc actcttgttg gtgagagtat taattggcat    8160
agcttctttt gaaatgaca tagcaatacc tgttaaaatt gcaaacatgc atgtcactta    8220
atccagtaat cccacttctg ggaatcaatg ctacaaaaac actgacaagt atacaaagat    8280
acattcaaga gtgttcactg ggccgggtgc ggtggcttca tgcctgtaat cccagggagg    8340
cagaggcaag acgatcgctt gaccccagga gttcaaggcc agcccgagaa acacagcaag    8400
accctgtctc tctttttttt atttaaaaaa taaatgttca ctgtatcagt tgttcacaaa    8460
aacaaaccaa catgtccatt aacagggaac catttaaatt aatcaagttc atctacacaa    8520
tgtaatacca tgcaactatt aaaaagcacc tgataatcca aagcacactg agacagaata    8580
atgctattaa aaaccaag tagtggaaca ctgtgttgcc tatgcaccat tttttattca    8640
acatttaaac aaatttgtaa cagcaattac atgagtagtg acaatggcgt ttatgagact    8700
tttcactttt atgtgcttct attttgtta tgcttctata tatacatcca tttattatgg    8760
agtgttactt tcaaaaatca caaatgggcc agtattattt ggtgttgcaa ggtgagcata    8820
tgacttctga tatcaacctt tgcatattac ttctcaattt agggaaatta cagacatccc    8880
ttattctaac taacttaaaa cccagcattt caaacataca gaattgatgg ggaaaaaaa    8940 gaaagaagaa agaaagaaaa ggcaacaagc ttcagatgac agtgactcac atcaaattat    9000
ttataaaatc tgttaaatag tgccatcttc tggagatacc tggtattaca gtccaactcc    9060
agttgatgtc tttacagaga caagaggaat aaaggaaaaa atattcaaga actgaaaagt    9120
atggagtcat ggaaaaattg ctgtgatcca aaggctacgg tgataggaca agaaacaaga    9180
gaactccaag cagtaagaca ctgctgttct attagcatcc aaacctccat actcctgttt    9240
gccccaaggc ttttttaaaa aatagagaca ggatctcact attttgctca ggctggtctt    9300
gaactcctgg actcaagcta tcctcctgcc tcggcctcct aaagtgccga gattacaggc    9360
ttgagtcacc atacctggct atttattttt tcttaactct cttgcctggc ctatagccac    9420
catggaagct aataaagaat attaatttaa gagtaatggt atagttcact acattggaat    9480
acaggtataa gtgcctacat tgtacatgaa tggcatacat ggatcaatta ccccacctgg    9540
gtggccaaag gaactgcgcg aacctccctc cttggctgtc tggaacaagc ttcccactag    9600 atcccttac tgagtgcctc cctcatcttt aattatggtt aagtctagga taacaggact    9660
ggcaaaggtg aggggaaagc ttcctccaga gttgctctac cctctcctct accgtcctat    9720
ctcctcactc ctctcagcca aggagtccaa tctgtcctga actcagagcg tcactgtcaa    9780
ctacataaaa ttgccagaga agctctttgg gactacaaac acatacccct aatgtcttta    9840
```

-continued

```
tttctatttt gtctacctct tcagtctagg tgaaaaaata ggaaggataa tagggaagaa    9900
ctttgtttat gcctacttat ccgccccctag gaattttgaa aacctctagg tagcaataag    9960
aactgcagca tggtatagaa aaagaggagg aaagctgtat agaaatgcat aataaatggg   10020
caggaaaaga actgcttgga acaaacaggg aggttgaact ataaggagag aaagcagaga   10080
ggctaatcaa caaggctggg ttcccaagag ggcatgatga gactattact aaggtaggaa   10140
ttactaaggg ctccatgtcc ccttagtggc ttagtactat gtagcttgct ttctgcagtg   10200
aacttcagac ccttctttta ggatcctaga atggactttt tttttttatc ggaaaacagt   10260
cattctctca acattcaagc aggccccaag tctaccacac tcaatcacat tttctcttca   10320
tatcataatc tctcaaccat tctctgtcct tttaactgtt tttctatacc ctgatcaaat   10380
gccaacaaaa gtgagaatgt tagaatcatg tatttttaga ggtagactgt atctcagata   10440
aaaaaaaagg gcagatattc cattttccaa aatatgtatg cagaaaaaat aagtatgaaa   10500
ggacatatgc tcaggtaaca agttaatttg tttacttgta ttttatgaat tccctaaaac   10560
ctacgtcacc cgccccgttc ccacgccccg cgccacgtca caaactccac ccctcatta   10620
tcatattggc ttcaatccaa aataaggtat attattgatg atgttaatta acatgcatgg   10680
atccatatgc ggtgtgaaat accgcacaga tgcgtaagga gaaataccg catcaggcgc   10740
tcttccgctt cctcgctcac tgactcgctg cgctcggtcg ttcggctgcg gcgagcggta   10800
tcagctcact caaaggcggt aatacggtta tccacagaat caggggataa cgcaggaaag   10860
aacatgtgag caaaaggcca gcaaaaggcc aggaaccgta aaaaggccgc gttgctggcg   10920
tttttccata ggctccgccc ccctgacgag catcacaaaa atcgacgctc aagtcagagg   10980
tggcgaaacc cgacaggact ataaagatac caggcgtttc ccctggaag ctccctcgtg   11040
cgctctcctg ttccgaccct gccgcttacc ggatacctgt ccgcctttct cccttcggga   11100
agcgtggcgc tttctcatag ctcacgctgt aggtatctca gttcggtgta ggtcgttcgc   11160
tccaagctgg gctgtgtgca cgaaccccc gttcagcccg accgctgcgc cttatccggt   11220
aactatcgtc ttgagtccaa cccggtaaga cacgacttat cgccactggc agcagccact   11280
ggtaacagga ttagcagagc gaggtatgta ggcggtgcta cagagttctt gaagtggtgg   11340
cctaactacg gctacactag aaggacagta tttggtatct gcgctctgct gaagccagtt   11400
accttcggaa aaagagttgg tagctcttga tccggcaaac aaaccaccgc tggtagcggt   11460
ggttttttg tttgcaagca gcagattacg cgcagaaaaa aaggatctca agaagatcct   11520
ttgatctttt ctacggggtc tgacgctcag tggaacgaaa actcacgtta agggattttg   11580
gtcatgagat tatcaaaaag gatcttcacc tagatccttt taaattaaaa atgaagtttt   11640
aaatcaatct aaagtatata tgagtaaact tggtctgaca gttaccaatg cttaatcagt   11700
gaggcaccta tctcagcgat ctgtctattt cgttcatcca tagttgcctg actccccgtc   11760
gtgtagataa ctacgatacg ggagggctta ccatctggcc ccagtgctgc aatgataccg   11820
cgagacccac gctcaccggc tccagattta tcagcaataa accagccagc cggaagggcc   11880
gagcgcagaa gtggtcctgc aactttatcc gcctccatcc agtctattaa ttgttgccgg   11940
gaagctagag taagtagttc gccagttaat agtttgcgca acgttgttgc cattgctgca   12000
gccatgagat tatcaaaaag gatcttcacc tagatccttt tcacgtagaa agccagtccg   12060
cagaaacggt gctgacccg gatgaatgtc agctactggg ctatctggac aagggaaaac   12120
gcaagcgcaa agagaaagca ggtagcttgc agtgggctta catggcgata gctagactgg   12180
```

```
gcggttttat ggacagcaag cgaaccggaa ttgccagctg gggcgccctc tggtaaggtt    12240 gggaagcccct gcaaagtaaa ctggatggct ttcttgccgc caaggatctg atggcgcagg    12300
ggatcaagct ctgatcaaga gacaggatga ggatcgtttc gcatgattga acaagatgga    12360
ttgcacgcag gttctccggc cgcttgggtg gagaggctat tcggctatga ctgggcacaa    12420
cagacaatcg gctgctctga tgccgccgtg ttccggctgt cagcgcaggg gcgcccggtt    12480 cttttttgtca agaccgacct gtccggtgcc ctgaatgaac tgcaagacga ggcagcgcgg    12540
ctatcgtggc tggccacgac gggcgttcct tgcgcagctg tgctcgacgt tgtcactgaa    12600
gcgggaaggg actggctgct attgggcgaa gtgccggggc aggatctcct gtcatctcac    12660
cttgctcctg ccgagaaagt atccatcatg gctgatgcaa tgcggcggct gcatacgctt    12720
gatccggcta cctgcccatt cgaccaccaa gcgaaacatc gcatcgagcg agcacgtact    12780
cggatggaag ccggtcttgt cgatcaggat gatctggacg aagagcatca ggggctcgcg    12840
ccagccgaac tgttcgccag gctcaaggcg agcatgcccg acggcgagga tctcgtcgtg    12900
acccatggcg atgcctgctt gccgaatatc atggtggaaa atggccgctt ttctggattc    12960
atcgactgtg gccggctggg tgtggcggac cgctatcagg acatagcgtt ggctacccgt    13020
gatattgctg aagagcttgg cggcgaatgg gctgaccgct tcctcgtgct ttacggtatc    13080
gccgctcccg attcgcagcg catcgccttc tatcgccttc ttgacgagtt cttctgaatt    13140
ttgttaaaat ttttgttaaa tcagctcatt ttttaaccaa taggccgaaa tcggcaaaat    13200
cccttataaa tcaaaagaat agaccgagat agggttgagt gttgttccag tttggaacaa    13260
gagtccacta ttaaagaacg tggactccaa cgtcaaaggg cgaaaaaccg tctatcaggg    13320
cgatggccca ctacgtgaac catcacccta atcaagtttt tgggggtcga ggtgccgtaa    13380
agcactaaat cggaaccctta agggagcccc cgatttagag cttgacggg gaaagccggc    13440 gaacgtggcg agaaaggaag ggaagaaagc gaaaggagcg ggcgctaggg cgctggcaag    13500
tgtagcggtc acgctgcgcg taaccaccac acccgccgcg cttaatgcgc cgctacaggg    13560
cgcgtccatt cgccattcag gatcgaatta attcttaatt aa                       13602
```

<210> SEQ ID NO 2
<211> LENGTH: 575
<212> TYPE: PRT
<213> ORGANISM: Homo sapiens

<400> SEQUENCE: 2

```
Met Leu Gly Val Leu Val Leu Gly Ala Leu Ala Leu Ala Gly Leu Gly
 1               5                  10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
           100                 105                 110

Gly Asp Asn Asn Thr Ser Tyr Ser Arg Trp Ala Arg Leu Asp Leu Asn
       115                 120                 125
```

```
Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
                180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
    210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
                260                 265                 270

Leu Gln Ala Asp Gly Arg Ser Cys Thr Ala Ser Ala Thr Gln Ser Cys
                275                 280                 285

Asn Asp Leu Cys Glu His Phe Cys Val Pro Asn Pro Asp Gln Pro Gly
                290                 295                 300

Ser Tyr Ser Cys Met Cys Glu Thr Gly Tyr Arg Leu Ala Ala Asp Gln
305                 310                 315                 320

His Arg Cys Glu Asp Val Asp Cys Ile Leu Glu Pro Ser Pro Cys
                325                 330                 335

Pro Gln Arg Cys Val Asn Thr Gln Gly Gly Phe Glu Cys His Cys Tyr
                340                 345                 350

Pro Asn Tyr Asp Leu Val Asp Gly Glu Cys Val Glu Pro Val Asp Pro
                355                 360                 365

Cys Phe Arg Ala Asn Cys Glu Tyr Gln Cys Gln Pro Leu Asn Gln Thr
                370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
                420                 425                 430

Leu Asp Asp Gly Phe Ile Cys Thr Asp Ile Asp Glu Cys Glu Asn Gly
                435                 440                 445

Gly Phe Cys Ser Gly Val Cys His Asn Leu Pro Gly Thr Phe Glu Cys
                450                 455                 460

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
                485                 490                 495

Pro Ser Pro Thr Pro Gly Ser Thr Leu Thr Pro Pro Ala Val Gly Leu
                500                 505                 510

Val His Ser Gly Leu Leu Ile Gly Ile Ser Ile Ala Ser Leu Cys Leu
                515                 520                 525

Val Val Ala Leu Leu Ala Leu Leu Cys His Leu Arg Lys Lys Gln Gly
                530                 535                 540
```

| Ala | Ala | Arg | Ala | Lys | Met | Glu | Tyr | Lys | Cys | Ala | Ala | Pro | Ser | Lys | Glu |
| 545 | | | | 550 | | | | | 555 | | | | | 560 | |

| Val | Val | Leu | Gln | His | Val | Arg | Thr | Glu | Arg | Thr | Pro | Gln | Arg | Leu |
| | | | | 565 | | | | | 570 | | | | | 575 |

<210> SEQ ID NO 3
<211> LENGTH: 1725
<212> TYPE: DNA
<213> ORGANISM: Homo sapiens

<400> SEQUENCE: 3

| atgcttgggg | tcctggtcct | tggcgcgctg | ccctggccg | gcctggggtt | ccccgcaccc | 60 |
| gcagagccgc | agccgggtgg | cagccagtgc | gtcgagcacg | actgcttcgc | gctctacccg | 120 |
| ggccccgcga | ccttcctcaa | tgccagtcag | atctgcgacg | gactgcgggg | ccacctaatg | 180 |
| acagtgcgct | cctcggtggc | tgccgatgtc | atttccttgc | tactgaacgg | cgacggcggc | 240 |
| gttggccgcc | ggcgcctctg | gatcggcctg | cagctgccac | ccggctgcgg | cgaccccaag | 300 |
| cgcctcgggc | ccctgcgcgg | cttccagtgg | gttacgggag | acaacaacac | cagctatagc | 360 |
| aggtgggcac | ggctcgacct | caatggggct | cccctctgcg | gcccgttgtg | cgtcgctgtc | 420 |
| tccgctgctg | aggccactgt | gcccagcgag | ccgatctggg | aggagcagca | gtgcgaagtg | 480 |
| aaggccgatg | gcttcctctg | cgagttccac | ttcccagcca | cctgcaggcc | actggctgtg | 540 |
| gagcccggcg | ccgcggctgc | cgccgtctcg | atcacctacg | gcaccccgtt | cgcggcccgc | 600 |
| ggagcggact | ccaggcgct | gccggtgggc | agctccgccg | cggtggctcc | cctcggctta | 660 |
| cagctaatgt | gcaccgcgcc | gcccggagcg | gtccaggggc | actgggccag | ggaggcgccg | 720 |
| ggcgcttggg | actgcagcgt | ggagaacggc | ggctgcgagc | acgcgtgcaa | tgcgatccct | 780 |
| ggggctcccc | gctgccagtg | cccagccggc | gccgccctgc | aggcagacgg | cgcgctcctgc | 840 |
| accgcatccg | cgacgcagtc | ctgcaacgac | ctctgcgagc | acttctgcgt | tcccaacccc | 900 |
| gaccagccgg | gctcctactc | gtgcatgtgc | gagaccggct | accggctggc | ggccgaccaa | 960 |
| caccggtgcg | aggacgtgga | tgactgcata | ctggagccca | gtccgtgtcc | gcagcgctgt | 1020 |
| gtcaacacac | agggtggctt | cgagtgccac | tgctacccta | actacgacct | ggtggacggc | 1080 |
| gagtgtgtgg | agcccgtgga | cccgtgcttc | agagccaact | gcgagtacca | gtgccagccc | 1140 |
| ctgaaccaaa | ctagctacct | ctgcgtctgc | gccgagggct | tcgcgcccat | tccccacgag | 1200 |
| ccgcacaggt | gccagatgtt | ttgcaaccag | actgcctgtc | cagccgactg | cgaccccaac | 1260 |
| acccaggcta | gctgtgagtg | ccctgaaggc | tacatcctgg | acgacggttt | catctgcacg | 1320 |
| gacatcgacg | agtgcgaaaa | cggcggcttc | tgctccgggg | tgtgccacaa | cctccccggt | 1380 |
| accttcgagt | gcatctgcgg | gcccgactcg | cccttgccc | gccacattgg | caccgactgt | 1440 |
| gactccggca | aggtggacgg | tggcgacagc | ggctctggcg | agccccgcc | cagcccgacg | 1500 |
| cccggctcca | ccttgactcc | tccggccgtg | gggctcgtgc | attcgggctt | gctcataggc | 1560 |
| atctccatcg | cgagcctgtg | cctggtggtg | gcgcttttgg | cgctcctctg | ccacctgcgc | 1620 |
| aagaagcagg | gcgccgccag | ggccaagatg | gagtacaagt | gcgcggcccc | ttccaaggag | 1680 |
| gtagtgctgc | agcacgtgcg | gaccgagcgg | acgccgcaga | gactc | | 1725 |

<210> SEQ ID NO 4
<211> LENGTH: 649
<212> TYPE: DNA
<213> ORGANISM: Homo sapiens
<220> FEATURE:
<221> NAME/KEY: modified_base
<222> LOCATION: (335)
<223> OTHER INFORMATION: a, c, g, t, unknown or other

<400> SEQUENCE: 4

```
tctagacgcg ttgacattga ttattgacta gttattaata gtaatcaatt acgggtcat     60
tagttcatag cccatgatat catatggagt tccgcgttac ataacttacg gtaaatggcc   120
cgcctggctg accgcccaac gaccccgcc cattgacgtc aataatgacg tatgttccca    180
tagtaacgcc aatagggact ttccattgac gtcaatgggt ggagtattta cggtaaactg   240
cccacttggc agtacatcaa gtgtatcata tgccaagtac gccccctat tgacgtcaat    300
gacggtaaat ggcccgcctg gcattatgcc cagtncatga ccttatggga ctttcctact   360
tggcagacat ctacgtatta gtcatcgcta ttaccatggt gatgcggttt tggcagtaca   420
tcaatgggcg tggatagcgg tttgactcac ggggattttc caagtctcca ccccattgac   480
gtcaatggga gtttgttttg gcaccaaaat caacgggact ttccaaaatg tcgtaacaac   540
tccgccccat tgacgcaaat gggcggtagg cgtgtacggt gggaggtcta tataagcaga   600
gctctctggc taactagaga acccctgctt actggcttat cgagatatc                649
```

<210> SEQ ID NO 5
<211> LENGTH: 3693
<212> TYPE: DNA
<213> ORGANISM: Homo sapiens

<400> SEQUENCE: 5

```
ggcagcgcgc agcggcaaga agtgtctggg ctgggacgga caggagaggc tgtcgccatc     60
ggcgtcctgt gccccctctgc tccggcacgg ccctgtcgca gtgcccgcgc tttccccggc   120
gcctgcacgg ggcgcgcctg ggtaacatgc ttggggtcct ggtccttggc gcgctggccc   180
tggccggcct ggggttcccc gcacccgcag agccgcagcc gggtggcagc cagtgcgtcg   240
agcacgactg cttcgcgctc tacccggggcc ccgcgaccctt cctcaatgcc agtcagatct   300
gcgacggact gcggggccac ctaatgacag tgcgctcctc ggtggctgcc gatgtcattt   360
ccttgctact gaacgcgac ggcggcgttg ccgccggcg cctctggatc ggcctgcagc    420
tgccacccgg ctgcggcgac cccaagcgcc tcgggcccct gcgcggcttc cagtgggtta   480
cgggagacaa caacaccagc tatagcaggt gggcacggct cgacctcaat ggggctcccc   540
tctgcggccc gttgtgcgtc gctgtctccg ctgctgaggc cactgtgccc agcgagccga   600
tctgggagga gcagcagtgc gaagtgaagg ccgatggctt cctctgcgag ttccacttcc   660
cagccacctg caggccactg gctgtggagc ccggcgccgc ggctgccgcc gtctcgatca   720
cctacgcac cccgttcgcg gcccgcggag cggacttcca ggcgctgccg gtgggcagct   780
ccgccgcgt ggctcccctc ggcttacagc taatgtgcac cgcgccgccc ggagcggtcc   840
aggggcactg ggtcagggag gcgcggggcg cttgggactg cagcgtggag aacgcggct   900
gcgagcacgc gtgcaatgcg atccctgggg ctccccgctg ccagtgccca gccggcgccg   960
ccctgcagga gacgggcgc tcctgcaccg catccgcgac gcagtcctgc aacgaccctct  1020
gcgagcactt ctgcgttccc aaccccgacc agccgggctc ctactcgtgc atgtgcgaga  1080
ccggctacgg ctgggcggcc gaccaacacc ggtgcgagga cgtggatgac tgcatactgg  1140
agcccagtcc gtgtccgcag cgctgtgtca acacacaggg tggcttcgag tgccactgct  1200
accctaacta cgacctggtg gacggcgagt gtgtggagcc cgtggaccg tgcttcagag  1260
ccaactgcga gtaccagtgc cagccctga accaaactag ctacctctgc gtctgcgccg   1320
```

-continued

```
agggcttcgc gcccattccc cacgagccgc acaggtgcca gatgttttgc aaccagactg    1380
cctgtccagc cgactgcgac cccaacaccc aggctagctg tgagtgccct gaaggctaca    1440
tcctggacga cggttttcatc tgcacggaca tcgacgagtg cgaaaacggc ggcttctgct    1500
ccggggtgtg ccacaacctc cccggtacct tcgagtgcat ctgcgggccc gactcggccc    1560
ttgcccgcca cattggcacc gactgtgact ccggcaaggt ggacggtggc dacagcggct    1620
ctggcgagcc cccgcccagc ccgacgcccg gctccacctt gactcctccg gccgtggggc    1680
tcgtgcattc gggcttgctc ataggcatct ccatcgcgag cctgtgcctg gtggtggcgc    1740
tttggcgct cctctgccac ctgcgcaaga agcagggcgc cgccagggcc aagatggagt    1800
acaagtgcgc ggccccttcc aaggaggtag tgctgcagca cgtgcggacc gagcggacgc    1860
cgcagagact ctgagcggcc tccgtccagg agcctggctc cgtccaggag cctgtgcctc    1920
ctcaccccca gctttgctac caaagcacct tagctggcat tacagctgga gaagaccctc    1980
cccgcacccc ccaagctgtt ttcttctatt ccatggctaa ctggcgaggg ggtgattaga    2040
gggaggagaa tgagcctcgg cctcttccgt gacgtcactg gaccactggg caatgatggc    2100
aattttgtaa cgaagacaca gactgcgatt tgtcccaggt cctcactacc gggcgcagga    2160
gggtgagcgt tattggtcgg cagccttctg ggcagacctt gacctcgtgg gctagggatg    2220
actaaaatat ttattttttt taagtattta ggttttttgtt tgtttccttt gttcttacct    2280
gtatgtctcc agtatccact ttgcacagct ctccggtctc tctctctcta caaactccca    2340
cttgtcatgt gacaggtaaa ctatcttggt gaatttttt ttcctagccc tctcacattt    2400
atgaagcaag ccccacttat tccccattct tcctagtttt ctcctcccag gaactgggcc    2460
aactcacctg agtcacccta cctgtgcctg accctacttc ttttgctctt agctgtctgc    2520
tcagacagaa cccctacatg aaacagaaac aaaaacacta aaataaaaa tggccatttg     2580
cttttttcacc agatttgcta atttatcctg aaatttcaga ttcccagagc aaaataattt    2640
taaacaaagg ttgagatgta aaaggtatta aattgatgtt gctggactgt catagaaatt    2700
acacccaaag aggtatttat ctttacttttt aaacagtgag cctgaatttt gttgctgttt    2760
tgatttgtac tgaaaaatgg taattgttgc taatcttctt atgcaatttc cttttttgtt    2820
attattactt attttttgaca gtgttgaaaa tgttcagaag gttgctctag attgagagaa    2880
gagacaaaca cctcccagga gacagttcaa gaaagcttca aactgcatga ttcatgccaa    2940
ttagcaattg actgtcactg ttccttgtca ctggtagacc aaaataaaac cagctctact    3000
ggtcttgtgg aattgggagc ttgggaatgg atcctggagg atgcccaatt agggcctagc    3060
cttaatcagg tcctcagaga atttctacca tttcagagag gccttttgga atgtggcccc    3120
tgaacaagaa ttggaagctg ccctgcccat gggagctggt tagaaatgca gaatcctagg    3180
ctccacccca tccagttcat gagaatctat atttaacaag atctgcaggg ggtgtgtctg    3240
ctcagtaatt tgaggacaac cattccagac tgcttccaat tttctggaat acatgaaata    3300
tagatcagtt ataagtagca ggccaagtca ggcccttatt ttcaagaaac tgaggaattt    3360
tctttgtgta gctttgctct ttggtagaaa aggctaggta cacagctcta gacactgcca    3420
cacagggtct gcaaggtctt tggttcagct aagctaggaa tgaaatcctg cttcagtgta    3480
tggaaataaa tgtatcatag aaatgtaact tttgtaagac aaaggttttc ctcttctatt    3540
ttgtaaactc aaaatatttg tacatagtta tttatttatt ggagataatc tagaacacag    3600
gcaaaatcct tgcttatgac atcacttgta caaaataaac aataacaat gtgaaaaaaa      3660
aaaaaaaaaa aaaaaaaaa aaaaaaaaa aaa                                   3693
```

<210> SEQ ID NO 6
<211> LENGTH: 4457
<212> TYPE: DNA
<213> ORGANISM: Homo sapiens
<220> FEATURE:
<221> NAME/KEY: modified_base
<222> LOCATION: (349)
<223> OTHER INFORMATION: a, c, g, t, unknown or other

<400> SEQUENCE: 6

```
gtttaaacgg gccctctaga cgcgttgaca ttgattattg actagttatt aatagtaatc      60
aattacgggg tcattagttc atagcccatg atatcatatg gagttccgcg ttacataact     120
tacggtaaat ggcccgcctg gctgaccgcc aacgacccc cgcccattga cgtcaataat      180
gacgtatgtt cccatagtaa cgccaatagg gactttccat tgacgtcaat gggtggagta     240
tttacggtaa actgcccact ggcagtaca tcaagtgtat catatgccaa gtacgccccc      300
ctattgacgt caatgacggt aaatggcccg cctggcatta tgcccagtnc atgaccttat     360
gggactttcc tacttggcag acatctacgt attagtcatc gctattacca tggtgatgcg     420
gttttggcag tacatcaatg ggcgtggata gcggtttgac tcacggggat tttccaagtc     480
tccaccccat tgacgtcaat gggagtttgt tttggcacca aaatcaacgg gactttccaa     540
aatgtcgtaa caactccgcc ccattgacgc aaatgggcgg taggcgtgta cggtgggagg     600
tctatataag cagagctctc tggctaacta gagaacccct gcttactggc ttatcgagat     660
atctgcagaa ttcatctgtc gactgctacc ggcagcgcg agcggcaaga agtgtctggg      720
ctgggacgga caggagaggc tgtcgccatc ggcgtcctgt gcccctctgc tccggcacgg     780
ccctgtcgca gtgcccgcgc tttccccggc gcctgcacgc ggcgcgcctg ggtaacatgc     840
ttggggtcct ggtccttggc gcgctggccc tggccggcct ggggttcccc gcacccgcag     900
agccgcagcc gggtggcagc cagtgcgtcg agcacgactt cttcgcgctc tacccggggcc    960
ccgcgacctt cctcaatgcc agtcagatct gcgacggact gcggggccac ctaatgacag    1020
tgcgctcctc ggtggctgcc gatgtcattt ccttgctact gaacggcgac ggcggcgttg    1080
gccgccggcg cctctggatc ggcctgcagc tgccacccgg ctgcggcgac cccaagcgcc    1140
tcgggcccct cgcgggcttc agtgggtta cgggagacaa caacaccagc tatagcaggt    1200
gggcacggct cgacctcaat ggggctcccc tctgcggccc gttgtgcgtc gctgtctccg    1260
ctgctgaggc cactgtgccc agcgagccga tctggggagga gcagcagtgc gaagtgaagg    1320
ccgatggctt cctctgcgag ttccacttcc cagccacctg caggccactg ctgtggagc     1380
ccggcgccgc ggctgccgcc gtctcgatca cctacggcac cccgttcgcg gcccgcggag    1440
cggacttcca ggcgctgccg gtgggcagct ccgccgcggt ggctcccctc ggcttacagc    1500
taatgtgcac cgcgccgccc ggagcggtcc aggggcactg gccagggag gcgccgggcg    1560
cttgggactg cagcgtggag aacggcggct gcgagcacgc gtgcaatgcg atccctgggg    1620
ctccccgctg ccagtgccca gccggcgccg ccctgcaggc agacgggcgc tcctgcaccg    1680
catccgcgac gcagtcctgc aacgacctct gcgagcactt ctgcgttccc aaccccgacc    1740
agccgggctc ctactcgtgc atgtgcgaga ccggctaccg gctggcggcc gaccaacacc    1800
ggtgcgagga cgtggatgac tgcatactgg agcccagtcc gtgtccgcag cgctgtgtca    1860
acacacaggg tggcttcgag tgccactgct accctaacta cgacctggtg gacggcgagt    1920
gtgtggagcc cgtggaccg tgcttcagag ccaactgcga gtaccagtgc cagccctga     1980
```

```
accaaactag ctacctctgc gtctgcgccg agggcttcgc gcccattccc cacgagccgc    2040
acaggtgcca gatgttttgc aaccagactg cctgtccagc cgactgcgac cccaacaccc    2100
aggctagctg tgagtgccct gaaggctaca tcctggacga cggtttcatc tgcacggaca    2160
tcgacgagtg cgaaaacggc ggcttctgct ccggggtgtg ccacaacctc cccggtacct    2220
tcgagtgcat ctgcgggccc gactcggccc ttgcccgcca cattggcacc gactgtgact    2280
ccggcaaggt ggacggtggc gacagcggct ctggcgagcc cccgcccagc ccgacgcccg    2340
gctccacctt gactcctccg gccgtggggc tcgtgcattc gggcttgctc ataggcatct    2400
ccatcgcgag cctgtgcctg gtggtggcgc ttttggcgct cctctgccac ctgcgcaaga    2460
agcagggcgc cgccagggcc aagatggagt acaagtgcgc ggccccttcc aaggaggtag    2520
tgctgcagca cgtgcggacc gagcggacgc cgcagagact ctgagcggcc tccgtccagg    2580
agcctggctc cgtccaggag cctgtgcctc ctcaccccca gctttgctac caaagcacct    2640
tagctggcat tacagctgga gaagaccctc cccgcacccc ccaagctgtt ttcttctatt    2700
ccatggctaa ctggcgaggg ggtgattaga gggaggagaa tgagcctcgg cctcttccgt    2760
gacgtcactg gaccactggg caatgatggc aattttgtaa cgaagacaca gactgcgatt    2820
tgtcccaggt cctcactacc gggcgcagga gggtgagcgt tattggtcgg cagccttctg    2880
ggcagacctt gacctcgtgg gctagggatg actaaaatat ttattttttt taagtattta    2940 ggttttgtt tgtttccttt gttcttacct gtatgtctcc agtatccact ttgcacagct    3000
ctccggtctc tctctctcta caaactccca cttgtcatgt gacaggtaaa ctatcttggt    3060
gaattttttt ttcctagccc tctcacattt atgaagcaag ccccacttat tccccattct    3120
tcctagtttt ctcctcccag gaactgggcc aactcacctg agtcacccta cctgtgcctg    3180
accctacttc ttttgctctt agctgtctgc tcagacagaa cccctacatg aaacagaaac    3240
aaaaacacta aaaataaaaa tggccatttg cttttttcacc agatttgcta atttatcctg    3300
aaatttcaga ttcccagagc aaaataattt taaacaaagg ttgagatgta aaaggtatta    3360
aattgatgtt gctggactgt catagaaatt acacccaaag aggtatttat ctttactttt    3420
aaacagtgag cctgaatttt gttgctgttt tgatttgtac tgaaaaatgg taattgttgc    3480
taatcttctt atgcaatttc ctttttttgtt attattactt attttttgaca gtgttgaaaa    3540 tgttcagaag gttgctctag attgagagaa gagacaaaca cctcccagga gacagttcaa    3600
gaaagcttca aactgcatga ttcatgccaa ttagcaattg actgtcactg ttccttgtca    3660
ctggtagacc aaaataaaac cagctctact ggtcttgtgg aattgggagc ttgggaatgg    3720
atcctggagg atgcccaatt agggcctagc cttaatcagg tcctcagaga atttctacca    3780
tttcagagag gccttttgga atgtggcccc tgaacaagaa ttggaagctg ccctgcccat    3840
gggagctggt tagaaatgca gaatcctagg ctccacccca tccagttcat gagaatctat    3900
atttaacaag atctgcaggg ggtgtgtctg ctcagtaatt tgaggacaac cattccagac    3960
tgcttccaat tttctggaat acatgaaata tagatcagtt ataagtagca ggccaagtca    4020
ggcccttatt ttcaagaaac tgaggaattt tctttgtgta gctttgctct ttggtagaaa    4080
aggctaggta cacagctcta gacactgcca cacagggtct gcaaggtctt tggttcagct    4140
aagctaggaa tgaaatcctg cttcagtgta tggaaataaa tgtatcatag aaatgtaact    4200
tttgtaagac aaaggttttc ctcttctatt ttgtaaactc aaaatatttg tacatagtta    4260
tttatttatt ggagataatc tagaacacag gcaaaatcct tgcttatgac atcacttgta    4320
caaaataaac aaataacaat gtgaaaaaaa aaaaaaaaa aaaaaaaaa aaaaaaaaa    4380
```

```
aaaggtagca gtcgacagat gaattccacc acactggact agtggatccg agctcggtac    4440
caagcttaag tttaaac                                                   4457

<210> SEQ ID NO 7
<211> LENGTH: 17534
<212> TYPE: DNA
<213> ORGANISM: Artificial Sequence
<220> FEATURE:
<221> NAME/KEY: modified_base
<222> LOCATION: (730)
<223> OTHER INFORMATION: a, c, g, t, unknown or other
<220> FEATURE:
<223> OTHER INFORMATION: Description of Artificial Sequence: Synthetic
      plasmid

<400> SEQUENCE: 7
catcatcaat aatataccct attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactggtacc gcggccgcct     360
cgagtctaga actagtggat cccccaaacg ggccctctag acgcgttgac attgattatt     420
gactagttat taatagtaat caattacggg gtcattagtt catagcccat gatatcatat     480
ggagttccgc gttacataac ttacggtaaa tggcccgcct ggctgaccgc ccaacgaccc     540
ccgcccattg acgtcaataa tgacgtatgt tcccatagta acgccaatag ggactttcca     600
ttgacgtcaa tgggtggagt atttacggta aactgcccac ttggcagtac atcaagtgta     660
tcatatgcca agtacgcccc cctattgacg tcaatgacgg taaatggccc gcctggcatt     720
atgcccagtn catgacctta tgggactttc ctacttggca gacatctacg tattagtcat     780
cgctattacc atggtgatgc ggttttggca gtacatcaat gggcgtggat agcggtttga     840
ctcacgggga ttttccaagt ctccacccca ttgacgtcaa tgggagtttg ttttggcacc     900
aaaatcaacg ggactttcca aaatgtcgta caactccgcc ccattgacgc aaatgggcg      960 gtaggcgtgt acggtgggag gtctatataa gcagagctct ctggctaact agagaacccc    1020
tgcttactgg cttatcgaga tatctgcaga attcatctgt cgactgctac cggcagcgcg    1080
cagcggcaag aagtgtctgg gctgggacgg acaggagagg ctgtcgccat cggcgtcctg    1140
tgcccctctg ctccggcacg gccctgtcgc agtgcccgcg cttccccgg cgcctgcacg     1200 cggcgcgcct gggtaacatg cttggggtcc tggtccttgg cgcgctggcc ctggccggcc    1260
tggggttccc cgcacccgca gagccgcagc cgggtggcag ccagtgcgtc gagcacgact    1320
gcttcgcgct ctacccgggc cccgcgacct tcctcaatgc cagtcagatc tgcgacggac    1380
tgcggggcca cctaatgaca gtgcgctcct cggtggctgc cgatgtcatt tccttgctac    1440
tgaacggcga cggcggcgtt ggccgccggc gcctctggat cggcctgcag ctgccacccg    1500
gctgcggcga ccccaagcgc ctcgggcccc tgcgcggctt ccagtgggtt acgggagaca    1560
acaacaccag ctatagcagg tgggcacggc tcgacctcaa tggggctccc tctgcggcc    1620 cgttgtgcgt cgctgtctcc gctgctgagg ccactgtgcc cagcgagccg atctgggagg    1680
agcagcagtg cgaagtgaag gccgatggct tcctctgcga gttccacttc ccagccacct    1740
gcaggccact ggctgtggag cccggcgccg cggctgccgc cgtctcgatc acctacggca    1800
```

```
ccccgttcgc ggcccgcgga gcggacttcc aggcgctgcc ggtgggcagc tccgccgcgg      1860
tggctcccct cggcttacag ctaatgtgca ccgcgccgcc cggagcggtc caggggcact      1920
gggccaggga ggcgccgggc gcttgggact gcagcgtgga gaacggcggc tgcgagcacg      1980
cgtgcaatgc gatccctggg gctccccgct gccagtgccc agccggcgcc gccctgcagg      2040
cagacgggcg ctcctgcacc gcatccgcga cgcagtcctg caacgacctc tgcgagcact      2100
tctgcgttcc caaccccgac cagccgggct cctactcgtg catgtgcgag accggctacc      2160
ggctggcggc cgaccaacac cggtgcgagg acgtggatga ctgcatactg gagcccagtc      2220
cgtgtccgca gcgctgtgtc aacacacagg gtggcttcga gtgccactgc taccctaact      2280
acgacctggt ggacggcgag tgtgtggagc ccgtggaccc gtgcttcaga gccaactgcg      2340
agtaccagtg ccagcccctg aaccaaacta gctacctctg cgtctgcgcc gagggcttcg      2400
cgcccattcc ccacgagccg cacaggtgcc agatgttttg caaccagact gcctgtccag      2460
ccgactgcga ccccaacacc caggctagct gtgagtgccc tgaaggctac atcctggacg      2520
acggtttcat ctgcacggac atcgacgagt gcgaaaacgg cggcttctgc tccggggtgt      2580
gccacaacct ccccggtacc ttcgagtgca tctgcgggcc cgactcggcc cttgcccgcc      2640
acattggcac cgactgtgac tccggcaagg tggacggtgg cgacagcggc tctggcgagc      2700
ccccgcccag cccgacgccc ggctccacct tgactcctcc ggccgtgggg ctcgtgcatt      2760
cgggcttgct cataggcatc tccatcgcga gcctgtgcct ggtggtggcg cttttggcgc      2820
tcctctgcca cctgcgcaag aagcagggcg ccgccagggc caagatggag tacaagtgcg      2880 cggcccctc caaggaggta gtgctgcagc acgtgcggac cgagcggacg ccgcagagac      2940
tctgagcggc ctccgtccag gagcctggct ccgtccagga gcctgtgcct cctcaccccc      3000
agctttgcta ccaaagcacc ttagctggca ttacagctgg agaagaccct ccccgcaccc      3060
cccaagctgt tttcttctat tccatggcta actggcgagg gggtgattag agggaggaga      3120
atgagcctcg gcctcttccg tgacgtcact ggaccactgg gcaatgatgg caattttgta      3180
acgaagacac agactgcgat ttgtcccagg tcctcactac cgggcgcagg agggtgagcg      3240
ttattggtcg gcagccttct gggcagacct tgacctcgtg ggctagggat gactaaaata      3300 tttattttt ttaagtattt aggttttgt ttgtttcctt tgttcttacc tgtatgtctc       3360
cagtatccac tttgcacagc tctccggtct ctctctctct acaaactccc acttgtcatg      3420
tgacaggtaa actatcttgg tgaattttt tttcctagcc ctctcacatt tatgaagcaa      3480
gccccactta ttcccattc ttcctagttt tctcctccca ggaactgggc caactcacct      3540
gagtcacccc acctgtgcct gaccctactt cttttgctct tagctgtctg ctcagacaga      3600 accctacat gaaacagaaa caaaaacact aaaaataaaa atggccattt gcttttcac       3660 cagatttgct aatttatcct gaaatttcag attcccagag caaataatt ttaaacaaag      3720 gttgagatgt aaaggtatt aaattgatgt tgctggactg tcatagaaat tacacccaaa      3780
gaggtattta tctttacttt taaacagtga gcctgaattt tgttgctgtt ttgatttgta      3840
ctgaaaaatg gtaattgttg ctaatcttct tatgcaattt ccttttttgt tattattact      3900 tattttgac agtgttgaaa atgttcagaa ggttgctcta gattgagaga agagacaaac      3960
acctcccagg agacagttca agaaagcttc aaactgcatg attcatgcca attagcaatt      4020
gactgtcact gttccttgtc actggtagac caaaataaaa ccagctctac tggtcttgtg      4080
gaattgggag cttgggaatg gatcctggag gatgcccaat tagggcctag ccttaatcag      4140
```

```
gtcctcagag aatttctacc atttcagaga ggccttttgg aatgtggccc ctgaacaaga    4200
attggaagct gccctgccca tgggagctgg ttagaaatgc agaatcctag gctccacccc    4260
atccagttca tgagaatcta tatttaacaa gatctgcagg gggtgtgtct gctcagtaat    4320
ttgaggacaa ccattccaga ctgcttccaa ttttctggaa tacatgaaat atagatcagt    4380
tataagtagc aggccaagtc aggcccttat tttcaagaaa ctgaggaatt ttctttgtgt    4440
agctttgctc tttggtagaa aaggctaggt acacagctct agacactgcc acacagggtc    4500
tgcaaggtct ttggttcagc taagctagga atgaaatcct gcttcagtgt atggaaataa    4560
atgtatcata gaaatgtaac ttttgtaaga caaaggtttt cctcttctat tttgtaaact    4620
caaaatattt gtacatagtt atttatttat tggagataat ctagaacaca ggcaaaatcc    4680
ttgcttatga catcacttgt acaaataaaa caaataacaa tgtgaaaaaa aaaaaaaaa    4740 aaaaaaaaaa aaaaaaaaa aaaaggtagc agtcgacaga tgaattccac cacactggac    4800
tagtggatcc gagctcggta ccaagcttaa gtttgggctg caggaattct gatggctctc    4860
aaaattcctg cctcctttag ggataaaaga ctttaagact ttttaacaaa aagaaaaag    4920 aaaaaaaaaa ttcctgcctc ctggtgtaca cacacagaag ggttccctcc ccttgaatgt    4980
gaccaggatc tgtgaaaata cgggatagc cgctcctgtg attaggttat gtggtagact    5040
agagcaagat tctcctgctg gttttgaaga agtcagctgc catgttgtga gactgtcatg    5100
ggctagggca tgagcccttta aatatctggg agcaacccct ggccagcagc cagtgagaaa    5160
acgggccctc agtcctacaa tcacaaggaa ctaaattctg ccaacaacct gaaggaactt    5220
tgaagaggat catgagtccc ttgattcagc ttgatgagcc cctgagcaga ggatacagct    5280
aacttgtact agggaagtat aaaaaacatg catgggaatg atatatatca actttaagga    5340
taattgtcat acttctggga atgaaggga agaaatgggg ctttagttgt attatgatct    5400
ttaatttctc aaaaaaaata agatcagaag caaatatggc aaaatgttaa tacttttgtg    5460
ggtacgtagg tattcagcat acccttttt ctgagttcaa aatatttat aattaaaatg    5520 aaatgcaggc caggcacagt ggctcatgcc tataatacca gcactttgcg aggccgaggt    5580
gggaggatgg cttgaggcca gaccagcctg gccaacatgg caaaacccca tctctactta    5640
aaaaaaaaaa aactatatat atatatatgt gtgtgtgtgt gtatatatat atatgtatat    5700
atatttatat atgtgtgtat atatatatat gtatatatat ttatatatgt gtgtgtatat    5760
atatatatac acacacacac atatatacat acatacatac acacacacac acacacaatt    5820
agccaggcat ggtggcgcac acctgtagtc ccagctactt gggaggctga gacatgagaa    5880
ttgcttgaac ctgggaggca gagtagttag tgagctgaga tcataccact gcactccagc    5940
ctggtgacag agtgagactc tgtcttaaaa aaaataaaaa ttaaaattaa atgcaaaagg    6000
tccaagtgaa ttgaagagga aaggggtatc aaggaaggtt ttgtggaggt gacgtttgag    6060
ctgggtctta aatgacttaa acatgggata agaagggagg gaataaggac atttcaggta    6120
cgagaaataa ggagcaaaca gtggaaacaa cctaacgtct gtcaaccagt gaatggataa    6180
caaaaatgta attcagatgg tatccaactt acgatggttc aacatgagat ttttctgact    6240
ttaggataga tttatcaaag tagtaaatcc attttcaact tatgatattt tcaacttcag    6300
atgggtttat caggacacag ttgaggaaca cctgtctatc catacaattt ggcaataaaa    6360
aggaaatgag tgcagatata ctccacaaca tgaatgaacc ttgaaaacat taagtgagag    6420
aagccagata caaaaggcca catattgtat gattctattt atacaaaatg tccagaataG    6480
gcaaatctta tagacagcaa gtaggtagat gatcagtttg ctaggtgctg ggggaagggg    6540
```

```
aaatggggag tgatggctaa ggggattggg tttctttgtg gggcaatgaa aatgttttaa    6600
aattgagcgt gataatgatt gcacaatgct gcatatatat ataatctata gattatatat    6660
atataaagag aggctgttag acagtgataa gtgatatata tatatatata catagagaga    6720
gagagagaga gagagagagg ctgttagtga taagtgatca ggaaaataaa agtattgagg    6780
aggaatacga agttgacggt gtgaaaacat gagattttat ataggatggc cagggaaggc    6840
cttaatgaga aagtgactta tgagtaaaaa caagggatcc taaaccttag catgcatcag    6900
aatcactcgg aaacttgtta aagcatagct tgctgggcct catcacagat attttgattc    6960
ggtaggttct tgtctgatat taatactttt ggtctaggga accacatttt gagaaccact    7020
gagctaaagg aagtaaaggt ttcccttagt ttactagctg gtaacactgg cccaggaggc    7080 cttttctggtg accctaagg aattatccaa actcttgttt ttagatgctt tattatatca    7140
aactctcctt taaacaagtg gcccatctgc tgggatttgg aagcctgtaa tactgaaatt    7200
ttcatcataa tggaaatttt aaaaacagaa tttgacccac ctgttttaa aacactttca    7260 ttacttaaca agaggtctaa tcttgggcaa gtcttgaaat ttctctggcc ttagtttccc    7320
atgtgttaaa tgaaacttga agcagttggt ctcttatagt ctcctgactc taacattcta    7380
agaattatat ttgtacaata actcaaaaat cacataattt aatttaccat atggactcca    7440
aaatatattt tctcattagg ctaaacttga tctgcatttt ctggatgtgt ccatattctt    7500 ggactcacact aaaacatgat accaatgctt cctctcacca taaaccctca cttcgctttc    7560
tacatttaag aattttatag ctggaagagt ccttaacaga aaataccatc taataattac    7620
ccctcaaaat cgagaaagtc ctatctgttc ttatgctagt tataagaatg aggcagcatt    7680
tcacataatg gttataaaca ctgccacaag aagattcatg atgtgttgtt tatctgtagc    7740
tctcatcata ctctgtcata taactatagc attaagattt taatgttcta tatattcttc    7800
taagacagtg tttaccagag taaggcacaa aagatccact ggtttgcaag aaagattaga    7860
acttttaaat ttttttacctc accttgttta atctatattt ttgtatgtat tttgtaacat    7920
atatattatt attaccataa atcatatata atttaaaatg catatattag gggtaaatgc    7980
tcaggaaact ttttataaat tgggcatgca aatacaagtt tgaagactca ctgttctagg    8040
tattaaaagt aaagttataa ccaagtaaag cttccacctt ttcatgtctc aaagcagttt    8100
attgttggag gtaagatctc ttagaagcct aaacaggtcc aagtacagaa tgaagtaagg    8160
ctagcccata acttgtggca agcaattcat actatttctc tcatgctgag ctctcctcag    8220
tgaagcagct actatagaca actgcagcct attggtagcc tattttacag gcaggaaaaa    8280
aattactttt tattcaaagt ggaactcagg acatggggag aaaatgaata caaaaaatag    8340
ggtcaatcca aaggcacaca gcaaatgagt aacacagtta tgttttttc ccatttgtat    8400 gaggtcccag taaattctaa gtaaactgca aatttaataa tacactaaaa aagccatgca    8460
attgttcaaa tgaatcccag catggtacaa ggagtacaga cactagagtc taaaaaacaa    8520
aagaatgcca ttattgagtt tttgaattat atcaagtagt tacatctcta cttaataaat    8580
gagaaaaacg aggataagag gccatttgat aaaatgaaaa tagccaagaa gtggtattag    8640
agacttgaat acaggtattc gggtccaaag ttcatctgct caaatactaa ctggggaaaa    8700
gagggaaaaa tatttatata catatatatc tgcacacaaa aataccccca aaagacaaaa    8760
tgaggccagg caggggtggct cacacccgta atcccggtac tttgggaggc tgaggcaggt    8820
ggatacctga gatcaggagt tggagatcag cctggtcaac atggtgaaac cctgtctcta    8880
```

```
ctaaagataa aaaaattagc caggcatggt ggcgtgcgcc tgtaatccca gctacttggg    8940
agtctgaggc aggagaatca cttgaactgg aagggggagg ttgcagtgag ccaagatcgt    9000
actactgcac tccagcctgg gcagcagagt gagactccat cacaaaaata aataaataaa    9060
taaaatacaa tgaaacagaa agttcaaata atcccataat cttaccacca agaaataact    9120
ttcactcgtt atacttattg attttttccat aataaatgta ctttactgtg actatcatga    9180
aaagaaagtt atttttagaaa cagagaactg tttcagatca aatctatgta gtagaacaga    9240
gccattaggt gggaaagacg agatcaaact aaatctcaga aggcctaaaa ggctaggtcc    9300
attccagcac taaaaactga ccagacaagt aatggcttca acagcttcta aatatggaca    9360
aagcatgctg aaagggaagg acaggtctaa cagtggtata tgaaatgaac aggaggggca    9420
aagctcattt ctcctctgaa gttttccaaa gatgctgagg aggacattag tttgacatga    9480
ccctgatatg ggacaagata atttcacaga agttttacat gttaaagttt tcttatagat    9540
actcattcaa gtaagcaatg aacactaaaa tctaaagaaa gaaagagct ttagagtcag    9600 gtctgtattc aaattcaagc tctaccactt actggttctg tgactttggg caagtctttt    9660
aaccttatta gtcttaatt tcctgatttg taaaatgggg atatcgtctc cctcacagga    9720
ttgttgtgaa acttttatga gattaatgcc tttatatttg gcatagtgta agtaaacaat    9780
aactggcagc ttcaaaaaaa aaaagcagta gcattccatc atttattatt ggttactctc    9840 aaaaagttttt tcaatgtact agaagataaa tattcaaata ccttaatatc tccattattt    9900
tcaggtaaac agcatgctcc tgaacaacca atgggtcaac aaataaatta aagggaaat    9960 ctaaaaacat cttgatatta aactacatgg aagcacaata taccaaaacc aatggttcac   10020
actaggagaa ttttaaggta caagaaaact ctttgagatt tcttaaaata atagtatgtc   10080
tgaatttatt gagtgattta ccagaaactg ttgtaagagc tctacttgca ttatagcact   10140
taatcctctt aactctatgg ctgctattat caacctcacc ctaatcacat atgggacaca   10200
gagaggttaa gtaacttgcc caaggtcaga gttaggaagt actaagccat gctttgaatc   10260
agttgtcagg ctccggaact cacactttca gccactacat aatactgctt tgctatcttt   10320
taggaaacta tgtgagtcta cctcacatag actcacatag gtttgttttt ttttttttttt   10380 taaaggctat cttttcccccc atcaatgttt tttgaaggat cccaaattag agtcccacag   10440
aggcagacag cagtacttga caatatggac atttaaggtt aatgttggat tctactgtct   10500
ttttactaca tgacctaggg aacgataatt aacctagact gcttccaagg gttaaataac   10560
ccatttagtt atactatgta aattatctct tagtgattga ttgaaagcac actgttacta   10620
attgactcgg tatgaagtgc tttttttttct tcccttcaa gatacatacc tttccagtta   10680
aagttgagag atcatctcca ccaattactt ttatgtcccc tgttgactgg tcattctagt   10740
taaaaaaaaa aaaactata tatatatata tctacacaca catatgtata tgtatatcct   10800
tatgtacaca cacaaacttc aaattaaatg agaactagaa gatttgagaa gttagctagc   10860
taatatccat agcattatga tattctaaat gatatgaatt ataagaatta ggtttcctga   10920
aatgaatgac tagaaaactt tcaagtagag attagtaaaa attaaaaagt cctaatcggc   10980
cattactgat ttgatgtttt taagagtcct aaaaaatggg ttacatccat ttttaagtgg   11040
gtagtattat aacagccacc catcttcaat cacagtgatt tctgaattgt gagggaagtt   11100
attagcatga caggtgtctg gttctggccc tgtacgattc ccatgagtca agcaaattgt   11160
aagggctggt ctatatcaca cccaacccca aggatatgtc cctcaaaagt ctagcccagg   11220 cccctgtcatc ttcagcatca tctgggaaac caggtctgat tagtagtcct ttaaggaata   11280
```

```
cctcttaggc tcccatttta ctgctatcac agaatccaat aaaaccctta caggagattc  11340
aatgggaaat gctcaacacc cactgtagtt ggtggtgaca atgaccataa tttggctgtg  11400
ctggattcag gacagaaaat ttgggtgaaa gagcaggtga acaaaagagc ttcgacttgc  11460
cctagcagag agcaagccat accataccac aaagccacag caattacaac ggtgcagtac  11520
cagcacagta aatgaacaaa gtagagccca gaaacagacc cagaactata tgaggattta  11580
gtatacaata aagatggtat ttcgagtcag tagggaaaag atgaattatt caataaatga  11640
tgtttggcca actagtaacc catttgggaa aaaataaaag tatggtccct acctcacagc  11700
atacacaaaa ataaattcca gacggattaa aatctaaatg taaaaaataa agccataagt  11760
ggactggaag aaaatagaga attttttttta acatccgtag aaagggtaaa acccaggca  11820 tgacatgaac caaaactgaa gaggttctgt aacaaatacc ccctttata tattgggctc  11880 caacaataag aacccatagg aaaatggaga atgaacacaa atagacaatt tatagaagag  11940
aaggttataa ggtgtaaaat tatatctatc tgagaaacaa acactaaaac aatgtgattc  12000
tactgttctc ccacccatac tggcaaaact taagcctgat aatatgctga ggggaaataa  12060
gcactcttgt tggtgagagt attaattggc atagcttctt ttgaaaatga catagcaata  12120
cctgttaaaa ttgcaaacat gcatgtcact taatccagta atcccacttc tgggaatcaa  12180
tgctacaaaa acactgacaa gtatacaaag atacattcaa gagtgttcac tgggccgggt  12240
gcggtggctt catgcctgta atcccaggga ggcagaggca agacgatcgc ttgaccccag  12300
gagttcaagg ccagcccgag aaacacagca agaccctgtc tctcttttt ttatttaaaa  12360 aataaatgtt cactgtatca gttgttcaca aaaacaaacc aacatgtcca ttaacaggga  12420
accatttaaa ttaatcaagt tcatctacac aatgtaatac catgcaacta ttaaaaagca  12480
cctgataatc caaagcacac tgagacagaa taatgctatt aaaaacacca agtagtggaa  12540
cactgtgttg cctatgacac catttttatt caacatttaa acaaatttgt aacagcaatt  12600
acatgagtag tgacaatggc gtttatgaga cttttcactt ttatgtgctt ctatttttgt  12660
tatgcttcta tatatacatc catttattat ggagtgttac tttcaaaaat cacaaatggg  12720
ccagtattat ttggtgttgc aaggtgagca tatgacttct gatatcaacc tttgcatatt  12780
acttctcaat ttagggaaat tacagacatc ccttattcta actaacttaa aacccagcat  12840
ttcaaacata cagaattgat ggggaaaaaa aagaaagaag aaagaaagaa aaggcaacaa  12900
gcttcagatg acagtgactc acatcaaatt atttataaaa tctgttaaat agtgccatct  12960
tctggagata cctggtatta cagtccaact ccagttgatg tctttacaga gacaagagga  13020
ataaaggaaa aaatattcaa gaactgaaaa gtatggagtc atggaaaaat tgctgtgatc  13080
caaaggctac ggtgatagga caagaaacaa gagaactcca agcagtaaga cactgctgtt  13140
ctattagcat ccaaacctcc atactcctgt ttgccccaag gcttttttaa aaaatagaga  13200
caggatctca ctattttgct caggctggtc ttgaactcct ggactcaagc tatcctcctg  13260
cctcggcctc ctaaagtgcc gagattacag gcttgagtca ccatacctgg ctatttattt  13320
tttcttaact ctcttgcctg gcctatagcc accatggaag ctaataaaga atattaattt  13380
aagagtaatg gtatagttca ctacattgga atacaggtat aagtgcctac attgtacatg  13440
aatggcatac atggatcaat taccccacct gggtggccaa aggaactgcg cgaacctccc  13500
tccttggctg tctggaacaa gcttcccact agatcccttt actgagtgcc tccctcatct  13560
ttaattatgg ttaagtctag gataacagga ctggcaaagg tgaggggaaa gcttcctcca  13620
```

```
gagttgctct accctctcct ctaccgtcct atctcctcac tcctctcagc caaggagtcc   13680
aatctgtcct gaactcagag cgtcactgtc aactacataa aattgccaga gaagctcttt   13740
gggactacaa acacataccc ttaatgtctt tatttctatt ttgtctacct cttcagtcta   13800
ggtgaaaaaa taggaaggat aatagggaag aactttgttt atgcctactt atccgcccct   13860
aggaattttg aaaacctcta ggtagcaata agaactgcag catggtatag aaaaagagga   13920
ggaaagctgt atagaaatgc ataataaatg ggcaggaaaa gaactgcttg gaacaaacag   13980
ggaggttgaa ctataaggag agaaagcaga gaggctaatc aacaaggctg ggttcccaag   14040
agggcatgat gagactatta ctaaggtagg aattactaag ggctccatgt ccccttagtg   14100
gcttagtact atgtagcttg ctttctgcag tgaacttcag acccttcttt taggatccta   14160
gaatggactt ttttttttta tcggaaaaca gtcattctct caacattcaa gcaggcccca   14220
agtctaccac actcaatcac attttctctt catatcataa tctctcaacc attctctgtc   14280
cttttaactg ttttttctata ccctgatcaa atgccaacaa agtgagaat gttagaatca   14340
tgtatttta gaggtagact gtatctcaga taaaaaaaaa gggcagatat tccatttcc   14400
aaaatatgta tgcagaaaaa ataagtatga aaggacatat gctcaggtaa caagttaatt   14460
tgtttacttg tattttatga attccctaaa acctacgtca cccgccccgt tcccacgccc   14520
cgcgccacgt cacaaactcc acccctcat tatcatattg gcttcaatcc aaaataaggt   14580
atattattga tgatgttaat taacatgcat ggatccatat gcggtgtgaa ataccgcaca   14640
gatgcgtaag gagaaaatac cgcatcaggc gctcttccgc ttcctcgctc actgactcgc   14700
tgcgctcggt cgttcggctg cggcgagcgg tatcagctca ctcaaaggcg gtaatacggt   14760
tatccacaga atcaggggat aacgcaggaa agaacatgtg agcaaaaggc cagcaaaagg   14820
ccaggaaccg taaaaaggcc gcgttgctgg cgtttttcca taggctccgc cccctgacg   14880
agcatcacaa aatcgacgc tcaagtcaga ggtggcgaaa cccgacagga ctataaagat   14940
accaggcgtt ccccctgga agctccctcg tgcgctctcc tgttccgacc ctgccgctta   15000
ccggatacct gtccgccttt ctcccttcgg gaagcgtggc gctttctcat agctcacgct   15060
gtaggtatct cagttcggtg taggtcgttc gctccaagct gggctgtgtg cacgaacccc   15120
ccgttcagcc cgaccgctgc gccttatccg gtaactatcg tcttgagtcc aacccggtaa   15180
gacacgactt atcgccactg gcagcagcca ctggtaacag gattagcaga gcgaggtatg   15240
taggcggtgc tacagagttc ttgaagtggt ggcctaacta cggctacact agaaggacag   15300
tatttggtat ctgcgctctg ctgaagccag ttaccttcgg aaaaagagtt ggtagctctt   15360
gatccggcaa acaaaccacc gctggtagcg gtggtttttt tgtttgcaag cagcagatta   15420
cgcgcagaaa aaaaggatct caagaagatc ctttgatctt ttctacgggg tctgacgctc   15480
agtggaacga aaactcacgt taagggattt tggtcatgag attatcaaaa aggatcttca   15540
cctagatcct tttaaattaa aaatgaagtt ttaaatcaat ctaaagtata tatgagtaaa   15600
cttggtctga cagttaccaa tgcttaatca gtgaggcacc tatctcagcg atctgtctat   15660
ttcgttcatc catagttgcc tgactccccg tcgtgtagat aactacgata cgggagggct   15720
taccatctgg ccccagtgct gcaatgatac cgcgagaccc acgctcaccg gctccagatt   15780
tatcagcaat aaaccagcca gccggaaggg ccgagcgcag aagtggtcct gcaactttat   15840
ccgcctccat ccagtctatt aattgttgcc gggaagctag agtaagtagt tcgccagtta   15900
atagtttgcg caacgttgtt gccattgctg cagccatgag attatcaaaa aggatcttca   15960
cctagatcct tttcacgtag aaagccagtc cgcagaaacg gtgctgaccc cggatgaatg   16020
```

-continued

```
tcagctactg ggctatctgg acaagggaaa acgcaagcgc aaagagaaag caggtagctt    16080
gcagtgggct tacatggcga tagctagact gggcggtttt atggacagca agcgaaccgg    16140
aattgccagc tggggcgccc tctggtaagg ttgggaagcc ctgcaaagta aactggatgg    16200
ctttcttgcc gccaaggatc tgatggcgca ggggatcaag ctctgatcaa gagacaggat    16260
gaggatcgtt tcgcatgatt gaacaagatg gattgcacgc aggttctccg gccgcttggg    16320
tggagaggct attcggctat gactgggcac aacagacaat cggctgctct gatgccgccg    16380
tgttccggct gtcagcgcag gggcgcccgg ttcttttttgt caagaccgac ctgtccggtg    16440
ccctgaatga actgcaagac gaggcagcgc ggctatcgtg gctggccacg acgggcgttc    16500
cttgcgcagc tgtgctcgac gttgtcactg aagcgggaag ggactggctg ctattgggcg    16560
aagtgccggg gcaggatctc ctgtcatctc accttgctcc tgccgagaaa gtatccatca    16620
tggctgatgc aatgcggcgg ctgcatacgc ttgatccggc tacctgccca ttcgaccacc    16680
aagcgaaaca tcgcatcgag cgagcacgta ctcggatgga agccggtctt gtcgatcagg    16740
atgatctgga cgaagagcat caggggctcg cgccagccga actgttcgcc aggctcaagg    16800
cgagcatgcc cgacggcgag gatctcgtcg tgacccatgg cgatgcctgc ttgccgaata    16860
tcatggtgga aaatggccgc ttttctggat tcatcgactg tggccggctg ggtgtggcgg    16920
accgctatca ggacatagcg ttggctaccc gtgatattgc tgaagagctt ggcggcgaat    16980
gggctgaccg cttcctcgtg ctttacggta tcgccgctcc cgattcgcag cgcatcgcct    17040
tctatcgcct tcttgacgag ttcttctgaa ttttgttaaa attttttgtta aatcagctca    17100 ttttttaacc aataggccga aatcggcaaa atcccttata aatcaaaaga atagaccgag    17160
atagggttga gtgttgttcc agtttggaac aagagtccac tattaaagaa cgtggactcc    17220
aacgtcaaag ggcgaaaaac cgtctatcag ggcgatggcc cactacgtga accatcaccc    17280
taatcaagtt ttttgggggtc gaggtgccgt aaagcactaa atcggaaccc taaagggagc    17340
ccccgattta gagcttgacg gggaaagccg gcgaacgtgg cgagaaagga agggaagaaa    17400
gcgaaaggag cgggcgctag ggcgctggca agtgtagcgg tcacgctgcg cgtaaccacc    17460
acacccgccg cgcttaatgc gccgctacag ggcgcgtcca ttcgccattc aggatcgaat    17520
taattcttaa ttaa                                                      17534
```

```
<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtaacactgg cccaggaggc ctttctggtg acccc                               35

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgaccgggtc ctccggaaag accactgggg att                                 33
```

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tagttccttc tgcctggaat ac                                              22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caagtcacaa ggatggacta ca                                              22

<210> SEQ ID NO 12
<211> LENGTH: 18524
<212> TYPE: DNA
<213> ORGANISM: Homo sapiens

<400> SEQUENCE: 12
tagttccttc tgcctggaat acttcctcat ctcacttgct ttcctgcctg gcagcttcct      60
acttgccctc tggaaccagc tctagggtca ccacatctct gcttctgagt gcctcctcag     120
acacagtctg tatttcctct tccaagctct catcacaaac attgtgctgt attatatgtt     180
tctgtgtggt cttccttcta tgaggaagcc ttggaaagca ggagacttat tttagtcttc     240
tttatgtttc ttttattccc aacacattat gtctgcccca tagacctttt caataaatga     300
ttattgagtt agtgactcct tttacatgct gacaaatgtg gctcttatta ctccccattt     360
cagtatcaca tatttgtaaa agtgaatcct tcttaatcgt tttacttttc tcctagtaaa     420
ttcctcatct atgcctgtct gctgctgttc tctgtgctgc tggcccttcg tttggatggc     480
atcatacagt ggagttactg ggctgtcttt gctccaatat ggctgtggaa gttaatggtc     540
attgttggag cctcagttgg aactggagtc tgggcacgaa atcctcaata tcggtaatac     600
tgctttatac aacccattgg tctctagcat gagggagcaa tatcttgact tttctcactt     660
ttgatgaagt aaggaccatt ttattttcta cctatctggg gtcttagaac tatagtataa     720
gctaacagat ctcttctgtg tttttgaaaa tttagtcttt ggtatgtatt ttcttacaaa     780
agcagtgcca tttgggggta agttgccagc cagctcacag atgcctatat aatccaaaat     840
gcacccaaaa tacagaactg gtatgccata ctagactaag cagcatgaaa ccaccctgtt     900
tttaggaaaa gacactcata ttatgtttgg tcatgaaaga tctttctcca atacagtttt     960
ggaactgggg ctccccttgt cccaccctcc agtcccaga gctttaggac tattagcagt    1020
gtaggggagg tggcttgacc aggagaccat gagtccctga dacagcagct ggggaatgag    1080
gaaagtcaaa gattggatgc cgagaaggaa agcagagcct ttgggggcag gggagagggg    1140 tacccttac cgtttccaac tcttgccctc cctgctcttg gatgcctccg ctggcccaaa     1200
ttcctgggag ttgctcacgc cagcatgcaa cctgcttgtt gctgggacct gcgagagtct    1260
ttcccttctc tgccacagag actgtaacta cataaaggga aaaaggggga cttaagactg    1320
ggaggctatt atgaacctcc actgggaaaa tgaggagtac aggaattccc agaaggcagc    1380

```
tgctcatgtg ggaaaagtgt aaagttgaaa ctaccgcacc tttttttttt tttttttttt    1440
tttttttttt ttgagacaga gtttcgctct tgttgcccag gctggagtgc aatggtgtga    1500
tctcggccca ctgcagcctc cacatcccgg gttcaagtga ttctcctgcc tcggcctcct    1560
gagtagctgg gattacaggc acctgccacc atgcccagct aattttttgt attttttagta   1620 gagatagggt ttcaccatgc caggctagtt ttgaactcct gacatcaggt gatccacccg    1680
ccttggcctc ctgaagtgct gggattacag gtgtgagcca ccacgtccgg ccactacatc    1740 aacttttttaa attttttgttt actaaatatg aaaatgattc agattgtgta aattacatat   1800
cacatacatg tctaagaact gtaaaacagt tacacagaga gccttggcag gtgagggaca    1860
ttcatgtata gctgtttcag agttcttaga tttttttga aagattgatg acctgtgtgg      1920
ctgtatgtgt tttattttt tatgagatat tttcagatat ctaatattaa ttgcttctca     1980
aagaatgcaa agttaaataa acatttaggt tctactaatt gatatttaga atatattcaa    2040
acttctcttt gttggtctta tttaagatgt tttgagcaag gaaaggaatt gtgtatgtgg    2100
ggttgaatgt aaggaatgta caggcgtggt cattctcatg ttaacattaa ccagtggaac    2160
atggttgggt cctacaggaa taacctctga tagcattttc tctatgatct aacttccggt    2220
gtatttgtca cccacaatac atgtatatca taaatgttca tctgtatttt gaataaacat    2280
tgtaggcctt tcagatgcat tatagagcct tttcctgatt agcggcctta ccattgctca    2340
attgtagatc tgttaaggtt attgtgcatg atacttagct aattaaactg attttgtttg    2400
agaacagttt taactcttgt tcttctttct ctttcatgtg caggtgttaa tttatcttaa    2460
tggaatagaa aggaaaatga aaatcattta tacgttttat ttgcatttaa aaatagcacc    2520
taacaatagt tactactatc ttgaaatata actggcactt gttcatagaa ctagagttat    2580
ttttataata ttgtgtgaag ggtggtttac atggtttctt gaaaaatgag gatcatgaga    2640
cttaaggggt atttgcctgg ttttagcagc agaagcaaat cagcttgaat aatcttggaa    2700
gtaactcttg ttgttgaatt taaagatgtg aacagaagtg tttatgtaca ttgtcaggga    2760
aataagaact ggctattact tttgagaata tccttatacg gttaaaacat taaattctgg    2820
tttggttgta atgttcattt tgtattatgt agtagttctt cgatgtttca gagattgcct    2880
accaaagctt aggtttaagt tagctttcta cctgatttcc ctttgctttt gtcaaatttt    2940
caagtaaaat tcaaagtata aatataagtt ggtatttgcc ctgaactgct tgcttatagt    3000
ggagattctg aactgagggt gttttcttct tctctcccctt ttttagagca gaaggagaaa   3060
cgtgtgtgga gtttaaagcc atgttgattg cagtgggcat ccacttgctc ttgttgatgt    3120
ttgaagttct ggtctgtgac agaatcgaga gaggaagcca tttctggctc ctggtcttca    3180
tgccgctgtt ctttgtttcc ccggtgtctg ttgcagcttg cgtttggggc tttcgacatg    3240
acaggtcact agaggtgaga tttcatatat ttaagaatgt tttccacttt gggaggtcaa    3300
ggcaggtgga tcacttgagg tcaggagttt gagaccagcc tggccaacat ggtgaaaccc    3360
catctctact aataatacaa aaattagccg ggtgtggtgg catgcgccag taatcccagc    3420
ttctccggag gctgaggcgg gagaatctct tgaacccagg aggcggaggt tgcagtgagc    3480
caagattgaa ccattgcact ccagcctggg tgacagaatg aaactccgtc ttaaaaaaaa    3540 aaaaaagaa tgttttcaaa agtaaaatat tttgctcagt tattcagatg tcaatttctt    3600 acccttttgtt aggaagagct tgatcattac caactctaca tcatgagaca acaaggcaac   3660
aaaagatgat ggaaataaca attttctttt cttcacttag aacactagct tttcacccag    3720
```

```
gacatcagcc ttctcccagc ttcacatcct gtatcaatca gacagaaaca gaactgatag    3780
gttagataca gatatatgta taaagagagt taaggaactg gctcacatta ctgtggggct    3840
ggcaagtctg aaatctccag ggcaggtgaa caggctggag acctaggagg agttgacact    3900
gcagtcctgg cacagaattt tttcctctcc aggaaaccac agttttttgct tttaaggcct   3960
tcacctgatt gcatgaggcc cacccatgct atggagggta gtctcctttta ttcaaagtca   4020
gtaccttcac tgcaacagca agcttagtgt ttgattaaat aactgggtac tatagcccag    4080
ccaagttgac actcaaaact gaccatctcc ccacctcaga ccccatgatt tagcacctcc    4140
cctgctgtct ggttagctta tcctgatgtg cccctgtgtt tgtttattca ttcaataaac    4200
atttatcaag tatttactag atgccaagcc cttttttccct aagcatagag gatatgcaga   4260
tgaataaaat accaggacta gtaataatag taatgaaagt aattgcagat aacgtttatt    4320
gagcacttac tgtgtgccag gcattgtgcg aggcacatta catgtggtag ttttcttact    4380
aactaactct gtgaggtagg tccagagaag ataagtcatt tgttcatggc cacatgtgaa    4440
ggggcaggac caggattccg tttgagtcag cccgactcta aagcccgggc acataactac    4500
ataactgcat agaagctgag ggcccaaagc tgaatactga tggttgagg ggagaactag     4560
aggctgtaga tgcctggttt tgagccgtgt ggatgaagag tgaagggaga agactgcagt    4620
tggcttagga agtaaacata gcagctgtag ggtgggtcag gcatataagc ctagacccca    4680
ggtatgggcg tgaggggaag gtatgtagac agagggacgg tgatggagca aggccctgtg    4740
ggactcaggg agaatgggac ctagagcacc aggaagggtt tggccttgaa caaggggagc    4800
tattccctga ttttcatgct ggtggaaagg ccacagcatg ggtatagtgg taggtaggag    4860
tgagccgtgg agggagagta tctgatggtc cactttcacc ctccctacaa ttcccagttt    4920
atatcaggga cttgagcatc catggatttt ggtatccaca gggggtcctg gaaccaatcc    4980
cccacagata ctgagggaca actatacaag gactaggact gcattgggcc tgaattacag    5040
aaagtaagtc tttcatatat tcacactcta ggcattcctg cccttggaag aaacaacata    5100
ccaggagctg agctccctcc tcctgtgatg caagaacagt acctatgttg gtgaggggt     5160
ggtctggagt aggctcatac agagatggga aggaggagtt gagggtctgc caggaagccc    5220
tgtgttggga gggaagggat ggcattttg ggacacattg aagcctagag gcaggaaaca    5280
ctccatcagc tgagtggact gtggcgattc agatccgacg ggagcacaag gtggaaagga    5340
aggaactgtg ggagttgaga agagaggag cctctacaga gggattgggg caaataggggg   5400
ccacgtcctc agcccacaga gcatgtgctg aagtgcccca ggcaccccag tgcactcaca    5460
gggcaccagg ggatagtgga cattttgagg aaaacagtaa tacctgacat tgttgggac    5520
accatacaaa ctactagctt gaaatagttt acaggtttat ttttaggcca cactgcattc    5580
ctttcagtga cgtcgtatct ttaagaagct gggttttcag cagttgctgt gaaaacaaaa    5640
aaggctaatg ctgtgtgaaa atccgggtga agaacaggta acgagtggga gcaccttgtc    5700
tgattccaag gcgtgggaaa tggtgagcta cctgacaggc acacgcatcc cactgggaat    5760
tagttttggt tatttaagaa taatattaac attttttcttt agatttatat gaattatttt   5820
ttctagtggc tacttagaaa tacttactaa gttagatgta attacttaaa tcagtgcaac    5880
tgttggcatt cccagccaca ttagggattt cttttggcct agaggtctat ggaggaatta    5940
ctaaattccc catgtaccta tgtactgaga acttttggga agctctgggc ctggtcccag    6000
atttcaattt tgtgggcaag aatgtacttt accagagtga ggagcagcct gcagggcgtt    6060
tgggctggag gcgggaggtt agtaaggggt tgctgaagtg gtaggcggat ggtgccgaag    6120
```

```
aaggcctcac taggcagtca tcatcaggat aggaagtggg cacgggattc aggagaaatc    6180
tggactttac agtggacagg atgtggtgac tgaacgtgac agtgtgggaa aaagaatgca    6240
gggtgattcc cgggctcatg gcttgagaaa tgagaccact gttgtgcctc caagtgacat    6300
gggaggctat agaaagtgac atgggaggct atagaaagtg acatgggagg ccatagaaag    6360
tgacatggga ggccatagaa agtgacatgg gaggccatag aaagtgacaa gggaggccat    6420
agaaagtgac atgggaggcc atagtgacat gggaggccat agaaagtgac atgggaggct    6480
atagaaagtg acatgggagg ccatagaaag tgacatggga ggccatagaa agtgacatgg    6540
gaggccatag tgacatggga ggccatagaa agtgacatgg gaggctatag aaagaggaga    6600
tacaaggttc taagtgcagg cgataatgat ctctatttgg gactggcttc atttgaggtg    6660
cctttaggag agccgagtgg cctatgcaca gctgggtctg ctatgcagca ggaaggctaa    6720
gttggagaca gatgtgagaa ctaaccatga aggaggtaat aatgcagacc aagggtctgg    6780
ttgaaatttc ttctccccca gtccagggtg cagcgggtga gtgaaaatat gtgtgtttgt    6840
gtgtctgtct cctagtcgg gagagaagac tgagtttgtg gctctgcgga gcatcaccat    6900
ttaaggaggg ggaaaaggag acagaaggaa ttaccagaac actccagagg gctccaagac    6960
tgtatggtgg gatctagatg gccaggagga ggggagcaaa aaggaaagag tcatccacag    7020
tatcagtagg atgccagttg aagtgttttt gctgcctccc ggttatcggt gactttgatg    7080
aaagctgtct tctggtggtc atgggggtgg aggccagatc acaaggaagc tgggaatggt    7140
agatgagata gtaggggctt gcatattcat tactgtctcg cagagagaaa cctgaggcta    7200
agaggggtct tggatcaaag gatggggtgg gtttatctgg tttcggggct tttgttttta    7260
atgagaagga gtcatttctg tgctgctagg agggatcaat ggaataggtg gggttaaaga    7320
tacagtacgg aatctacagt tgatggcttg atgtgacaag gtcctcaagg agcctgaaag    7380
gaaggggtgg ggtccaaggg caaaaccgag gtatgagaag aaggatgcac aaggatggtt    7440
tcgagtagac agtattgttg gtagggacat gaaggaagtt tagtggtcta ttgcagctag    7500
cctgtgttcc cagtgaacct ggaaacaagg ttctcatctg tgctcaggcc tcaggccaga    7560
aagggcaagg cagcagaggg gcaaggcagc aggctgagcc ccatttcccc ttgccataat    7620
actgctgtgc ccctctggta ccgaaaatca ggagtttcca gtgcaatata atattataca    7680
agttacactg tattataatg tgtattgtct tttagtgtgt taaccaaatt actgcagtat    7740
taaatgcaaa ttatactttg tttaactgat tcttctcttc attttttagtt agaaatcctg    7800 tgttctgtca acattctcca gtttatattc attgccttaa gactggacaa gatcatccac    7860
tggccctggc ttgtatgtaa cttttaaaat ccttaaataa acttctttt tattataaaa    7920 gtaattcata ttcactgtac aaagcttgga aaagacggac aagcagaagt aatagcctaa    7980
tagtcaccca taatcccacc atggggagat aacatggtta tgttttat gtctgtgttt    8040 tatacaaaca gtttggatat aactgtgtgc accatttgt atcctgattt ttttgtttta    8100
atgttgtatc ataaacattt tatcatgtta ataaaggtc tttataaaca tgacttctaa    8160
agtttaattg atacaaaata ttcttcaagt gcatgtatca gaccatcctc ttatttctaa    8220
aatatggtat ttccattgtt gccagtgttg aatgatttta aatcatactg cagtatatat    8280
gtttatgcat taaaattttt gccttttgtt ttttggttgt tttcttagga aatagtccag    8340
aaatagtgtt actgagctag aggttgggaa ctatttgaga ttcctatata cgtatactgc    8400
actgccaact tgcttttcca aaagccatac ctggccaggc gcagtggctt acacttacag    8460
```

```
tcccagcact ttgggaggcc gaggtgagct gatcacttga gctcaggagt tcgagaccaa   8520
cctgtgcaat gtagcaagac cctgtctcaa aagaaaaaaa aaaaaagcca tacccattta   8580
cactcttgct ggtggtggca tctatgtcat gcttctaaac tgtgacttca gttactgggc   8640
atttggttga aattaactgt gaataaatgg gtagatggat gcagagatag aaagataagt   8700
ggcaaggtag aaattagaga acacagtata gattccacta ttaaatgcat ggaaaaaaga   8760
tggagactaa aggcagaaga gttccattgc cactgggagg taaggtcatg ctagtgtttt   8820
tgttcggttt tattttctct gttgtttgat gtataatttt gcatacaata tattttatgt   8880
attaaatata gctacccttca aaagtgaaaa agtatagtaa agaattggga gcagagaaga   8940
aatgaaggga acctaagtat actccatatt taaagatggg aataatcact tctgcccaaa   9000
gtctttgata aacattcat aataaaaaat attcagtcac tcatcctaca acttcacagt   9060
gctgtatctg gagaatggtc attgggttca aaactgtttc tgttgtgacg tgaaggaaac   9120
atatctaaac aagaccaaat tttttcgtat aagatactgt cagggaaaaa aaagattagt   9180
aattttgaga gctttccaca aatgagaaga aagatttttt ctgcccttca tcctctgtag   9240
atcccagttg atgaagcagt ctgagtacat gtttcccata gtgagcaaga gaaacaagg    9300
aagcctattg agatctaaca ttccacccat gaagggaact tcagtaaaaa ggagaatctc   9360
atcacagaat ggggaacggg gaagaaaggc tgtgcataga ctctgcagag aaacctacaa   9420
tcaagaactg gtcaggagaa gtaaaattcg tatgccaact caaatcatag atctaaaaga   9480
aaatgtaaaa ctatagatct gttaggaaat aacataggac agaatctttg gggtttgcaa   9540
ttaggcagag agtacttaga aatggcactg ttaatatggt ccatacgaga gagaaatcat   9600
aaatttggac ttcctcaaaa ttaaaatgaa atgaagacag gccacagact gggagaaaat   9660
atttgcaaag cacacatcaa aacactgact tgcacccaga acatacagag aactcttaaa   9720
aactcaaaac tgcaaaaaga aacacctaaa aattggcaaa agagttgaca atttgcgaag   9780
gggatataca catggcgaaa aagcacagga aaagatgctc aacgccatta caggttaggg   9840
aagacaaact acaaccagga tgagggcccg aaacacatgg cttcagaatg gtgaaactca   9900
gcaacactga cgaggccacg tgcctgggag gatgcagagg aactgggaca ctccagtgtt   9960
actggcggga aggcaggtgg tacgggcact gtagaaaatg gtttggccat ctctgatgca  10020
gttaaaagcg cacttcccgt gggacttggc tgccccactc ctgggtataa gatttacccc  10080
cagagaagtg aaagcgcgca gccttgtaga aacccacaca ccagtgtttg tagcagtctt  10140
gtttgcattt tggatagcgg ccttgtttgg ttttcacaaa ccaccctcag cggacagtca  10200
gataaactgt aggcatccat acaatggaat accactcaga tctgagaggg aacgacctgt  10260
ggatacaggg agggaacaac ttggatgaat ctcattagac acattatgtg gatggcggga  10320
agccagtctc aacaggttac ttgtctcgcg atgccatcta cataaagttc cagcagagac  10380
aaaagtacag tgagagaaca gatcagtgtt tgccggggct aatggtgggg acggtgtgat  10440
agtgaaggga cagcacggag agttttgcag ggtgacagac ctcttctgca tcctgccaac  10500
ggctgtgtga atctacttgt gtgaagactc agggaactca caccaaagga agacggtcac  10560
ttttcctact gtatgataga taattaataa aaagggagaa cggaggagtg tcgtcccagg  10620
aggcagggca ggagggcgaa gacgtgtcac agggggagcct ggccaagtgg cgccccgga   10680
actcgtcctc tgggcttgtg tgtggatgag acaaggtcta cctggtacga cagggacata  10740
ctgggaatgc gcccttgccg tggaggcggg gacccggcag cgctacgtat ccagcatcaa  10800
cctgtatcca gcatcaaccc gccaagttca ctaacttggt aggggtgagg ttagggatcc  10860
```

```
ttaggagccc aggcagccag actttctggg gagcccattc ccatttgtgt tgccaaagta   10920
cccccagcag gttgtgggaa tgttgcctgt gaagagagtc tgttggggtg agatcttgtg   10980
tgtgtgcaca gggtgacagt tgtgtcccat ttcccgggaa gctgtgatgg cagcagaacc   11040
tagaggagcc tgagagagtg tgggagagtg ggcctctgga agagtagagg ctgcggagcc   11100
aggtgcaggg ctgtctgtca cccaaaggaa gagggactga tgactcactg agcgtgtgtg   11160
tcccctggtg gcagcaggcc ccatagtgaa cataccatac cttttctgtc ctgagcgatg   11220
ctcccagcag tcctgggaga tggaacggtc cttattcggc tcacaggaag daccgcctta   11280
actggacaga cacagcaagg tgctaaagat gccttccatc agaggccagg ttggaagctc   11340
taaagagact tctcttgctg ttctctcacc cacccccagg ttgtgtgtgt cccgctgtgg   11400
attctcatgt cctttctgtg cctggtggtc ctctactaca ttgtgtggtc cgtcttgttc   11460
ttgcgctcta tggatgtgat tgcggacagc gcaggacaca cataaccatg gccctgagct   11520
ggatgaccat cgtcgtgccc cttcttacat ttgaggtaag cgttccacgg gaagcctctt   11580
cagcccctga agcttgcgct tccccctgaca ggattctgca ccctagaaa ggcagcctct   11640
gtccctcgag ctcacagtga gcccactcca ggagagggga gagaacacag ccatctccga   11700
gagggagctt cggtgaaagg agagcatcct tcctttctct tggggcagc acgtggggct   11760
ggcagggaga agagtgcacc ttttagcca tggtgcctct gtatggctcc agtttccact   11820
ctggggaaag cagagtggga tgtcagattt gtgtattgga gtcacgtgga gaattctaga   11880
atgggagctg ttgactcctt agaacaaaca cccggaggaa tttgccataa aactgctggc   11940
actgggaact tttcaagtgg ataggctatt gccgagctct gaagagggac ataaaagctc   12000
atttcgagct ttccccaggg ataggtggtt tcctgccttt ttctggcggt gctgatgttc   12060
cctcttgtgg gagctcacgc gggggtgggg tggtggggag gaactgccta atgaagtctg   12120
gcttccgcct ctgcccattt tcggtgctgg catcaaccgg gactatgtct ctttctttag   12180
attctgctgg ttcacaaact ggatggccac aacgccttct cctgcatccc gatctttgtc   12240
ccccttggc tctcgttgat cacgctgatg gcaaccacat ttggacagaa gggaggaaac   12300
cactgtatgt actcagcatt tcagaagtcc ttggtgtgtg tctgggggg gaccaggggg   12360
tgggggtgg cggatagaag tctaggaagg gatgagtccc cgagggcccc aatttagaag   12420
cttgtgtggg aaagtgaggg ctgaggaaat tctgggacct tctaagggaa gggcatgccg   12480
taactctggt gttctgctgg cctgcaccgg gactttctc gcagtgcacg ctgccatttg   12540
aggtagaacc agacacggca ggcaacctct cagagatccc gttccctcct ctgcaaaatg   12600
gggatcaaga cagattcttc ccaggcccgg gagggtttga tggaaaatcc acatctccca   12660
cccaaacctg ggattcatcc taggtccctg ttggccgctc tgcctccccc atatccttgc   12720
tgccatcacc cgagtcttgc ctgtcttgcc ttgctaacac tctattcccc tccacctgct   12780
tgctgaggca gacacttcca aaacgatctc tgcagagggt gccttcctgg caaggctgtg   12840
ggctccatgg cacggaagcc cagagcattg cccttcggaa agccagtggg tttgggggca   12900
gggcctcact gcagcccagc agcccgggct gtgcttgctg tttgtgcctc tgcccctac   12960
cccgcacccg ggagcaggga gggcttgcac cgagctgaca ctccagtagc ctacagagag   13020
gagtagtggg actgggaaag tggctttaag gtggctccat gagttcaggc cccctcctgg   13080
ccaacccgtg catgactacc gccctcacg attccagagg gtgacagaaa tcttgttctt   13140
gggtggcact gtcatccatg agtttatcct ggctggagaa gattagcgga agacaccgta   13200
```

```
gtctgcgcac cacagatatt ttgagactca ctggagcagt agttctcaaa tttgggcatc   13260
cagcagaatc ccaaaagggc caggaaaagg ggaccgctgg agcccaccct agcccgactc   13320
agtttctgga ggtctgggct ggggcccgag aatggcatcc ctaactaggc cccgtggacg   13380
ctgtccctgc cggtccggga accccactcc aagcaccaca gagctagcat ttgcacttct   13440
tccccatttt gggtactcaa gccctgttca ggctttgtga ctcaggagtc tggataaagt   13500
atgttatgac attgtaggag tgaaacttct tgttacggaa agaaagttaa caggaaggtc   13560
agttgagcct cgtgtgtgaa ataaaaaatt cttattttc agggtggttt ggtatccgca    13620
aagatttctg tcagtttctg cttgaaatct tcccatttct acgagaatat ggaaacattt   13680
cctatgatct ccatcacgaa gataatgaag aaaccgaaga gaccccagtt ccggagcccc   13740
ctaaaatcgc acccatgttt cgaaagaagg ccagggtggt cattacccag agccctggga   13800
agtatgtgct cccacctccc aaattaaata tcgaaatgcc agattagatg ccacttccgg   13860
ggacagagct taagtggact gggacgcact ctctccgcct tcctctgccc cctcgttcac   13920
cccgcagacc agaaccagta ctggagctgg gtctccaggt acgtccatct catgccttgt   13980
ttgcatccag cgcctatcag ccactcacca cgacgggacg cggaagtggc aggtgacggg   14040
ggtgtgtgcc agcagatgcg gatgccagga agagtgtgag aacaggggtg ggattaccgt   14100
ctgtctggga ggggctccag gtaccctct tcccgtcag acccactggg agatggctgc     14160
ttgccaggcc cccagaagga acatctgtct atacggtgct gaaatcccaa tcaaaagtat   14220
tgtttagaaa tgtatttctc cacagggctg acctcctgca gctcgctgag cactcccagg   14280
tcctcagcac tcccaggtcg tggctggggc agtcagtagg aactgtaact atgtctctga   14340
tgcaccacgt gtttagacac agcacagtcc ttttttctgt tcctactgtg gaagtagttt   14400
ctctttgggc atgctgacag cagttttttca tagcctcacg gatgagccct ttctacggga   14460
gtgactccat gcttgtatac agagtattta tacaaatgtt ttagcatctt catatgcggt   14520
gttaacccct agttctgtac agcatattct gttcaagtat ttttttacaa gcttgtgctg   14580
taggcacatg ccttctgctg cagaagtgga cgcccgtggc acactccccc cccccccg     14640 tggggtgcca cgccttcatg ggacattgcc acttctgccc tggaactcgt gcaggtacgt   14700
agtagctgct actgccacaa cggcaacacc aagcaagaga tggtccatgc ttttctgacg   14760
ttctcagaat agtggctagc ttcaaacctg acaagcgctg cttgaagccg gaacactaga   14820
gaatgttgct gagagcagaa acggccacgc gggtcacgac tatgcgtggg aaagtctcaa   14880
gcttccctcc tgccagcaac aagaaggctt tggagtaggc atgatgtttt cacgtgtgcg   14940
tgccgtttct ccaagcactg caggttccac cgtgtgtcag aggctgcaag tttaacatcc   15000
tcctgcctga aaacaaatag gtcctttgct gaaaagaggg taaaaaaaga gctttgatct   15060
tctcagccag gagaagaggg tggtgttttc acgcgggcaa ctgctcgccg gcctacatgg   15120
ggttaattca agtctgctgc gagcacgact ccgcccttgg cactggcctc cagcaagccc   15180
tgttctcttt ggggtacagg gaacgggat ggtttagact ttcctgctca gtgtgtaaaa     15240
aatgtagcta aagccactat ttttgctctc cttaagctgt tcaataaacc ggttcctcat   15300
tttacacgtg catgatgtgt atcttctttg ctggatgggc caggaaactg gagtggtcct   15360
ctcagccagc ctcagaggaa agaaatctct agctggcaca gcagccagt gagtgaggct     15420 ggcggctgca ggggcacagc ctttagaatg agtccttcag tgcacaggtc cagggtata    15480 cggggtagtg ggaggaagga ggggacgcct cgcagatgcc actgttggct gggctacacc   15540
ttgccacact tgttactgct taggaggctt tctggagtgt tccttgggtg ctacgacaat   15600
```

```
ctgcagcaga cactgtcctt tcaccgctcc tggtcctcgt ttgctcccca gtgatgtcaa    15660
cagctgagga ctgctcacgc tgcaacaaaa ggctctgcag tcgctgtcta gcttgcccta    15720
gtcgtctcta gagttctgcc tgaactgaaa ctcaagtggg gttcagctca tgacttgtgg    15780
caattgacca ggaaattcac cagttgctgt ggctggaagg attttcagtc ctgtgggttg    15840
taaccagagg ccacaggtgg attctgcctt aggctcatga gatttccgac ttgctgttga    15900
agaaaatgcc ttgtgaagtg acaacagtag ctctgaccca actgccggtg cctcgctagt    15960
tcctatacgt cccactggat cctcacagcc cgggaagca ggtgctacta ctcttatccc    16020
cgggaggaga cagaggccga gagaggttaa gtgacgtgcc caagtcacac agctcggcag    16080
cggccgggtt gagcatcagc agtctgtttg cagacccctc actgtcaccc cctgagccag    16140
tgcgccttgg gccctgcggt caggatgtct caagcgtgga ggcatcaccg gttcgtggca    16200
gtctctggaa ggtcactgag ctctgtgccc agaatcgagt cggggagtc tgtgcagagg    16260 tggccctgtg tgtggggaca gtgtgtgaca cagacactgc tttggatgga cacctctccc    16320
gtgacctcct agcatccaat cccaaaggaa caactgttgc agagatggac cgctggacac    16380
aaacccacgt gcgtttctct ggagacactg gccaaggaaa acaaaacatg ctcgaaggcc    16440
aacagctgca tgccccaccg cgatgtgacc gcagacaccc ggggtgtaga agggtctctg    16500
cctggtgggg ggacacgtgc aggccgagga gaggcaggaa ggaggctgcc tccgactccc    16560
cactggactg catggcgacg cgtgtggtg gggcagtcag ctaagccatt tgcctaaggg    16620
gctgtcgggc atctgcgtgc tggggaccga cagtgtgggt gtgttaggag gatctgtatg    16680
gagcacattg ctgcctctgg ctaggacagg gtggaaaggg tggcgtggct acagcctgac    16740
ccatgggcac cgtcctaccc tttgttctgt gcttccgagt gtcagtcatg tgctggggtc    16800
tgtgggccca tgactcagac ggtgagctct gaccttcctg agccagggct ttgctgtagt    16860
tgtgcctggc tcaggagctc taggacaagg ggaccgctcc aggtctgcat ctacggtgtg    16920
gcagggcccc tcggcactct tgtgcactag tgtcatcttt cccattgaaa tgactgtgag    16980
gaccagaatg tgcacatgca gatgggcagc tacttgtctg ccttggccct ttattacaca    17040
acttgctggg ggtggagatg ccaccccccg gcagtcagag ccccttatg atgtcatggg    17100 gctggttaca tgactgccaa ggggtgctgc tggccacact gcactagcaa gtttgccaga    17160
tggaggacaa gcgatcattg agtatggctc gctgtgaaga aagaaattcg agaggacagg    17220
atcatggctt ggaaagggtg ccttctccctc cccagttgca gtcagagacc taccttcacc    17280
cagcagatcc ttcccctgcc tgggacgacc cggggtccac tgggagccct aacttgaggc    17340
tgctgacaga agaaatcgct ttccaacctc tggccgagga agcttcgttc agaaggccgc    17400
accctgacgg tgacgtcccg ccccagggag aagataatct cctctccctc cccttttccac    17460 agaaactgtg gagactggtc agcagcaacc agttttcgtc catctggtgg gatgacagtg    17520
gggcttgtag agtgatcaat caaaaactct ttgaaaagga gattctcaaa agggacgtcg    17580
cacacaaagt gtttgccaca acttcgataa agagcttctt ccgccagcta aacttgtatg    17640
gcttccgaaa acggcgtcaa tgcactttca ggaccttcac ccgcatttt tccgcaaaaa    17700 ggctggtctc catcttgaat aaggtaatga acgacaagcc tctggagggg ttaagtcggt    17760
gggctctggg gcctggtcgg gtggaagtcc caggactgcc tcctgggaag tgggcgacct    17820
caggcagggt gtgggccat cgctgtgggc ctgtgtcccc ctctgggtgg aggtgacatg    17880
aactaagagt gaatgtgggg agagggctga ggatggtgcg ggcccctctc gagtgtgtaa    17940
```

| | | | | |
|---|---|---|---|---|
| aatatcacag | gtgccaagta | gccgtatctg | cgtgtcgtcc | tccccggggc cagccatgtc 18000 |
| atctggtggt | tgctgtgtcc | ccctgactcc | acagcacatt | accctgtgag gtgagcaggc 18060 |
| caggggagtc | tggtatttgt | accactgtca | ccctagctgg | tgtctggaga ggtgctcaag 18120 |
| tggaagcact | gaagggcgcc | tggcgcagga | ggtgcagatg | ctcctgctgc ccttggtagg 18180 |
| tgggcccctg | tgtggaaga | gccagtaccc | agggcctcca | acccagccgg ggtgcattct 18240 |
| gttgccagct | gacactgcat | gggggaggcc | agaatcttc | ttccctcctg gtctgcaact 18300 |
| tcaaagaccc | tttccgccgg | ccatggacac | cctaatctgc | cattttgagg cttttttccaa 18360 |
| gacgaaagg | cccgccacaa | cttggtaaac | cttgacgatg | tgaacgcgag tccccagctt 18420 |
| cctttgggga | ctgggacctt | tccagaaaag | gcctcctggg | ccagtagagt tctcttgcac 18480 |
| aggggcgtag | atggttggta | gttgtagtcc | atccttgtga | cttg 18524 |

```
<210> SEQ ID NO 13
<211> LENGTH: 7695
<212> TYPE: DNA
<213> ORGANISM: Homo sapiens

<400> SEQUENCE: 13
```

| | | | | |
|---|---|---|---|---|
| ggcccaggag | gcctttctgg | aaaaggtccc | agtccccaaa | ggaagctggg gactcgcgtt 60 |
| cacatcgtca | aggtttacca | agttgtggcg | ggccttccg | tcttggaaaa agcctcaaaa 120 |
| tggcagatta | gggtgtccat | ggccggcgga | aagggtcttt | gaagttgcag accaggaggg 180 |
| aagaagattc | tgggcctccc | ccatgcagtg | tcagctggca | acagaatgca ccccggctgg 240 |
| gttggaggcc | ctgggtactg | gctcttccac | accaggggcc | cacctaccaa gggcagcagg 300 |
| agcatctgca | cctcctgcgc | caggcgccct | tcagtgcttc | cacttgagca cctctccaga 360 |
| caccagctag | ggtgacagtg | gtacaaatac | cagactcccc | tggcctgctc acctcacagg 420 |
| gtaatgtgct | gtggagtcag | ggggacacag | caaccaccag | atgacatggc tggccccggg 480 |
| gaggacgaca | cgcagatacg | gctacttggc | acctgtgata | ttttacacac tcgagagggg 540 |
| cccgcaccat | cctcagccct | ctccccacat | tcactcttag | ttcatgtcac ctccacccag 600 |
| aggggacac | aggcccacag | cgatggcccc | acaccctgcc | tgaggtcgcc cacttcccag 660 |
| gaggcagtcc | tgggacttcc | acccgaccag | gccccagagc | ccaccgactt aaccctcca 720 |
| gaggcttgtc | gttcattacc | ttattcaaga | tggagaccag | ccttttttgcg gagaaaatgc 780 |
| gggtgaaggt | cctgaaagtg | cattgacgcc | gttttcggaa | gccatacaag tttagctggc 840 |
| ggaagaagct | ctttatcgaa | gttgtggcaa | acactttgtg | tgcgacgtcc cttttgagaa 900 |
| tctccttttc | aaagagtttt | tgattgatca | ctctacaagc | cccactgtca tcccaccaga 960 |
| tggacgaaaa | ctggttgctg | ctgaccagtc | tccacagttt | ctgtggaaag ggagggaga 1020 |
| ggagattatc | ttctccctgg | ggcgggacgt | caccgtcagg | gtgcggcctt ctgaacgaag 1080 |
| cttcctcggc | cagaggttgg | aaagcgattt | cttctgtcag | cagcctcaag ttagggctcc 1140 |
| cagtggaccc | cgggtcgtcc | caggcagggg | aaggatctgc | tgggtgaagg taggtctctg 1200 |
| actgcaactg | ggagggaaa | ggcacccttt | ccaagccatg | atcctgtcct ctcgaatttc 1260 |
| tttcttcaca | gcgagccata | ctcaatgatc | gcttgtcctc | catctggcaa acttgctagt 1320 |
| gcagtgtggc | cagcagcacc | ccttggcagt | catgtaacca | gccccatgac atcataaagg 1380 |
| ggctctgact | gccggggggt | ggcatctcca | cccccagcaa | gttgtgtaat aaagggccaa 1440 |
| ggcagacaag | tagctgccca | tctgcatgtg | cacattctgg | tcctcacagt catttcaatg 1500 |
| ggaaagatga | cactagtgca | caagagtgcc | gaggggccct | gccacaccgt agatgcagac 1560 |

```
ctggagcggt ccccttgtcc tagagctcct gagccaggca caactacagc aaagccctgg    1620
ctcaggaagg tcagagctca ccgtctgagt catgggccca cagaccccag cacatgactg    1680
acactcggaa gcacagaaca aagggtagga cggtgcccat gggtcaggct gtagccacgc    1740
cacccttccc accctgtcct agccagaggc agcaatgtgc tccatacaga tcctcctaac    1800
acacccacac tgtcggtccc cagcacgcag atgcccgaca gcccttagg caaatggctt     1860 agctgactgc cccaccacac gccgtcgcca tgcagtccag tggggagtcg gaggcagcct    1920
ccttcctgcc tctcctcggc ctgcacgtgt cccccacca gcagagacc cttctacacc      1980 ccgggtgtct gcggtcacat cgcggtgggg catgcagctg ttggccttcg agcatgtttt    2040
gttttccttg gccagtgtct ccagagaaac gcacgtgggt ttgtgtccag cggtccatct    2100
ctgcaacagt tgttcctttg ggattggatg ctaggaggtc acgggagagg tgtccatcca    2160
aagcagtgtc tgtgtcacac actgtcccca cacacagggc cacctctgca cagactcccc    2220
cgactcgatt ctgggcacag agctcagtga ccttccagag actgccacga accggtgatg    2280
cctccacgct tgagacatcc tgaccgcagg gcccaaggcg cactggctca ggggtgaca     2340 gtgaggggtc tgcaaacaga ctgctgatgc tcaacccggc cgctgccgag ctgtgtgact    2400
tgggcacgtc acttaacctc tctcggcctc tgtctcctcc cggggataag agtagtagca    2460
cctgcttccc ggggctgtga ggatccagtg ggacgtatag gaactagcga ggcaccggca    2520
gttgggtcag agctactgtt gtcacttcac aaggcatttt cttcaacagc aagtcggaaa    2580
tctcatgagc ctaaggcaga atccacctgt ggcctctggt acaacccac aggactgaaa     2640 atccttccag ccacagcaac tggtgaattt cctggtcaat tgccacaagt catgagctga    2700
accccacttg agtttcagtt caggcagaac tctagacg actagggcaa gctagacagc       2760
gactgcagag ccttttgttg cagcgtgagc agtcctcagc tgttgacatc actggggagc    2820
aaacgaggac caggagcggt gaaaggacag tgtctgctgc agattgtcgt agcacccaag    2880
gaacactcca gaaagcctcc taagcagtaa caagtgtggc aaggtgtagc ccagccaaca    2940
gtggcatctg cgaggcgtcc cctccttcct cccactaccc cgtatacct gggacctgtg      3000 cactgaagga ctcattctaa aggctgtgcc cctgcagccg ccagcctcac tcactggctg    3060
cctgtgccag ctagagattt cttcctctg aggctggctg agaggaccac tccagtttcc      3120
tggcccatcc agcaaagaag atacacatca tgcacgtgta aaatgaggaa ccggtttatt    3180
gaacagctta aggagagcaa aaatagtggc tttagctaca tttttacac actgagcagg      3240 aaagtctaaa ccatcccgtt ccctgtacc caaagagaa cagggcttgc tggaggccag       3300
tgccaagggc ggagtcgtgc tcgcagcaga cttgaattaa ccccatgtag gccggcgagc    3360
agttgcccgc gtgaaaacac caccctcttc tcctggctga aagatcaaa gctctttttt      3420 taccctcttt tcagcaaagg acctatttgt tttcaggcag gaggatgtta aacttgcagc    3480
ctctgacaca cggtggaacc tgcagtgctt ggagaaacgg cacgcacacg tgaaaacatc    3540
atgcctactc caaagccttc ttgttgctgg caggagggaa gcttgagact ttcccacgca    3600
tagtcgtgac ccgcgtggcc gtttctgctc tcagcaacat tctctagtgt tccggcttca    3660
agcagcgctt gtcaggtttg aagctagcca ctattctgag aacgtcagaa aagcatggac    3720
catctcttgc ttggtgttgc cgttgtggca gtagcagcta ctacgtacct gcacgagttc    3780
cagggcagaa gtggcaatgt cccatgaagg cgtggcaccc cacgggggg ggggggagt      3840 gtgccacggg cgtccacttc tgcagcagaa ggcatgtgcc tacagcacaa gcttgtaaaa    3900
```

```
aaatacttga acagaatatg ctgtacagaa ctaggggtta acaccgcata tgaagatgct    3960
aaaacatttg tataaatact ctgtatacaa gcatggagtc actcccgtag aaagggctca    4020
tccgtgaggc tatgaaaaac tgctgtcagc atgcccaaag agaaactact tccacagtag    4080
gaacagaaaa aaggactgtg ctgtgtctaa acacgtggtg catcagagac atagttacag    4140
ttcctactga ctgccccagc cacgacctgg gagtgctgag gacctgggag tgctcagcga    4200
gctgcaggag gtcagccctg tggagaaata catttctaaa caatacttt gattgggatt     4260 tcagcaccgt atagacagat gttccttctg ggggcctggc aagcagccat tcccagtgg     4320 gtctgacggg gaagagggt acctggagcc cctcccagac agacggtaat cccacccctg     4380
ttctcacact cttcctggca tccgcatctg ctggcacaca cccccgtcac ctgccacttc    4440
cgcgtcccgt cgtggtgagt ggctgatagg cgctggatgc aaacaaggca tgagatggac    4500
gtacctggag acccagctcc agtactggtt ctggtctgcg gggtgaacga gggggcagag    4560 gaaggcgag agagtgcgtc ccagtccact taagctctgt ccccggaagt ggcatctaat     4620
ctggcatttc gatatttaat ttgggaggtg ggagcacata cttcccaggg ctctgggtaa    4680
tgaccaccct ggccttcttt cgaaacatgg gtgcgatttt aggggctcc ggaactgggg     4740 tctcttcggt ttcttcatta tcttcgtgat ggagatcata ggaaatgttt ccatattctc    4800
gtagaaatgg gaagatttca agcagaaact gacagaaatc tttgcggata ccaaaccacc    4860
ctgaaaaata agaatttttt atttcacaca cgaggctcaa ctgaccttcc tgttaacttt    4920 cttccgtaa caagaagttt cactcctaca atgtcataac atactttatc cagactcctg     4980
agtcacaaag cctgaacagg gcttgagtac ccaaaatggg gaagaagtgc aaatgctagc    5040
tctgtggtgc ttggagtggg gttcccggac cggcagggac agcgtccacg gggcctagtt    5100
agggatgcca ttctcgggcc ccagcccaga cctccagaaa ctgagtcggg ctagggtggg    5160
ctccagcggt ccccttttcc tggcccttt gggattctgc tggatgccca aatttgagaa     5220
ctactgctcc agtgagtctc aaaatatctg tggtgcgcag actacggtgt cttccgctaa    5280
tcttctccag ccaggataaa ctcatggatg acagtgccac ccaagaacaa gatttctgtc    5340
accctctgga atccgtgagg gcggtagtca tgcacgggtt ggccaggagg gggcctgaac    5400
tcatggagcc accttaaagc cactttccca gtcccactac tcctctctgt aggctactgg    5460
agtgtcagct cggtgcaagc cctccctgct cccgggtgcg gggtaggggg cagaggcaca    5520
aacagcaagc acagcccggg ctgctgggct gcagtgaggc cctgccccca aacccactgg    5580 cttttccgaag ggcaatgctc tgggcttccg tgccatggag cccacagcct tgccaggaag   5640
gcaccctctg cagagatcgt tttggaagtg tctgcctcag caagcaggtg gaggggaata    5700
gagtgttagc aaggcaagac aggcaagact cgggtgatgg cagcaaggat atgggggagg    5760
cagagcggcc aacagggacc taggatgaat cccaggtttg ggtgggagat gtggattttc    5820
catcaaaccc tcccgggcct gggaagaatc tgtcttgatc cccatttgc agaggaggga    5880 acgggatctc tgagaggttg cctgccgtgt ctggttctac ctcaaatggc agcgtgcact    5940
gcgagaaaag tcccggtgca ggccagcaga acaccagagt tacggcatgc ccttccctta    6000
gaaggtccca gaatttcctc agccctcact ttcccacaca gcttctaaa ttggggccct     6060 cggggactca tcccttccta gacttctatc cgccacccc cacccctgg tccccccca      6120 gacacacacc aaggacttct gaaatgctga gtacatacag tggtttcctc ccttctgtcc    6180
aaatgtggtt gccatcagcg tgatcaacga gagccaaagg gggacaaaga tcgggatgca    6240
ggagaaggcg ttgtggccat ccagtttgtg aaccagcaga atctaaagaa agagacatag    6300
```

```
tcccggttga tgccagcacc gaaaatgggc agaggcggaa gccagacttc attaggcagt    6360
tcctccccac caccccaccc ccgcgtgagc tcccacaaga gggaacatca gcaccgccag    6420
aaaaaggcag gaaaccacct atccctgggg aaagctcgaa atgagctttt atgtccctct    6480
tcagagctcg gcaatagcct atccacttga aaagttccca gtgccagcag ttttatggca    6540
aactcctccg ggtgtttgtt ctaaggagtc aacagctccc attctagaat tctccacgtg    6600
actccaatac acaaatctga catcccactc tgctttcccc agagtggaaa ctggagccat    6660
acagaggcac catggctaaa aaggtgcact cttctccctg ccagccccac gtgctgcccc    6720
caagagaaag gaaggatgct ctcctttcac cgaagctccc tctcggagat ggctgtgttc    6780
tctcccctct cctggagtgg gctcactgtg agctcgaggg acagaggctg cctttctagg    6840
ggtgcagaat cctgtcaggg gaagcgcaag cttcaggggc tgaagaggct tcccgtggaa    6900
cgcttacctc aaatgtaaga aggggcacga cgatggtcat ccagctcagg gccatggtta    6960
tgtgtgtcct gcgctgtccg caatcacatc catagagcgc aagaacaaga cggaccacac    7020
aatgtagtag aggaccacca ggcacagaaa ggacatgaga atccacagcg ggacacacac    7080
aacctggggg tgggtgagag aacagcaaga gaagtctctt tagagcttcc aacctggcct    7140
ctgatggaag gcatctttag caccttgctg tgtctgtcca gttaaggcgg tccttcctgt    7200
gagccgaata aggaccgttc catctcccag gactgctggg agcatcgctc aggacagaaa    7260
aggtatggta tgttcactat ggggcctgct gccaccaggg gacacacacg ctcagtgagt    7320
catcagtccc tcttcctttg ggtgacagac agccctgcac ctggctccgc agcctctact    7380
cttccagagg cccactctcc cacactctct caggctcctc taggttctgc tgccatcaca    7440
gcttcccggg aaatgggaca caactgtcac cctgtgcaca cacaagat  ctcaccccaa    7500 cagactctct tcacaggcaa cattcccaca acctgctggg ggtactttgg caacacaaat    7560
gggaatgggc tccccagaaa gtctggctgc ctgggctcct aaggatccct aacctcaccc    7620
ctaccaagtt agtgaacttg gcgggttgat gctggataca ggttgatgct ggatacgtag    7680
cgctgccggg tgacc                                                     7695
```

<210> SEQ ID NO 14
<211> LENGTH: 9014
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 14

```
gggcgaattg ggcccgacgt cgcatgctcc cggccgccat ggcggccgcg ggaattcgat     60
atcactagtg aattcgcggc cggcgattgg gcccgacgtc gcatgctccc ggccgccatg    120
gcggccgcgg gaattcgatt ccttaattaa gtcgactggg acccaaactt ggagtcgtt    180 gacagatgtg acaggtgaag cctgggatga catcgccaaa aatgcaacgt ctcactcatt    240
gtcactactc ccagggctca gtcgtcactg ggaaaatct  ccagaaggta gcgcgggcca    300
aggtgacagg tgtctgccaa gatctgcccg ccagactccc gggcggcgcg ctccctccct    360
gcaggccttc agcccgtcag catccccttc ctcggggccc tgctcactcc cagcctccat    420
ccccctgcca tctcctccgc cggtcgcgtg cggacacaag gatgggacc  tcccagcgag    480 gagcgctctg ggcggggctc cggacgcatg gcgcgccctc gtacggaagc ccggaaggag    540
gggcaggggg cggtggctca ggtttctccg ggcggcggcg gcggcggcgg cggcgacggc    600
```

```
gacggcgacg gcagcgggga cggcagcagt agcgggagca gcagcgtgga cgcggctggc    660
gctggcgcca tgaacccgct gtaaggcgca ggctgtgcag cacggggtgc ggggaggag     720
gaggaggacg ccgcggtgaa gttctccgcc atgaacctga ggggcctctt ccaggacttc    780
aacccgaggt gaggcggcgt cgttggcgcc cccgggagtc cgcgctgcgg gctcgggcgc    840
gggctggtgt tcggctccgg ggaggcacgg cgggcgagat gctgcagccc gaggacccgg    900
gcgcctgccc gagcctccct gcgggtgcaa gcggtcccca ggcaaaacag tcggcctcgg    960
cgcccgcccg cttcctcctc ccgtgccggg tgctttcagc ccctgcccgg ccacggccgg   1020
aagggcccgg ccgcgagccc cgtcctgccc caagggaacc ccattctttt ctgcttgctg   1080
tccctcattg gtgtcccaac ttcttcgtct cggttccatc ctcttctgcg ccgctgcggg   1140
ccctccattc tccgcgtcag ggccgtctca ctcgacccaa cacccctacc cccacccag    1200
ctgtttcctc cagttcctcg cagtccttgg ggttttcctt gggtttatgc ccatccctct   1260
cttgtttgct tctttgttga acggatacct gaaacactgt tgaatccttg gagtcagtgt   1320
cggggtatgg caataccttg tataatgcat ttctgggtga gcctgatcat tttccatact   1380
cattttctca tcagtcttca ctacaagttt atttgcagga agtagatatt gctgtccttc   1440
ttttccagat ggggaacacc cagtggacag tgtggagaaa acactggcta agcactcaag   1500
cgcctgtcct tgcacttgcc cgactgtttt gtaactgttc tttaccccag gctgtgagct   1560
ccctgaagct gagaccatct cctgctcatc tcagtgtccc cagcgcctcc cacccaccgt   1620
atctggcaca tagtaggcac atataaaatg tttgtggaac taaactgagc ccaaagactt   1680
ggattggaga cgaggccata tgtaactggg tgattctctg cccttctttg gcccttctgt   1740
aaaatgagga gttggcctaa ctgatctctt aaatgcacta ctctccgaaa ggagtatccg   1800
tttcccttat ttgccagttg ggaagacgtg ctcagtaaat atttgtgtgc tgtaacctat   1860
gttaggtgct ttagatgctg gcggtctcag catggggtga agaagggctt gtacacttaa   1920
gatgccttac agtactgtgc agtgctgtac tgcgggggcc aactctgggg acctatgcct   1980
tggctgcttg ttgaggatga aaggaagttt taggggagta tttgtatgtt gagggtgcag   2040
tctccctagg gatggtgaca ttttaacttg tgagtcattg tgactttgta tgtgcccta    2100
ttccactttg agttcatgtt ctggttagga gtgccagtgt ctctaacacg gtgcagacat   2160
tatcattgtt ggcttcgaag gcatagagga ggtaacagaa ctaactgcag tcccttcctc   2220
tgctgcatca gggggttaag attggtctgc agggtagtag ggttggtgct gtggctggac   2280
aagccctgta tgtcttctat ttggagatgg tgataagaaa gttaagtaaa aactgaattg   2340
ttttgtgccc ttgggcaact cacttatcta ttgtttatc tgtagaatga gtataatctc    2400
tcagtggggt agggaggcca attaaggatt gattacaaag tgccttacaa atagaaagct   2460
acagtgactt gtttgcaagg tgacagagaa ttcagaagcc tcaagaaact gccttaagtg   2520
atcaaacagg ctaacggagt tgccaaagca aaatagtgct gcactgatac tacctttaac   2580
cgttttttcc tttagcccctt ttccccccaa aaaattagt atatgaaatt acagtgaaat   2640
acctggtatc taagcagatt tatagtaatt ctcaacatat tcatcaatct cttaattcta   2700
cctgcattaa aatgtatttc tacctgaaaa gtttaaaggt cttttatact gtgccatttt   2760
cctgattcat tgttgccaga ggtagtgagt tccttaattt tacagatatt tcaagaggac   2820
attggccagg tattattggt aaatcagatt tgttttttta gctggtagtg tttcacctct   2880
cctgagcact cctagttttt gacagtgtgc tttagtctcc ttccatgctg aggaaggcct   2940
```

```
tctctatagg agaaagaaaa ctgaggggtg tacacaggaa gttacctttat gctgggggact    3000 caaaccttga tgctactgct ttgctccctg cctctatttt tgaaccaatt caacatctcc    3060
ctcctacccc aggaccttgt cacacactgt tctctttacc aggaatgttt ccctctcttt    3120
tcctctcctc cagacctagt gaactcctat ttatcctcac ttggcacttg ctaagggaag    3180
cattcctgac ttccctgacc agatttactg ctccctgttt ctacagttcc tgtagtattt    3240
actactcctc catcatagtg catatttgta cccttgtgtc tgtctggatg cttatttgat    3300
taatacctgc ctcccccact aaactttaag ctccatgggg tcaaggccgt gactgtgtca    3360
gtatcgtagc ctgcatactt ggaatagtac ctggctcaat aaatatttgt ggagtaaata    3420
actgaataac tctccagagc ctataagata aatctagagc tgctgctttc aatcactgct    3480
ttcctggtgg tctgtggcct ggttctcttt cttctcacac tcttcccacc ttcagagtgc    3540
agccattgct ttggagagat gggagagaac atggcactaa ggcagaatat ggctatattt    3600
actttgaaga gcatgtcttt gtcatagaaa tagtcactgt catggtttgg tgggtcccaa    3660
ggcatgggtc atggctccag atccccttc cagccttttg gatcttggta agtctgaacc    3720
cactgctgcg ttggcaaggc tctggaaact atagtgacag agaatgattc acaagtgtca    3780
acactcagat gtacagggct gccagctgac ccactctacc tatttccatc tggcactgaa    3840
ctggttgatc atgaacttct tttcataatt gcttttagt tatgcaggtt aagacatgcc    3900
gaaacagatg taccggaccc acaaacaagt ccttccttga atgcctgagg cttcctaaca    3960
gtgaaagagc cctgttctta gagtaggcaa actgattctg aggcattgta ggtggtaggg    4020
atctggtagt aggtagcatt aggtgggctc ccggcactca ccatggagcc ttgaaatttt    4080
ctgctacttt gggggagttg ctggttcaga gaaggcccctt ccaccctggt agccatgtgg    4140
cactggaagg ctgtgaaaac tctgctgggc cttcttagtc atctgttgtg agctcctgat    4200
gggagtgtgg tgtatccctc aggtgtgcta gactggaaca aaggctgaga agtgttgctc    4260
tgggggttcc aacttgtggg catggggtac tgatgagatc agtagtgttt ggagacttct    4320
gtatgctcca tcttcagaag acattctgga gtccatataa gttatcttgt ctcttgtttg    4380
aagcaggaaa aaggaatgcg attgctggta atatagttca ctaaagtcag ctacctggcc    4440
tctaacagtt atttgcaaag tatattataa cattgattcc tcaaacatct agattcctat    4500
ctcgtgccaa gtgatgtact aggtgctcta agtacaaaaa taaggaata tagtcctcct    4560 ctcaatgcgt aagcctagtg gaagaagcag aaatgaaagg gaaataagaa ttcaatagag    4620
tatgaggcat tacagtgaaa gaaaccaaat gtcttagaag tacaaatggc agagctacta    4680
attctgtctc gagcaggcag ggaagagtct atagtggaaa tgacttttga gctagatttt    4740
gaattgagct agtcttttga gccagacttt tgagctagaa ttgtagggtt gtcatcagac    4800
cagagagtag gaagggtacc ttgtgaggaa gagagagaga gatcagattg ttactgtgtc    4860
tatgtagaaa aggaagacat aagaaactcc attttgatct gtactaagaa aaattgtttc    4920
tgctttgaga tgctgttaac ctgtaactttt agtcccaacc ctgtgctcac agaaacctgt    4980
gctgtaatga atcaaggttt aatggattta gggctgtgca ggatgtacct tgttaacaat    5040
atgtttgcag gcagtatgct tggtaaaagt catcgccatt tccattctc gattaaccag    5100 ggacacagtg cactgcggaa ggccgcaggg acatctgccc aagaaagcct gggtattgtc    5160
caaggtttcc ccccactgag acagcctgag atatggcctt gtgggaaagg aaagaccta    5220 ccaccccca gcccgacacc cgtaaagtgt ctgtgctgag gaggagtagt gaaagagcgg    5280
ggcctctttg cagttgagat aagaggaagg cttctgtctc ctgctcatcc ctgggaatgg    5340
```

-continued

```
aatgtctctg tgtaaagctg accattccca ttcgttctat tctgagatag gagaaaacca    5400
ccctgtggct ggaggcgaag tatgctggca gcaatactgc tctgttactc tttgctacac    5460
tgagttgttt gggtaaagag aaacataaat ctagcctgcg tgcacatcca ggcacagtac    5520
ctttccttga acttattcat gatacagatt cctttgctca cgtttccctg ctgaccttct    5580
ccccacctgt tgccctgcta cactcccctc gctaagatag taaaaataat gatcagtaaa    5640
tactgaggta actcagaggc tagcgctggt gcgggtcctc cgtatgctga gtgccggtcc    5700
cctgggccca ctgttctttc tctatacttt gtttctgtgt cttatttctt ttctcagtct    5760
cgtcccacct gacgagaaat acccacaggt gtggaggggc tggccccttt cagtatctca    5820
gaagggacaa agtacacaaa ggcatggggt catgatagtg cctggtatgt tcaggtagtg    5880
aagaggtcca tgtggtatga gcactgcaga tgatatgtgt cgtatgaatt aaaaatacat    5940
agttactgca aatagttttt acaggttatt gtttttaaga aagcagtatc taatgcacga    6000
gtgtactgtc agtactgtca atgaactact taccactcaa gtgactgctt acgcgtcgaa    6060
tcactagtga attcgcggcc gcctgcaggt cgaccatatg ggagagctcc caacgcgttg    6120
gatgcatagc ttgagtattc tatagtgtca cctaaatagc ttggcgtaat catggtcata    6180
gctgtttcct gtgtgaaatt gttatccgct cacaattcca cacaacatac gagccggaag    6240
cataaagtgt aaagcctggg gtgcctaatg agtgagctaa ctcacattaa ttgcgttgcg    6300
ctcactgccc gctttccagt cgggaaacct gtcgtgccag ctgcattaat gaatcggcca    6360
acgcgcgggg agaggcggtt tgcgtattgg gcgctcttcc gcttcctcgc tcactgactc    6420
gctgcgctcg tcgttcggc tgcggcgagc ggtatcagct cactcaaagg cggtaatacg    6480
gttatccaca gaatcagggg ataacgcagg aaagaacatg tgagcaaaag gccagcaaaa    6540
ggccaggaac cgtaaaaagg ccgcgttgct ggcgtttttc cataggctcc gcccccctga    6600
cgagcatcac aaaaatcgac gctcaagtca gaggtggcga aacccgacag gactataaag    6660
ataccaggcg tttccccctg gaagctccct cgtgcgctct cctgttccga ccctgccgct    6720
taccggatac ctgtccgcct ttctcccttc gggaagcgtg gcgctttctc atagctcacg    6780
ctgtaggtat ctcagttcgg tgtaggtcgt tcgctccaag ctgggctgtg tgcacgaacc    6840
ccccgttcag cccgaccgct gcgccttatc cggtaactat cgtcttgagt ccaacccggt    6900
aagacacgac ttatcgccac tggcagcagc cactggtaac aggattagca gagcgaggta    6960
tgtaggcggt gctacagagt tcttgaagtg gtggcctaac tacggctaca ctagaagaac    7020
agtatttggt atctgcgctc tgctgaagcc agttaccttc ggaaaaagag ttggtagctc    7080
ttgatccggc aaacaaacca ccgctggtag cggtggtttt tttgtttgca agcagcagat    7140
tacgcgcaga aaaaaggat ctcaagaaga tcctttgatc ttttctacgg ggtctgacgc    7200
tcagtggaac gaaaactcac gttaagggat tttggtcatg agattatcaa aaaggatctt    7260
cacctagatc cttttaaatt aaaaatgaag ttttaaatca atctaaagta tatatgagta    7320
aacttggtct gacagttacc aatgcttaat cagtgaggca cctatctcag cgatctgtct    7380
atttcgttca tccatagttg cctgactccc cgtcgtgtag ataactacga tacgggaggg    7440
cttaccatct ggccccagtg ctgcaatgat accgcgagac ccacgctcac cggctccaga    7500
tttatcagca ataaaccagc cagccggaag ggccgagcgc agaagtggtc ctgcaacttt    7560
atccgcctcc atccagtcta ttaattgttg ccgggaagct agagtaagta gttcgccagt    7620
taatagtttg cgcaacgttg ttgccattgc tacaggcatc gtggtgtcac gctcgtcgtt    7680
```

```
tggtatggct tcattcagct ccggttccca acgatcaagg cgagttacat gatcccccat    7740
gttgtgcaaa aaagcggtta gctccttcgg tcctccgatc gttgtcagaa gtaagttggc    7800
cgcagtgtta tcactcatgg ttatggcagc actgcataat tctcttactg tcatgccatc    7860
cgtaagatgc ttttctgtga ctggtgagta ctcaaccaag tcattctgag aatagtgtat    7920
gcggcgaccg agttgctctt gcccggcgtc aatacgggat aataccgcgc cacatagcag    7980
aactttaaaa gtgctcatca ttggaaaacg ttcttcgggg cgaaaactct caaggatctt    8040
accgctgttg agatccagtt cgatgtaacc cactcgtgca cccaactgat cttcagcatc    8100
ttttactttc accagcgttt ctgggtgagc aaaaacagga aggcaaaatg ccgcaaaaaa    8160
gggaataagg gcgacacgga aatgttgaat actcatactc ttccttttc aatattattg    8220
aagcatttat cagggttatt gtctcatgag cggatacata tttgaatgta tttagaaaaa    8280
taaacaaata ggggttccgc gcacatttcc ccgaaaagtg ccacctgatg cggtgtgaaa    8340
taccgcacag atgcgtaagg agaaaatacc gcatcaggaa attgtaagcg ttaatatttt    8400
gttaaaattc gcgttaaatt tttgttaaat cagctcattt tttaaccaat aggccgaaat    8460
cggcaaaatc ccttataaat caaaagaata daccgagata gggttgagtg ttgttccagt    8520
ttggaacaag agtccactat taagaacgt ggactccaac gtcaaagggc gaaaaaccgt    8580
ctatcagggc gatggcccac tacgtgaacc atcaccctaa tcaagttttt tggggtcgag    8640
gtgccgtaaa gcactaaatc ggaaccctaa agggagcccc cgatttagag cttgacgggg    8700
aaagccggcg aacgtggcga gaaggaagg gaagaaagcg aaaggagcgg cgctagggc    8760
gctggcaagt gtagcggtca cgctgcgcgt aaccaccaca cccgccgcgc ttaatgcgcc    8820
gctacagggc gcgtccattc gccattcagg ctgcgcaact gttgggaagg gcgatcggtg    8880
cgggcctctt cgctattacg ccagctggcg aaaggggat gtgctgcaag gcgattaagt    8940
tgggtaacgc cagggtttc ccagtcacga cgttgtaaaa cgacggccag tgaattgtaa    9000
tacgactcac tata                                                     9014
```

<210> SEQ ID NO 15
<211> LENGTH: 5954
<212> TYPE: DNA
<213> ORGANISM: Homo sapiens

<400> SEQUENCE: 15

```
ggccgcggga attcgattcc ttaattaagt cgactgggac ccaaactttg gagtcgttga      60
cagatgtgac aggtgaagcc tgggatgaca tcgccaaaaa tgcaacgtct cactcattgt     120
cactactccc agggctcagt cgtcactggg gaaaatctcc agaaggtagc gcgggccaag     180
gtgacaggtg tctgccaaga tctgcccgcc agactcccgg gcggcgcgct ccctccctgc     240
aggccttcag cccgtcagca tccccttcct cggggccctg ctcactccca gcctccatcc     300
ccctgccatc tcctccgccg gtcgcgtgcg gacacaagga tggggacctc ccagcgagga     360
gcgctctggg cggggctccg gacgcatgcg cggccctcgt acggaagccc ggaaggaggg     420
gcaggggcg gtggctcagg tttctccggg cggcggcggc ggcggcggcg cgacggcga      480
cggcgacggc agcggggacg gcagcagtag cgggagcagc agcgtggacg cggctggcgc     540
tggcgccatg aacccgctgt aaggcgcagg ctgtgcagca cggggtgcgg gggaggagga     600
ggaggacgcc gcggtgaagt tctccgccat gaacctgagg ggcctcttcc aggacttcaa     660
cccgaggtga ggcggcgtcg ttggcgcccc cgggagtccg cgctgcgggc tcggcgcgg      720
gctggtgttc ggctccgggg aggcacggcg ggcgagatgc tgcagcccga ggacccgggc     780
```

-continued

```
gcctgcccga gcctccctgc gggtgcaagc ggtccccagg caaaacagtc ggcctcggcg    840
cccgcccgct tcctcctccc gtgcccggtg ctttcagccc ctgcccggcc acggccggaa    900
gggcccggcc gcgagccccg tcctgcccca agggaacccc attcttttct gcttgctgtc    960
cctcattggt gtcccaactt cttcgtctcg gttccatcct cttctgcgcc gctgcgggcc   1020
ctccattctc cgcgtcaggg ccgtctcact cgacccaaca cccctacccc caccccagct   1080
gtttcctcca gttcctcgca gtccttgggg ttttccttgg gtttatgccc atccctctct   1140
tgtttgcttc tttgttgaac ggatacctga aacactgttg aatccttgga gtcagtgtcg   1200
gggtatggca ataccttata taatgcattt ctgggtgagc ctgatcattt ccatactca    1260
ttttctcatc agtcttcact acaagtttat ttgcaggaag tagatattgc tgtccttctt   1320
ttccagatgg ggaacaccca gtggacagtg tggagaaaac actggctaag cactcaagcg   1380
cctgtccttg cacttgcccg actgttttgt aactgttctt taccccaggc tgtgagctcc   1440
ctgaagctga gaccatctcc tgctcatctc agtgtcccca gcgcctccca cccaccgtat   1500
ctggcacata gtaggcacat ataaaatgtt tgtggaacta aactgagccc aaagacttgg   1560
attggagacg aggccatatg taactgggtg attctctgcc cttcttttgc ccttctgtaa   1620
aatgaggagt tggcctaact gatctcttaa atgcactact ctccgaaagg agtatccgtt   1680
tcccttattt gccagttggg aagacgtgct cagtaaatat ttgtgtgctg taacctatgt   1740
taggtgcttt agatgctggc ggtctcagca tggggtgaag aagggcttgt acacttaaga   1800
tgccttacag tactgtgcag tgctgtactg cgggggccaa ctctggggac ctatgccttg   1860
gctgcttgtt gaggatgaaa ggaagtttta ggggagtatt tgtatgttga gggtgcagtc   1920
tccctaggga tggtgacatt ttaacttgtg agtcattgtg actttgtatg tgcccttatt   1980
ccactttgag ttcatgttct ggttaggagt gccagtgtct ctaacacggt gcagacatta   2040
tcattgttgg cttcgaaggc atagaggagg taacagaact aactgcagtc ccttcctctg   2100
ctgcatcagg gggttaagat tggtctgcag ggtagtaggg ttggtgctgt ggctggacaa   2160
gccctgtatg tcttctattt ggagatggtg ataagaaagt taagtaaaaa ctgaattgtt   2220
ttgtgccctt gggcaactca cttatctatt gttttatctg tagaatgagt ataatctctc   2280
agtggggtag ggaggccaat taaggattga ttacaaagtg ccttacaaat agaaagctac   2340
agtgacttgt ttgcaaggtg acagagaatt cagaagcctc aagaaactgc cttaagtgat   2400
caaacaggct aacggagttg ccaaagcaaa atagtgctgc actgatacta cctttaaccg   2460
ttttttcctt tagcccttttt ccccccaaaa aaattagtat atgaaattac agtgaaatac   2520
ctggtatcta agcagattta tagtaattct caacatattc atcaatctct taattctacc   2580
tgcattaaaa tgtatttcta cctgaaaagt ttaaggtct tttatactgt gccattttcc    2640
tgattcattg ttgccagagg tagtgagttc cttaattttta cagatatttc aagaggacat   2700
tggccaggta ttattggtaa atcagatttg tttttttagc tggtagtgtt tcacctctcc   2760
tgagcactcc tagttttttga cagtgtgctt tagtctcctt ccatgctgag gaaggccttc   2820
tctataggag aaagaaaact gagggggtgta cacaggaagt taccttatgc tggggactca   2880
aaccttgatg ctactgcttt gctccctgcc tctattttg aaccaattca acatctccct    2940
cctacccccag gaccttgtca cacactgttc tctttaccag gaatgtttcc ctctcttttc   3000
ctctcctcca gacctagtga actcctattt atcctcactt ggcacttgct aagggaagca   3060
ttcctgactt ccctgaccag atttactgct ccctgttcct acagttcctg tagtatttac   3120
```

```
tactcctcca tcatagtgca tatttgtacc cttgtgtctg tctggatgct tatttgatta    3180
ataccctgcct cccccactaa actttaagct ccatgggggtc aaggccgtga ctgtgtcagt   3240
atcgtagcct gcatacttgg aatagtacct ggctcaataa atatttgtgg agtaaataac    3300
tgaataactc tccagagcct ataagataaa tctagagctg ctgctttcaa tcactgcttt    3360
cctggtggtc tgtggcctgg ttctctttct tctcacactc ttcccacctt cagagtgcag    3420
ccattgcttt ggagagatgg gagagaacat ggcactaagg cagaatatgg ctatatttac    3480
tttgaagagc atgtctttgt catagaaata gtcactgtca tggtttggtg ggtcccaagg    3540
catgggtcat ggctccagat cccctttcca gccttttgga tcttggtaag tctgaaccca    3600
ctgctgcgtt ggcaaggctc tggaaactat agtgacagag aatgattcac aagtgtcaac    3660
actcagatgt acagggctgc cagctgaccc actctaccta tttccatctg cactgaact     3720
ggttgatcat gaacttcttt tcataattgc tttttagtta tgcaggttaa gacatgccga    3780
aacagatgta ccgacccac aaacaagtcc ttccttgaat gcctgaggct tcctaacagt     3840
gaaagagccc tgttcttaga gtaggcaaac tgattctgag gcattgtagg tggtagggat    3900
ctggtagtag gtagcattag gtgggctccc ggcactcacc atggagcctt gaaattttct    3960
gctactttgg gggagttgct ggttcagaga aggcccttcc accctggtag ccatgtggca    4020
ctggaaggct gtgaaaactc tgctgggcct tcttagtcat ctgttgtgag ctcctgatgg    4080
gagtgtggtg tatccctcag gtgtgctaga ctggaacaaa ggctgagaag tgttgctctg    4140
ggggttccaa cttgtgggca tggggtactg atgagatcag tagtgtttgg agacttctgt    4200
atgctccatc ttcagaagac attctggagt ccatataagt tatcttgtct cttgtttgaa    4260
gcaggaaaaa ggaatgcgat tgctggtaat atagttcact aaagtcagct acctggcctc    4320
taacagttat ttgcaaagta tattataaca ttgattcctc aaacatctag attcctatct    4380
cgtgccaagt gatgtactag gtgctctaag tacaaaaata aaggaatata gtcctcctct    4440
caatgcgtaa gcctagtgga agaagcagaa atgaaaggga aataagaatt caatagagta    4500
tgaggcatta cagtgaaaga aaccaaatgt cttagaagta caaatggcag agctactaat    4560
tctgtctcga gcaggcaggg aagagtctat agtggaaatg acttttgagc tagattttga    4620
attgagctag tcttttgagc cagacttttg agctagaatt gtagggttgt catcagacca    4680
gagagtagga agggtacctt gtgaggaaga gagagagaga tcagattgtt actgtgtcta    4740
tgtagaaaag gaagacataa gaaactccat tttgatctgt actaagaaaa attgtttctg    4800
cttttgagatg ctgttaacct gtaactttag tcccaaccct gtgctcacag aaacctgtgc   4860
tgtaatgaat caaggtttaa tggatttagg gctgtgcagg atgtaccttg ttaacaatat    4920
gtttgcaggc agtatgcttg gtaaaagtca tcgccattct ccattctcga ttaaccaggg    4980
acacagtgca ctgcggaagg ccgcagggac atctgcccaa gaaagcctgg gtattgtcca    5040
aggtttcccc ccactgagac agcctgagat atggccttgt gggaaaggaa agaccttacc    5100
acccccagc ccgacacccg taaagtgtct gtgctgagga ggagtagtga aagagcgggg     5160
cctctttgca gttgagataa gaggaaggct tctgtctcct gctcatccct gggaatggaa    5220
tgtctctgtg taaagctgac cattcccatt cgttctattc tgagatagga gaaaccacc    5280
ctgtggctgg aggcgaagta tgctggcagc aatactgctc tgttactctt tgctacactg    5340
agttgtttgg gtaaagagaa acataaatct agcctgcgtg cacatccagg cacagtacct    5400
ttccttgaac ttattcatga tacagattcc tttgctcacg tttccctgct gaccttctcc    5460
ccacctgttg ccctgctaca ctcccctcgc taagatagta aaaataatga tcagtaaata    5520
```

```
ctgaggtaac tcagaggcta gcgctggtgc gggtcctccg tatgctgagt gccggtcccc    5580
tgggcccact gttctttctc tatactttgt ttctgtgtct tatttctttt ctcagtctcg    5640
tcccacctga cgagaaatac ccacaggtgt ggaggggctg gccccttca gtatctcaga    5700 agggacaaag tacacaaagg catggggtca tgatagtgcc tggtatgttc aggtagtgaa    5760
gaggtccatg tggtatgagc actgcagatg atatgtgtcg tatgaattaa aaatacatag    5820
ttactgcaaa tagtttttac aggttattgt ttttaagaaa gcagtatcta atgcacgagt    5880
gtactgtcag tactgtcaat gaactactta ccactcaagt gactgcttac gcgtcgaatc    5940
actagtgaat tcgc                                                      5954
```

<210> SEQ ID NO 16
<211> LENGTH: 30756
<212> TYPE: DNA
<213> ORGANISM: Homo sapiens
<220> FEATURE:
<221> NAME/KEY: modified_base
<222> LOCATION: (5934)
<223> OTHER INFORMATION: a, c, g, t, unknown or other

<400> SEQUENCE: 16

```
gtacggaagc ccggaaggag gggcaggggg cggtggctca ggtttctccg ggcggcggcg      60
gcggcggcgg cggcgacggc gacggcgacg gcagcgggga cggcagcagt agcgggagca     120
gcagcgtgga cgcggctggc gctggcgcca tgaacccgct gtaaggcgca ggctgtgcag     180
cacggggtgc gggggaggag gaggaggacg ccgcggtgaa gttctccgcc atgaacctga     240
ggggcctctt ccaggacttc aacccgaggt gaggcggcgt cgttggcgcc cccgggagtc     300
cgcgctgcgg gctcgggcgc gggctggtgt tcggctccgg ggaggcacgg cgggcgagat     360
gctgcagccc gaggacccgg gcgcctgccc gagcctccct gcgggtgcaa gcggtcccca     420
ggcaaaacag tcggcctcgg cgcccgcccg cttcctcctc ccgtgcccgg tgctttcagc     480
ccctgcccgg ccacggccgg aagggcccgg ccgcgagccc cgtcctgccc caagggaacc     540
ccattctttt ctgcttgctg tccctcattg gtgtcccaac ttcttcgtct cggttccatc     600
ctcttctgcg ccgctgcggg ccctccattc tccgcgtcag ggccgtctca ctcgacccaa     660 caccccctacc cccaccccag ctgtttcctc cagttcctcg cagtccttgg ggttttcctt    720
gggtttatgc ccatccctct cttgtttgct tctttgttga acggataccct gaaacactgt    780 tgaatccttg gagtcagtgt cggggtatgg caataccctta tataatgcat ttctgggtga    840
gcctgatcat tttccatact cattttctca tcagtcttca ctacaagttt atttgcagga    900
agtagatatt gctgtccttc ttttccagat ggggaacacc cagtgacag tgtggagaaa     960 acactggcta agcactcaag cgcctgtcct tgcacttgcc cgactgtttt gtaactgttc    1020
tttaccccag gctgtgagct ccctgaagct gagaccatct cctgctcatc tcagtgtccc    1080
cagcgcctcc cacccaccgt atctggcaca tagtaggcac atataaaatg tttgtggaac    1140
taaactgagc ccaaagactt ggattggaga cgaggccata tgtaactggg tgattctctg    1200
cccttctttg gcccttctgt aaaatgagga gttggcctaa ctgatctctt aaatgcacta    1260
ctctccgaaa ggagtatccg tttcccttat ttgccagttg ggaagacgtg ctcagtaaat    1320
atttgtgtgc tgtaacctat gttaggtgct ttagatgctg gcggtctcag catggggtga    1380
agaagggctt gtacacttaa gatgcctttac agtactgtgc agtgctgtac tgcgggggcc    1440
aactctgggg acctatgcct tggctgcttg ttgaggatga aggaagttt tagggagta     1500
```

```
tttgtatgtt gagggtgcag tctccctagg gatggtgaca ttttaacttg tgagtcattg    1560
tgactttgta tgtgcccttc ttccactttg agttcatgtt ctggttagga gtgccagtgt    1620
ctctaacacg gtgcagacat tatcattgtt ggcttcgaag gcatagagga ggtaacagaa    1680
ctaactgcag tcccttcctc tgctgcatca gggggttaag attggtctgc agggtagtag    1740
ggttggtgct gtggctggac aagccctgta tgtcttctat ttggagatgg tgataagaaa    1800
gttaagtaaa aactgaattg ttttgtgccc ttgggcaact cacttatcta ttgttttatc    1860
tgtagaatga gtataatctc tcagtggggt agggaggcca attaaggatt gattacaaag    1920
tgccttacaa atagaaagct acagtgactt gtttgcaagg tgacagagaa ttcagaagcc    1980
tcaagaaact gccttaagtg atcaaacagg ctaacggagt tgccaaagca aaatagtgct    2040
gcactgatac tacctttaac cgttttttcc tttagcccct tccccccaa aaaaattagt    2100 atatgaaatt acagtgaaat acctggtatc taagcagatt tatagtaatt ctcaacatat    2160
tcatcaatct cttaattcta cctgcattaa aatgtatttc tacctgaaaa gtttaaaggt    2220
cttttatact gtgccatttt cctgattcat tgttgccaga ggtagtgagt tccttaattt    2280
tacagatatt tcaagaggac attggccagg tattattggt aaatcagatt tgtttttta    2340 gctggtagtg tttcacctct cctgagcact cctagttttt gacagtgtgc tttagtctcc    2400
ttccatgctg aggaaggcct tctctatagg agaaagaaaa ctgaggggtg tacacaggaa    2460
gttaccttat gctggggact caaaccttga tgctactgct ttgctccctg cctctatttt    2520
tgaaccaatt caacatctcc ctcctacccc aggaccttgt cacacactgt tctcttacc     2580 aggaatgttt ccctctcttt tcctctcctc cagacctagt gaactcctat ttatcctcac    2640
ttggcacttg ctaagggaag cattcctgac ttccctgacc agatttactg ctccctgttt    2700
ctacagttcc tgtagtattt actactcctc catcatagtg catatttgta cccttgtgtc    2760
tgtctggatg cttatttgat taatacctgc ctcccccact aaactttaag ctccatgggg    2820
tcaaggccgt gactgtgtca gtatcgtagc ctgcatactt ggaatagtac ctggctcaat    2880
aaatatttgt ggagtaaata actgaataac tctccagagc ctataagata aatctagagc    2940
tgctgctttc aatcactgct ttcctggtgg tctgtggcct ggttctcttt cttctcacac    3000
tcttcccacc ttcagagtgc agccattgct ttggagagat gggagagaac atggcactaa    3060
ggcagaatat ggctatattt actttgaaga gcatgtcttt gtcatagaaa tagtcactgt    3120
catggtttgg tgggtcccaa ggcatgggtc atggctccag atccccttc cagccttttg     3180 gatcttggta agtctgaacc cactgctgcg ttggcaaggc tctggaaact atagtgacag    3240
agaatgattc acaagtgtca acactccagat gtacagggct gccagctgac ccactctacc    3300
tatttccatc tggcactgaa ctggttgatc atgaacttct tttcataatt gcttttagt     3360 tatgcaggtt aagacatgcc gaaacagatg taccggaccc acaaacaagt ccttccttga    3420
atgcctgagg cttcctaaca gtgaaagagc cctgttctta gagtaggcaa actgattctg    3480
aggcattgta ggtggtaggg atctggtagt aggtagcatt aggtgggctc ccggcactca    3540
ccatggagcc ttgaaatttt ctgctacttt gggggagttg ctggttcaga gaaggccctt    3600
ccaccctggt agccatgtgg cactggaagg ctgtgaaaac tctgctgggc cttcttagtc    3660
atctgttgtg agctcctgat gggagtgtgg tgtatccctc aggtgtgcta gactggaaca    3720
aaggctgaga agtgttgctc tgggggttcc aacttgtggg catgggtac tgatgagatc     3780 agtagtgttt ggagacttct gtatgctcca tcttcagaag acattctgga gtccatataa    3840
gttatcttgt ctcttgtttg aagcaggaaa aaggaatgcg attgctggta atatagttca    3900
```

```
ctaaagtcag ctacctggcc tctaacagtt atttgcaaag tatattataa cattgattcc    3960
tcaaacatct agattcctat ctcgtgccaa gtgatgtact aggtgctcta agtacaaaaa    4020
taaaggaata tagtcctcct ctcaatgcgt aagcctagtg gaagaagcag aaatgaaagg    4080
gaaataagaa ttcaatagag tatgaggcat tacagtgaaa gaaaccaaat gtcttagaag    4140
tacaaatggc agagctacta attctgtctc gagcaggcag ggaagagtct atagtggaaa    4200
tgacttttga gctagatttt gaattgagct agtcttttga gccagacttt tgagctagaa    4260
ttgtagggtt gtcatcagac cagagagtag gaagggtacc ttgtgaggaa gagagagaga    4320
gatcagattg ttactgtgtc tatgtagaaa aggaagacat aagaaactcc attttgatct    4380
gtactaagaa aaattgtttc tgctttgaga tgctgttaac ctgtaacttt agtcccaacc    4440
ctgtgctcac agaaacctgt gctgtaatga atcaaggttt aatggattta gggctgtgca    4500
ggatgtacct tgttaacaat atgtttgcag gcagtatgct tggtaaaagt catcgccatt    4560
ctccattctc gattaaccag ggacacagtg cactgcggaa ggccgcaggg acatctgccc    4620
aagaaagcct gggtattgtc caaggtttcc ccccactgag acagcctgag atatggcctt    4680
gtgggaaagg aaagacctta ccaccccccca gcccgacacc cgtaaagtgt ctgtgctgag    4740
gaggagtagt gaaagagcgg ggcctctttg cagttgagat aagaggaagg cttctgtctc    4800
ctgctcatcc ctgggaatgg aatgtctctg tgtaaagctg accattccca ttcgttctat    4860
tctgagatag gagaaaacca ccctgtggct ggaggcgaag tatgctggca gcaatactgc    4920
tctgttactc tttgctacac tgagttgttt gggtaaagag aaacataaat ctagcctgcg    4980
tgcacatcca ggcacagtac cttcccttga acttattcat gatacagatt cctttgctca    5040
cgtttccctg ctgaccttct ccccacctgt tgccctgcta cactcccctc gctaagatag    5100
taaaaataat gatcagtaaa tactgaggta actcagaggc tagcgctggt gcgggtcctc    5160
cgtatgctga gtgccggtcc cctgggccca ctgttctttc tctatacttt gtttctgtgt    5220
cttatttctt ttctcagtct cgtcccacct gacgagaaat acccacaggt gtggagggc    5280 tggccccttt cagtatctca gaagggacaa agtacacaaa ggcatgggt catgatagtg    5340 cctggtatgt tcaggtagtg aagaggtcca tgtggtatga gcactgcaga tgatatgtgt    5400
cgtatgaatt aaaaatacat agttactgca aatagttttt acaggttatt gttttttaaga    5460 aagcagtatc taatgcacga gtgtactgtc agtactgtca atgaactact taccactcaa    5520
gtgactgctt acgcgtcgaa tcactagtga attcgcggcc gctcgagtc tagaactagt    5580 ggatccccca aacgggccct ctagacgcgt tgacattgat tattgactag ttattaatag    5640
taatcaatta cggggtcatt agttcatagc ccatgatatc atatggagtt ccgcgttaca    5700
taacttacgg taaatggccc gcctggctga ccgcccaacg acccccgccc attgacgtca    5760
ataatgacgt atgttcccat agtaacgcca taggggactt tccattgacg tcaatgggtg    5820
gagtatttac ggtaaactgc ccacttggca gtacatcaag tgtatcatat gccaagtacg    5880 ccccccctatt gacgtcaatg acggtaaatg gcccgcctgg cattatgccc agtncatgac    5940
cttatgggac tttcctactt ggcagacatc tacgtattag tcatcgctat taccatggtg    6000
atgcggtttt ggcagtacat caatgggcgt ggatagcggt ttgactcacg ggatttttcc    6060
aagtctccac cccattgacg tcaatgggag tttgttttgg caccaaaatc aacgggactt    6120
tccaaaatgt cgtaacaact ccgccccatt gacgcaaatg ggcggtaggc gtgtacggtg    6180
ggaggtctat ataagcagag ctctctggct aactagagaa cccctgctta ctggcttatc    6240
```

```
gagatatctg cagaattcat ctgtcgactg ctaccggcag cgcgcagcgg caagaagtgt    6300
ctgggctggg acggacagga gaggctgtcg ccatcggcgt cctgtgcccc tctgctccgg    6360
cacggccctg tcgcagtgcc cgcgctttcc ccggcgcctg cacgcggcgc gcctgggtaa    6420
catgcttggg gtcctggtcc ttggcgcgct ggccctggcc ggcctggggt tccccgcacc    6480
cgcagagccg cagccgggtg gcagccagtg cgtcgagcac gactgcttcg cgctctaccc    6540
gggccccgcg accttcctca atgccagtca gatctgcgac ggactgcggg gccacctaat    6600
gacagtgcgc tcctcggtgg ctgccgatgt catttccttg ctactgaacg gcgacggcgg    6660
cgttggccgc cggcgcctct ggatcggcct gcagctgcca cccggctgcg gcgacccccaa   6720 gcgcctcggg ccctgcgcg gcttccagtg ggttacggga gacaacaaca ccagctatag    6780
caggtgggca cggctcgacc tcaatggggc tcccctctgc ggcccgttgt gcgtcgctgt    6840
ctccgctgct gaggccactg tgcccagcga ccgatctgg gaggagcagc agtgcgaagt     6900
gaaggccgat ggcttcctct gcgagttcca cttcccagcc acctgcaggc cactggctgt    6960
ggagcccggc gccgcggctg ccgccgtctc gatcacctac ggcacccccgt tcgcggcccg    7020 cggagcggac ttccaggcgc tgccggtggg cagctccgcc gcggtggctc ccctcggctt    7080
acagctaatg tgcaccgcgc cgcccggagc ggtccagggg cactgggcca gggaggcgcc    7140
gggcgcttgg gactgcagcg tggagaacgg cggctgcgag cacgcgtgca atgcgatccc    7200
tggggctccc cgctgccagt gcccagccgg cgccgccctg caggcagacg ggcgctcctg    7260
caccgcatcc gcgacgcagt cctgcaacga cctctgcgag cacttctgcg ttcccaaccc    7320
cgaccagccg ggctcctact cgtgcatgtg cgagaccggc taccggctgg cggccgacca    7380
acaccggtgc gaggacgtgg atgactgcat actggagccc agtccgtgtc cgcagcgctg    7440
tgtcaacaca cagggtggct tcgagtgcca ctgctaccct aactacgacc tggtggacgg    7500
cgagtgtgtg gagcccgtgg acccgtgctt cagagccaac tgcgagtacc agtgccagcc    7560
cctgaaccaa actagctacc tctgcgtctg cgccgagggc ttcgcgccca ttccccacga    7620
gccgcacagg tgccagatgt tttgcaacca gactgcctgt ccagccgact gcgaccccaa    7680
cacccaggct agctgtgagt gccctgaagg ctacatcctg gacgacggtt tcatctgcac    7740
ggacatcgac gagtgcgaaa acggcggctt ctgctccggg gtgtgccaca acctccccgg    7800
taccttcgag tgcatctgcg ggcccgactc ggcccttgcc cgccacattg gcaccgactg    7860
tgactccggc aaggtggacg gtggcgacag cggctctggc gagcccccgc ccagcccgac    7920
gcccggctcc accttgactc ctccggccgt ggggctcgtg cattcgggct tgctcatagg    7980
catctccatc gcgagcctgt gcctggtggt ggcgcttttg gcgctcctct gccacctgcg    8040
caagaagcag ggcgccgcca gggccaagat ggagtacaag tgcgcggccc cttccaagga    8100
ggtagtgctg cagcacgtgc ggaccgagcg gacgccgcag agactctgag cggcctccgt    8160
ccaggagcct ggctccgtcc aggagcctgt gcctcctcac ccccagcttt gctaccaaag    8220
caccttagct ggcattacag ctggagaaga ccctccccgc acccccaag ctgttttctt    8280 ctattccatg gctaactggc gagggggtga ttagagggag gagaatgagc ctcggcctct    8340
tccgtgacgt cactggacca ctgggcaatg atggcaattt tgtaacgaag acacagactg    8400
cgatttgtcc caggtcctca ctaccggcg caggagggtg agcgttattg gtcggcagcc    8460
ttctgggcag accttgacct cgtgggctag ggatgactaa aatatttatt ttttttaagt    8520
atttaggttt ttgtttgttt cctttgttct tacctgtatg tctccagtat ccactttgca    8580
cagctctccg gtctctctct ctctacaaac tcccacttgt catgtgacag gtaaactatc    8640
```

```
ttggtgaatt ttttttttcct agccctctca catttatgaa gcaagcccca cttattcccc    8700
attcttccta gttttctcct cccaggaact gggccaactc acctgagtca ccctacctgt    8760
gcctgaccct acttcttttg ctcttagctg tctgctcaga cagaacccct acatgaaaca    8820
gaaacaaaaa cactaaaaat aaaaatggcc atttgctttt tcaccagatt tgctaattta    8880
tcctgaaatt tcagattccc agagcaaaat aattttaaac aaaggttgag atgtaaaagg    8940
tattaaattg atgttgctgg actgtcatag aaattacacc caagaggta tttatcttta     9000
cttttaaaca gtgagcctga attttgttgc tgttttgatt tgtactgaaa aatggtaatt    9060
gttgctaatc ttcttatgca atttccttt ttgttattat tacttatttt tgacagtgtt     9120
gaaaatgttc agaaggttgc tctagattga gagaagagac aaacacctcc caggagacag    9180
ttcaagaaag cttcaaactg catgattcat gccaattagc aattgactgt cactgttcct    9240
tgtcactggt agaccaaaat aaaaccagct ctactggtct tgtggaattg ggagcttggg    9300
aatggatcct ggaggatgcc caattagggc ctagccttaa tcaggtcctc agagaatttc    9360
taccatttca gagaggcctt ttggaatgtg gcccctgaac aagaattgga agctgccctg    9420
cccatgggag ctggttagaa atgcagaatc ctaggctcca ccccatccag ttcatgagaa    9480
tctatattta acaagatctg caggggtgt gtctgctcag taatttgagg acaaccattc     9540
cagactgctt ccaattttct ggaatacatg aaatatagat cagttataag tagcaggcca    9600
agtcaggccc ttattttcaa gaaactgagg aattttcttt gtgtagcttt gctctttggt    9660
agaaaaggct aggtacacag ctctagacac tgccacacag ggtctgcaag gtctttggtt    9720
cagctaagct aggaatgaaa tcctgcttca gtgtatggaa ataaatgtat catagaaatg    9780
taacttttgt aagacaaagg ttttcctctt ctattttgta aactcaaaat atttgtacat    9840
agttatttat ttattggaga taatctagaa cacaggcaaa atccttgctt atgacatcac    9900
ttgtacaaaa taaacaaata acaatgtgaa aaaaaaaaa aaaaaaaaaa aaaaaaaaa      9960
aaaaaaaagg tagcagtcga cagatgaatt ccaccacact ggactagtgg atccgagctc   10020
ggtaccaagc ttaagtttgg gctgcaggaa ttctgatggc tctcaaaatt cctgcctcct   10080
ttagggataa aagactttaa gacttttttaa caaaaagaa aaagaaaaaa aaaattcctg   10140
cctcctggtg tacacacaca gaagggttcc ctcccctga atgtgaccag gatctgtgaa   10200
aataacggga tagccgctcc tgtgattagg ttatgtggta gactagagca agattctcct   10260
gctggttttg aagaagtcag ctgccatgtt gtgagactgt catgggctag ggcatgagcc   10320
tttaaatatc tgggagcaac ccctggccag cagccagtga gaaaacgggc cctcagtcct   10380
acaatcacaa ggaactaaat tctgccaaca acctgaagga actttgaaga ggatcatgag   10440
tcccttgatt cagcttgatg agcccctgag cagaggatac agctaacttg tactagggaa   10500
gtataaaaaa catgcatggg aatgatatat atcaacttta aggataattg tcatacttct   10560
gggaatgaag ggaaagaaat ggggctttag ttgtattatg atctttaatt tctcaaaaaa   10620
aataagatca gaagcaaata tggcaaaatg ttaatacttt tgtgggtacg taggtattca   10680
gcatacccctt ttttctgagt tcaaaatatt ttataattaa aatgaaatgc aggccaggca   10740
cagtggctca tgcctataat accagcactt tgcgaggccg aggtgggagg atggcttgag   10800
gccagaccag cctggccaac atggcaaaac cccatctcta cttaaaaaaa aaaaaactat   10860
atatatatat atgtgtgtgt gtgtgtatat atatatatgt atatatattt atatatgtgt   10920
gtatatatat atatgtatat atatttatat atgtgtgtgt atatatatat atacacacac   10980
```

```
acacatatat acatacatac atacacacac acacacacac aattagccag gcatggtggc    11040
gcacacctgt agtcccagct acttgggagg ctgagacatg agaattgctt gaacctggga    11100
ggcagagtag ttagtgagct gagatcatac cactgcactc cagcctggtg acagagtgag    11160
actctgtctt aaaaaaaata aaaattaaaa ttaaatgcaa aaggtccaag tgaattgaag    11220
aggaaagggg tatcaaggaa ggttttgtgg aggtgacgtt tgagctgggt cttaaatgac    11280
ttaaacatgg gataagaagg gagggaataa ggacatttca ggtacgagaa ataaggagca    11340
aacagtggaa acaacctaac gtctgtcaac cagtgaatgg ataacaaaaa tgtaattcag    11400
atggtatcca acttacgatg gttcaacatg agattttttct gactttagga tagatttatc    11460
aaagtagtaa atccattttc aacttatgat attttcaact tcagatgggt ttatcaggac    11520
acagttgagg aacacctgtc tatccataca atttggcaat aaaaaggaaa tgagtgcaga    11580
tatactccac aacatgaatg aaccttgaaa acattaagtg agagaagcca gatacaaaag    11640
gccacatatt gtatgattct atttatacaa aatgtccaga ataggcaaat cttatagaca    11700
gcaagtaggt agatgatcag tttgctaggt gctgggggaa ggggaaatgg ggagtgatgg    11760
ctaaggggat tgggtttctt tgtggggcaa tgaaaatgtt ttaaaattga gcgtgataat    11820
gattgcacaa tgctgcatat atatataatc tatagattat atatatataa agagaggctg    11880
ttagacagtg ataagtgata tatatatata tatacataga gagagagaga gagagagaga    11940
gaggctgtta gtgataagtg atcaggaaaa taaaagtatt gaggaggaat acgaagttga    12000
cggtgtgaaa acatgagatt ttatatagga tggccaggga aggccttaat gagaaagtga    12060
cttatgagta aaaacaaggg atcctaaacc ttagcatgca tcagaatcac tcggaaactt    12120
gttaaagcat agcttgctgg gcctcatcac agatattttg attcggtagg ttcttgtctg    12180
atattaatac ttttggtcta gggaaccaca ttttgagaac cactgagcta aaggaagtaa    12240
aggtttccct tagtttacta gctggtaaca ctggcccagg aggccttttct ggaaaaggtc    12300
ccagtcccca aaggaagctg gggactcgcg ttcacatcgt caaggtttac caagttgtgg    12360
cgggcctttc cgtcttggaa aaagcctcaa aatggcagat tagggtgtcc atggccggcg    12420
gaaagggtct ttgaagttgc agaccaggag ggaagaagat tctgggcctc ccccatgcag    12480
tgtcagctgg caacagaatg cacccccggct gggttggagg ccctgggtac tggctcttcc    12540
acaccagggg cccacctacc aagggcagca ggagcatctg cacctcctgc gccaggcgcc    12600
cttcagtgct tccacttgag cacctctcca gacaccagct agggtgacag tggtacaaat    12660
accagactcc cctggcctgc tcacctcaca gggtaatgtg ctgtggagtc aggggacac    12720
agcaaccacc agatgacatg gctggccccg gggaggacga cacgcagata cggctacttg    12780
gcacctgtga tattttacac actcgagagg ggcccgcacc atcctcagcc ctctccccac    12840
attcactctt agttcatgtc acctccaccc agaggggggac acaggcccac agcgatggcc    12900
ccacaccctg cctgaggtcg cccacttccc aggaggcagt cctgggactt ccacccgacc    12960
aggccccaga gcccaccgac ttaaccccct cagaggcttg tcgttcatta ccttattcaa    13020
gatgagacc agccttttttg cggagaaaat gcgggtgaag gtcctgaaag tgcattgacg    13080
ccgttttcgg aagccataca agtttagctg gcggaagaag ctctttatcg aagttgtggc    13140
aaacactttg tgtgcgacgt cccttttgag aatctccttt tcaaagagtt tttgattgat    13200
cactctacaa gccccactgt catcccacca gatggacgaa aactggttgc tgctgaccag    13260
tctccacagt ttctgtggaa agggaggga gaggagatta tcttctccct ggggcggac    13320
gtcaccgtca gggtgcggcc ttctgaacga agcttcctcg gccagaggtt ggaaagcgat    13380
```

```
ttcttctgtc agcagcctca agttagggct cccagtggac cccgggtcgt cccaggcagg    13440
ggaaggatct gctgggtgaa ggtaggtctc tgactgcaac tggggaggga aaggcaccct    13500
ttccaagcca tgatcctgtc ctctcgaatt tctttcttca cagcgagcca tactcaatga    13560
tcgcttgtcc tccatctggc aaacttgcta gtgcagtgtg gccagcagca ccccttggca    13620
gtcatgtaac cagccccatg acatcataaa ggggctctga ctgccggggg gtggcatctc    13680
cacccccagc aagttgtgta ataaagggcc aaggcagaca agtagctgcc catctgcatg    13740
tgcacattct ggtcctcaca gtcatttcaa tgggaaagat gacactagtg cacaagagtg    13800
ccgaggggcc ctgccacacc gtagatgcag acctggagcg gtccccttgt cctagagctc    13860
ctgagccagg cacaactaca gcaaagccct ggctcaggaa ggtcagagct caccgtctga    13920
gtcatgggcc cacagacccc agcacatgac tgacactcgg aagcacagaa caaagggtag    13980
gacggtgccc atgggtcagg ctgtagccac gccacccttt ccaccctgtc ctagccagag    14040
gcagcaatgt gctccataca gatcctccta acacacccac actgtcggtc cccagcacgc    14100
agatgcccga cagccccta ggcaaatggc ttagctgact gccccaccac acgccgtcgc    14160
catgcagtcc agtggggagt cggaggcagc ctccttcctg cctctcctcg gcctgcacgt    14220 gtcccccac caggcagaga cccttctaca ccccgggtgt ctgcggtcac atcgcggtgg    14280
ggcatgcagc tgttggcctt cgagcatgtt ttgttttcct tggccagtgt ctccagagaa    14340
acgcacgtgg gtttgtgtcc agcggtccat ctctgcaaca gttgttcctt gggattgga    14400 tgctaggagg tcacgggaga ggtgtccatc caaagcagtg tctgtgtcac acactgtccc    14460
cacacacagg gccacctctg cacagactcc cccgactcga ttctgggcac agagctcagt    14520
gaccttccag agactgccac gaaccggtga tgcctccacg cttgagacat cctgaccgca    14580
gggcccaagg cgcactggct caggggtga cagtgagggg tctgcaaaca gactgctgat    14640
gctcaacccg gccgctgccg agctgtgtga cttgggcacg tcacttaacc tctctcggcc    14700
tctgtctcct cccggggata agagtagtag cacctgcttc ccggggctgt gaggatccag    14760
tgggacgtat aggaactagc gaggcaccgg cagttgggtc agagctactg ttgtcacttc    14820
acaaggcatt tcttcaaca gcaagtcgga aatctcatga gcctaaggca gaatccacct    14880
gtggcctctg gttacaaccc acaggactga aaatccttcc agccacagca actggtgaat    14940
ttcctggtca attgccacaa gtcatgagct gaaccccact tgagtttcag ttcaggcaga    15000
actctagaga cgactagggc aagctagaca gcgactgcag agccttttgt tgcagcgtga    15060
gcagtcctca gctgttgaca tcactgggga gcaaacgagg accaggagcg gtgaaaggac    15120
agtgtctgct gcagattgtc gtagcaccca aggaacactc cagaaagcct cctaagcagt    15180
aacaagtgtg gcaaggtgta gcccagccaa cagtggcatc tgcgaggcgt cccctccttc    15240
ctcccactac cccgtatacc ctgggacctg tgcactgaag gactcattct aaaggctgtg    15300
cccctgcagc cgccagcctc actcactggc tgcctgtgcc agctagagat ttcttttcctc   15360 tgaggctggc tgagaggacc actccagttt cctggcccat ccagcaaaga agatacacat   15420
catgcacgtg taaaatgagg aaccggttta ttgaacagct taaggagagc aaaaatagtg   15480
gctttagcta cattttttac acactgagca ggaaagtcta aaccatcccg ttcccctgta   15540
ccccaaagag aacagggctt gctggaggcc agtgccaagg gcggagtcgt gctcgcagca   15600
gacttgaatt aaccccatgt aggcggcga gcagttgccc gcgtgaaaac accaccctct   15660
tctcctggct gagaagatca aagctctttt tttaccctct tttcagcaaa ggacctattt   15720
```

```
gttttcaggc aggaggatgt taaacttgca gcctctgaca cacggtggaa cctgcagtgc  15780
ttggagaaac ggcacgcaca cgtgaaaaca tcatgcctac tccaaagcct tcttgttgct  15840
ggcaggaggg aagcttgaga cttttcccacg catagtcgtg acccgcgtgg ccgtttctgc  15900
tctcagcaac attctctagt gttccggctt caagcagcgc ttgtcaggtt tgaagctagc  15960
cactattctg agaacgtcag aaaagcatgg accatctctt gcttggtgtt gccgttgtgg  16020
cagtagcagc tactacgtac ctgcacgagt tccagggcag aagtggcaat gtcccatgaa  16080
ggcgtggcac cccacggggg ggggggggga gtgtgccacg ggcgtccact tctgcagcag  16140
aaggcatgtg cctacagcac aagcttgtaa aaaatactt gaacagaata tgctgtacag  16200
aactaggggt taacaccgca tatgaagatg ctaaaacatt tgtataaata ctctgtatac  16260
aagcatggag tcactcccgt agaaagggct catccgtgag gctatgaaaa actgctgtca  16320
gcatgcccaa agagaaacta cttccacagt aggaacagaa aaaggactg tgctgtgtct  16380 aaacacgtgg tgcatcagag acatagttac agttcctact gactgcccca gccacgacct  16440
gggagtgctg aggacctggg agtgctcagc gagctgcagg aggtcagccc tgtggagaaa  16500
tacatttcta aacaatactt ttgattggga tttcagcacc gtatagacag atgttccttc  16560
tgggggcctg gcaagcagcc atctcccagt gggtctgacg gggaagaggg gtacctggag  16620
cccctcccag acagacggta atcccacccc tgttctcaca ctcttcctgg catccgcatc  16680
tgctggcaca caccccgtc acctgccact tccgcgtccc gtcgtggtga gtggctgata  16740
ggcgctggat gcaaacaagg catgagatgg acgtacctgg agacccagct ccagtactgg  16800
ttctggtctg cggggtgaac gaggggggcag aggaaggcgg agagagtgcg tcccagtcca  16860
cttaagctct gtccccggaa gtggcatcta atctggcatt tcgatattta atttgggagg  16920
tgggagcaca tacttcccag ggctctgggt aatgaccacc ctggccttct ttcgaaacat  16980
gggtgcgatt ttaggggggct ccggaactgg ggtctcttcg gtttcttcat tatcttcgtg  17040
atggagatca taggaaatgt ttccatattc tcgtagaaat gggaagattt caagcagaaa  17100
ctgacagaaa tctttgcgga taccaaacca ccctgaaaaa taagaatttt ttatttcaca  17160
cacgaggctc aactgaccctt cctgttaact ttctttccgt aacaagaagt ttcactccta  17220
caatgtcata acatacttta tccagactcc tgagtcacaa agcctgaaca gggcttgagt  17280
acccaaaatg gggaagaagt gcaaatgcta gctctgtggt gcttggagtg gggttcccgg  17340
accggcaggg acagcgtcca cggggcctag ttagggatgc cattctcggg ccccagccca  17400
gacctccaga aactgagtcg ggctagggtg ggctccagcg gtccccttt cctggccctt  17460 ttgggattct gctggatgcc caaatttgag aactactgct ccagtgagtc tcaaaatatc  17520 tgtggtcgc agactacggt gtcttccgct aatcttctcc agccaggata aactcatgga  17580
tgacagtgcc acccaagaac aagatttctg tcaccctctg gaatccgtga gggcggtagt  17640
catgcacggg ttggccagga gggggcctga actcatggag ccaccttaaa gccactttcc  17700
cagtcccact actcctctct gtaggctact ggagtgtcag ctcggtgcaa gccctccctg  17760
ctcccgggtg cggggtaggg ggcagaggca caaacagcaa gcacagcccg ggctgctggg  17820
ctgcagtgag gccctgcccc caaacccact ggctttccga agggcaatgc tctgggcttc  17880
cgtgccatgg agcccacagc cttgccagga aggcaccctc tgcagagatc gttttggaag  17940
tgtctgcctc agcaagcagg tggagggaa tagagtgtta gcaaggcaag acaggcaaga  18000
ctcgggtgat ggcagcaagg atatggggga ggcagagcgg ccaacaggga cctaggatga  18060
atcccaggtt tgggtgggag atgtggattt tccatcaaac cctcccgggc ctgggaagaa  18120
```

```
tctgtcttga tccccatttt gcagaggagg gaacgggatc tctgagaggt tgcctgccgt    18180
gtctggttct acctcaaatg gcagcgtgca ctgcgagaaa agtcccggtg caggccagca    18240
gaacaccaga gttacggcat gcccttccct tagaaggtcc cagaatttcc tcagccctca    18300
ctttcccaca caagcttcta aattggggcc ctcggggact catcccttcc tagacttcta    18360
tccgccaccc cccaccccct ggtccccccc cagacacaca ccaaggactt ctgaaatgct    18420
gagtacatac agtggtttcc tcccttctgt ccaaatgtgg ttgccatcag cgtgatcaac    18480
gagagccaaa gggggacaaa gatcgggatg caggagaagg cgttgtggcc atccagtttg    18540
tgaaccagca gaatctaaag aaagagacat agtcccggtt gatgccagca ccgaaaatgg    18600
gcagaggcgg aagccagact tcattaggca gttcctcccc accacccac cccgcgtga    18660
gctcccacaa gagggaacat cagcaccgcc agaaaaaggc aggaaaccac ctatccctgg    18720
ggaaagctcg aaatgagctt ttatgtccct cttcagagct cggcaatagc ctatccactt    18780
gaaaagttcc cagtgccagc agttttatgg caaactcctc cgggtgtttg ttctaaggag    18840
tcaacagctc ccattctaga attctccacg tgactccaat acacaaatct gacatcccac    18900
tctgctttcc ccagagtgga aactggagcc atacagaggc accatggcta aaaaggtgca    18960
ctcttctccc tgccagcccc acgtgctgcc cccaagagaa aggaaggatg ctctcctttc    19020
accgaagctc cctctcggag atggctgtgt tctctcccct ctcctggagt gggctcactg    19080
tgagctcgag ggacagaggc tgcctttcta ggggtgcaga atcctgtcag gggaagcgca    19140
agcttcaggg gctgaagagg cttcccgtgg aacgcttacc tcaaatgtaa gaaggggcac    19200
gacgatggtc atccagctca gggccatggt tatgtgtgtc ctgcgctgtc cgcaatcaca    19260
tccatagagc gcaagaacaa gacggaccac acaatgtagt agaggaccac caggcacaga    19320
aaggacatga gaatccacag cgggacacac acaacctggg ggtgggtgag agaacagcaa    19380
gagaagtctc tttagagctt ccaacctggc ctctgatgga aggcatcttt agcaccttgc    19440
tgtgtctgtc cagttaaggc ggtccttcct gtgagccgaa taaggaccgt tccatctccc    19500
aggactgctg ggagcatcgc tcaggacaga aaaggtatgg tatgttcact atggggcctg    19560
ctgccaccag gggacacaca cgctcagtga gtcatcagtc cctcttcctt tgggtgacag    19620
acagccctgc acctggctcc gcagcctcta ctcttccaga ggcccactct cccacactct    19680
ctcaggctcc tctaggttct gctgccatca cagcttcccg ggaaatggga cacaactgtc    19740
accctgtgca cacacacaag atctcacccc aacagactct cttcacaggc aacattccca    19800
caacctgctg ggggtacttt ggcaacacaa atgggaatgg gctccccaga aagtctggct    19860
gcctgggctc ctaaggatcc ctaacctcac ccctaccaag ttagtgaact tggcgggttg    19920
atgctggata caggttgatg ctggatacgt agcgctgccg ggtcgtgacc cctaaggaat    19980
tatccaaact cttgttttta gatgctttat tatatcaaac tctcctttaa caagtggcc    20040
catctgctgg gatttggaag cctgtaatac tgaaattttc atcataatgg aaattttaaa    20100
aacagaattt gacccacctg tttttaaaac actttcatta cttaacaaga ggtctaatct    20160
tgggcaagtc ttgaaatttc tctggcctta gtttcccatg tgttaaatga aacttgaagc    20220
agttggtctc ttatagtctc ctgactctaa cattctaaga attatatttg tacaataact    20280
caaaaatcac ataatttaat ttaccatatg gactccaaaa tatattttct cattaggcta    20340
aacttgatct gcattttctg gatgtgtcca tattcttgga ctacactaaa acatgatacc    20400
aatgcttcct ctcaccataa accctcactt cgctttctac atttaagaat tttatagctg    20460
```

```
gaagagtcct taacagaaaa taccatctaa taattacccc tcaaaatcga gaaagtccta   20520
tctgttctta tgctagttat aagaatgagg cagcatttca cataatggtt ataaacactg   20580
ccacaagaag attcatgatg tgttgtttat ctgtagctct catcatactc tgtcatataa   20640
ctatagcatt aagattttaa tgttctatat attcttctaa gacagtgttt accagagtaa   20700
ggcacaaaag atccactggt ttgcaagaaa gattagaact tttaaatttt ttacctcacc   20760
ttgtttaatc tatattttg tatgtattt gtaacatata tattattatt accataaatc   20820
atatataatt taaatgcat atattagggg taaatgctca ggaaactttt tataaattgg   20880
gcatgcaaat acaagtttga agactcactg ttctaggtat taaaagtaaa gttataacca   20940
agtaaagctt ccacctttc atgtctcaaa gcagtttatt gttggaggta agatctctta   21000
gaagcctaaa caggtccaag tacagaatga agtaaggcta gcccataact tgtggcaagc   21060
aattcatact atttctctca tgctgagctc tcctcagtga agcagctact atagacaact   21120 gcagccatt ggtagcctat tttacaggca ggaaaaaaat tacttttat tcaaagtgga   21180 actcaggaca tggggagaaa atgaatacaa aaaatagggt caatccaaag gcacacagca   21240
aatgagtaac acagttatgt ttttttccca tttgtatgag gtcccagtaa attctaagta   21300
aactgcaaat ttaataatac actaaaaag ccatgcaatt gttcaaatga atcccagcat   21360
ggtacaagga gtacagacac tagagtctaa aaaacaaaag aatgccatta ttgagttttt   21420
gaattatatc aagtagttac atctctactt aataaatgag aaaaacgagg ataagaggcc   21480
atttgataaa atgaaaatag ccaagaagtg gtattagaga cttgaataca ggtattcggg   21540
tccaaagttc atctgctcaa atactaactg gggaaaagag ggaaaatat ttatatacat   21600 atatatctgc acacaaaat accccaaaa gacaaaatga ggccaggcag ggtggctcac   21660
acccgtaatc ccggtacttt gggaggctga ggcaggtgga tacctgagat caggagttgg   21720
agatcagcct ggtcaacatg gtgaaaccct gtctctacta agataaaaaa aattagccag   21780
gcatggtggc gtgcgcctgt aatcccagct acttgggagt ctgaggcagg agaatcactt   21840
gaactgggaa gggaggttg cagtgagcca agatcgtact actgcactcc agcctgggca   21900
gcagagtgag actccatcac aaaaataaat aaataaataa aatacaatga aacagaaagt   21960
tcaaataatc ccataatctt accaccaaga aataactttc actcgttata cttattgatt   22020
tttccataat aaatgtactt tactgtgact atcatgaaaa gaaagttatt ttagaaacag   22080
agaactgttt cagatcaaat ctatgtagta gaacagagcc attaggtggg aaagacgaga   22140
tcaaactaaa tctcagaagg cctaaaaggc taggtccatt ccagcactaa aaactgacca   22200
gacaagtaat ggcttcaaca gcttctaaat atggacaaag catgctgaaa gggaaggaca   22260
ggtctaacag tggtatatga aatgaacagg aggggcaaag ctcatttctc ctctgaagtt   22320
ttccaaagat gctgaggagg acattagttt gacatgaccc tgatatggga caagataatt   22380
tcacagaagt tttacatgtt aaagtttct tatagatact cattcaagta agcaatgaac   22440
actaaaatct aaagaaagaa aagagcttta gagtcaggtc tgtattcaaa ttcaagctct   22500
accacttact ggttctgtga ctttgggcaa gtcttttaac cttattaagt cttaatttcc   22560
tgatttgtaa aatggggata tcgtctccct cacaggattg ttgtgaaact tttatgagat   22620
taatgccttt atatttggca tagtgtaagt aaacaataac tggcagcttc aaaaaaaaaa   22680
agcagtagca ttccatcatt tattattggt tactctcaaa aagttttca atgtactaga   22740 agataaaatat tcaaataccct taatatctcc attattttca ggtaaacagc atgctcctga   22800
acaaccaatg ggtcaacaaa taaattaaaa gggaaatcta aaaacatctt gatattaaac   22860
```

```
tacatggaag cacaatatac caaaaccaat ggttcacact aggagaattt taaggtacaa   22920
gaaaactctt tgagatttct taaaataata gtatgtctga atttattgag tgatttacca   22980
gaaactgttg taagagctct acttgcatta tagcacttaa tcctcttaac tctatggctg   23040
ctattatcaa cctcacccta atcacatatg ggacacagag aggttaagta acttgcccaa   23100
ggtcagagtt aggaagtact aagccatgct ttgaatcagt tgtcaggctc cggaactcac   23160
actttcagcc actacataat actgctttgc tatcttttag gaaactatgt gagtctacct   23220
cacatagact cacataggtt tgtttttttt ttttttttaa aggctatctt ttccccatc    23280 aatgttttt gaaggatccc aaattagagt cccacagagg cagacagcag tacttgacaa   23340 tatgacatt taaggttaat gttggattct actgtctttt tactacatga cctagggaac    23400
gataattaac ctagactgct tccaagggtt aaataaccca tttagttata ctatgtaaat   23460
tatctcttag tgattgattg aaagcacact gttactaatt gactcggtat gaagtgcttt   23520
tttttcttcc ctttcaagat ataccttt ccagttaaag ttgagagatc atctccacca     23580
attactttta tgtcccctgt tgactggtca ttctagttaa aaaaaaaaaa aactatatat   23640
atatatatct acacacacat atgtatatgt atatccttat gtacacacac aaacttcaaa   23700
ttaaatgaga actagaagat ttgagaagtt agctagctaa tatccatagc attatgatat    23760
tctaaatgat atgaattata agaattaggt ttcctgaaat gaatgactag aaaactttca   23820
agtagagatt agtaaaaatt aaaaagtcct aatcggccat tactgatttg atgttttaa    23880 gagtcctaaa aaatgggtta catccatttt taagtgggta gtattataac agccacccat   23940
cttcaatcac agtgatttct gaattgtgag ggaagttatt agcatgacag gtgtctggtt   24000
ctggccctgt acgattccca tgagtcaagc aaattgtaag ggctggtcta tatcacaccc   24060
aaccccaagg atatgtccct caaaagtcta gcccaggccc cgtcatcttc agcatcatct   24120
gggaaaccag gtctgattag tagtccttta aggaatacct cttaggctcc cattttactg    24180
ctatcacaga atccaataaa acccttacag gagattcaat gggaaatgct caacacccac    24240
tgtagttggt ggtgacaatg accataattt ggctgtgctg gattcaggac agaaaatttg    24300
ggtgaaagag caggtgaaca aaagagcttc gacttgccct agcagagagc aagccatacc    24360
ataccacaaa gccacagcaa ttacaacggt gcagtaccag cacagtaaat gaacaaagta    24420
gagcccagaa acagacccag aactatatga ggatttagta tacaataaag atggtatttc    24480
gagtcagtag ggaaaagatg aattattcaa taaatgatgt ttggccaact agtaacccat    24540
ttgggaaaaa ataaaagtat ggtccctacc tcacagcata cacaaaaata aattccagac    24600
ggattaaaat ctaaatgtaa aaaataaagc cataagtgga ctggaagaaa atagagaatt   24660 tttttaaca tccgtagaaa gggtaaaaac ccaggcatga catgaaccaa aactgaagag    24720
gttctgtaac aaatacccc ttttatatat tgggctccaa caataagaac ccataggaaa    24780
atggagaatg aacacaaata gacaatttat agaagagaag gttataaggt gtaaaattat    24840
atctatctga gaaacaaaca ctaaacaat gtgattctac tgttctccca cccatactgg    24900
caaaacttaa gcctgataat atgctgaggg gaaataagca ctcttgttgg tgagagtatt    24960
aattggcata gcttctttg aaaatgacat agcaatacct gttaaaattg caaacatgca    25020
tgtcacttaa tccagtaatc ccacttctgg gaatcaatgc tacaaaaaca ctgacaagta    25080
tacaaagata cattcaagag tgttcactgg gccgggtgcg gtggcttcat gcctgtaatc    25140
ccagggaggc agaggcaaga cgatcgcttg accccaggag ttcaaggcca gcccgagaaa    25200
```

```
cacagcaaga ccctgtctct cttttttttta tttaaaaaat aaatgttcac tgtatcagtt   25260
gttcacaaaa acaaaccaac atgtccatta acagggaacc atttaaatta atcaagttca   25320
tctacacaat gtaataccat gcaactatta aaaagcacct gataatccaa agcacactga   25380
gacagaataa tgctattaaa aacaccaagt agtggaacac tgtgttgcct atgacaccat   25440
ttttattcaa catttaaaca aatttgtaac agcaattaca tgagtagtga caatggcgtt   25500
tatgagactt ttcactttta tgtgcttcta tttttgttat gcttctatat atacatccat   25560
ttattatgga gtgttacttt caaaaatcac aaatgggcca gtattatttg gtgttgcaag   25620
gtgagcatat gacttctgat atcaaccttt gcatattact tctcaattta gggaaattac   25680
agacatccct tattctaact aacttaaaac ccagcatttc aaacatacag aattgatggg   25740 gaaaaaaag aaagaagaaa gaaagaaaag gcaacaagct tcagatgaca gtgactcaca   25800
tcaaattatt tataaaatct gttaaatagt gccatcttct ggagatacct ggtattacag   25860
tccaactcca gttgatgtct ttacagagac aagaggaata aaggaaaaaa tattcaagaa   25920
ctgaaaagta tggagtcatg gaaaaattgc tgtgatccaa aggctacggt gataggacaa   25980
gaaacaagag aactccaagc agtaagacac tgctgttcta ttagcatcca aacctccata   26040
ctcctgtttg ccccaaggct ttttttaaaaa atagagacag gatctcacta ttttgctcag   26100
gctggtcttg aactcctgga ctcaagctat cctcctgcct cggcctccta aagtgccgag   26160
attacaggct tgagtcacca tacctggcta ttttatttttt cttaactctc ttgcctggcc   26220
tatagccacc atggaagcta ataagaata ttaatttaag agtaatggta tagttcacta   26280
cattggaata caggtataag tgcctacatt gtacatgaat ggcatacatg gatcaattac   26340
cccacctggg tggccaaagg aactgcgcga acctccctcc ttggctgtct ggaacaagct   26400
tcccactaga tcccttact gagtgcctcc ctcatcttta attatggtta agtctaggat   26460
aacaggactg gcaaaggtga ggggaaagct tcctccagag ttgctctacc ctctcctcta   26520
ccgtcctatc tcctcactcc tctcagccaa ggagtccaat ctgtcctgaa ctcagagcgt   26580
cactgtcaac tacataaaat tgccagagaa gctctttggg actacaaaca catacccta   26640 atgtctttat ttctattttg tctacctctt cagtctaggt gaaaaaatag gaaggataat   26700
agggaagaac tttgtttatg cctacttatc cgccccctagg aattttgaaa acctctaggt   26760
agcaataaga actgcagcat ggtatagaaa aagaggagga aagctgtata gaaatgcata   26820
ataaatgggc aggaaaagaa ctgcttggaa caaacaggga ggttgaacta taaggagaga   26880
aagcagagag gctaatcaac aaggctgggt tcccaagagg gcatgatgag actattacta   26940
aggtaggaat tactaagggc tccatgtccc cttagtggct tagtactatg tagcttgctt   27000
tctgcagtga acttcagacc cttcttttag gatcctagaa tggactttt ttttttatcg   27060 gaaacagtc attctctcaa cattcaagca ggccccaagt ctaccacact caatcacatt   27120
ttctcttcat atcataatct ctcaaccatt ctctgtcctt ttaactgttt ttctataccc   27180
tgatcaaatg ccaacaaaag tgagaatgtt agaatcatgt atttttagag gtagactgta   27240
tctcagataa aaaaaaggg cagatattcc attttccaaa atatgtatgc agaaaaaata   27300
agtatgaaag gacatatgct caggtaacaa gttaatttgt ttacttgtat tttatgaatt   27360
ccctaaaacc tacgtcaccc gccccgttcc cacgccccgc gccacgtcac aaactccacc   27420
ccctcattat catattggct tcaatccaaa ataaggtata ttattgatga tgttaattaa   27480
catgcatgga tccatatgcg gtgtgaaata ccgcacagat gcgtaaggag aaaataccgc   27540
atcaggcgct cttccgcttc ctcgctcact gactcgctgc gctcggtcgt tcggctgcgg   27600
```

-continued

```
cgagcggtat cagctcactc aaaggcggta atacggttat ccacagaatc agggggataac    27660
gcaggaaaga acatgtgagc aaaaggccag caaaaggcca ggaaccgtaa aaaggccgcg    27720
ttgctggcgt ttttccatag gctccgcccc cctgacgagc atcacaaaaa tcgacgctca    27780
agtcagaggt ggcgaaaccc gacaggacta taaagatacc aggcgtttcc ccctggaagc    27840
tccctcgtgc gctctcctgt tccgaccctg ccgcttaccg gatacctgtc cgcctttctc    27900
ccttcgggaa gcgtggcgct ttctcatagc tcacgctgta ggtatctcag ttcggtgtag    27960
gtcgttcgct ccaagctggg ctgtgtgcac gaaccccccg ttcagcccga ccgctgcgcc    28020
ttatccggta actatcgtct tgagtccaac ccggtaagac acgacttatc gccactggca    28080
gcagccactg gtaacaggat tagcagagcg aggtatgtag gcggtgctac agagttcttg    28140
aagtggtggc ctaactacgg ctacactaga aggacagtat ttggtatctg cgctctgctg    28200
aagccagtta ccttcggaaa aagagttggt agctcttgat ccggcaaaca aaccaccgct    28260
ggtagcggtg gttttttgt ttgcaagcag cagattacgc gcagaaaaaa aggatctcaa    28320
gaagatcctt tgatctttc tacggggtct gacgctcagt ggaacgaaaa ctcacgttaa    28380
gggattttgg tcatgagatt atcaaaaagg atcttcacct agatcctttt aaattaaaaa    28440
tgaagtttta aatcaatcta agtatatat gagtaaactt ggtctgacag ttaccaatgc    28500
ttaatcagtg aggcacctat ctcagcgatc tgtctatttc gttcatccat agttgcctga    28560
ctccccgtcg tgtagataac tacgatacgg gagggcttac catctggccc cagtgctgca    28620
atgataccgc gagacccacg ctcaccggct ccagatttat cagcaataaa ccagccagcc    28680
ggaagggccg agcgcagaag tggtcctgca actttatccg cctccatcca gtctattaat    28740
tgttgccggg aagctagagt aagtagttcg ccagttaata gtttgcgcaa cgttgttgcc    28800
attgctgcag ccatgagatt atcaaaaagg atcttcacct agatcctttt cacgtagaaa    28860
gccagtccgc agaaacggtg ctgaccccgg atgaatgtca gctactgggc tatctggaca    28920
agggaaaacg caagcgcaaa gagaaagcag gtagcttgca gtgggcttac atggcgatag    28980
ctagactggg cggttttatg gacagcaagc gaaccggaat tgccagctgg ggcgccctct    29040
ggtaaggttg ggaagccctg caaagtaaac tggatggctt tcttgccgcc aaggatctga    29100
tggcgcaggg gatcaagctc tgatcaagag acaggatgag gatcgtttcg catgattgaa    29160
caagatggat tgcacgcagg ttctccggcc gcttgggtgg agaggctatt cggctatgac    29220
tgggcacaac agacaatcgg ctgctctgat gccgccgtgt tccggctgtc agcgcagggg    29280
cgcccggttc ttttttgtcaa gaccgacctg tccggtgccc tgaatgaact gcaagacgag    29340
gcagcgcggc tatcgtggct ggccacgacg ggcgttcctt gcgcagctgt gctcgacgtt    29400
gtcactgaag cgggaaggga ctggctgcta ttgggcgaag tgccggggca ggatctcctg    29460
tcatctcacc ttgctcctgc cgagaaagta tccatcatgg ctgatgcaat gcggcggctg    29520
catacgcttg atccggctac ctgcccattc gaccaccaag cgaaacatcg catcgagcga    29580
gcacgtactc ggatggaagc cggtcttgtc gatcaggatg atctggacga agagcatcag    29640
gggctcgcgc cagccgaact gttcgccagg ctcaaggcga gcatgcccga cggcgaggat    29700
ctcgtcgtga cccatggcga tgcctgcttg ccgaatatca tggtggaaaa tggccgcttt    29760
tctggattca tcgactgtgg ccggctgggt gtggcggacc gctatcagga catagcgttg    29820
gctacccgtg atattgctga agagcttggc ggcgaatggg ctgaccgctt cctcgtgctt    29880
tacggtatcg ccgctcccga ttcgcagcgc atcgccttct atcgccttct tgacgagttc    29940
```

-continued

```
ttctgaattt tgttaaaatt tttgttaaat cagctcattt tttaaccaat aggccgaaat    30000
cggcaaaatc ccttataaat caaaagaata gaccgagata gggttgagtg ttgttccagt    30060
ttggaacaag agtccactat taaagaacgt ggactccaac gtcaaagggc gaaaaaccgt    30120
ctatcagggc gatggcccac tacgtgaacc atcaccctaa tcaagttttt tggggtcgag    30180
gtgccgtaaa gcactaaatc ggaaccctaa agggagcccc cgatttagag cttgacgggg    30240
aaagccggcg aacgtggcga gaaaggaagg gaagaaagcg aaaggagcgg gcgctagggc    30300
gctggcaagt gtagcggtca cgctgcgcgt aaccaccaca cccgccgcgc ttaatgcgcc    30360
gctacagggc gcgtccattc gccattcagg atcgaattaa ttcttaatta acatcatcaa    30420
taatatacct tattttggat tgaagccaat atgataatga gggggtggag tttgtgacgt    30480 ggcgcgggc gtgggaacgg ggcgggtgac gtagtagtgt ggcggaagtg tgatgttgca    30540
agtgtggcgg aacacatgta agcgacggat gtggcaaaag tgacgttttt ggtgtgcgcc    30600
ggtgtacaca ggaagtgaca attttcgcgc ggttttaggc ggatgttgta gtaaatttgg    30660
gcgtaaccga gtaagatttg gccattttcg cgggaaaact gaataagagg aagtgaaatc    30720
tgaataattt tgtgttactc atagcgcgta atactg                              30756
```